US010568650B2

(12) United States Patent
Goble et al.

(10) Patent No.: US 10,568,650 B2
(45) Date of Patent: Feb. 25, 2020

(54) KNEE INSTRUMENTS AND METHODS

(71) Applicant: E. Marlowe Goble, Logan, UT (US)

(72) Inventors: E. Marlowe Goble, Logan, UT (US);
Carlyle J. Creger, Wellsville, UT (US);
Daniel J. Triplett, Providence, UT (US)

(73) Assignee: E. Marlowe Goble, Logan, UT (US)

( * ) Notice: Subject to any disclaimer, the term of this patent is extended or adjusted under 35 U.S.C. 154(b) by 0 days.

(21) Appl. No.: 15/630,555

(22) Filed: Jun. 22, 2017

(65) Prior Publication Data

US 2017/0290597 A1   Oct. 12, 2017

Related U.S. Application Data

(63) Continuation-in-part of application No. 15/081,828, filed on Mar. 25, 2016, now Pat. No. 10,426,565.

(60) Provisional application No. 62/353,553, filed on Jun. 22, 2016, provisional application No. 62/138,307, filed on Mar. 25, 2015, provisional application No. 62/302,787, filed on Mar. 2, 2016.

(51) Int. Cl.
*A61B 17/17* (2006.01)
*A61B 90/00* (2016.01)
*A61B 17/15* (2006.01)

(52) U.S. Cl.
CPC ........ *A61B 17/1764* (2013.01); *A61B 17/155* (2013.01); *A61B 17/157* (2013.01); *A61B 17/1717* (2013.01); *A61B 90/06* (2016.02); *A61B 2090/067* (2016.02)

(58) Field of Classification Search
CPC .................................................. A61B 17/1717
See application file for complete search history.

(56) References Cited

U.S. PATENT DOCUMENTS

| | | | |
|---|---|---|---|
| 3,949,428 | A | 4/1976 | Cavendish |
| 4,187,559 | A | 2/1980 | Grell |
| 4,242,758 | A | 1/1981 | Amis |
| 4,364,389 | A | 12/1982 | Keller |
| 4,426,071 | A | 1/1984 | Klevstad |

(Continued)

FOREIGN PATENT DOCUMENTS

| | | |
|---|---|---|
| EP | 2145590 | 5/2012 |
| EP | 2626044 | 12/2016 |

(Continued)

OTHER PUBLICATIONS

Insall, John N. Surgery of the Knee. New York: Churchill Livingstone, 1984. pp. 631-365.

(Continued)

*Primary Examiner* — Samuel S Hanna
(74) *Attorney, Agent, or Firm* — Maywood IP Law; G. Jo Hays; David W. Meibos

(57) ABSTRACT

Knee arthroplasty instrument systems directly reference and align with the anterior distal femoral cortex and the mechanical axis of the leg. The anterior femoral resection is aligned in the same plane as the anterior distal femoral cortex. The center of the femoral head, the medial/lateral center of the distal femur, the medial/lateral center of the proximal tibia, and the second toe, medial/lateral center of the ankle, or anterior tibial spine are all aligned to the mechanical axis of the leg. Methods of using the instrument systems are disclosed.

22 Claims, 155 Drawing Sheets

(56) References Cited

U.S. PATENT DOCUMENTS

| | | |
|---|---|---|
| 4,457,307 A | 7/1984 | Stillwell |
| 4,502,474 A | 3/1985 | Comparetto |
| 4,509,511 A | 4/1985 | Neufeld |
| 4,524,766 A | 6/1985 | Petersen |
| 4,565,192 A | 1/1986 | Shapiro |
| 4,566,448 A | 1/1986 | Rohr, Jr. |
| 4,567,885 A | 2/1986 | Androphy |
| 4,567,886 A | 2/1986 | Petersen |
| 4,624,250 A | 11/1986 | Saunders |
| 4,627,425 A | 12/1986 | Reese |
| 4,677,973 A | 7/1987 | Slocum |
| 4,703,751 A | 11/1987 | Pohl |
| 4,718,414 A | 1/1988 | Saunders |
| 4,722,330 A | 2/1988 | Russell |
| 4,736,737 A | 4/1988 | Fargie |
| 4,759,350 A | 7/1988 | Dunn |
| 4,773,407 A | 9/1988 | Petersen |
| 4,892,093 A | 1/1990 | Zarnowski |
| 4,893,619 A | 1/1990 | Dale |
| 4,907,578 A | 3/1990 | Petersen |
| 4,926,847 A | 5/1990 | Luckman |
| 4,938,762 A | 7/1990 | Wehrli |
| 4,944,756 A | 7/1990 | Kenna |
| 4,944,760 A | 7/1990 | Kenna |
| 4,952,213 A | 8/1990 | Bowman |
| 5,002,545 A | 3/1991 | Whiteside |
| 5,007,912 A | 4/1991 | Albrektsson |
| 5,021,055 A | 6/1991 | Burkinshaw |
| 5,037,423 A | 8/1991 | Kenna |
| 5,047,032 A * | 9/1991 | Jellicoe ............ A61B 17/1764 409/179 |
| 5,049,149 A | 9/1991 | Schmidt |
| 5,053,037 A | 10/1991 | Lackey |
| 5,053,039 A | 10/1991 | Hofmann |
| 5,062,852 A | 11/1991 | Dorr |
| 5,395,377 A | 3/1995 | Petersen |
| 5,472,415 A | 12/1995 | King |
| 5,514,143 A | 5/1996 | Bonutti |
| 5,601,563 A | 2/1997 | Burke |
| 5,624,444 A | 4/1997 | Wixon |
| 5,688,281 A * | 11/1997 | Cripe ............... A61B 17/155 606/88 |
| 5,709,689 A | 1/1998 | Ferrante |
| 5,720,752 A | 2/1998 | Elliott |
| 5,749,876 A | 5/1998 | Duvillier |
| 5,925,049 A | 7/1999 | Gustilo |
| 6,013,081 A | 1/2000 | Burkinshaw |
| 6,022,332 A | 2/2000 | Nelson |
| 6,234,173 B1 | 5/2001 | Hajianpour |
| 6,258,096 B1 | 7/2001 | Seki |
| 6,852,115 B2 | 2/2005 | Kinnett |
| 7,104,997 B2 | 9/2006 | Lionberger |
| 7,547,307 B2 | 6/2009 | Carson |
| 7,621,920 B2 | 11/2009 | Claypool |
| 7,641,660 B2 | 1/2010 | Lakin |
| 7,658,741 B2 | 2/2010 | Claypool |
| 7,665,167 B2 | 2/2010 | Branch |
| 7,780,672 B2 | 8/2010 | Metzger |
| 7,947,862 B2 | 5/2011 | Livorsi |
| 8,052,692 B2 | 11/2011 | Lionberger |
| 8,070,752 B2 | 12/2011 | Metzger |
| 8,382,766 B2 | 2/2013 | Warkentine |
| 8,518,051 B2 | 8/2013 | Shoham |
| 9,005,207 B2 | 4/2015 | Dodds |
| 9,572,586 B2 | 2/2017 | van der Walt |
| 10,405,871 B1 * | 9/2019 | Bini .................... A61B 17/154 |
| 2002/0173797 A1 | 11/2002 | Van Zile |
| 2005/0149037 A1 | 7/2005 | Steffensmeier |
| 2007/0197944 A1 | 8/2007 | Bruce |
| 2009/0088768 A1 | 4/2009 | Grant |
| 2010/0016858 A1 | 1/2010 | Michel |
| 2011/0009868 A1 * | 1/2011 | Sato .................... A61B 17/1764 606/87 |
| 2011/0245835 A1 * | 10/2011 | Dodds ................. A61B 17/155 606/87 |
| 2012/0136359 A1 | 5/2012 | Grunder |
| 2012/0259335 A1 * | 10/2012 | Scifert ................ A61B 17/155 606/80 |
| 2012/0316564 A1 * | 12/2012 | Serbousek ......... A61B 17/1764 606/80 |
| 2014/0114319 A1 | 4/2014 | Wilkinson |
| 2014/0243991 A1 | 8/2014 | Collazo |
| 2015/0157337 A1 | 6/2015 | Wolf |
| 2015/0305754 A1 | 10/2015 | Metzger |
| 2016/0051268 A1 | 2/2016 | Seitlinger |
| 2016/0278938 A1 | 9/2016 | Goble |
| 2016/0287238 A1 | 10/2016 | DeMayo |
| 2016/0361178 A1 | 12/2016 | Budhabhatti |
| 2017/0100132 A1 | 4/2017 | Collazo |
| 2018/0280038 A1 | 10/2018 | Goble |
| 2018/0296232 A1 | 10/2018 | Nielsen |
| 2019/0274696 A1 | 9/2019 | Goble |

FOREIGN PATENT DOCUMENTS

| | | |
|---|---|---|
| WO | WO2016154606 | 9/2016 |
| WO | WO2017223353 | 12/2017 |

OTHER PUBLICATIONS

DePuy Synthes. P.F.C. Sigma Knee Systems. Surgical Technique. 2013. pp. 19-23.

Tiftikçi U, Serbest S, Burulday V. Can Achilles tendon be used as a new distal landmark for coronal tibial component alignment in total knee replacement surgery? An observational MRI study. Therapeutics and Clinical Risk Management. 2017:13. pp. 81-86.

\* cited by examiner

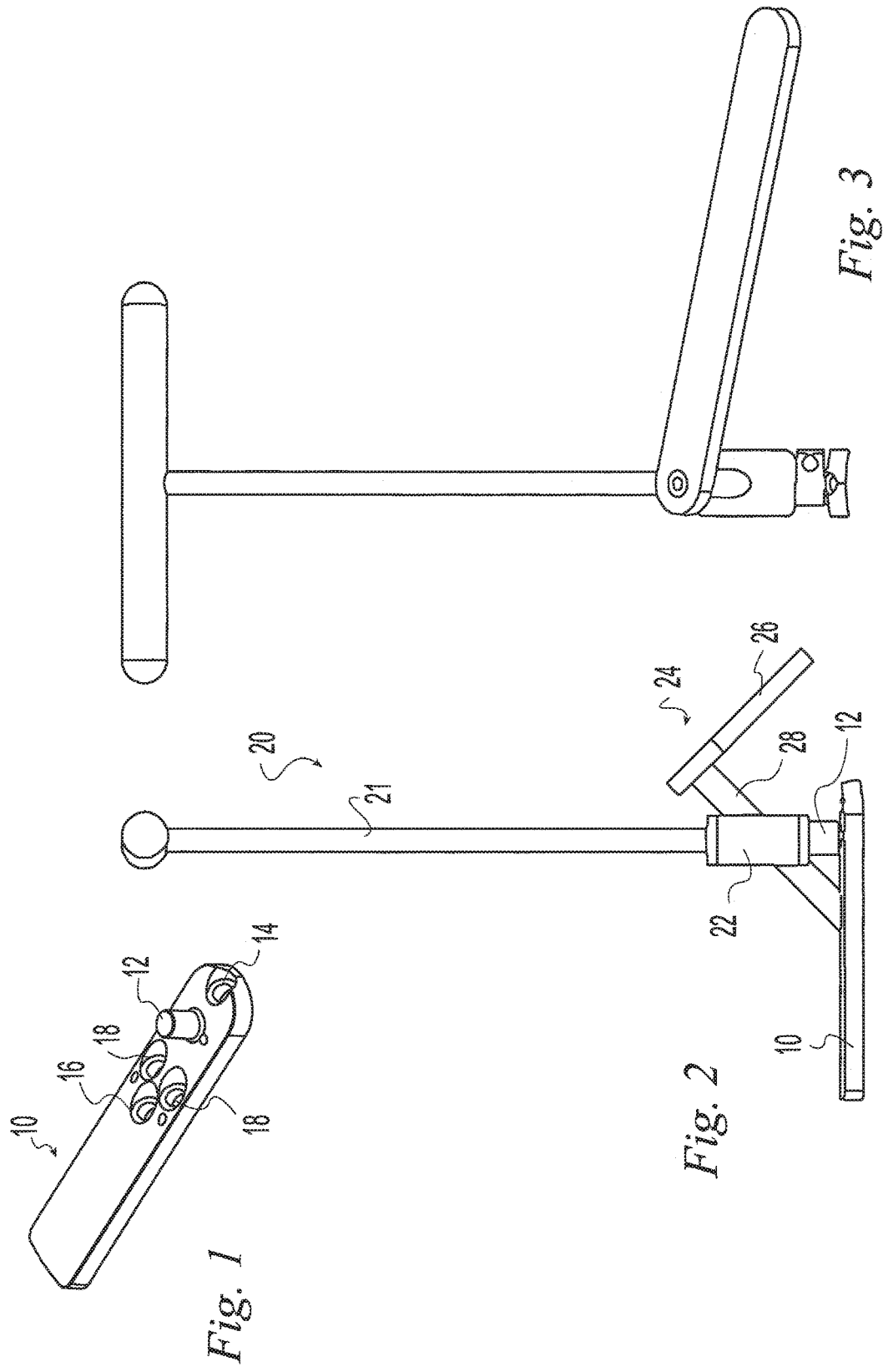

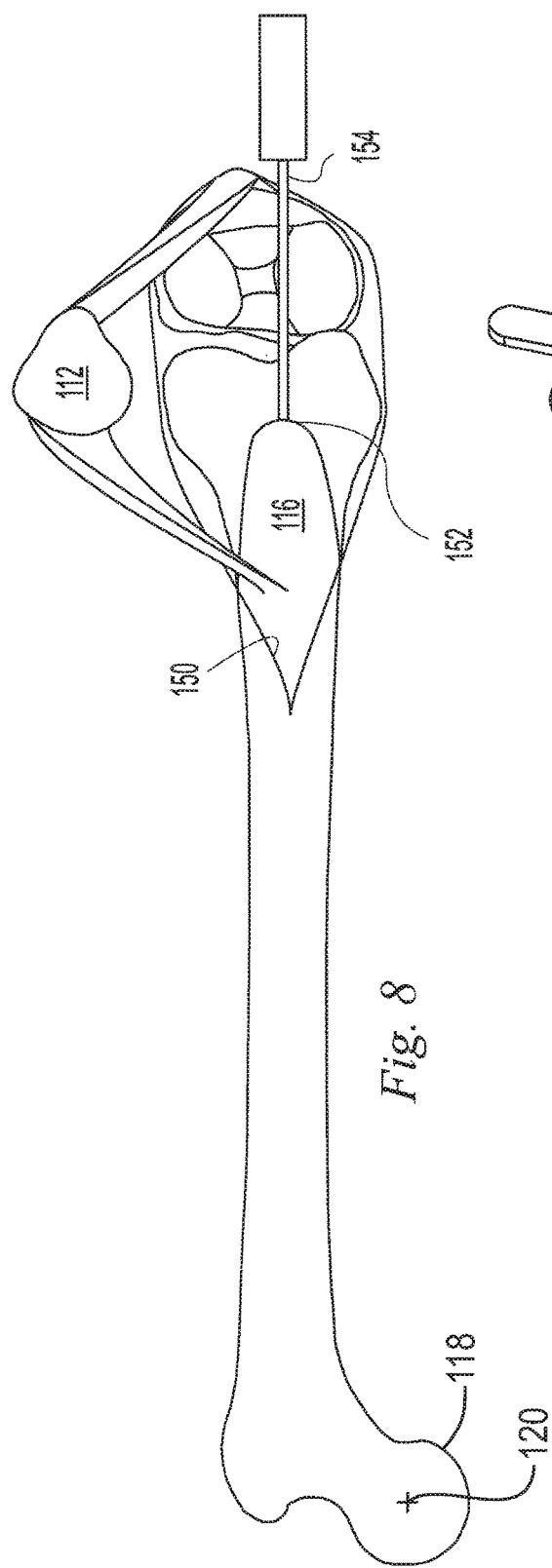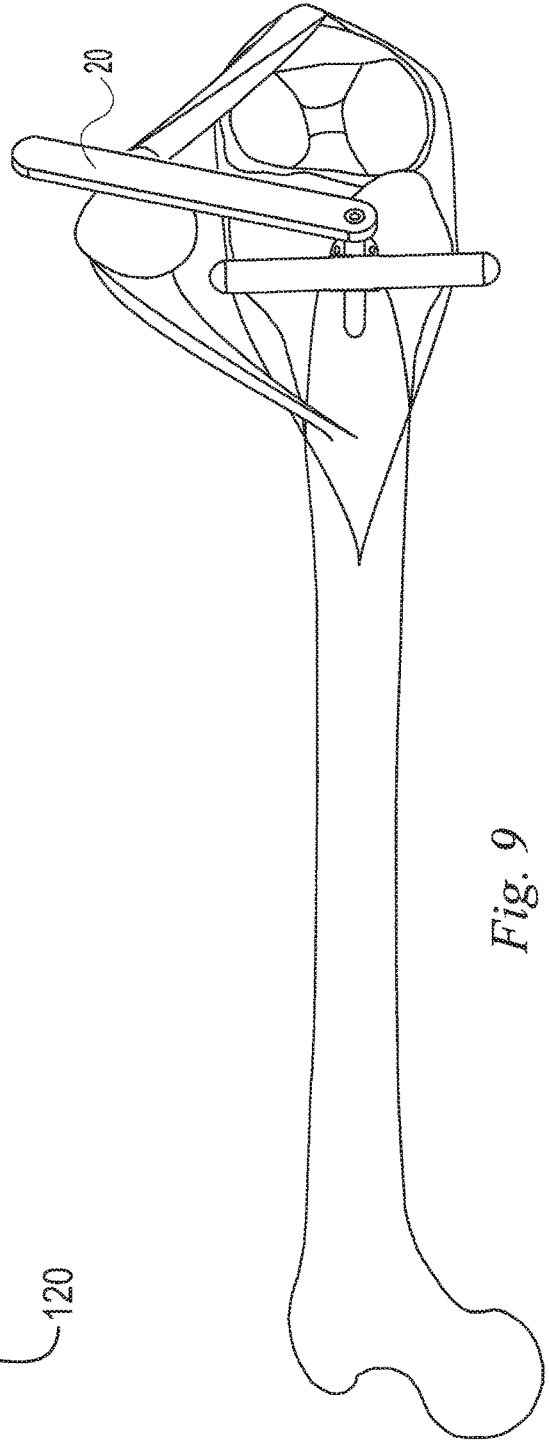
Fig. 8
Fig. 9

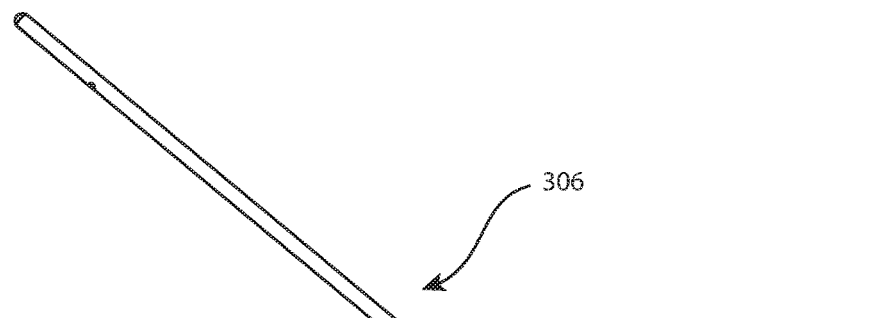
FIG. 26A
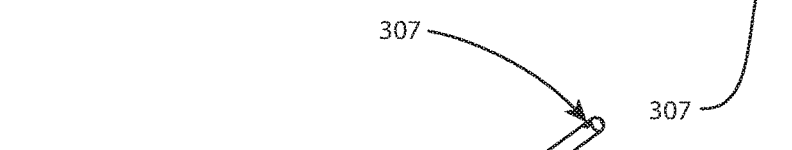
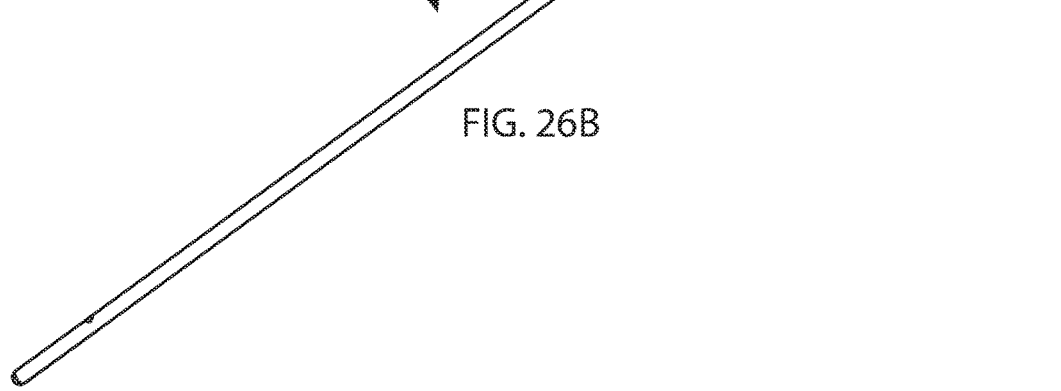
FIG. 26B

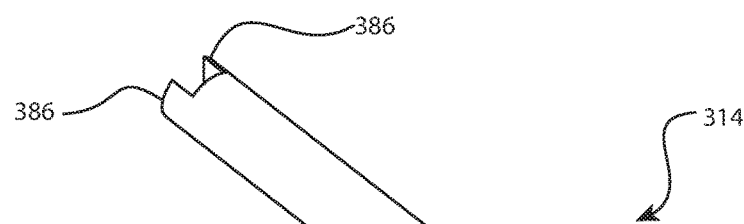
FIG. 30A
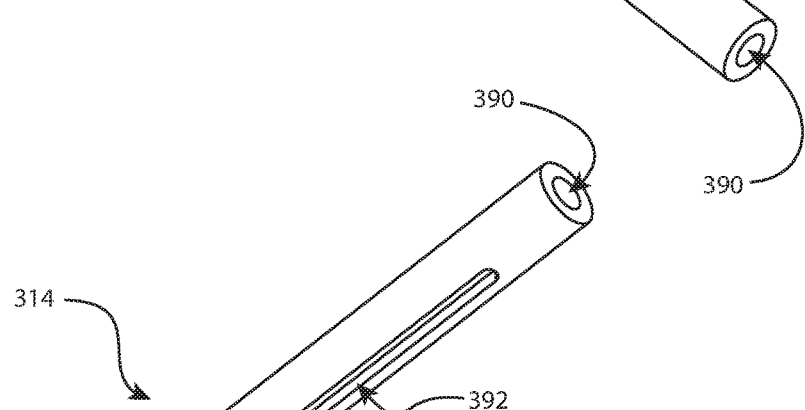
FIG. 30B
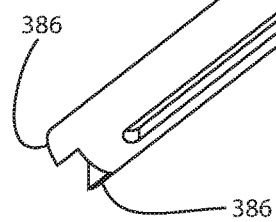

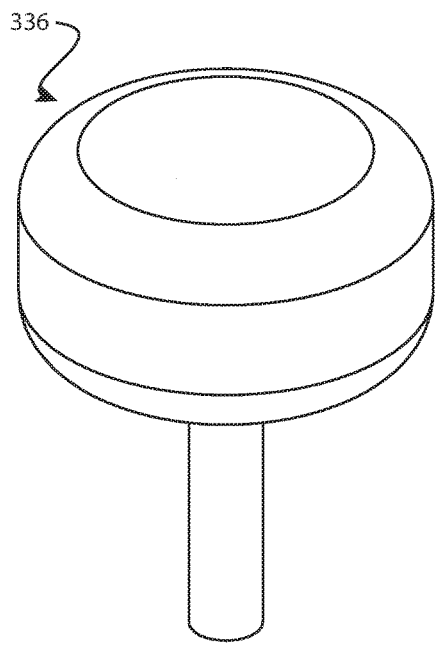
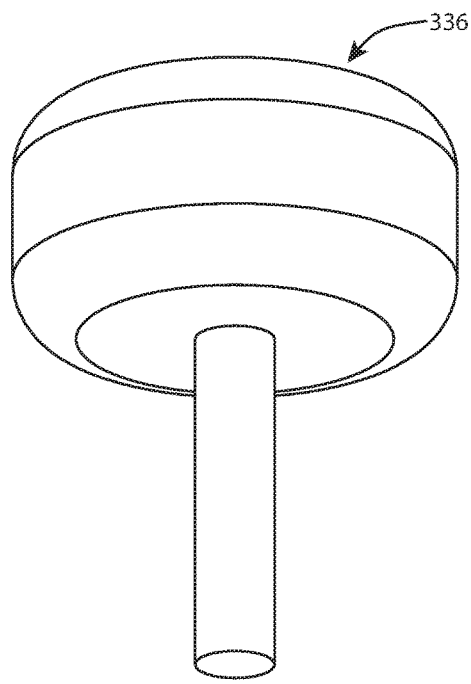
FIG. 38A
FIG. 38B
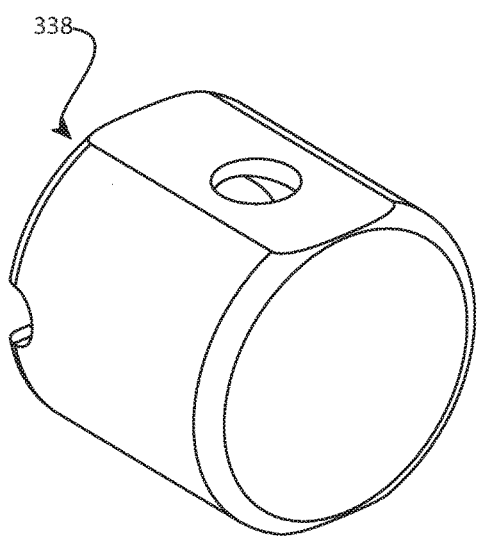
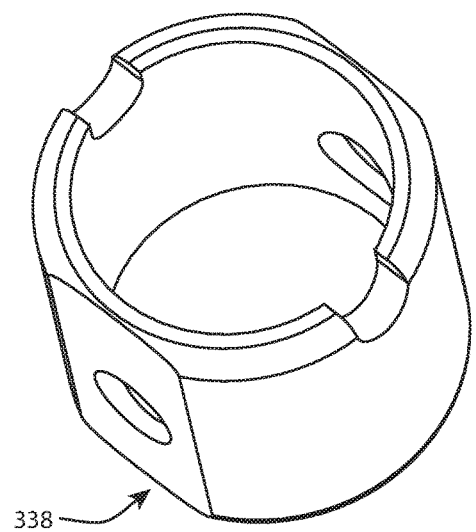
FIG. 39A
FIG. 39B

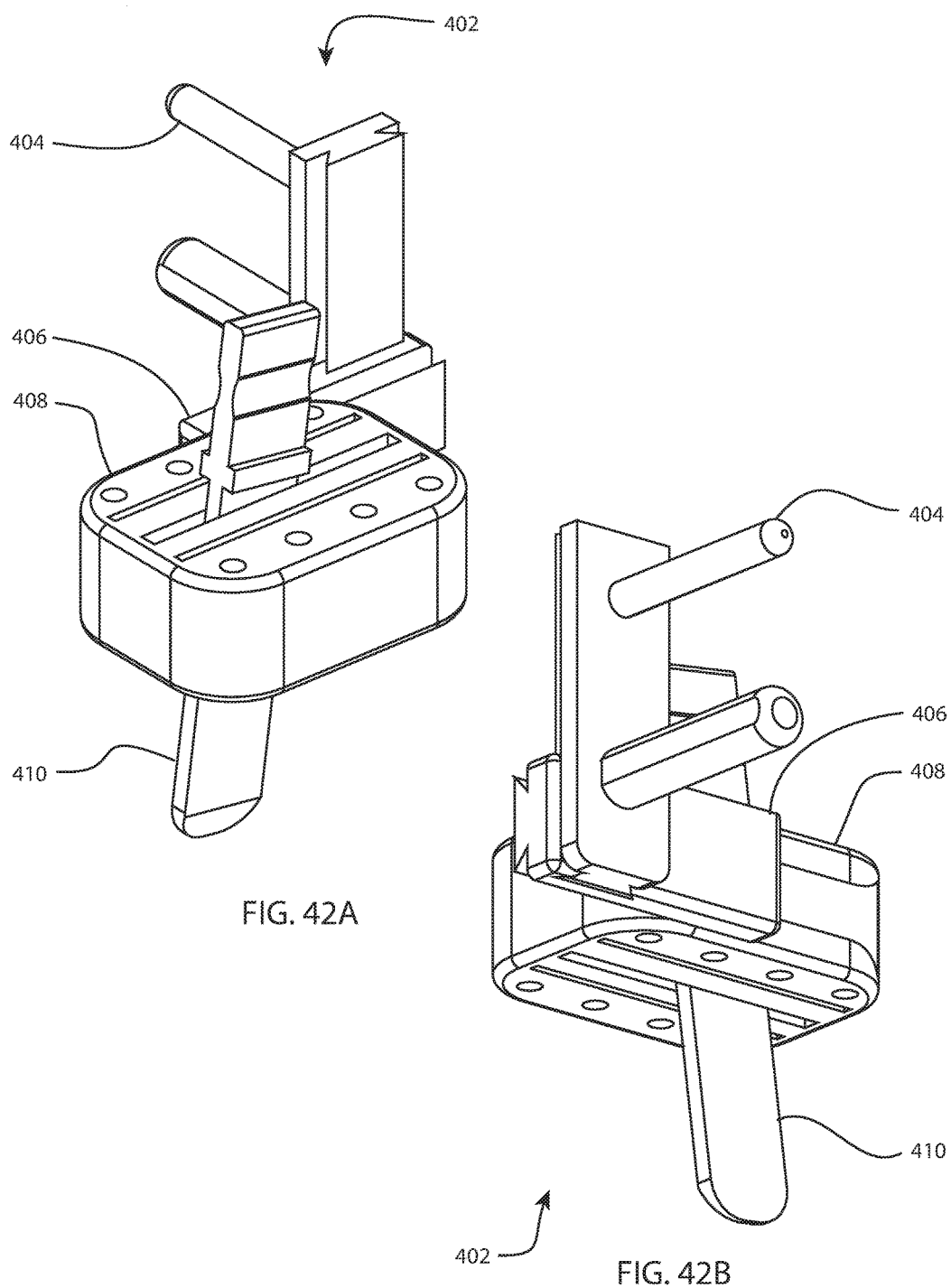

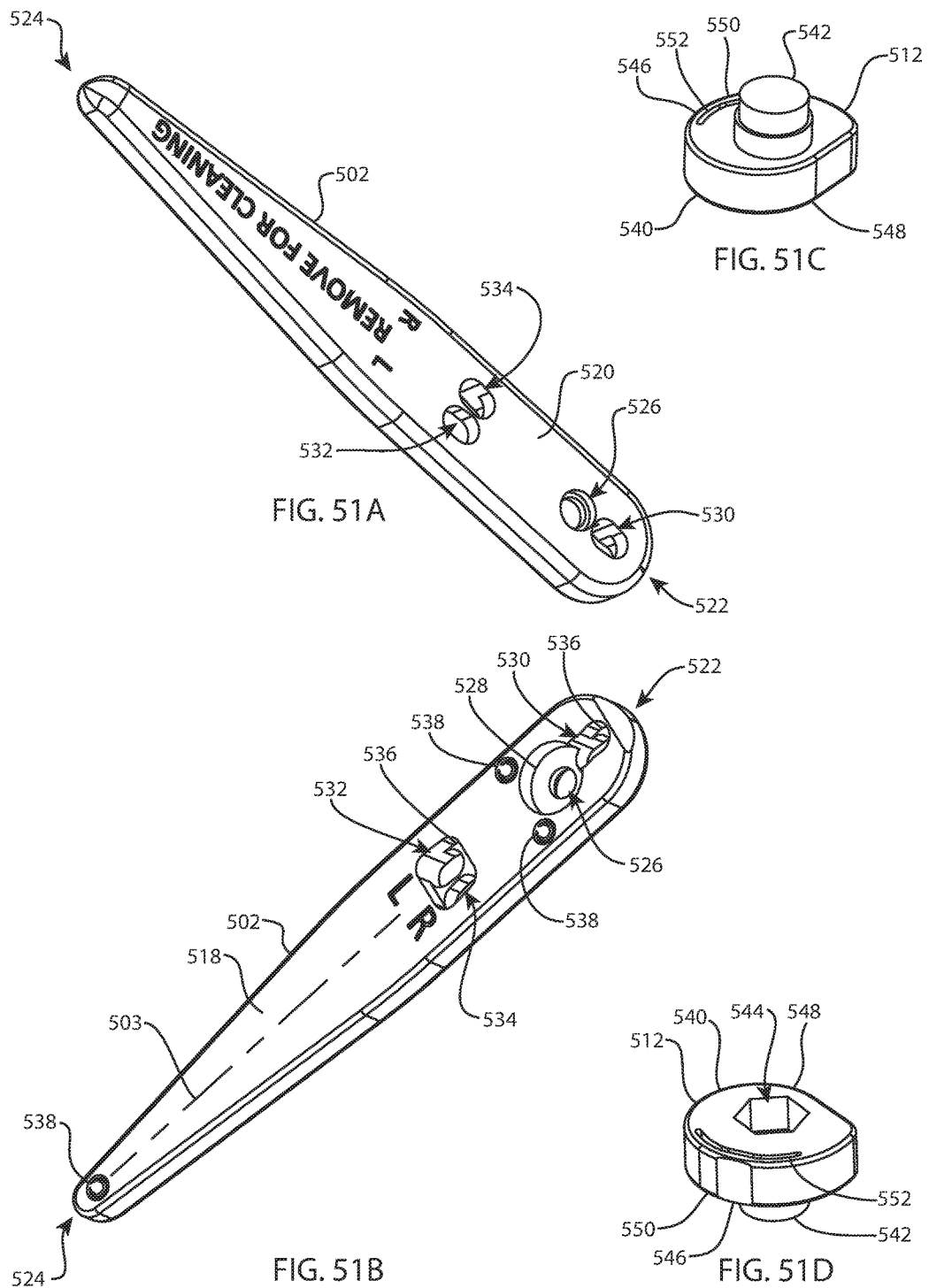

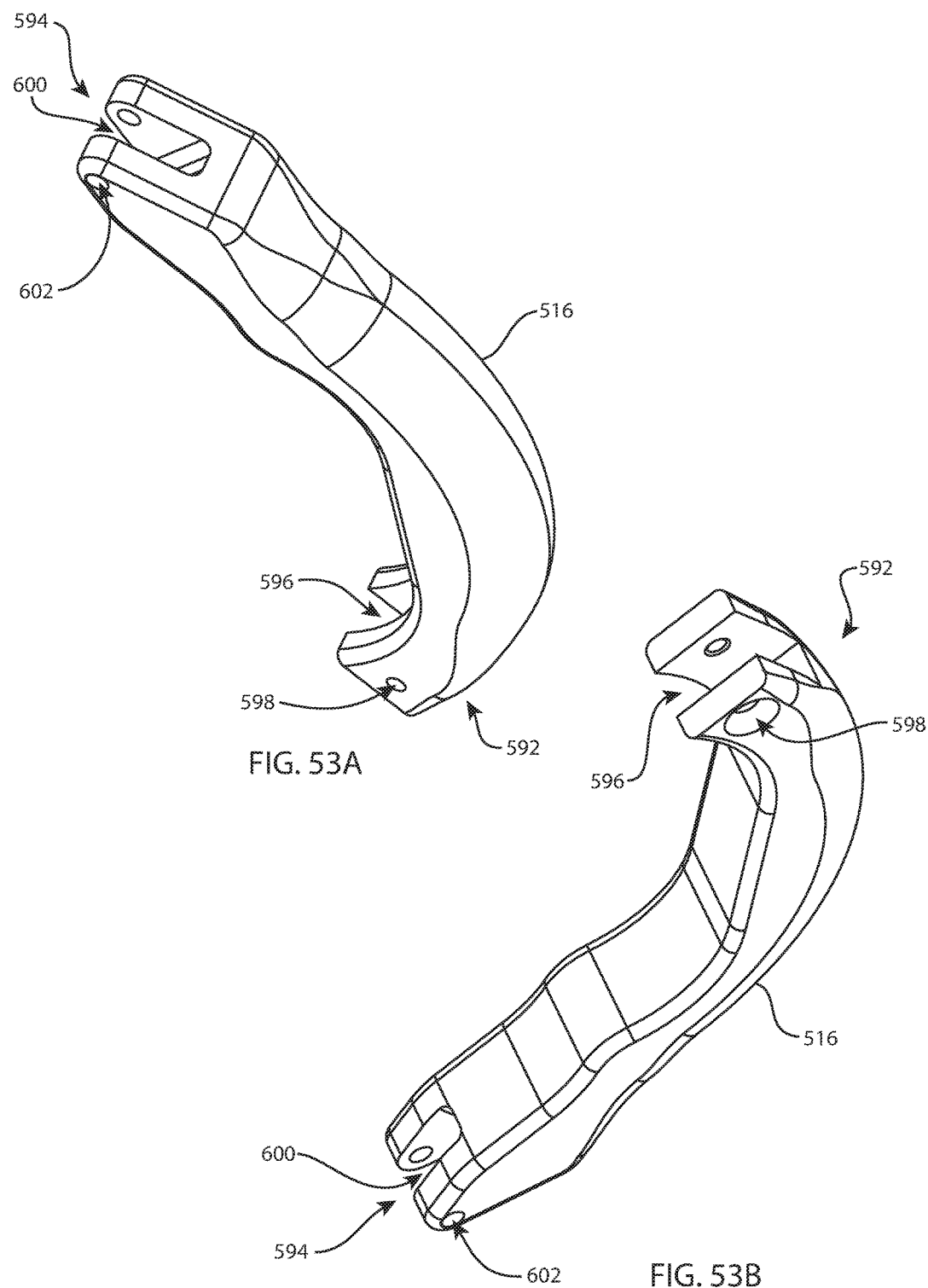

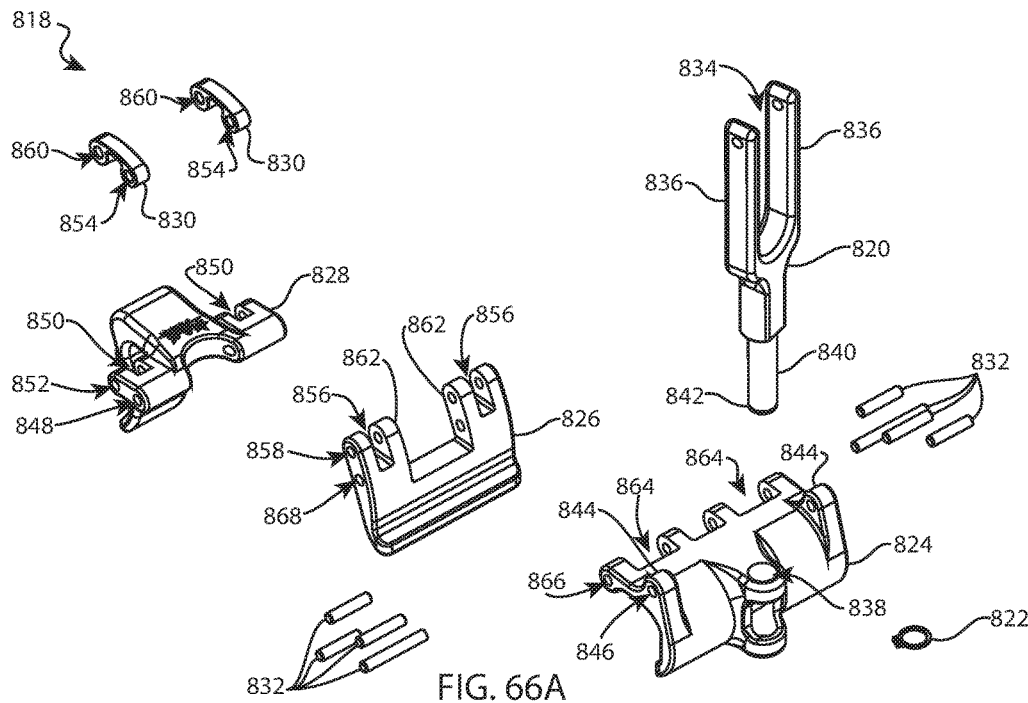
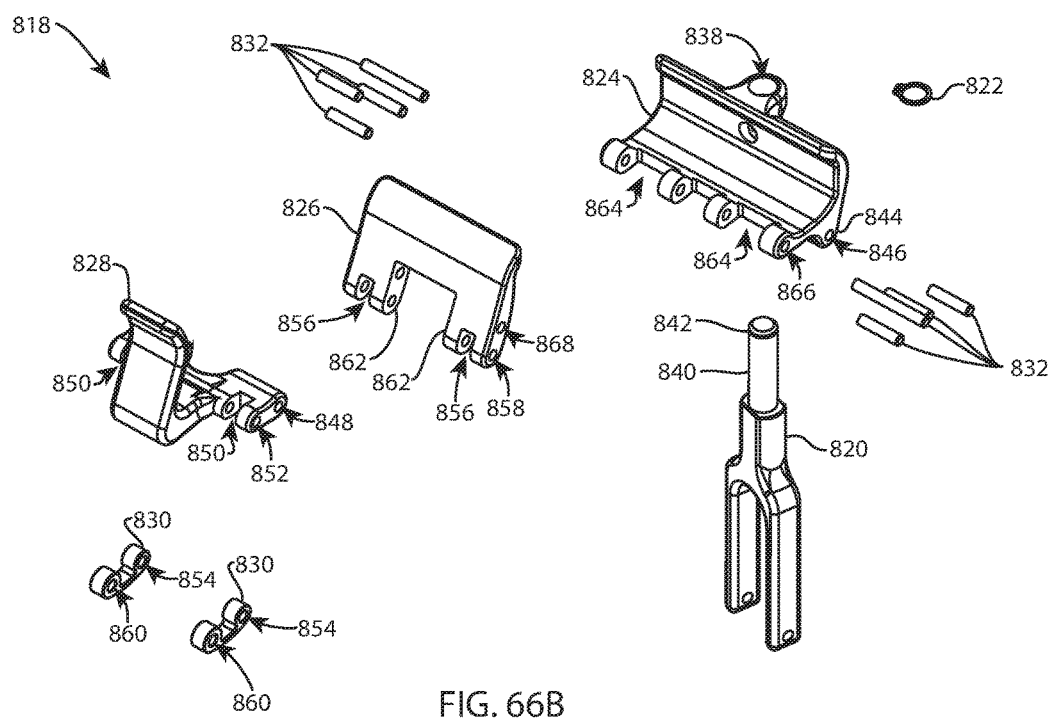

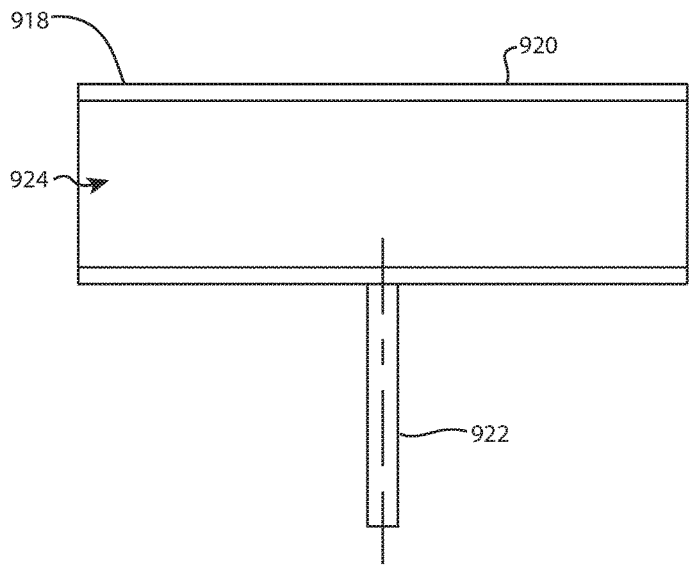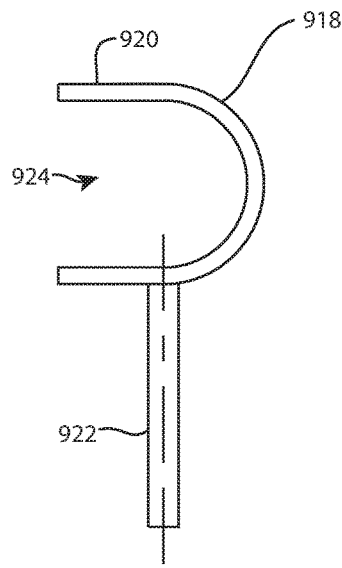
FIG. 86A    FIG. 86B
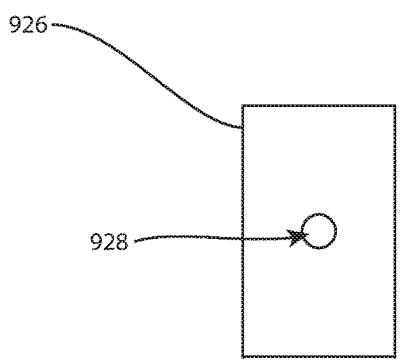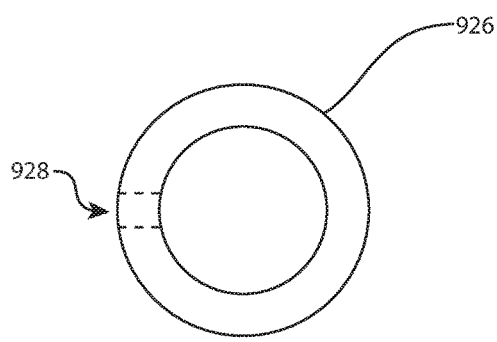
FIG. 87A    FIG. 87B

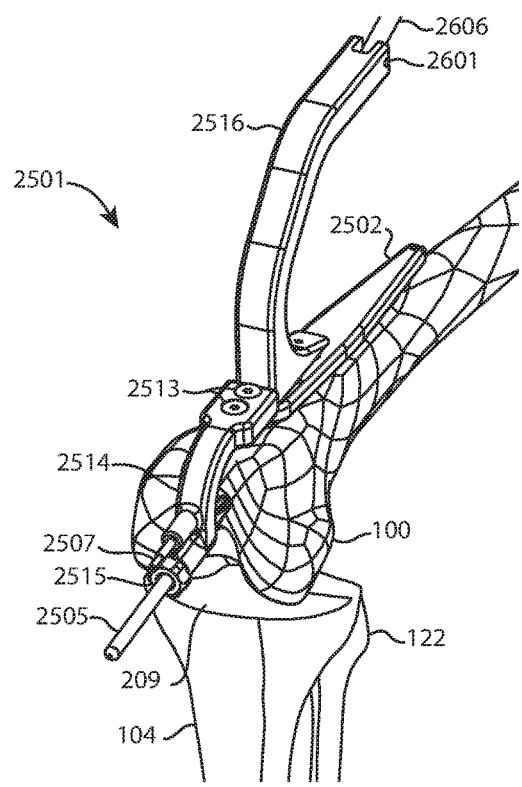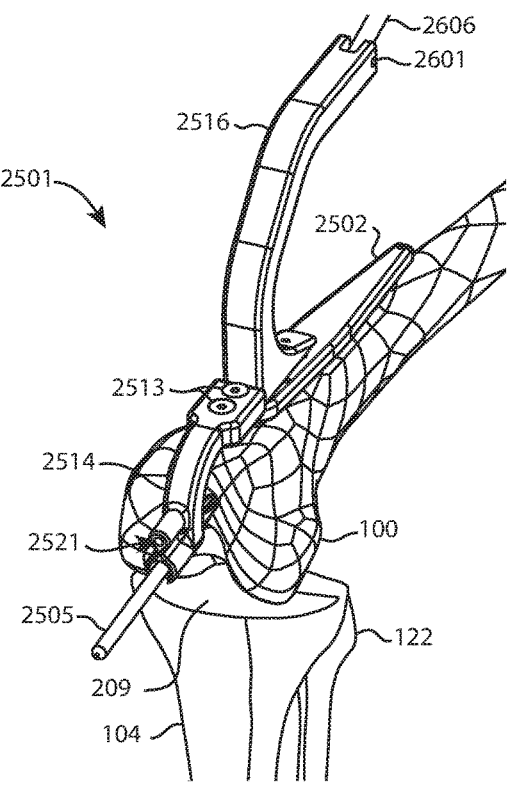
FIG. 130     FIG. 131
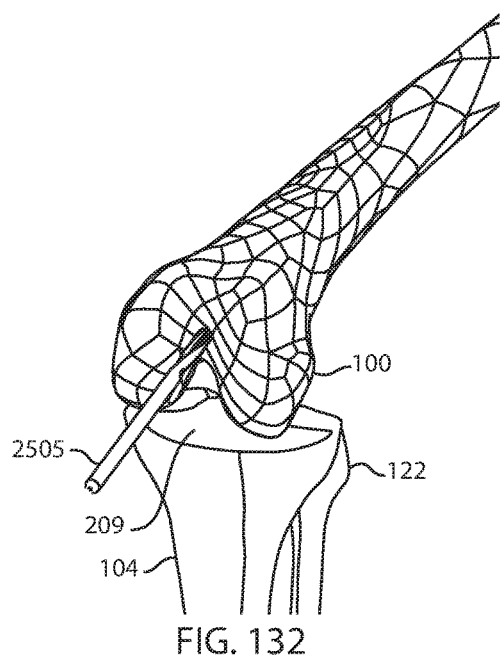
FIG. 132

KNEE INSTRUMENTS AND METHODS

CROSS-REFERENCE TO RELATED APPLICATIONS

The present application claims the benefit of:

U.S. Provisional Application Ser. No. 62/353,553, entitled KNEE INSTRUMENTS AND METHODS, which was filed on Jun. 22, 2016.

The present application is a continuation-in-part of:

U.S. application Ser. No. 15/081,828, entitled KNEE INSTRUMENTS AND METHODS, which was filed on Mar. 25, 2016, which is pending.

U.S. application Ser. No. 15/081,828 claims the benefit of:

U.S. Provisional Application Ser. No. 62/138,307, entitled KNEE INSTRUMENTS AND METHODS, which was filed on Mar. 25, 2015; and U.S. Provisional Application Ser. No. 62/302,787, entitled KNEE INSTRUMENTS AND METHODS, which was filed on Mar. 2, 2016.

The foregoing are incorporated by reference as though set forth herein in their entirety.

TECHNICAL FIELD

The present disclosure relates to instruments and methods to improve femoral and tibial alignment during knee arthroplasty. More specifically, the present disclosure relates to instruments and methods to reference and align with the anterior distal femoral cortex, the mechanical axis of the leg, and Whiteside's line (while intact, prior to any distal femoral resection). While this disclosure is made in the context of knee arthroplasty, the principles are applicable to alignment during other arthroplasty procedures.

BACKGROUND

Traditional total knee arthroplasty instruments utilize intramedullary instruments to determine proper distal femur saw cut alignment, and extramedullary instruments to align the saw cut for the proximal tibia. Therefore it is acceptable to prepare the distal femur separate from the proximal tibia. There exists no conjoined effort to cut the distal femur and the proximal tibia as the single lower extremity body part which constitutes the knee joint.

This contemporary instrumentation process violates the principles established by Insall in the 1970s. Popular total knee arthroplasty instruments teaches this inexact intramedullary instrument process because it is simpler to teach, understand and utilize by most surgeons.

Dr. Insall recognized the need for external rotation (ER) of the femoral component when performing a total knee arthroplasty (TKA). In 1990 Dr. Insall attributed the need for approximately 3 degrees of ER to an "abundance of soft tissue in the posteromedial corner of the knee."

Indeed in the absence of this prescribed ER of the femoral component 1) patellar tracking will be unbalanced, related to the trochlear groove and 2) the medial compartment will be compressed significantly greater than the lateral compartment with the knee flexed beyond 40 degrees and 3) the patella would track laterally.

The reason for alteration of the normal morphology of the distal femur when performing a TKA is not well understood.

The reason for the need to externally rotate the femoral condyle approximately 3 degrees relative to the normal morphology of the femoral condyles is the clue to surgical alteration of normal morphology of the proximal tibia.

Normal Anatomy of the Proximal Tibia

As is well known, in a lateral xray of a normal proximal tibia, the plane of the medial tibial plateau exists approximately 3 mm more distal than the lateral tibial plateau.

Evident in a CAT scan of a normal knee is the elevation difference between the planes of the two tibial plateaus.

If a saw cut is made at the proximal tibia, at a right angle to the vertical axis of the tibia, the medial tibial compartment will be elevated relative to the lateral tibial plateau. This relative elevation will, in turn, elevate the medial femoral condyle, necessitating removal of an equal amount of posterior medial femoral condyle (equal to the relative elevation of the medial tibial plateau) in order to maintain proper tracking of the patellar throughout flexion and extension of the knee. It is the external rotation of approximately 3 degrees (3 mm) that accomplishes about 3 mm more removal of the condyle on the medial side than the lateral side.

The most common adjustment position for "external rotation guides" is 3 degrees. This position will remove about 3 mm more off the medial femoral condyle than the lateral femoral condyle. The reality is, and therefore the error is, that condylar and plateau articular cartilage wear, and differences in plateau height between the medial and lateral plateaus, will require external rotation adjustments between 1 degree and 6 degrees in order to balance compression forces in the medial and lateral compartments for both flexion and extension.

It is only after equal compartment compression is accomplished through proper external rotation that proper ligament releases can be accomplished.

Method for Getting External Rotation Right

Equal compression of the medial and lateral compartments can only be obtained by causing the posterior femoral condylar cut to be parallel to the proximal tibial cut.

To accomplish this:

Pin the tibial cut guide in place with the tibial alignment rod centering distally over the middle of the plafond. The plafond is the ceiling of the ankle joint, that is, the articular surface of the distal end of the tibia.

After resecting the distal femur, place the 4-in-1 femoral cut guide in place over the cut surface of the distal femur. Hang the 4-in-1 cutting guide on a centrally placed pin on Whiteside's line located just below the cut slot for the anterior femoral resection. This cut slot location references the distal/anterior femoral cortex for proper anterior resection. The centrally placed pin may optionally be replaced by a protruding post located on the bone-contacting side of the 4-in-1 cut guide that fits into a corresponding hole in the femur.

Utilizing the proper sized 4-in-1 cut guide, this guide is now "rotated" until the posterior cut slot is parallel with the cut slot on the tibial cut guide.

Appropriate fixation pins/screws secure the femoral and tibial cut guides. All cuts can now be made, assuring proper patellar tracking.

Equal and rectangular gaps can be expected in both flexion and extension. Soft tissue releases are now performed to further balance compression forces in the medial and lateral compartments.

At least the following aspects of this disclosure are believed to be novel and non-obvious contributions over the prior art of knee arthroplasty:

Reference of distal anterior femur (DAF) and exact location of femoral head to accomplish exact knowledge of 1)

varus/valgus of distal femoral cut, and 2) flexion/extension of anterior and posterior femoral cuts. Both data points are contained in the position of a distal femoral pin or hole.

Determination of proper External Rotation of femur by "hanging" the upper-center portion of a 4-in-1 femoral cutting block on the distal femoral pin, which is in the center of the trochlear groove. The proximal/distal axis through the center of the block is aligned with the longitudinal axis of the tibia, which aligns the trochlear groove of the femur (Whiteside's line) with the axis of the tibia at 90 degrees flexion of the knee. The distal femoral pin may optionally be replaced by a protruding post located on the bone-contacting side of the 4-in-1 cut guide that fits into a corresponding hole in the femur.

With proper ER of the femoral component, the posterior femoral cut and the proximal tibial cut will be parallel at 90 degrees knee flexion. Therefore the 4-in-1 femoral cutting block can be extended to a 5-in-1 cutting block by adding the proximal tibial cut slot.

The 5-in-1 (effective) block is attached superiorly (proximally) at the distal femoral pin or hole and distally to the tibial alignment rod extending to the middle of the ankle. The patellar will now track properly.

With the rectangular gap at the femur and tibia, equal compression will exist between medial and lateral compartments of the knee both in flexion and extension.

Other:

Finding the femoral head.

Bar fixed to operating table over the area of the femoral head with goal post marker/target.

Ultrasound method of locating femoral head.

Guide to reference DAF and then connect to femoral head goal post/target to determine distal femoral pin location. Arthroscopic procedure contemplated.

Adjustable 4-in-1 femoral cut guide.

This disclosure teaches bony and soft tissue preparation of the knee joint utilizing instruments and techniques consistent with proven total knee arthroplasty instruments principles.

SUMMARY

The various systems and methods of the present technology have been developed in response to the present state of the art, and in particular, in response to the problems and needs in the art that have not yet been fully solved by currently available knee arthroplasty instrument systems and methods. The systems and methods of the present technology may provide more objective, repeatable alignment relative to important biomechanical features, compared to current systems and methods.

More specifically, the present disclosure relates to instruments and methods to reference and align with the anterior distal femoral cortex, the mechanical axis of the leg, and Whiteside's line (while intact, prior to any distal femoral resection). The anterior femoral resection is aligned in the same plane as the anterior distal femoral cortex. The center of the femoral head, the medial/lateral center of the distal femur, the medial/lateral center of the proximal tibia, and the second toe, medial/lateral center of the ankle, or anterior tibial spine or crest are all simultaneously aligned to the mechanical axis of the leg while the leg is in full extension and the knee joint is distracted. The distal femoral and proximal tibial resections are aligned relative to the mechanical axis of the leg. Since the distal femoral and proximal tibial resections may be made with the leg in full extension, a much smaller incision may be required, particularly in the quadriceps region. An eight to ten inch long incision, typical of the current state of the art, may be shortened to about six inches, with most of the savings occurring proximally in the quadriceps region. Whiteside's line is referenced while the distal femur is intact, before any distal femoral resection, and the anterior and posterior femoral resections and chamfer cuts are aligned to this reference using a jig.

The systems and methods disclosed herein provide a simple and fast way to objectively and precisely align the knee joint during arthroplasty procedures. This is inherently advantageous because malalignment predisposes a reconstructed knee to premature failure. This is particularly advantageous for those surgeons who must perform knee arthroplasty from time to time, but whose knee arthroplasty procedure volume is low. Eighty percent of knee arthroplasty procedures are performed by surgeons who do no more than two knee arthroplasty procedures per month.

The systems disclosed herein provide a cost-effective mechanical alternative to surgical navigation systems, particularly because the disclosed systems include components that are readily made as disposable items. The femoral and tibial alignment components, for example, are contemplated to be disposable items.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1 is a perspective view of an instrument base;

FIG. 2 is a side view of the base of FIG. 1 assembled with a handle and a drill guide;

FIG. 3 is a front view of the assembly of FIG. 2;

FIG. 8 is a top view of a step in a surgical procedure, elevating the suprapatellar fat pad;

FIG. 9 is a top view of a step in a surgical procedure, inserting the base of FIG. 1 against the anterior distal femoral cortex;

FIG. 26A is a perspective view of a femoral extension rod of the instrument system of FIG. 21A; and FIG. 26B is another perspective view of the femoral extension rod of FIG. 26A from a different direction;

FIG. 30A is a perspective view of a tibial outer extension rod of the instrument system of FIG. 21A; and FIG. 30B is another perspective view of the tibial outer extension rod of FIG. 30A from a different direction;

FIG. 38A is a perspective view of a knob of the femoral base block assembly of FIG. 35; and FIG. 38B is another perspective view of the knob of FIG. 38A from a different direction;

FIG. 39A is a perspective view of a top component of the femoral base block assembly of FIG. 35; and FIG. 39B is another perspective view of the top component of FIG. 39A from a different direction;

FIG. 42A is a perspective view of another translation bar, a slide, a cut guide, and a condyle probe, all for substitution into the femoral base block assembly of FIG. 35; and FIG. 42B is another perspective view of the translation bar, slide, cut guide, and condyle probe of FIG. 42A from a different direction;

FIG. 51A is a perspective view of the base of FIG. 50A; FIG. 51B is another perspective view of the base of FIG. 51A from a different direction; FIG. 51C is a perspective view of a cam for use with the base of FIG. 50A; and FIG. 51D is another perspective view of the cam from a different direction;

FIG. 53A is a perspective view of a handle of the femoral riser assembly of FIG. 50A; and FIG. 53B is another perspective view of the handle of FIG. 53A from a different direction;

FIG. 66A is an exploded perspective view of the target clamp assembly of FIG. 65A; and FIG. 66B is another exploded perspective view of the target clamp assembly of FIG. 66A from a different direction;

FIG. 86A is a bottom view of a femoral head finder; and FIG. 86B is a side view of the femoral head finder of FIG. 86A;

FIG. 87A is a front view of a collar; and FIG. 87B is a side view of the collar of FIG. 87A;

Figure 17:
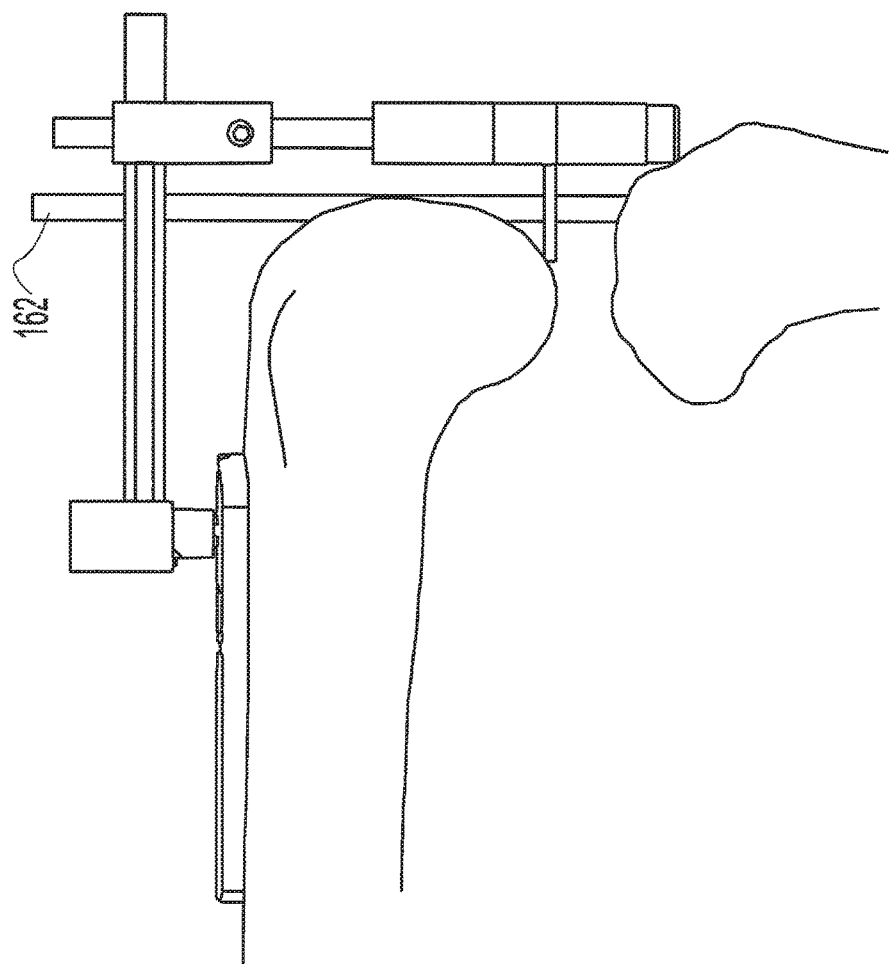
FIG. 17 is a side view of the surgical step of FIG. 14 illustrating the use of another joint distraction member.
Figure 105:
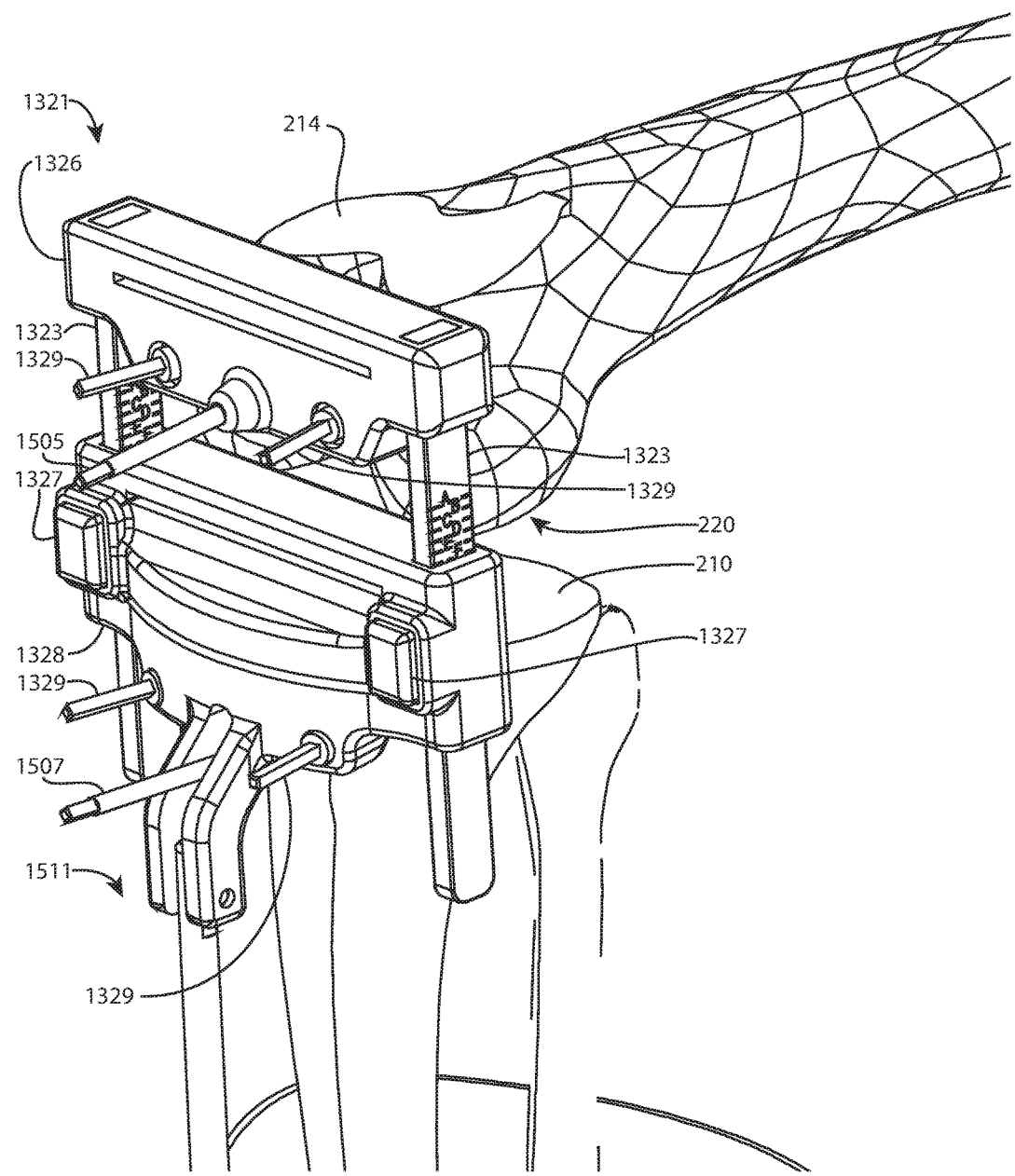
FIG. 105 is a perspective view of the femur, tibia, fibula, femoral pin, tibial pin, three in one cut guide assembly, tibial extension rod assembly, and pins of FIG. 104 after making an anterior femoral resection, a posterior femoral resection, and a proximal tibial resection through the three in one cut guide assembly.
Figure 109:
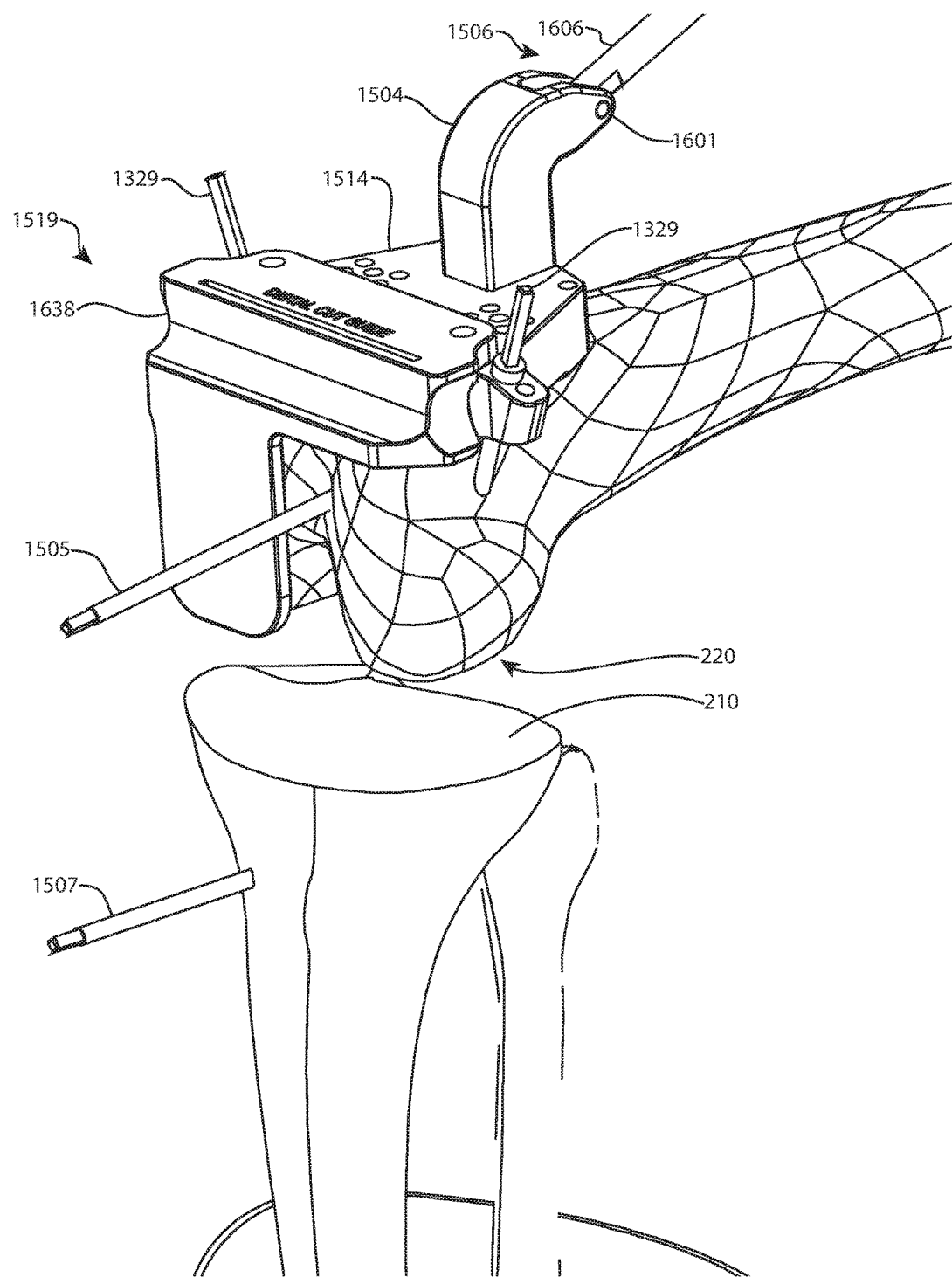
FIG. 109 is a perspective view of the femur, tibia, fibula, femoral pin, tibial pin, distal femoral cut guide assembly, and a portion of the femoral extension rod assembly of FIG.
Figure 110:
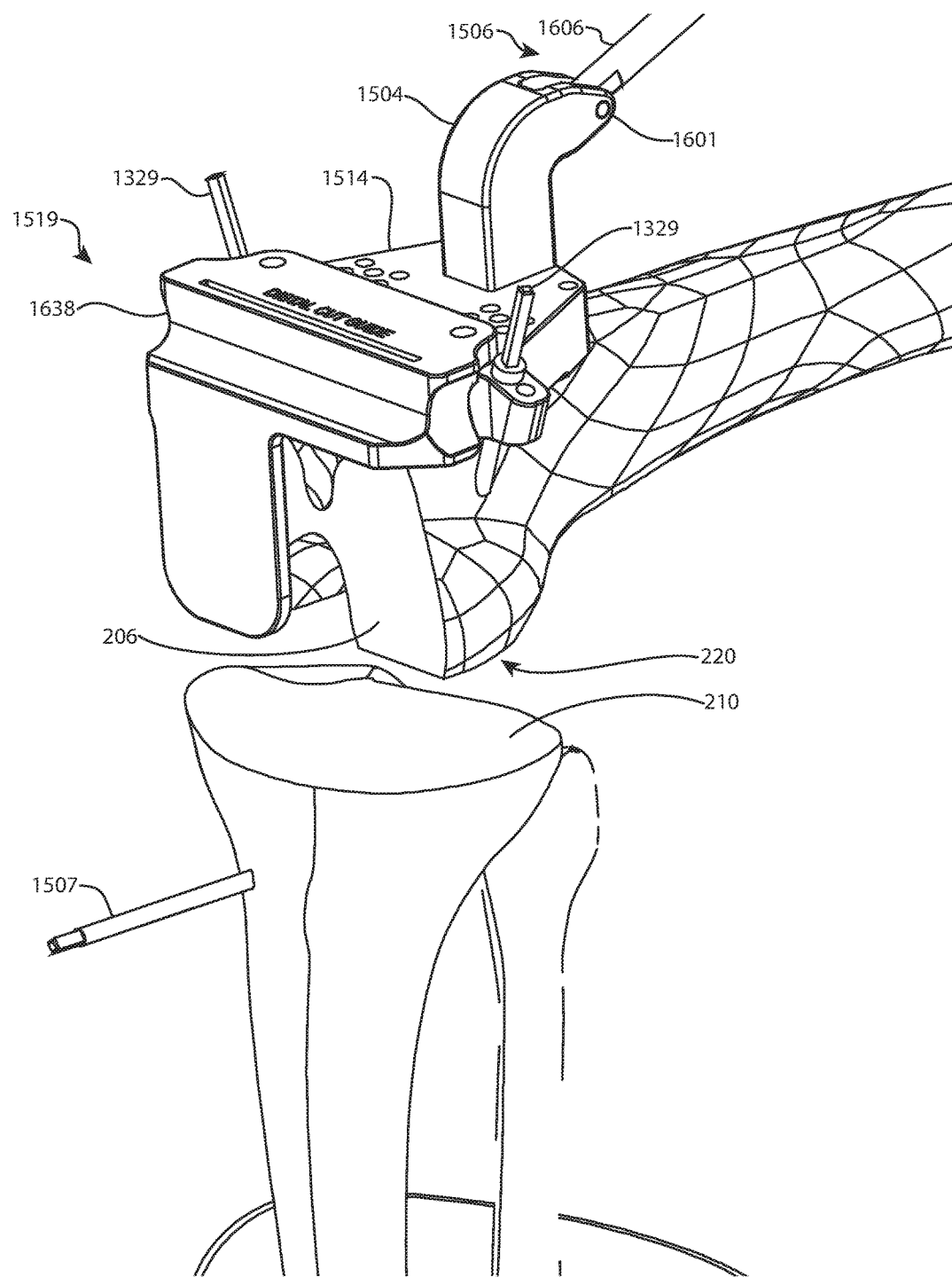
Figure 111A:
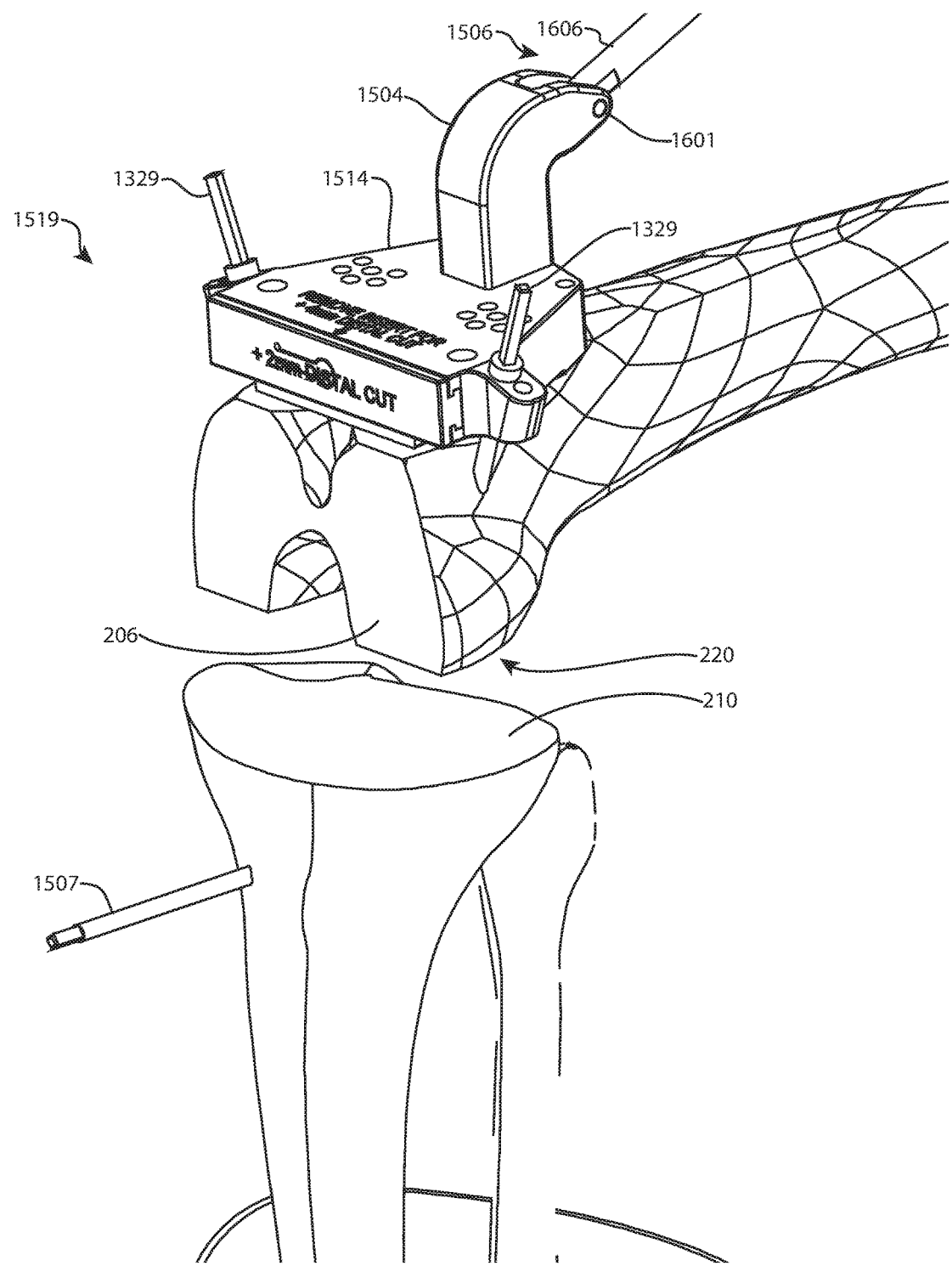
Figure 111B:
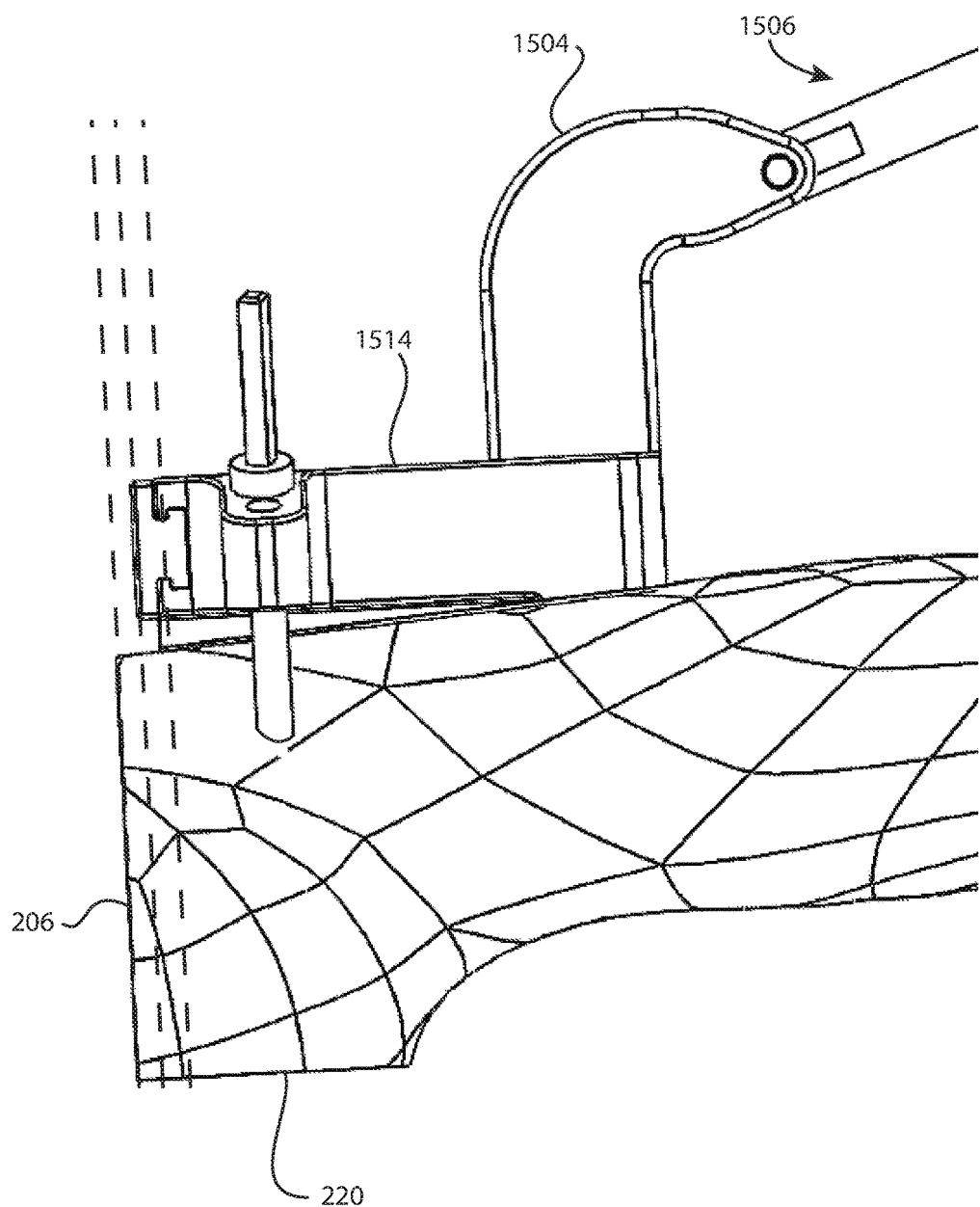
Figure 112:
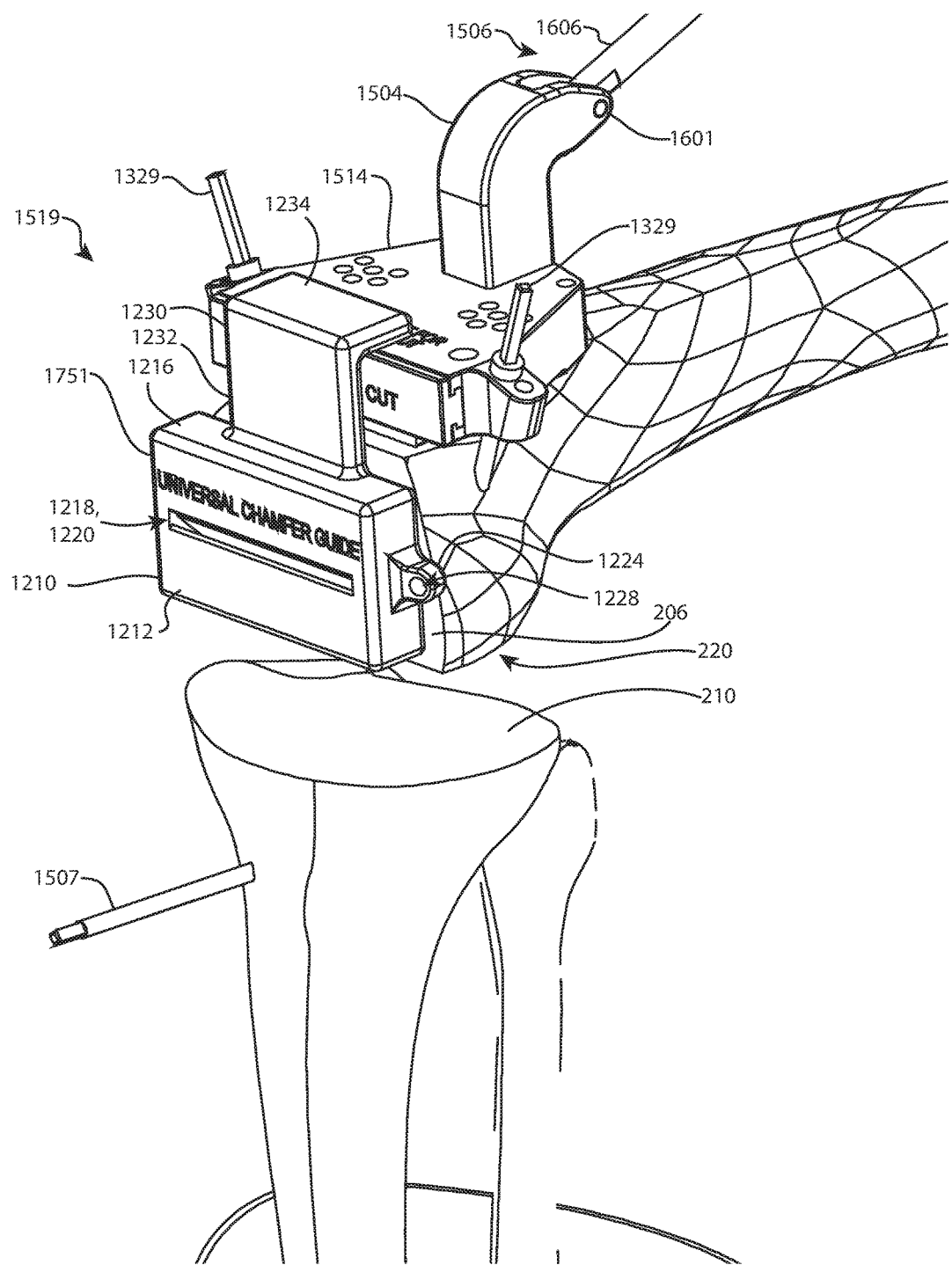
Figure 113:
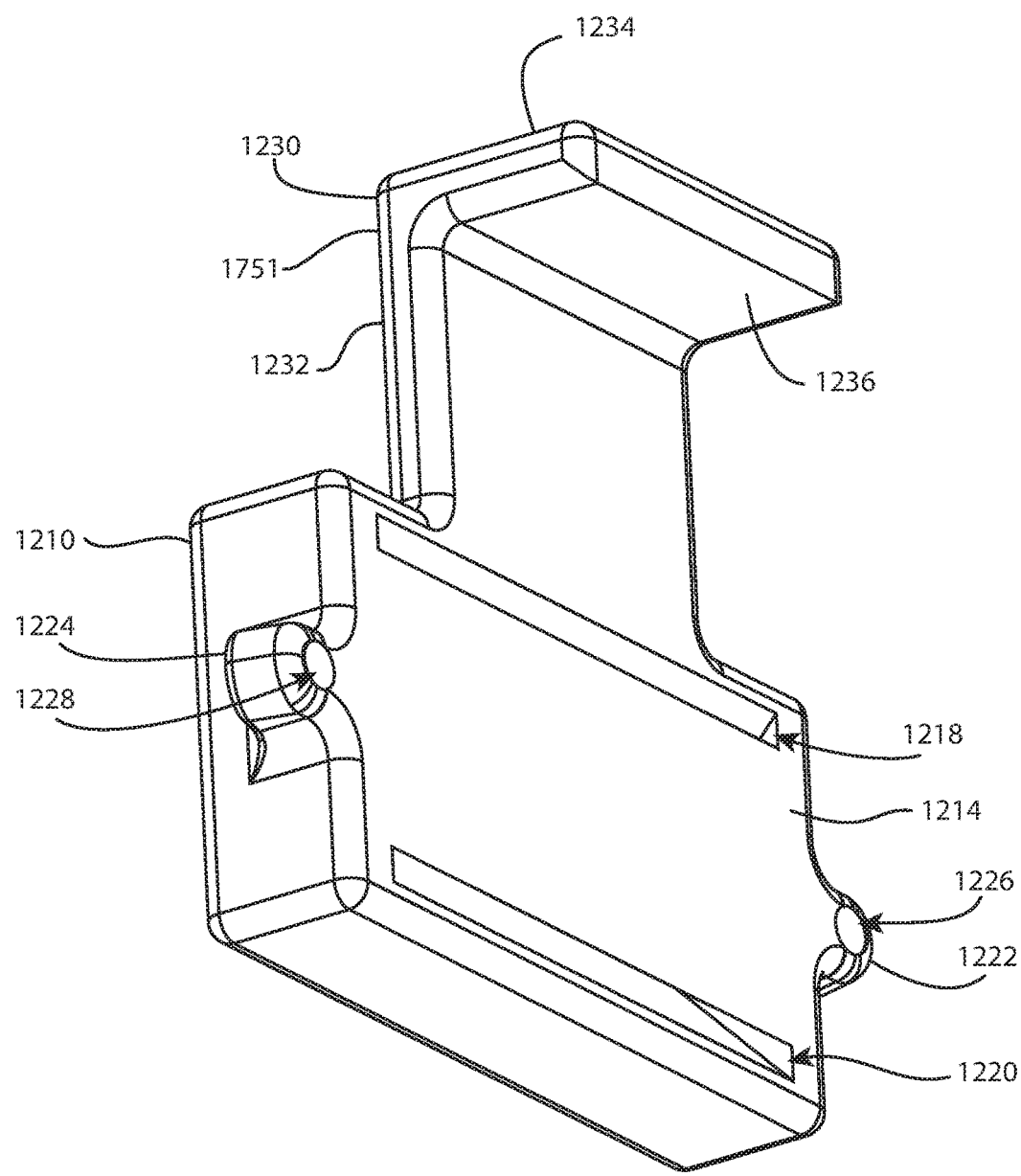
Figure 114:
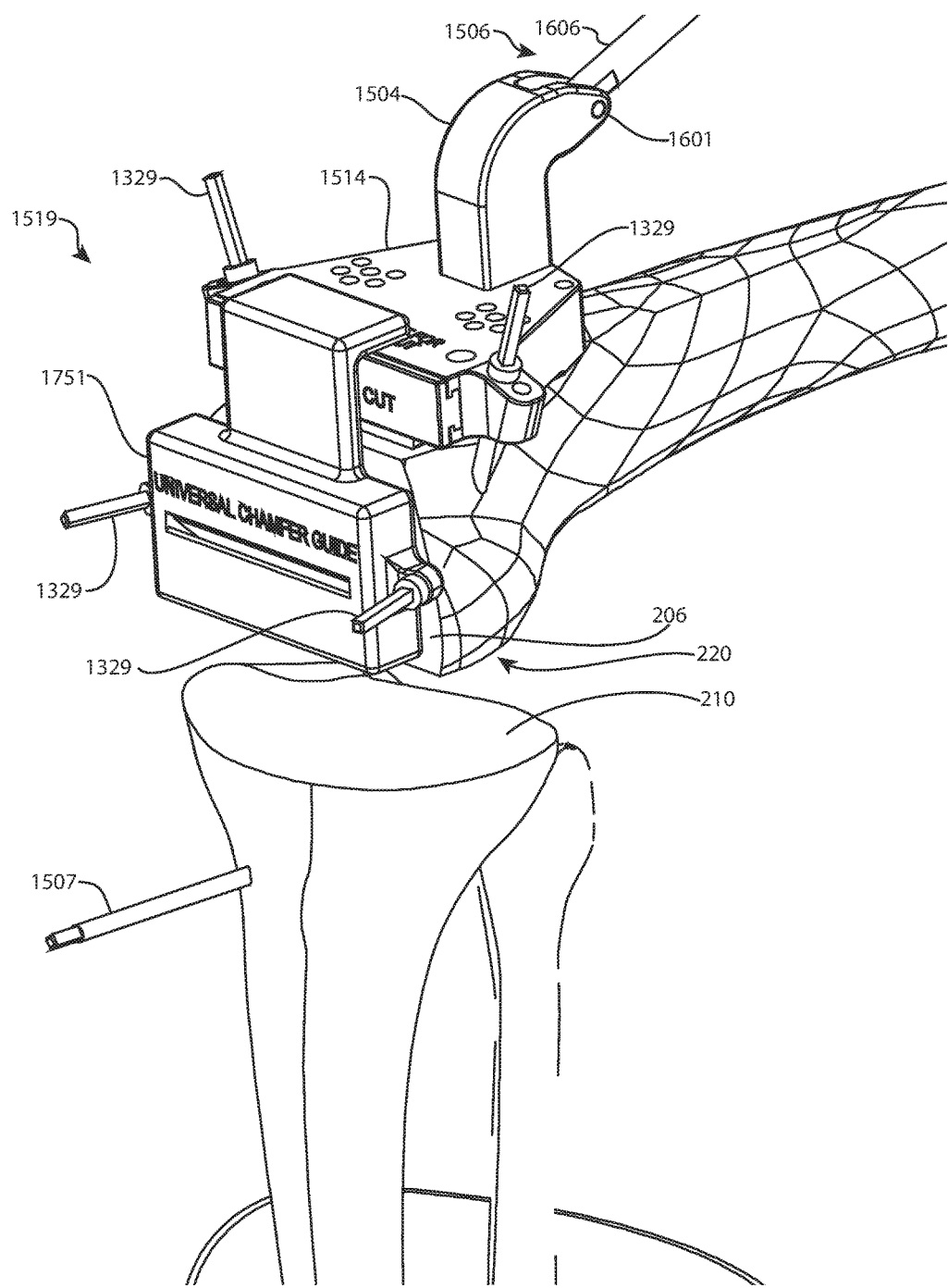
Figure 115A:
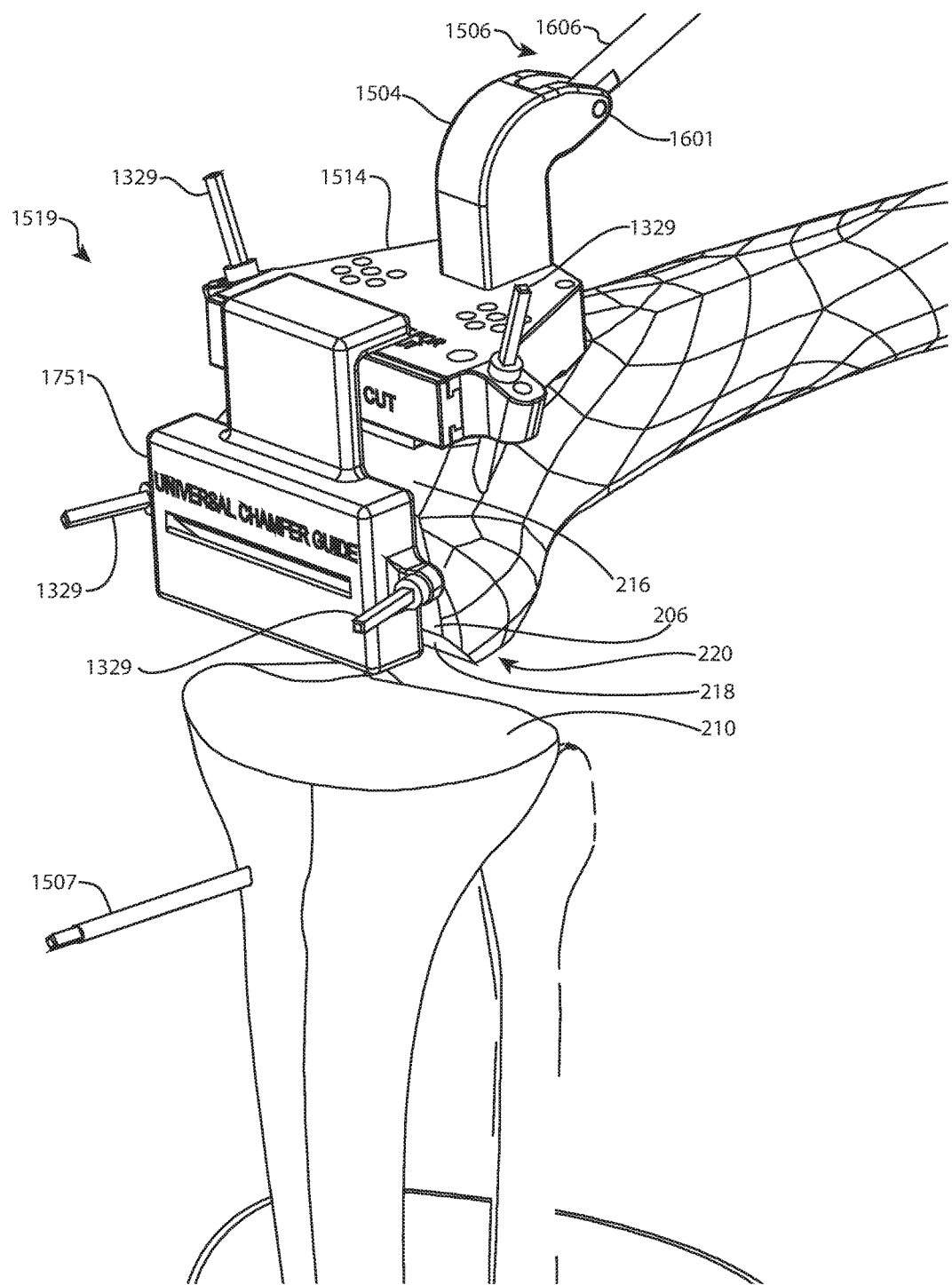
Figure 115B:
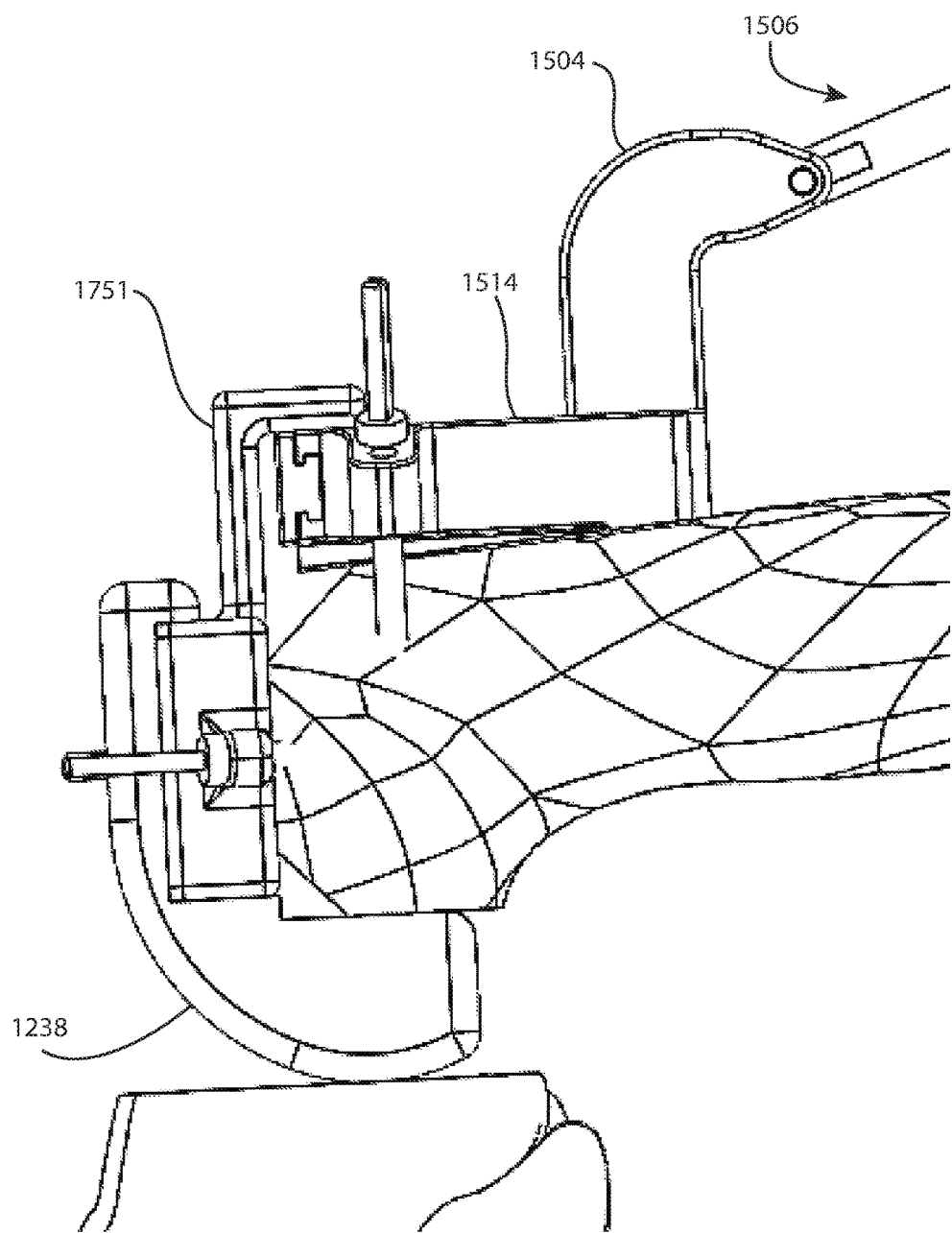
Figure 116A:
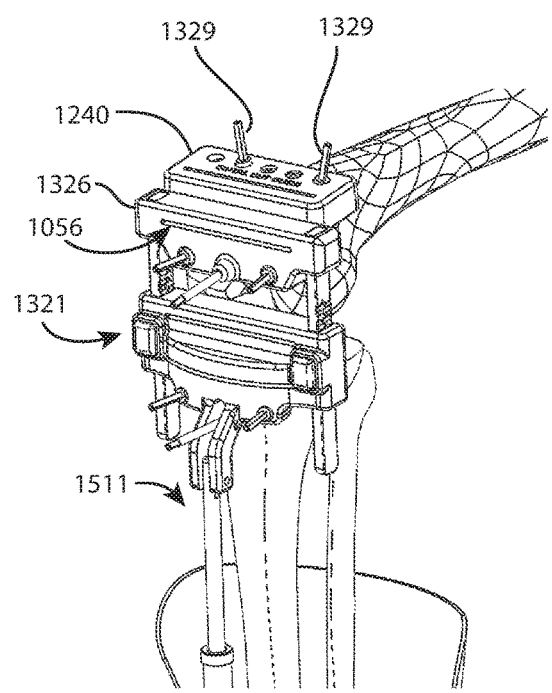
Figure 116B:
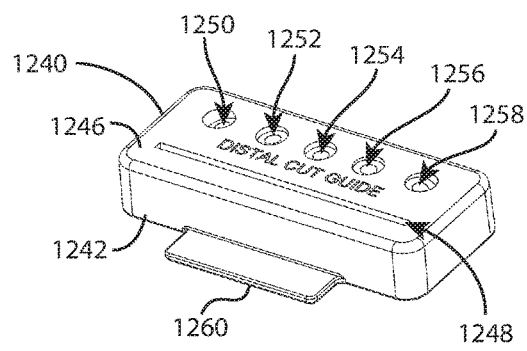
Figure 116C:
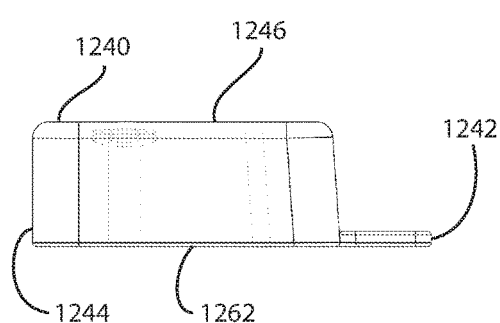
Figure 117A:
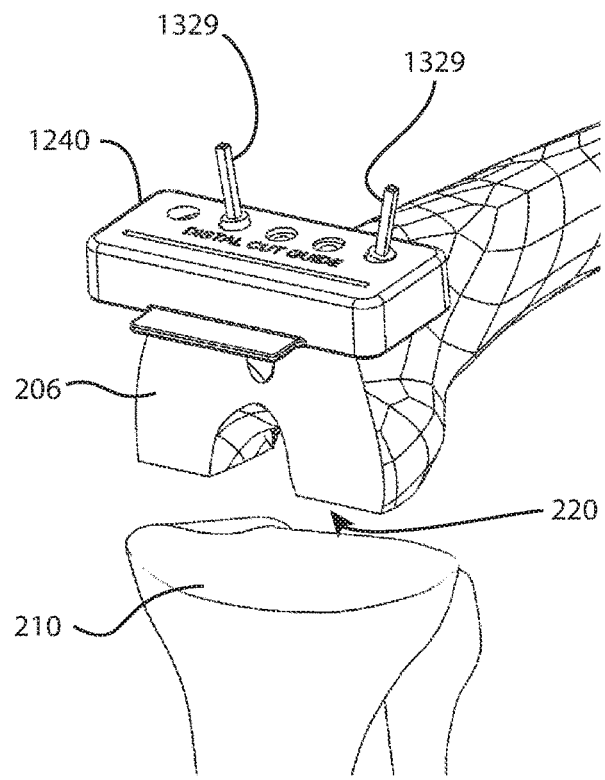
Figure 117B:
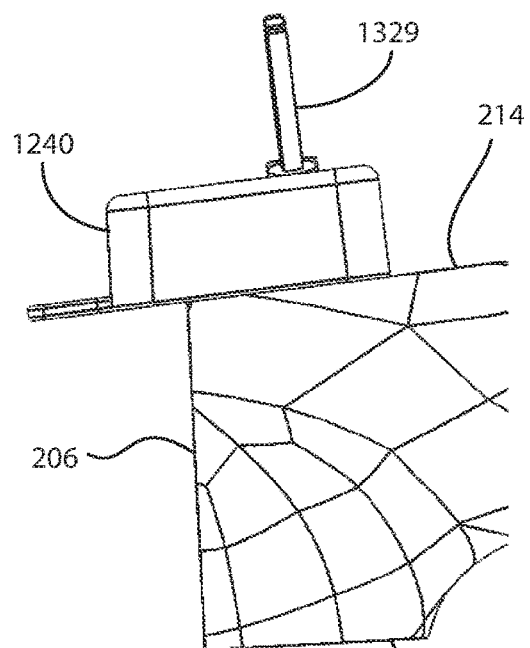
Figure 118A:
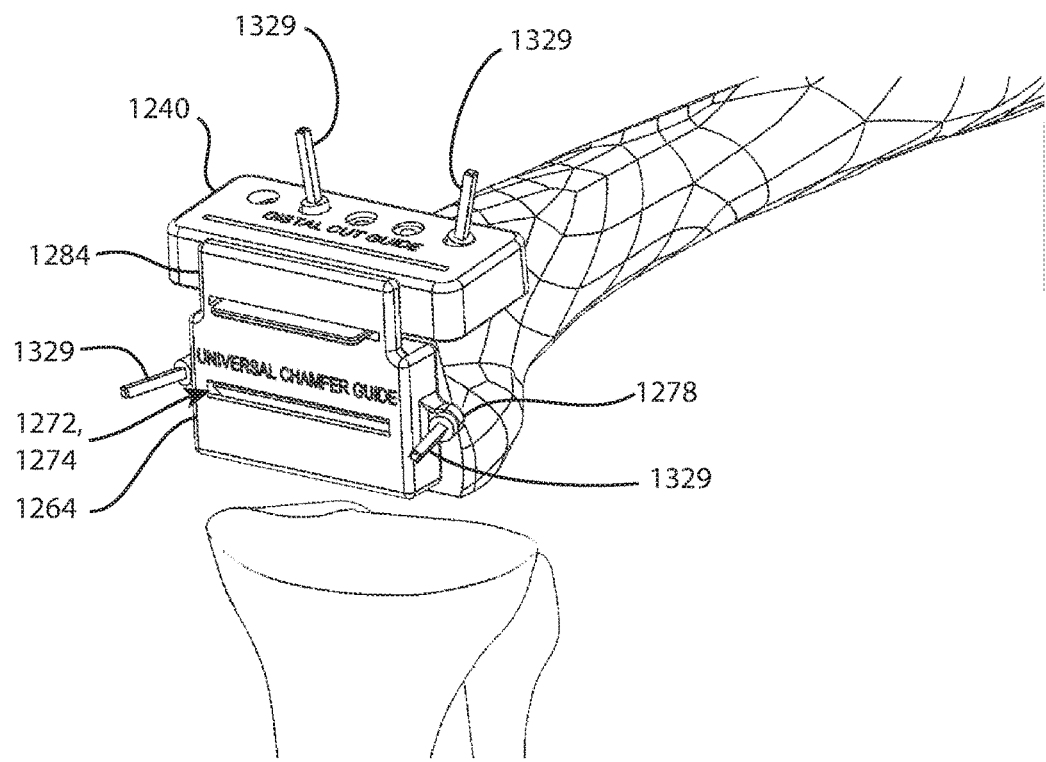
Figure 118B:
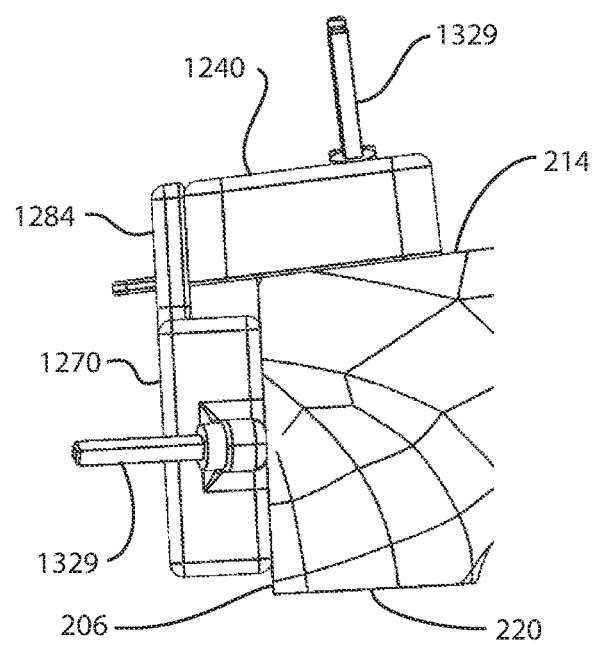
Figure 119A:
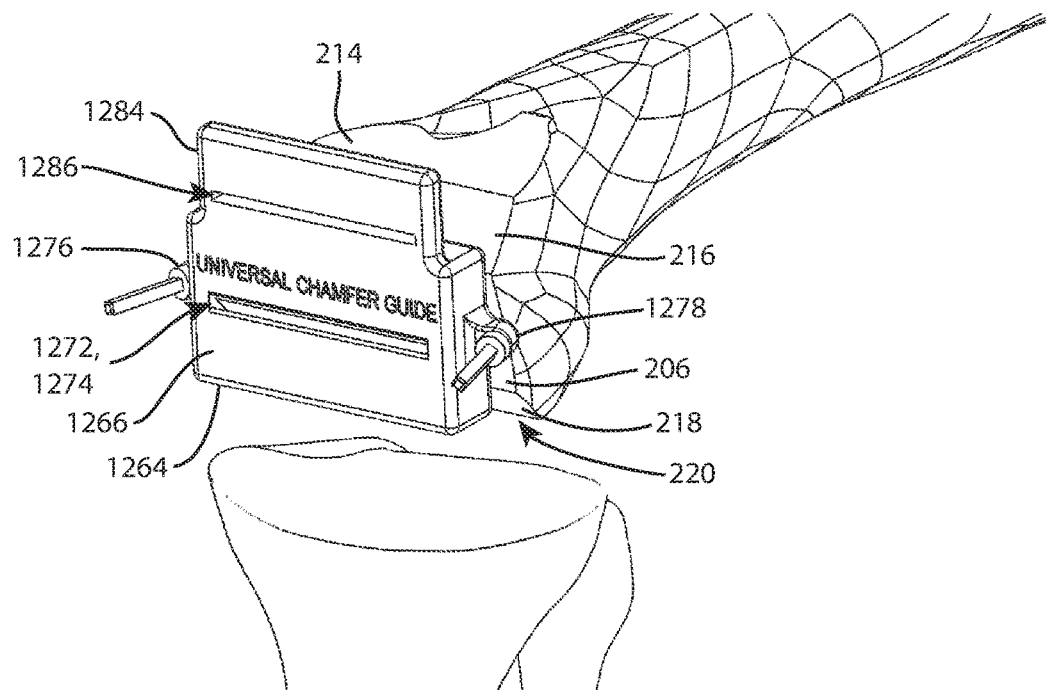
Figure 119B:
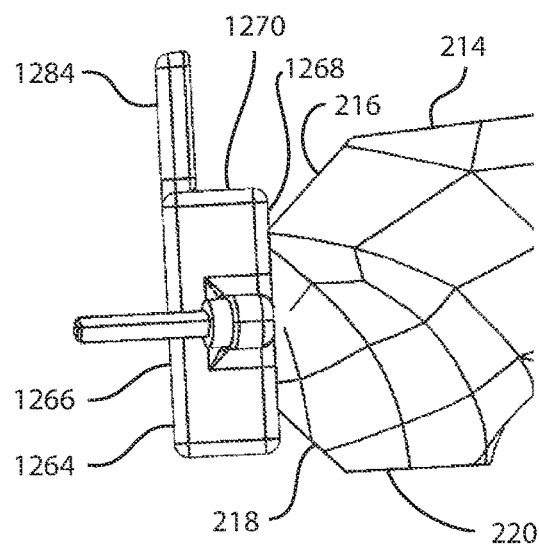
Figure 120:
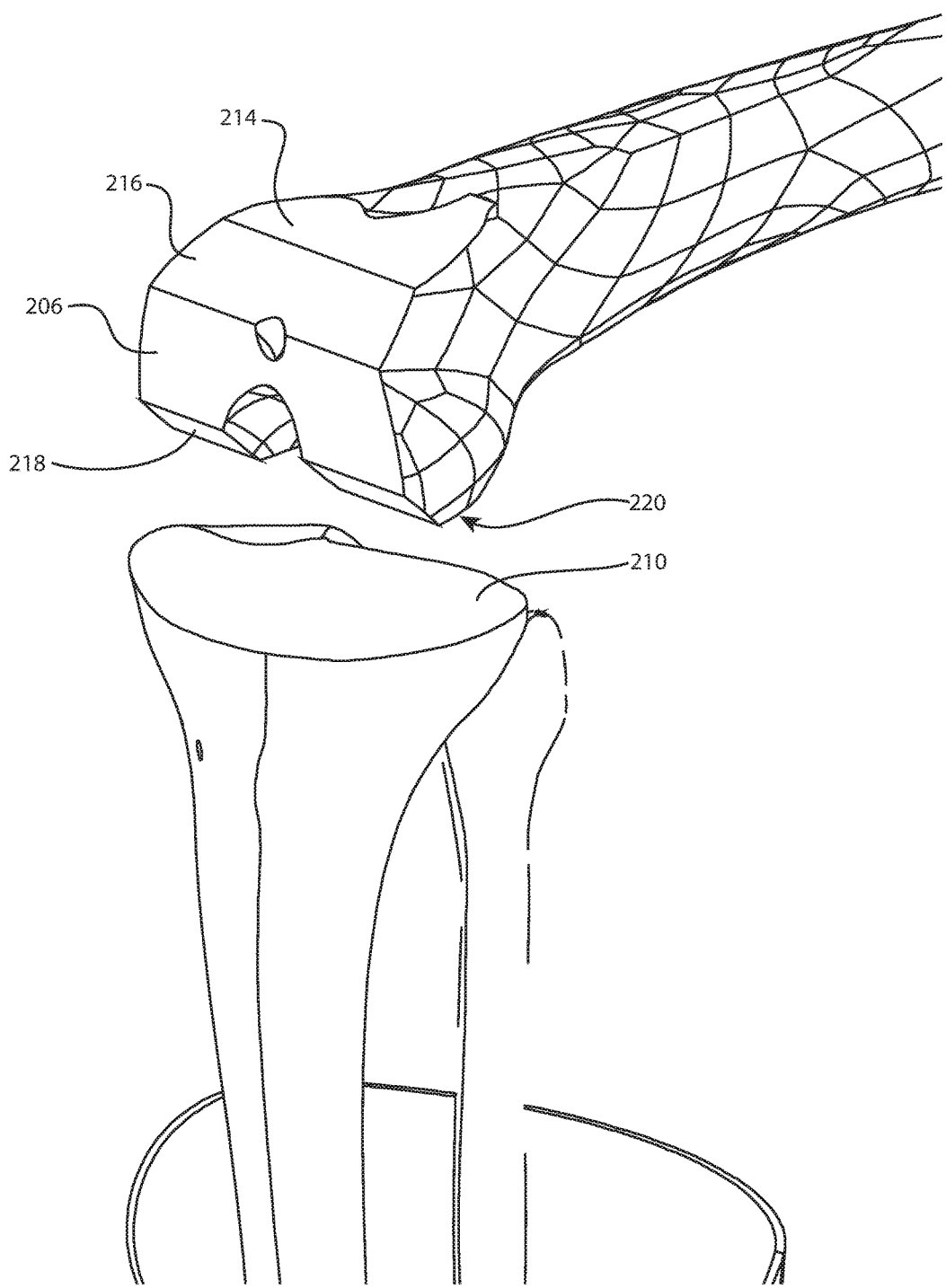
Figure 121:
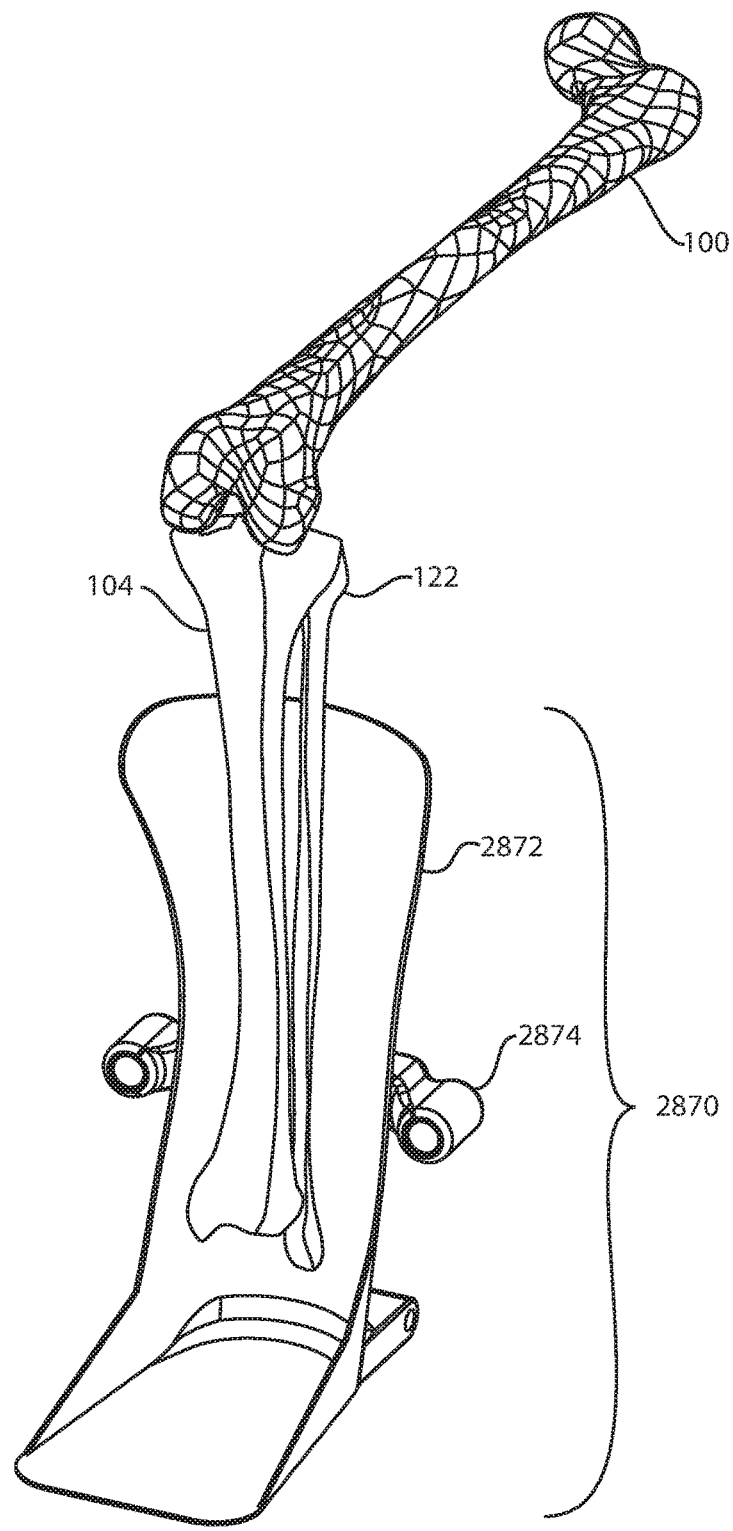
Figure 122:
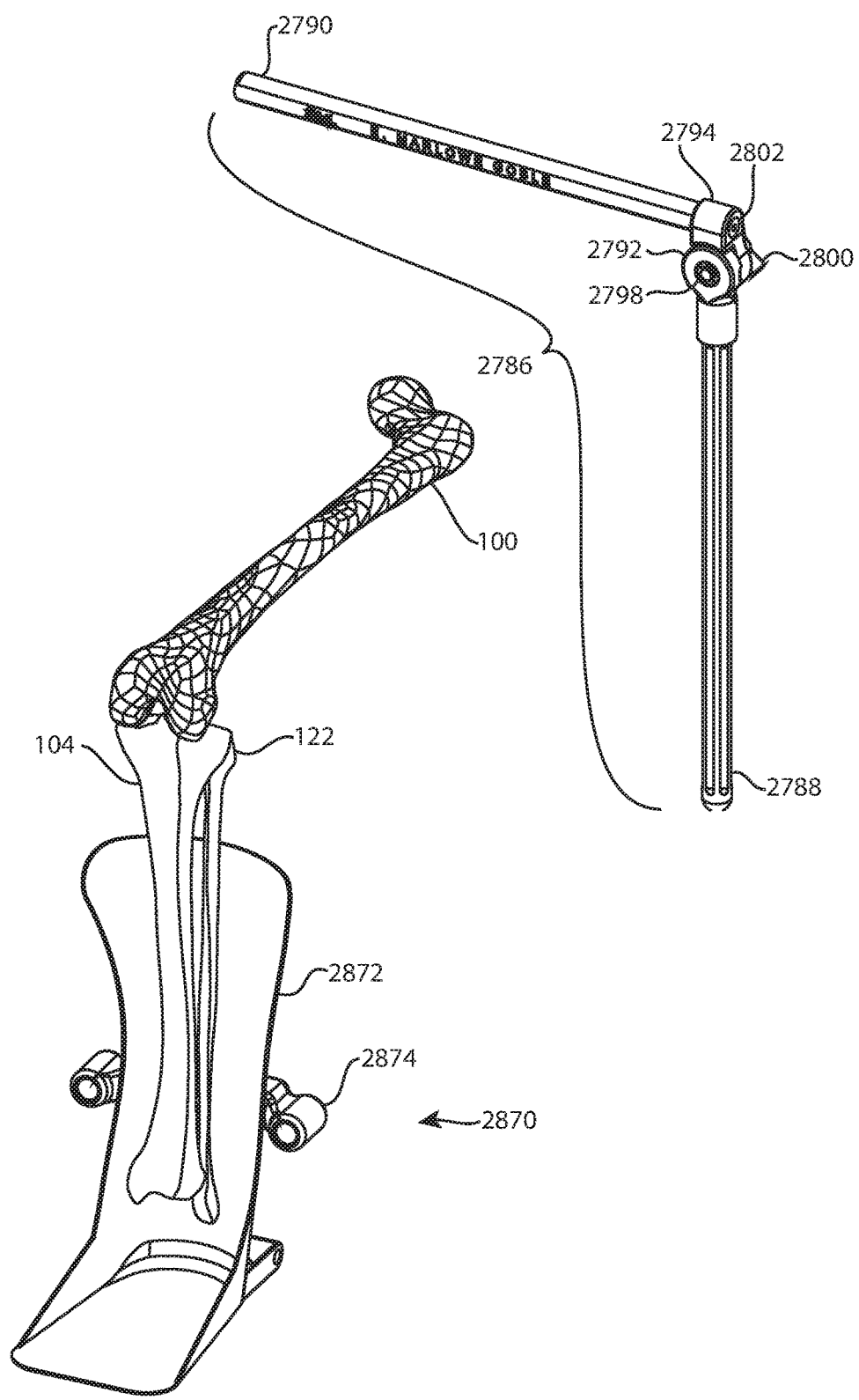
Figure 123A:
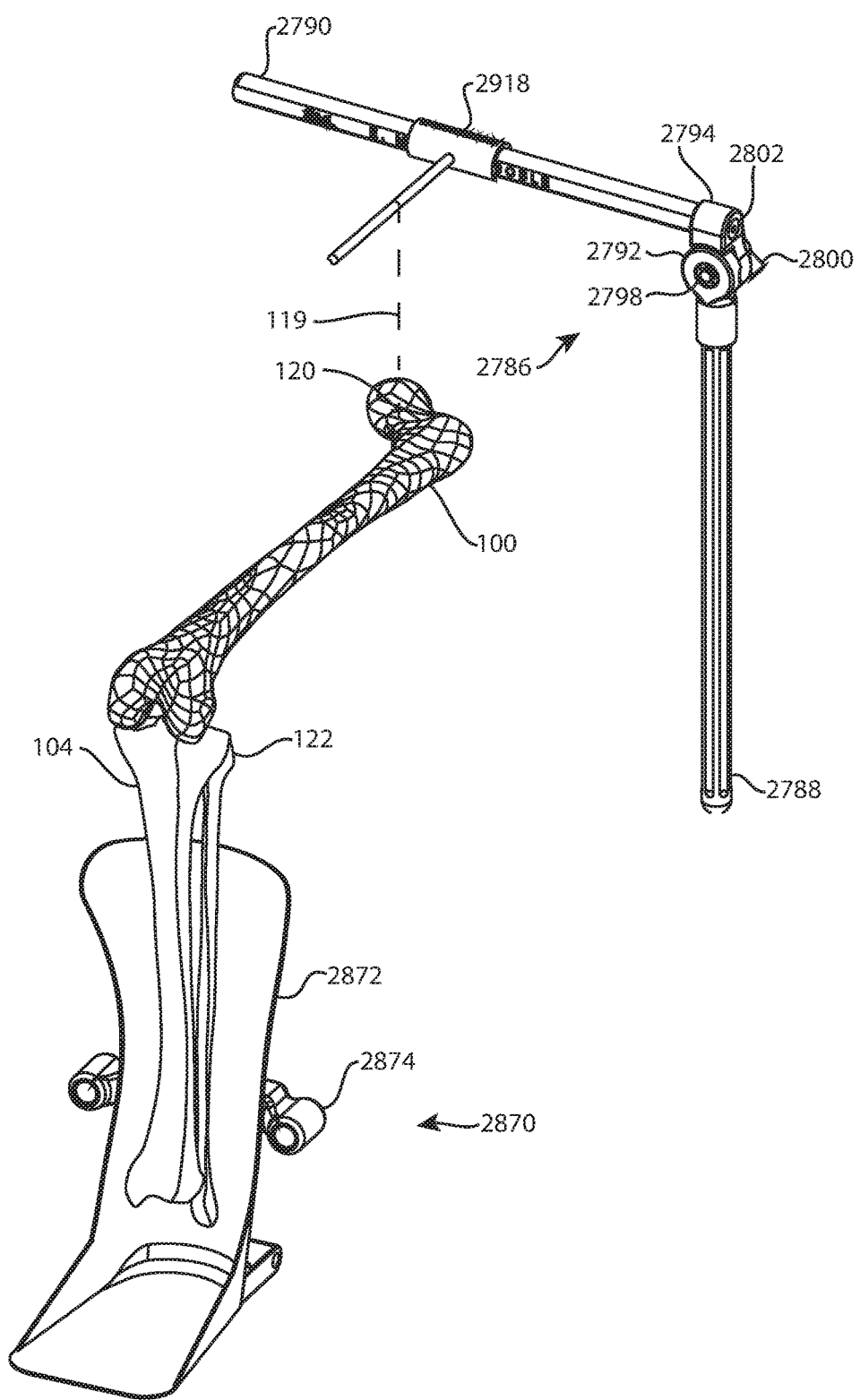
Figure 123B:
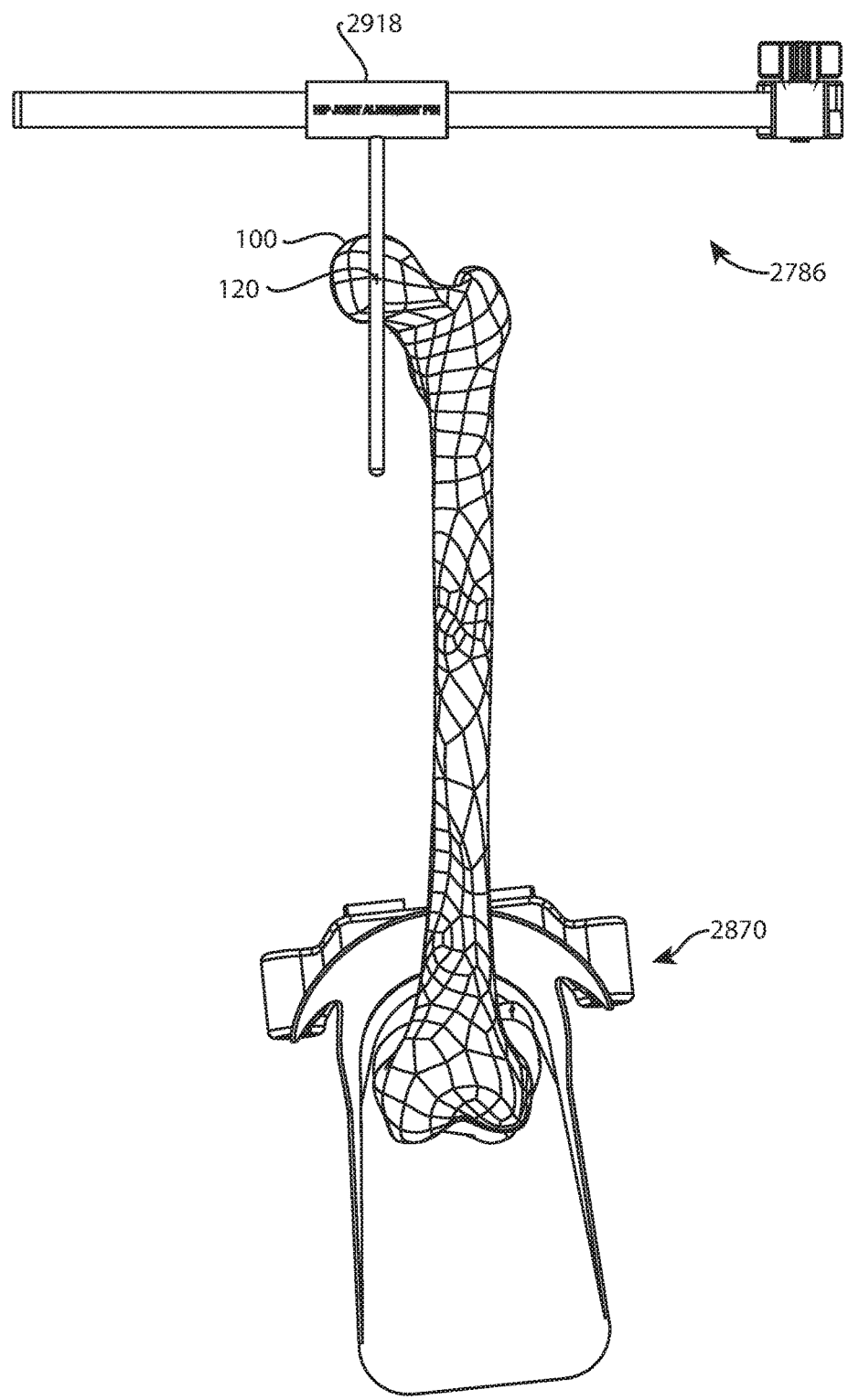
Figure 124:
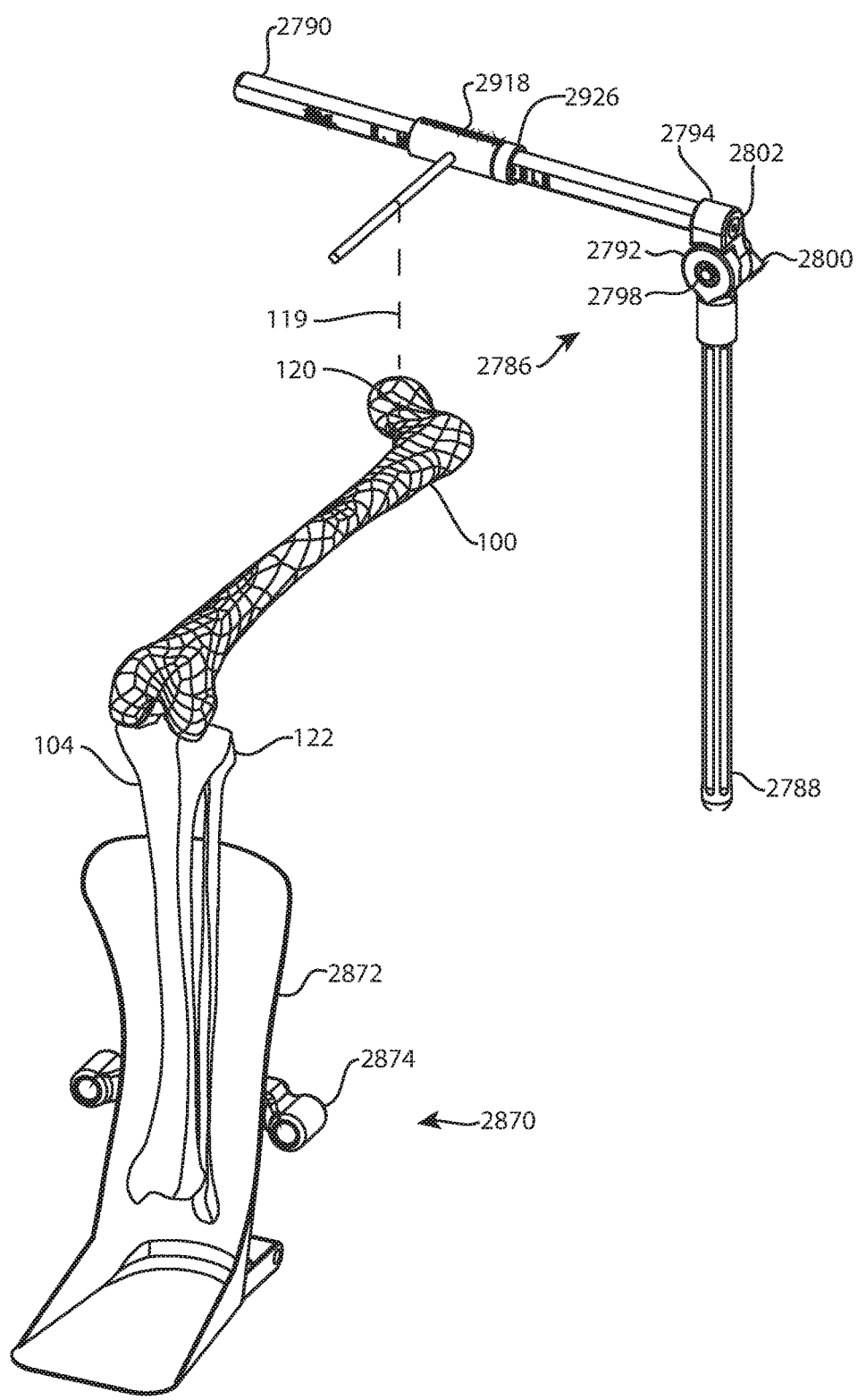
Figure 125:
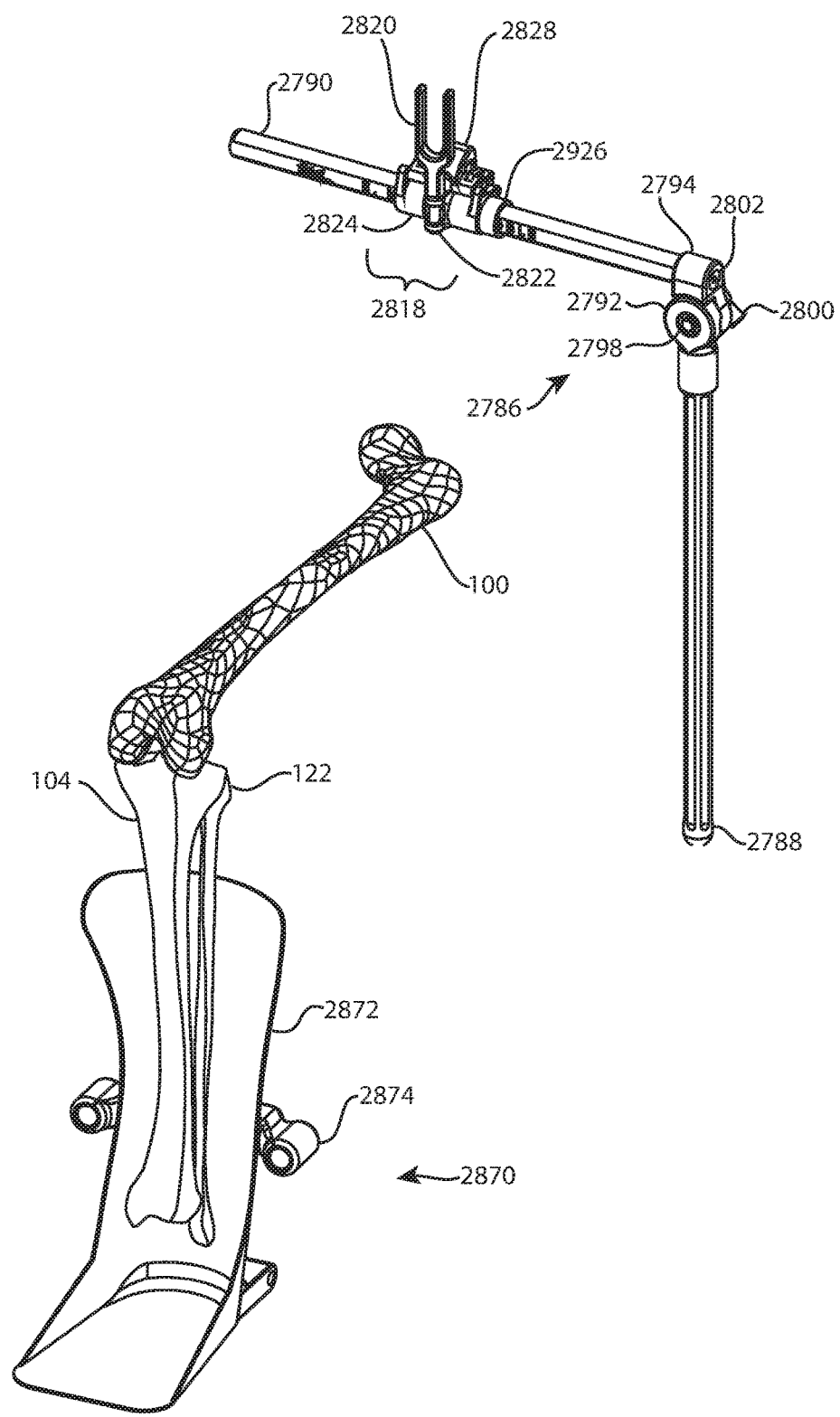
Figure 126:
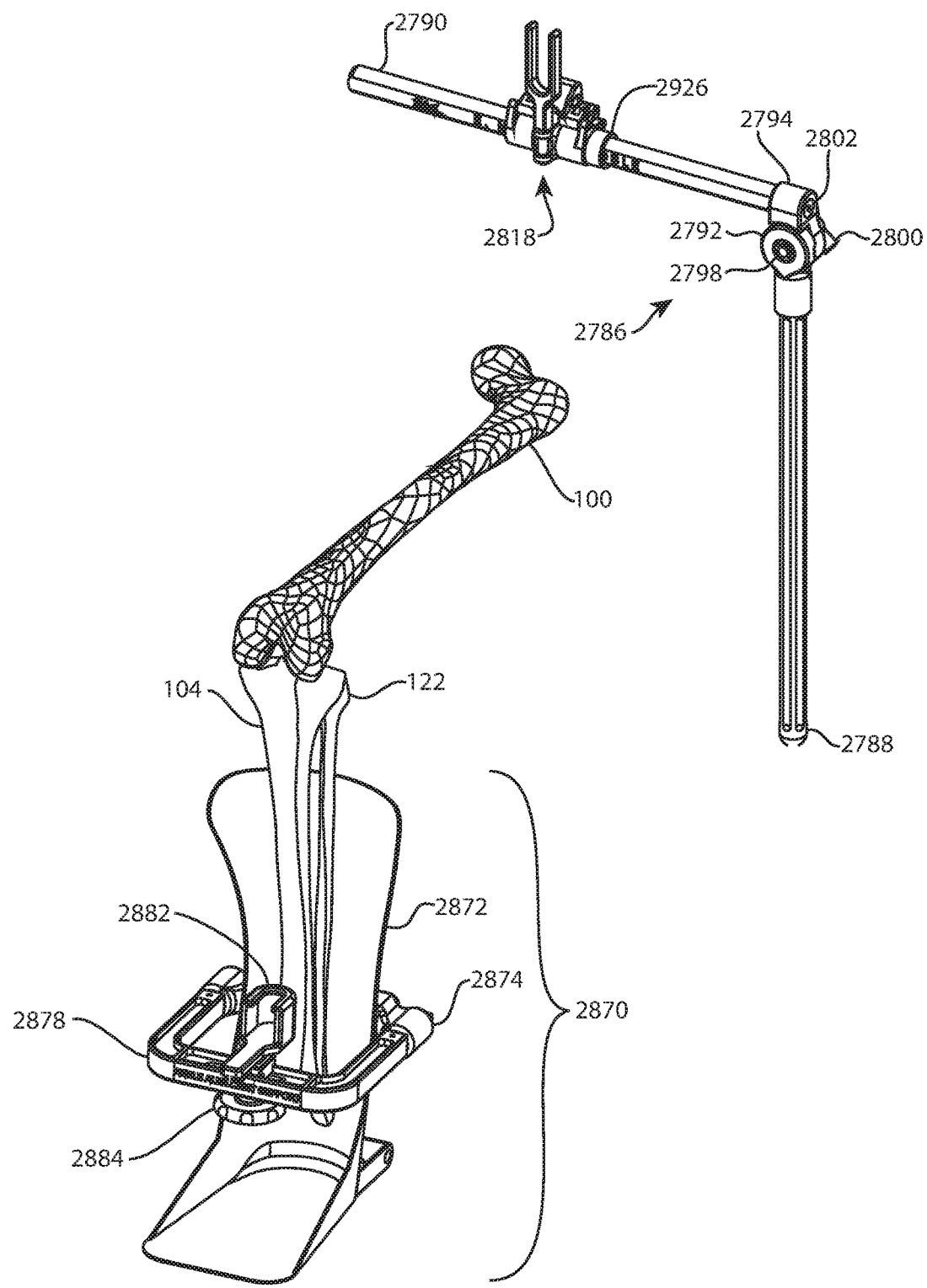
Figure 127:
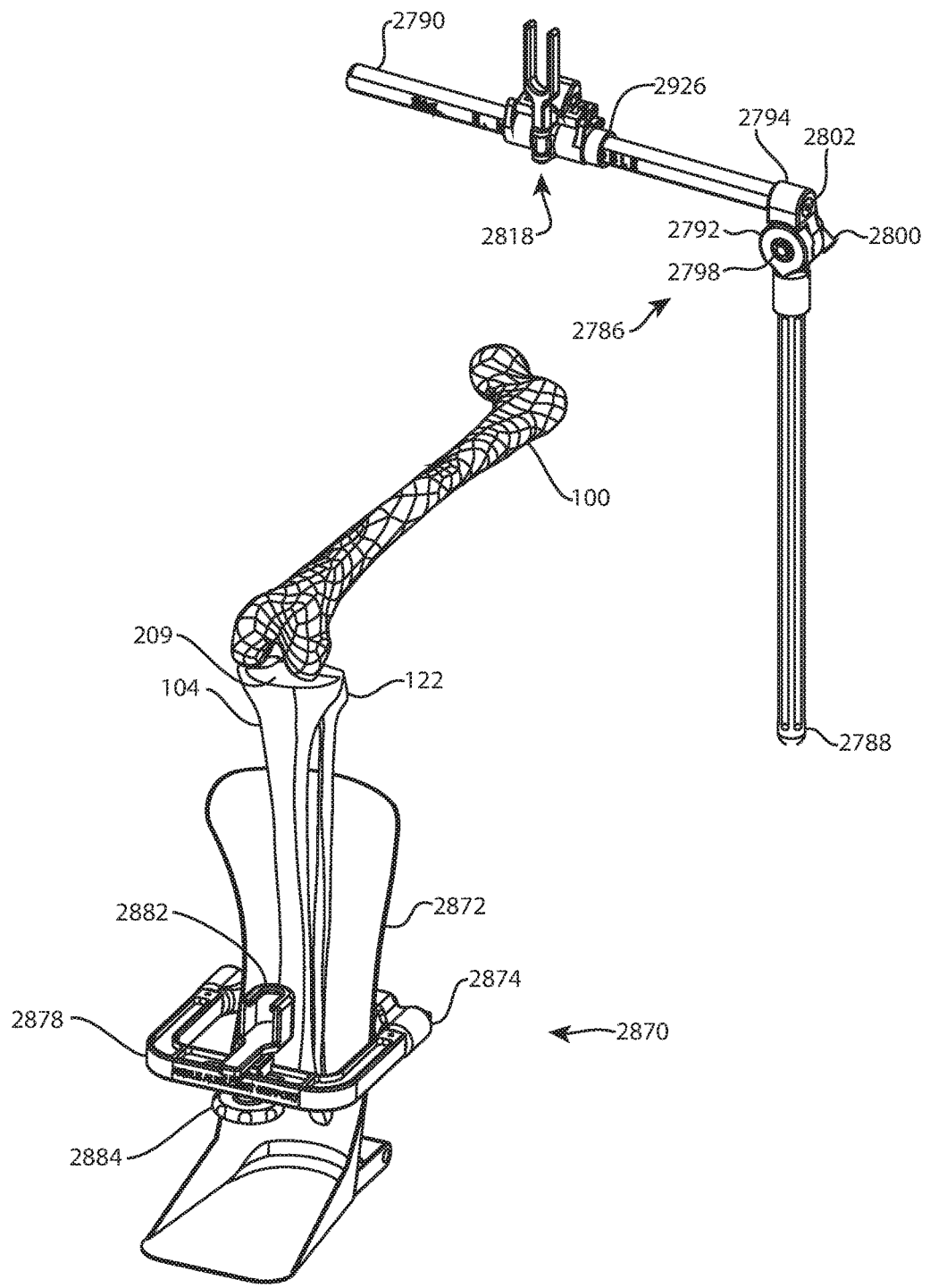
Figure 128A:
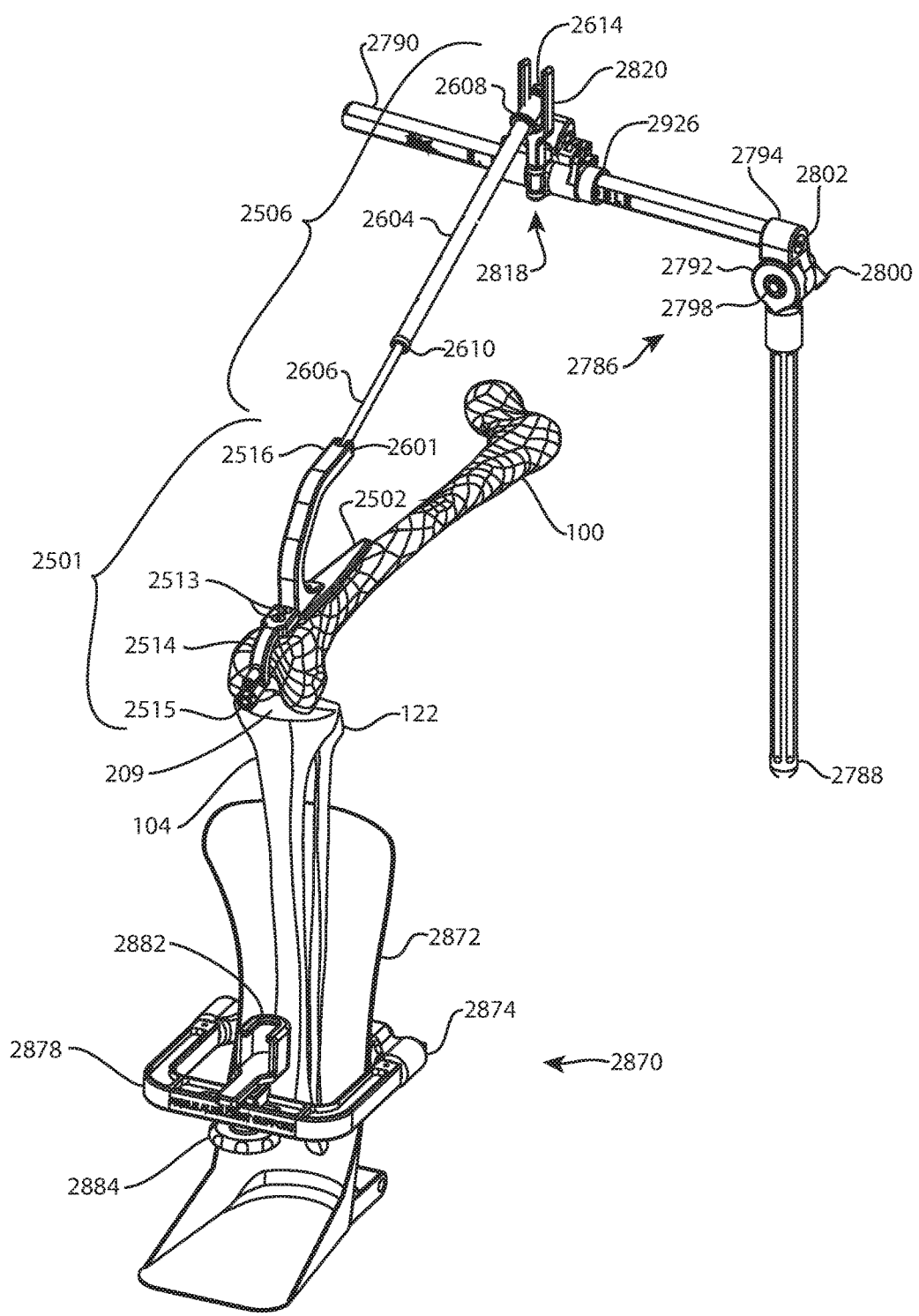
Figure 128B:
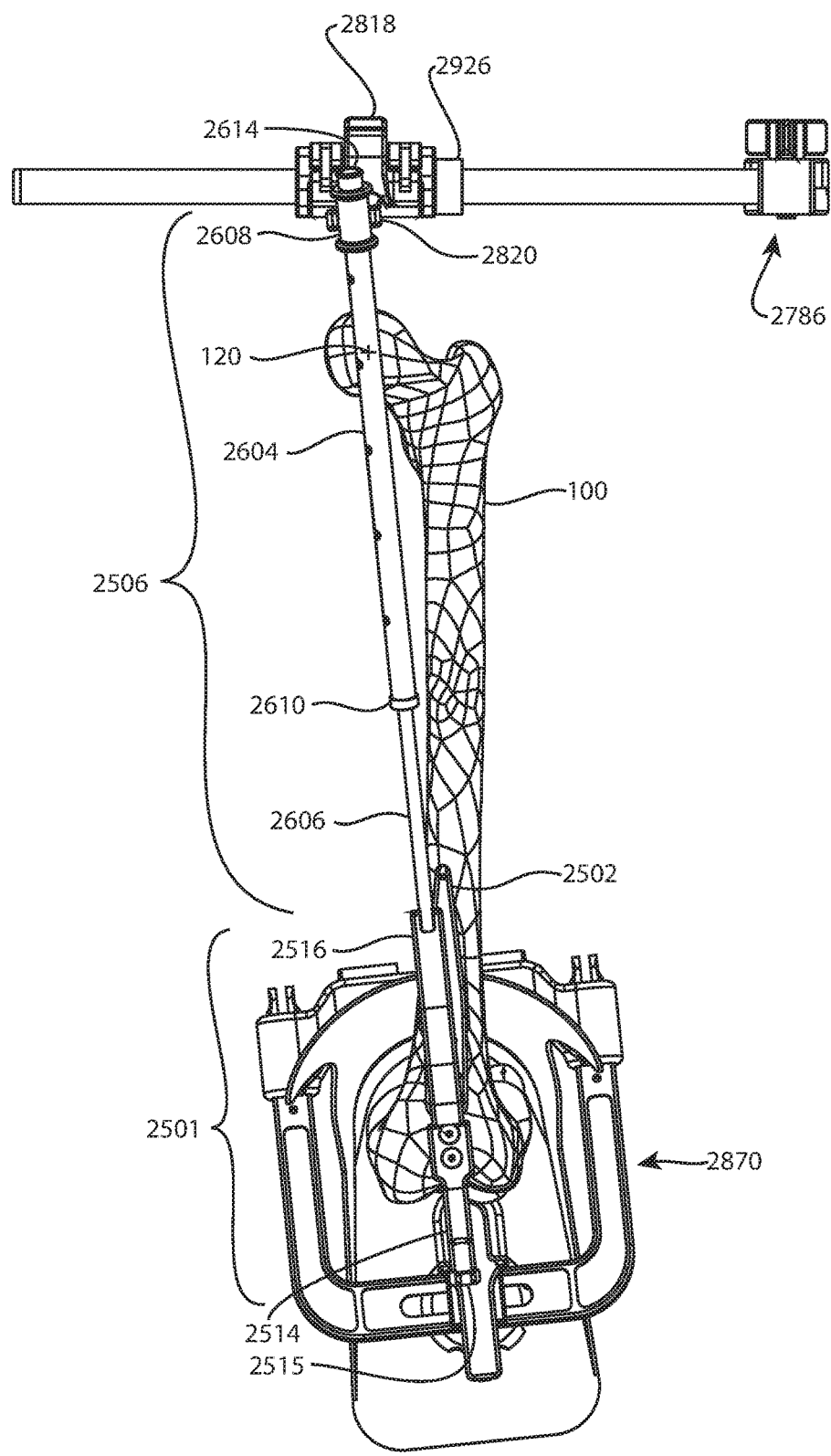
Figure 129A:
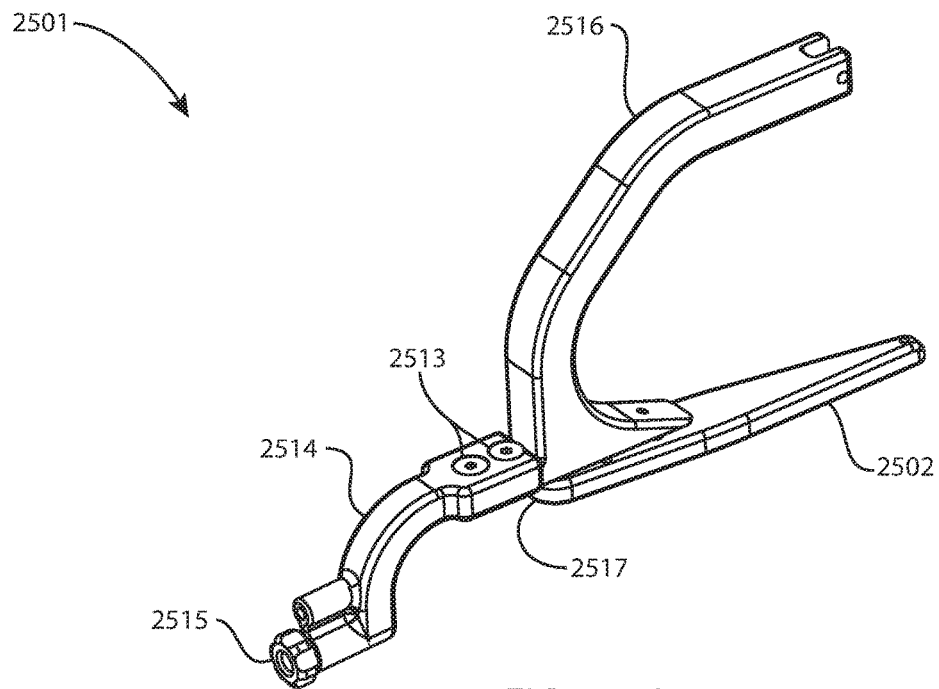
Figure 129B:
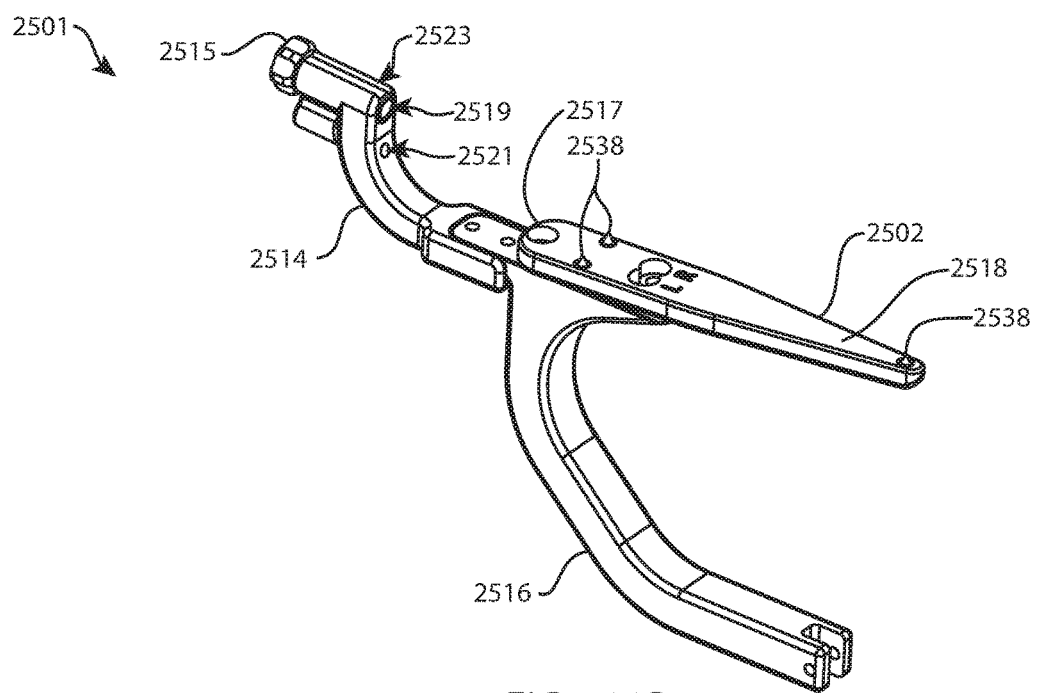
Figure 133A:
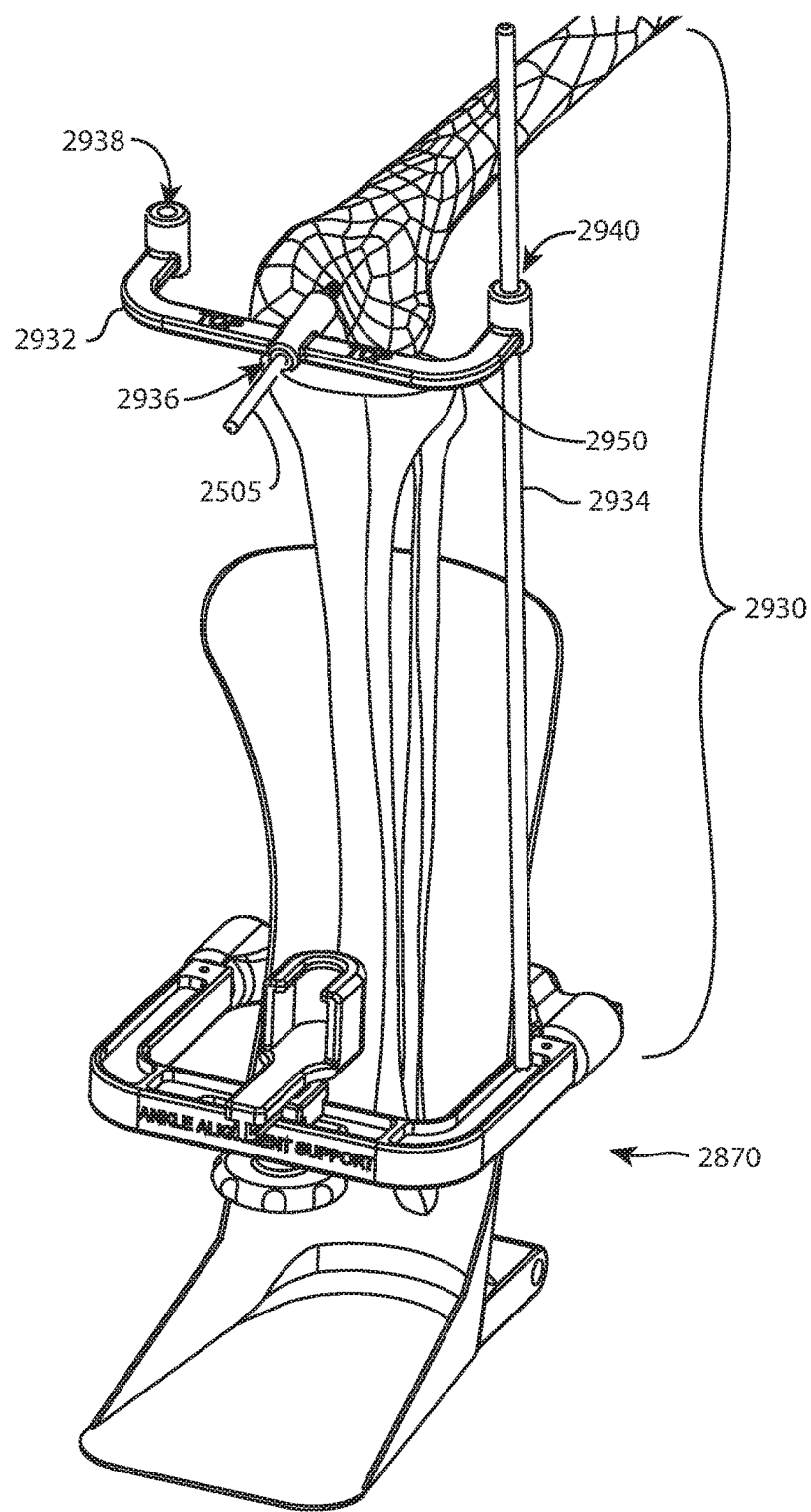
Figure 133B:
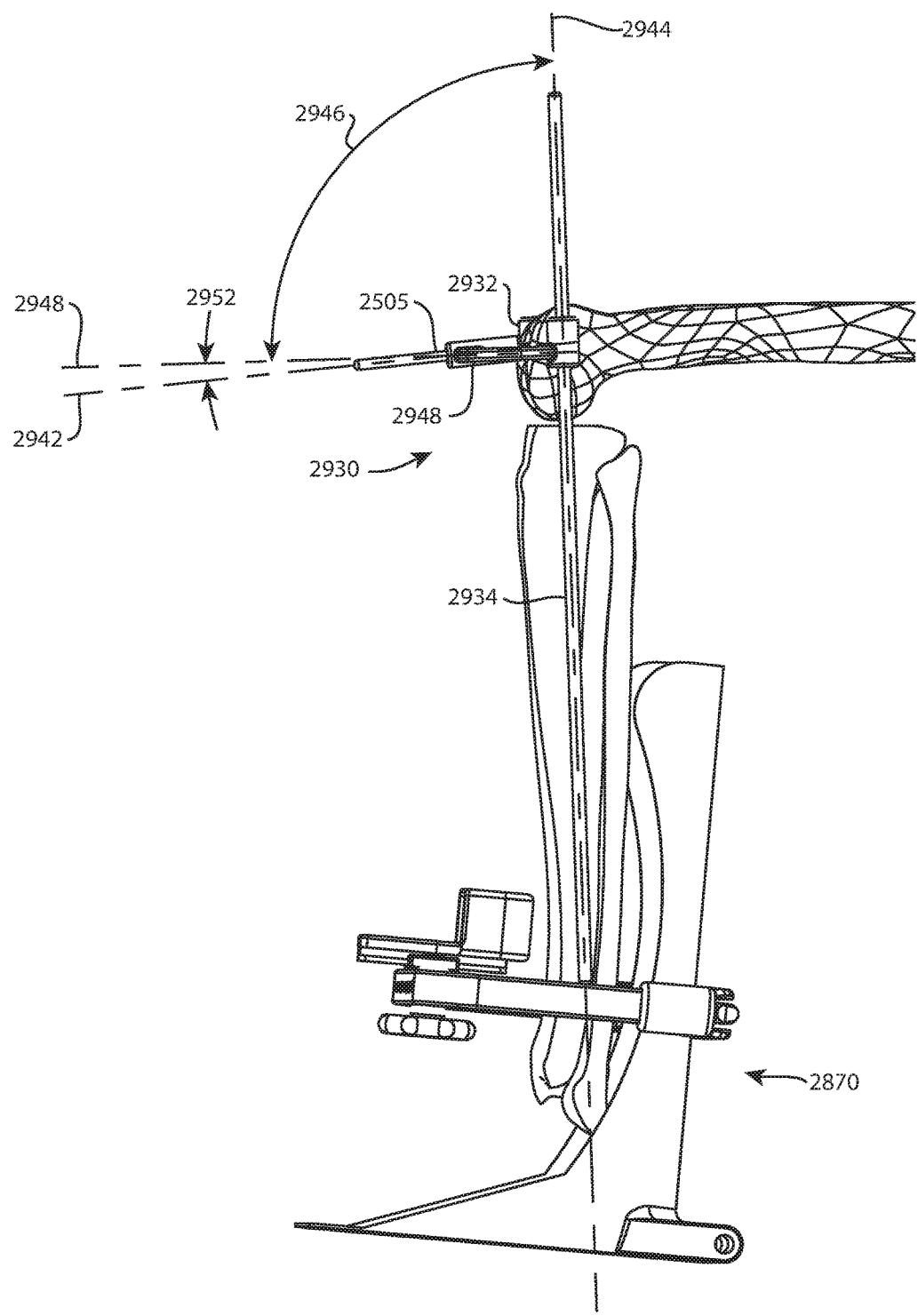
Figure 134:
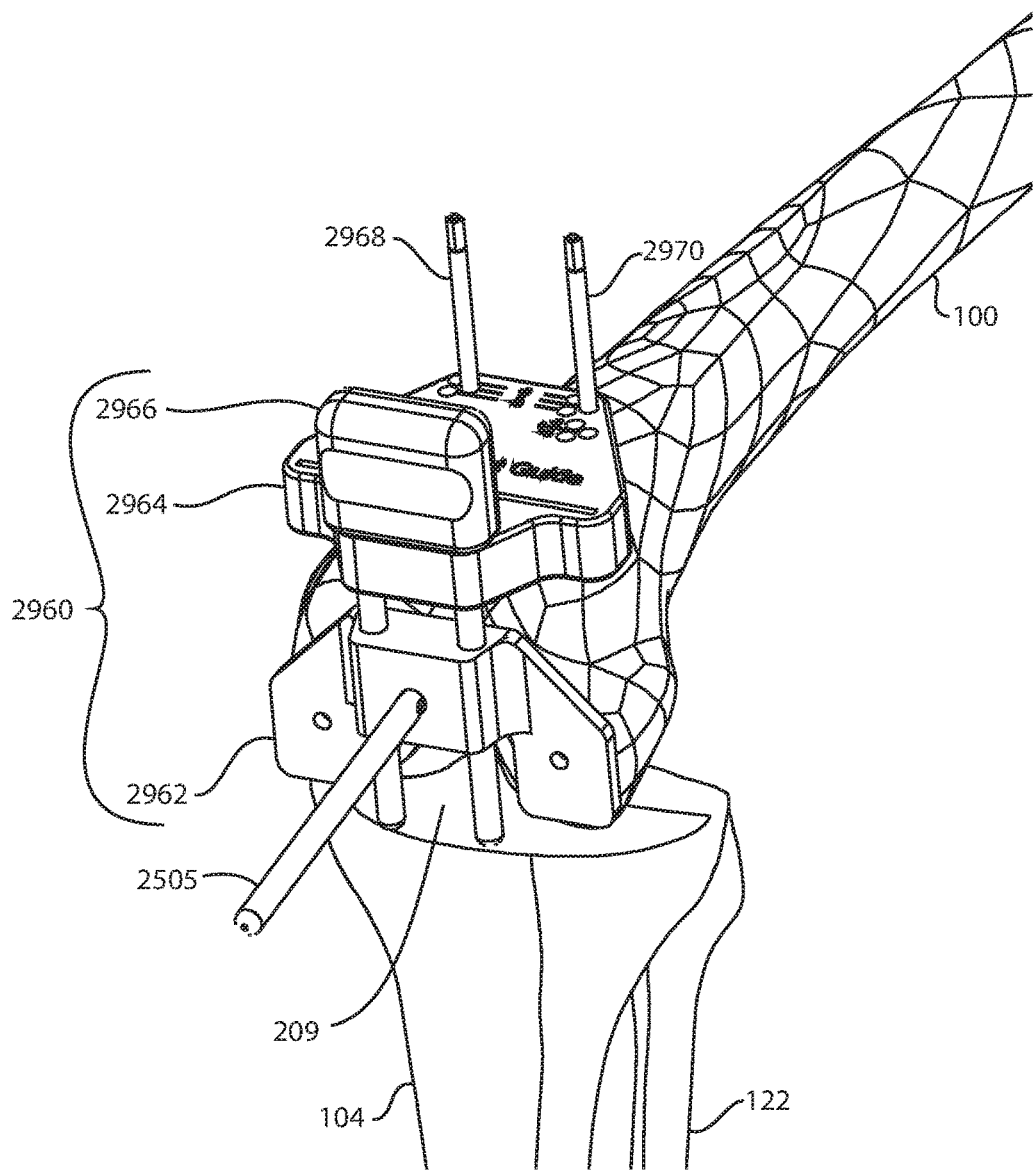
Figure 135A:
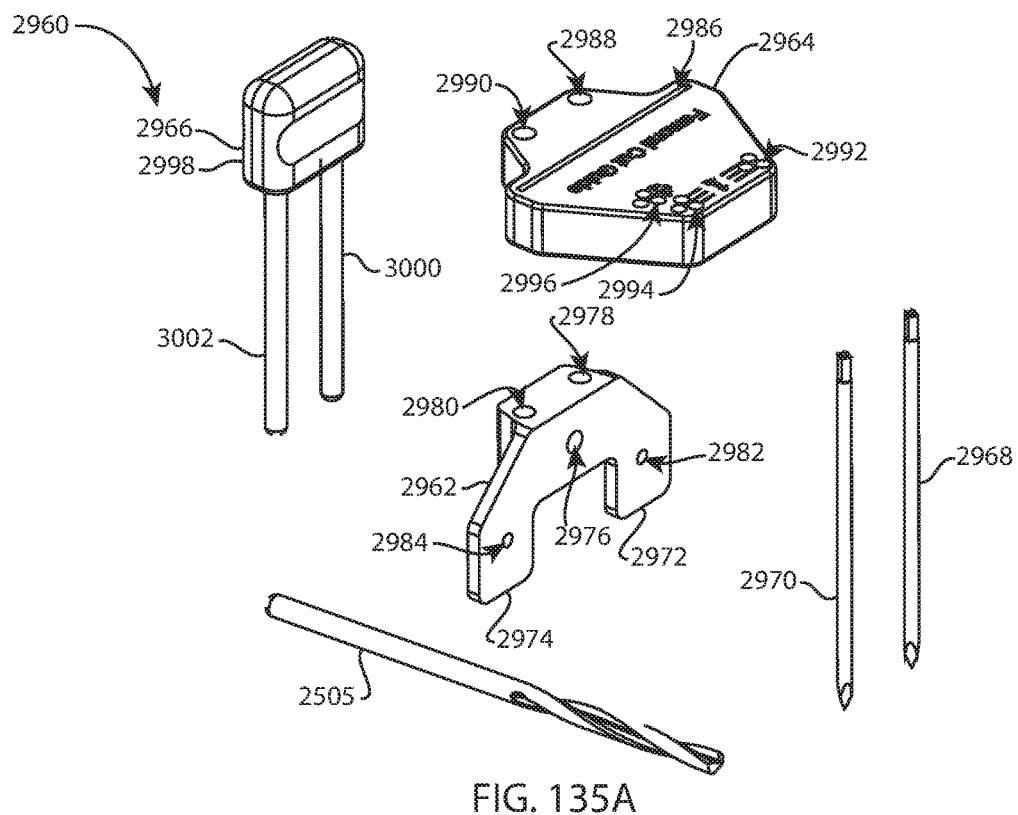
Figure 135B:
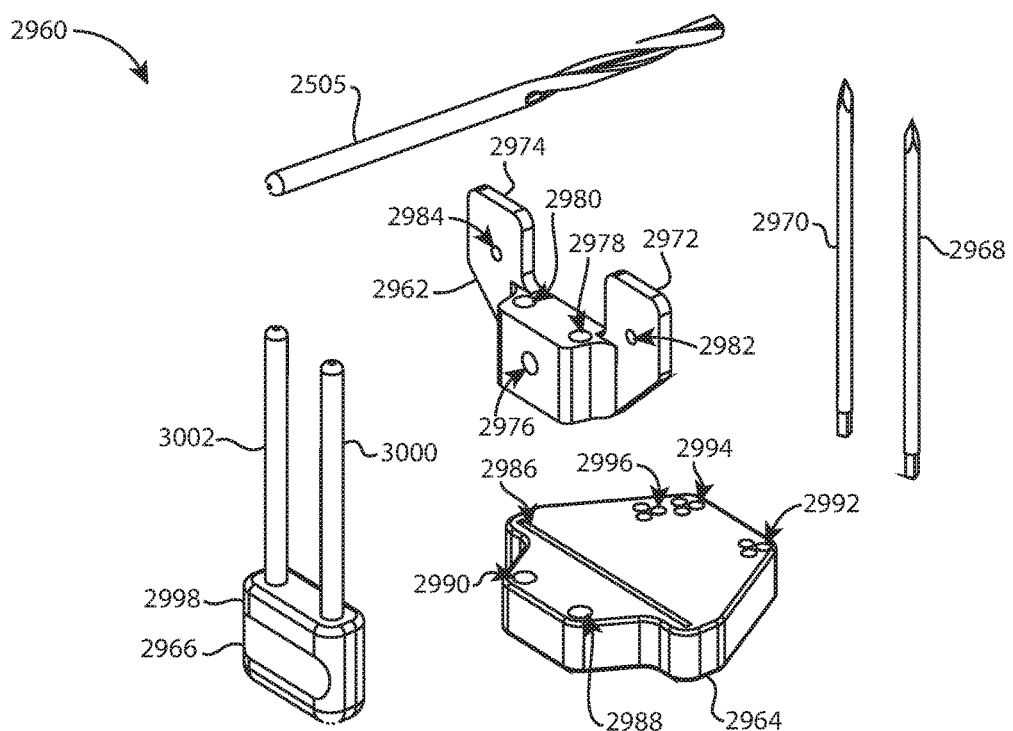
Figure 136:
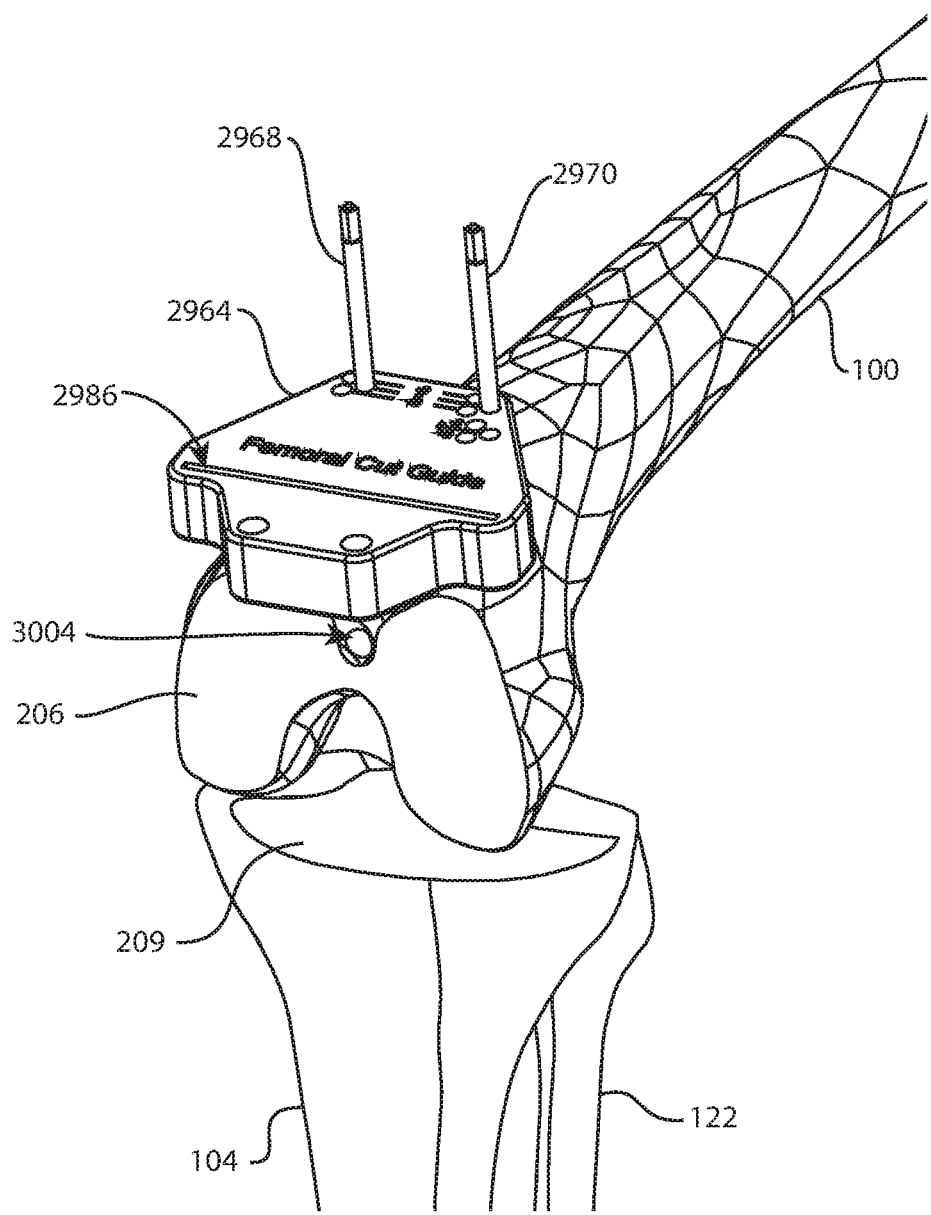
Figure 137A:
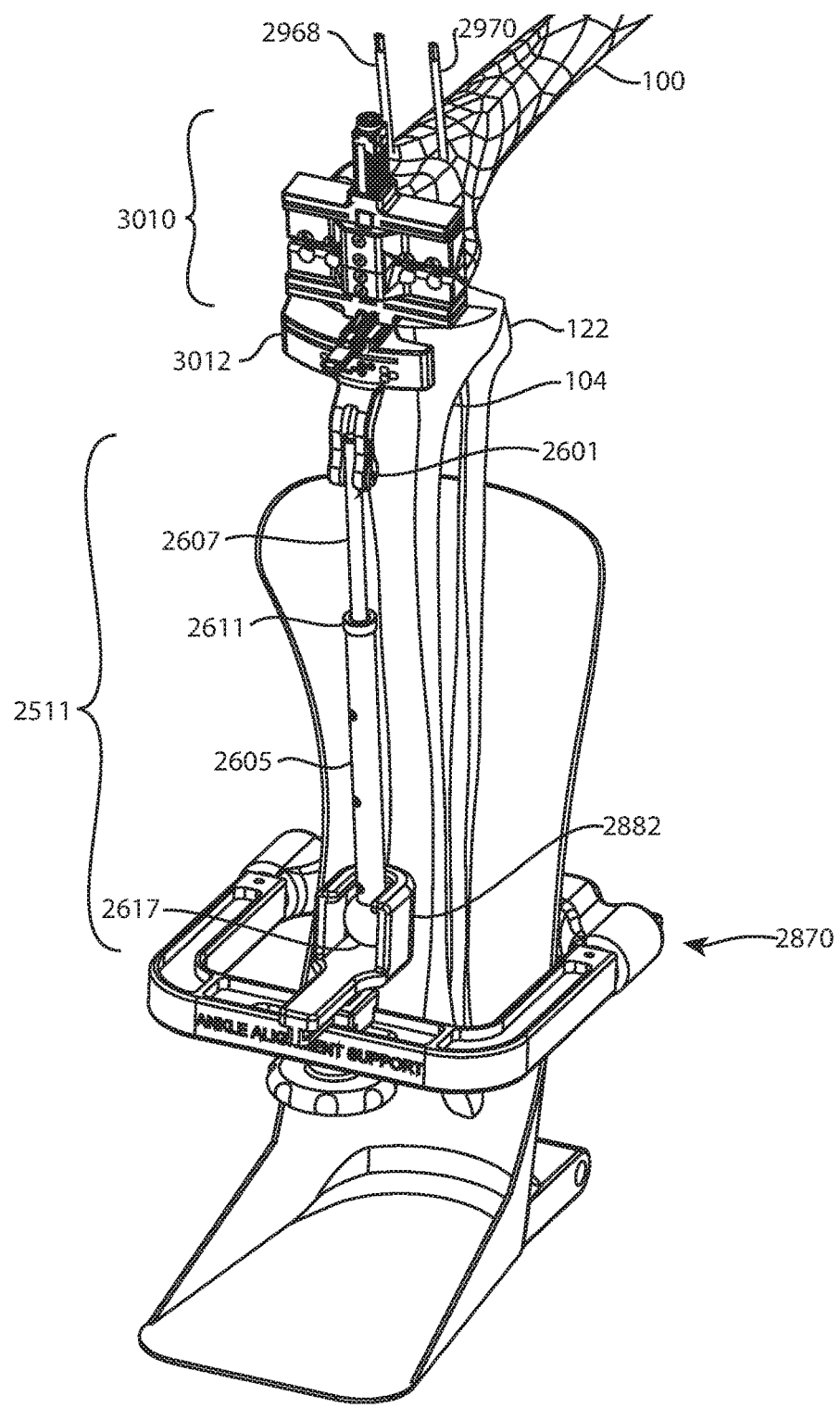
Figure 137B:
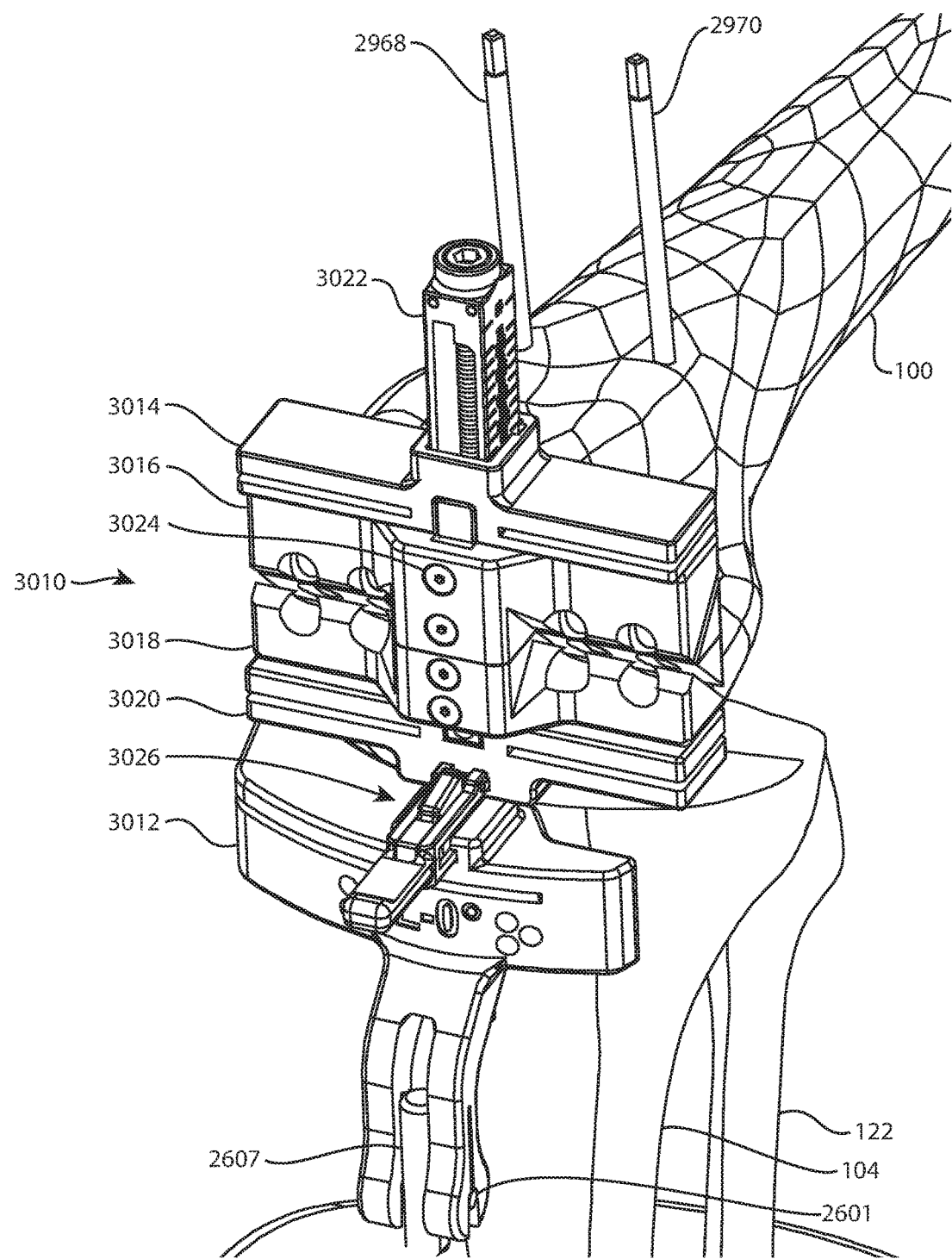
Figure 137C:
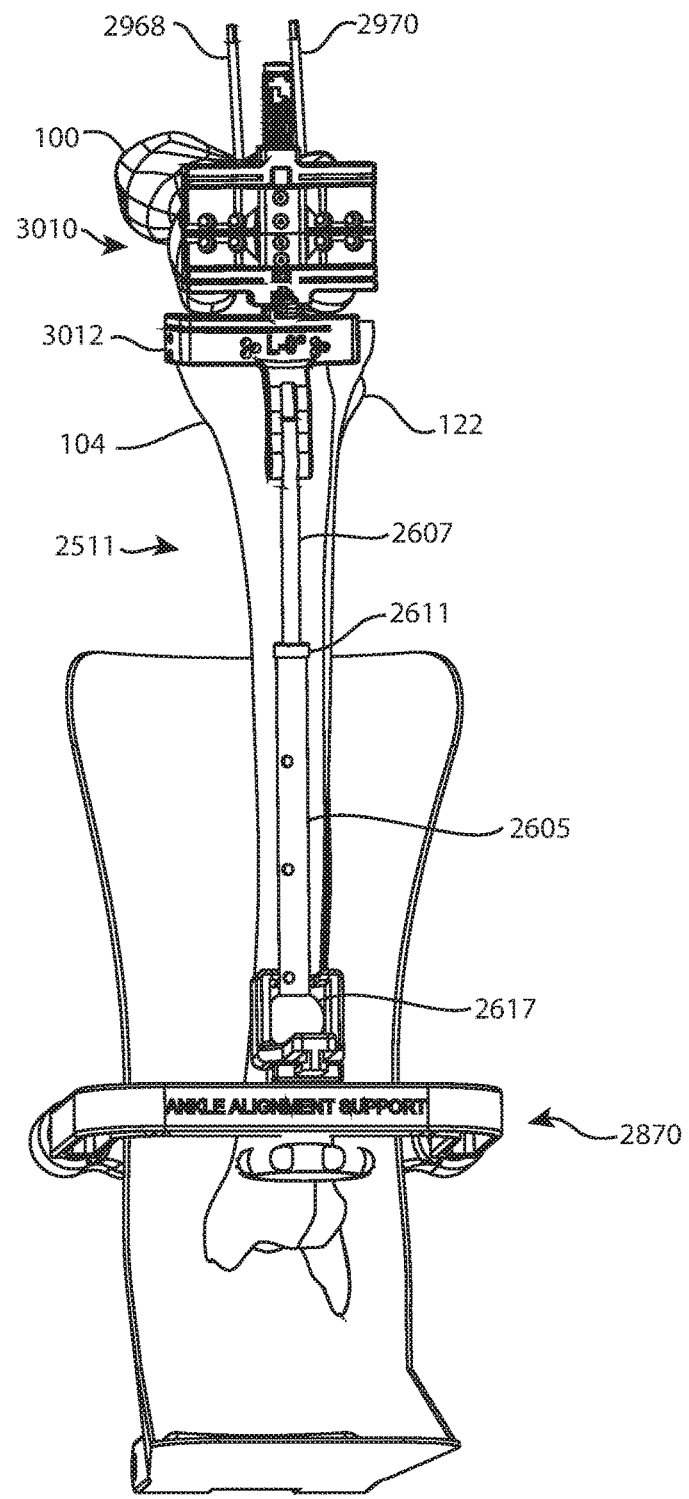
Figure 137D:
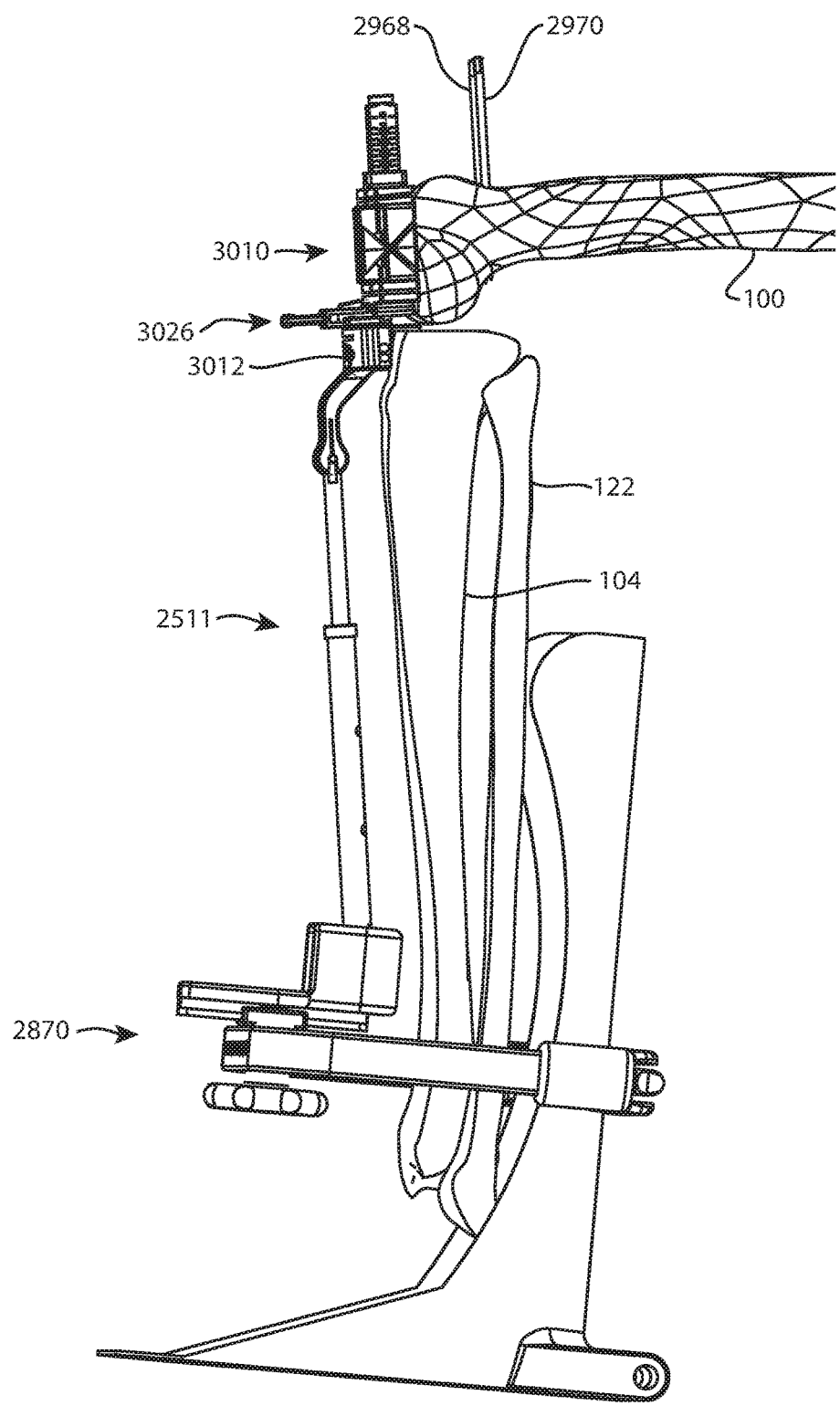
Figure 138A:
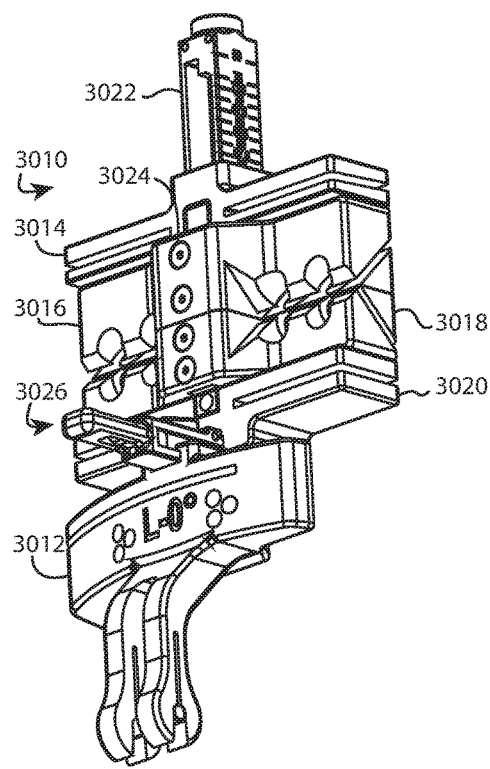
Figure 138B:
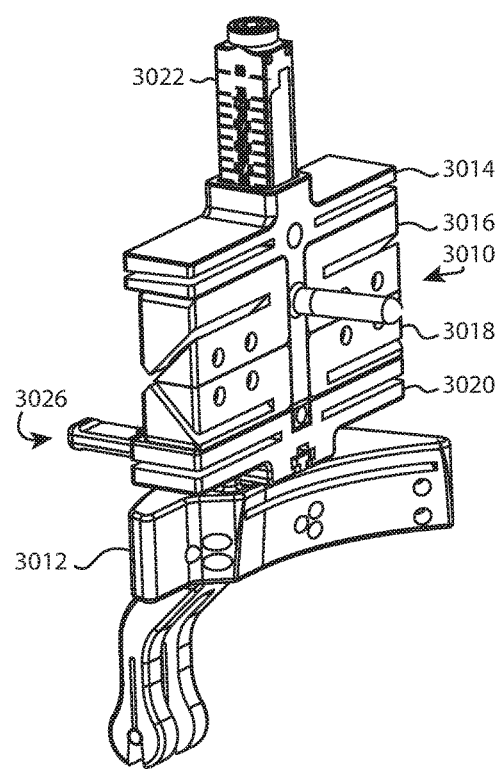
Figure 138C:
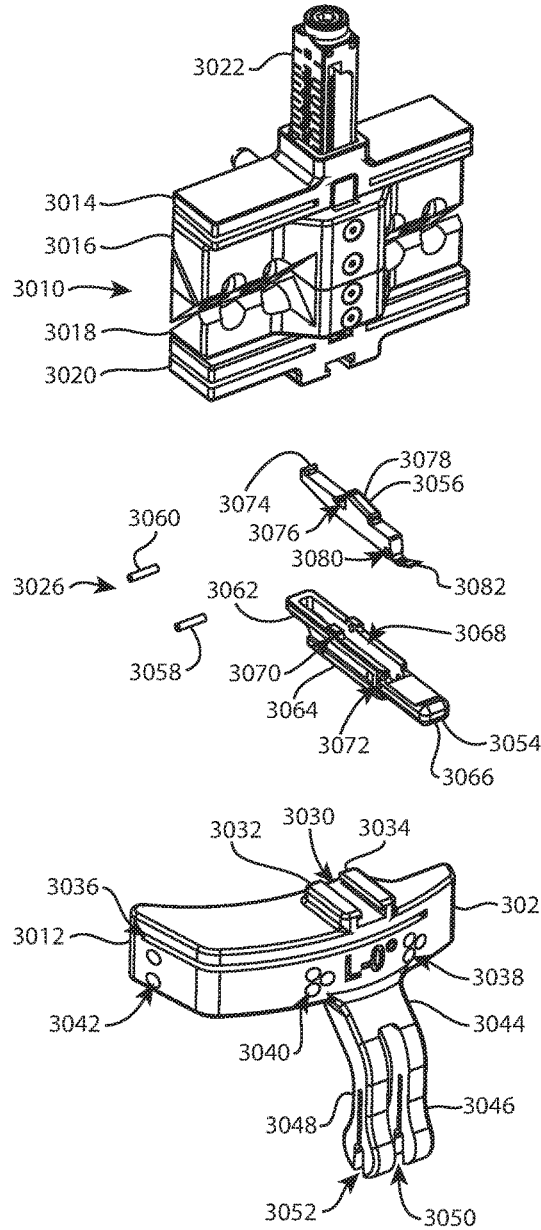
Figure 138D:
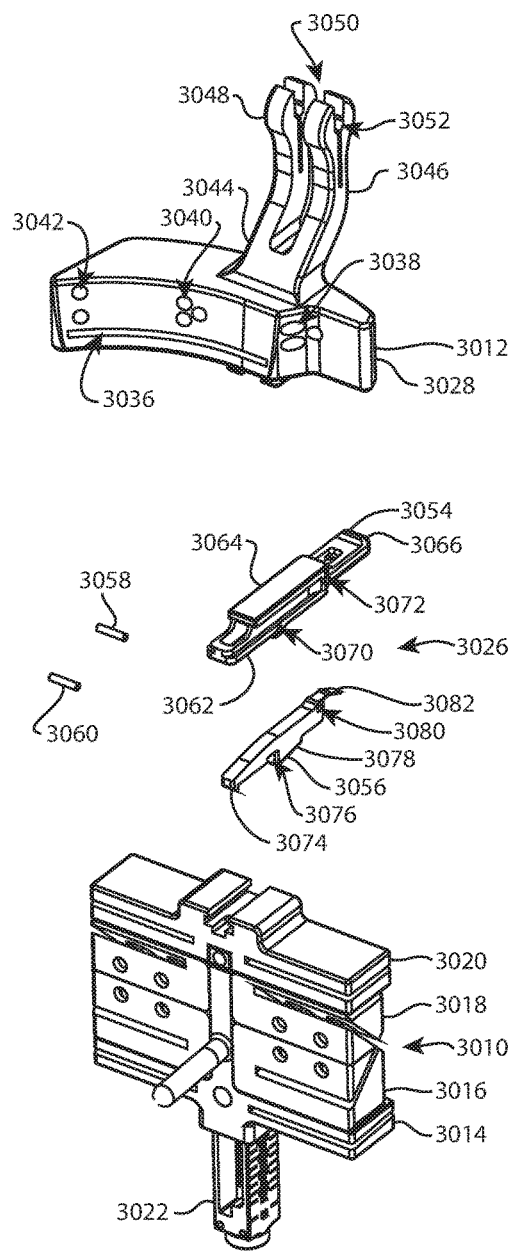
Figure 139A:
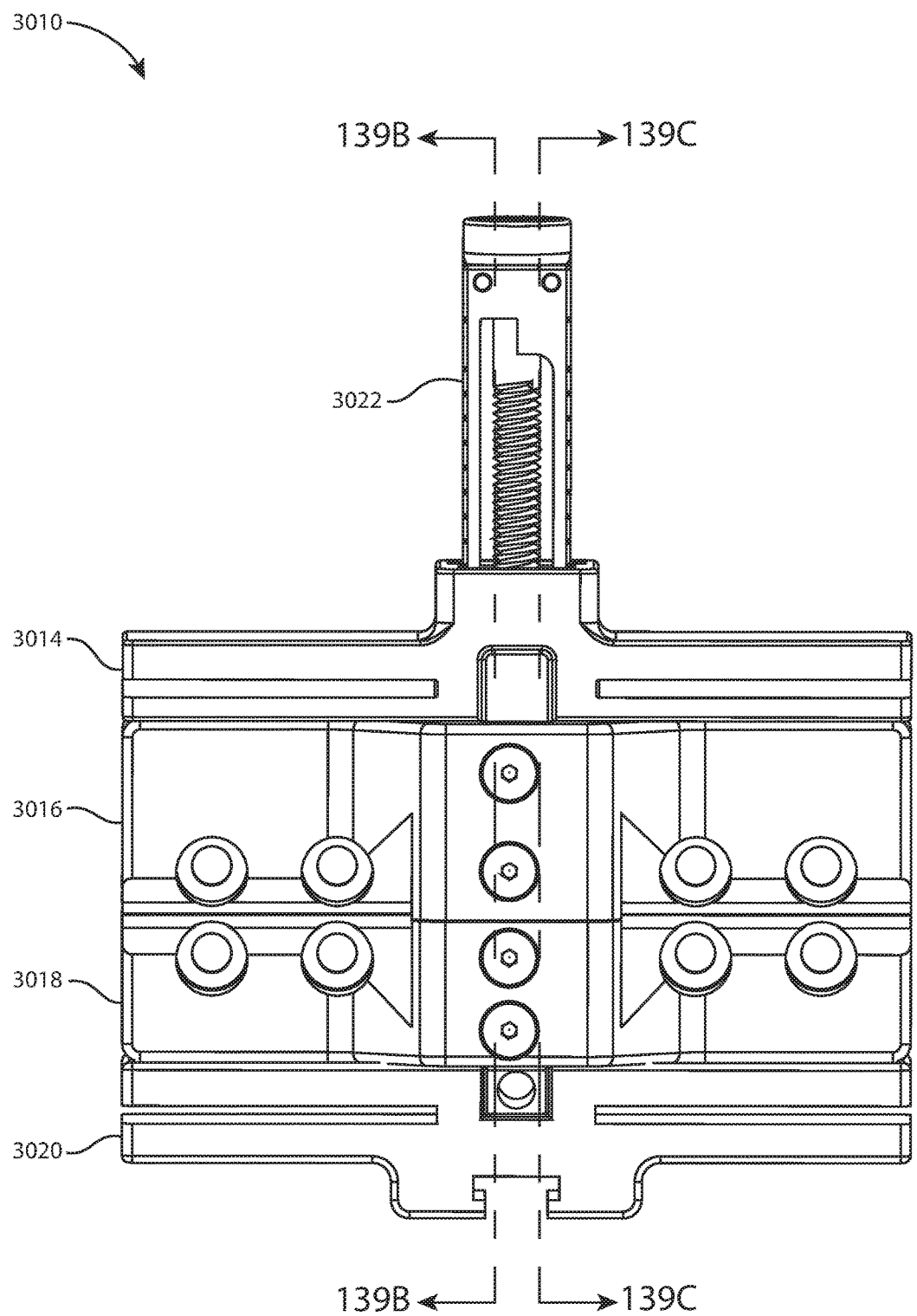
Figures 139B, 139C:
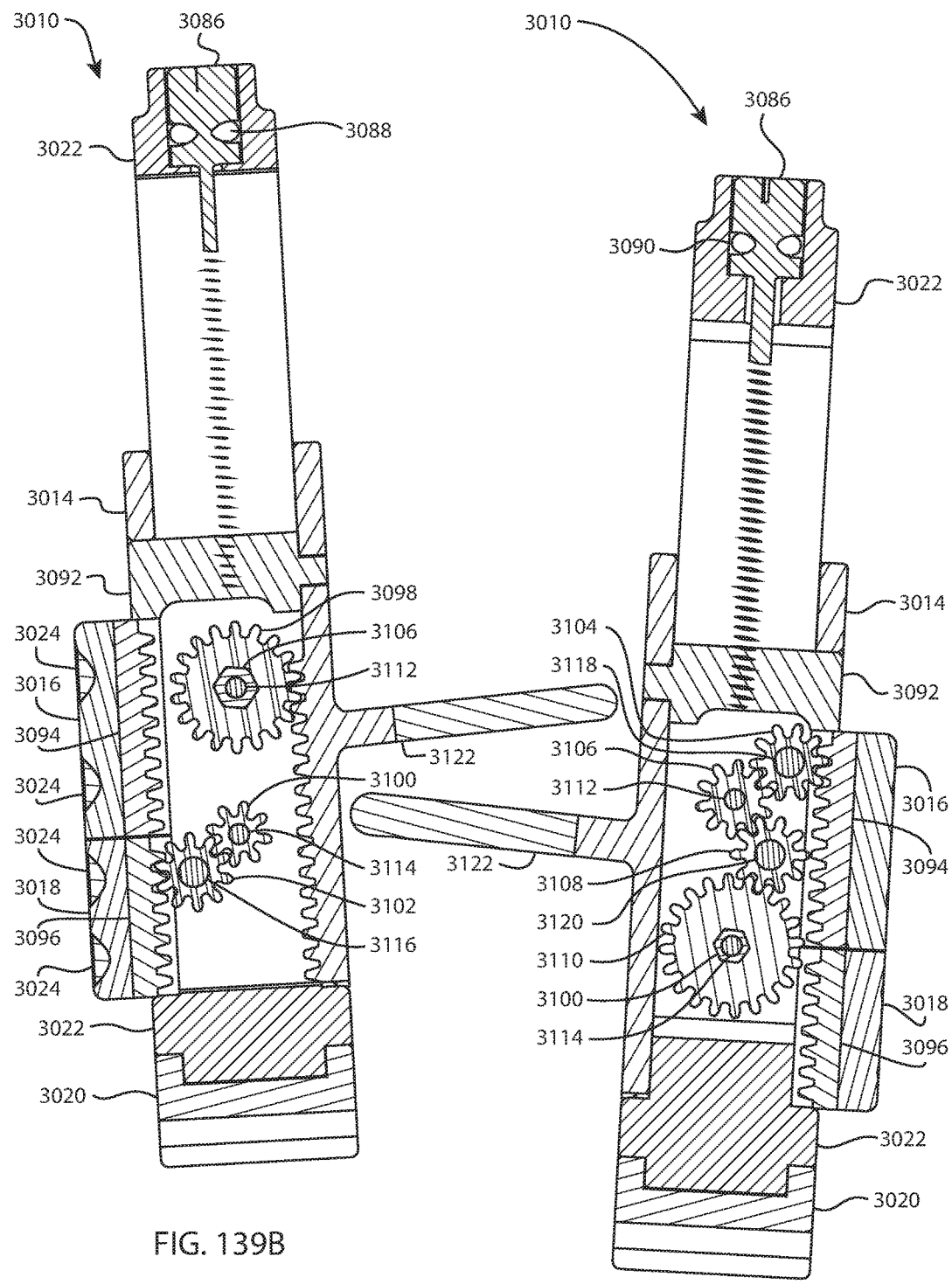
Figure 139D:
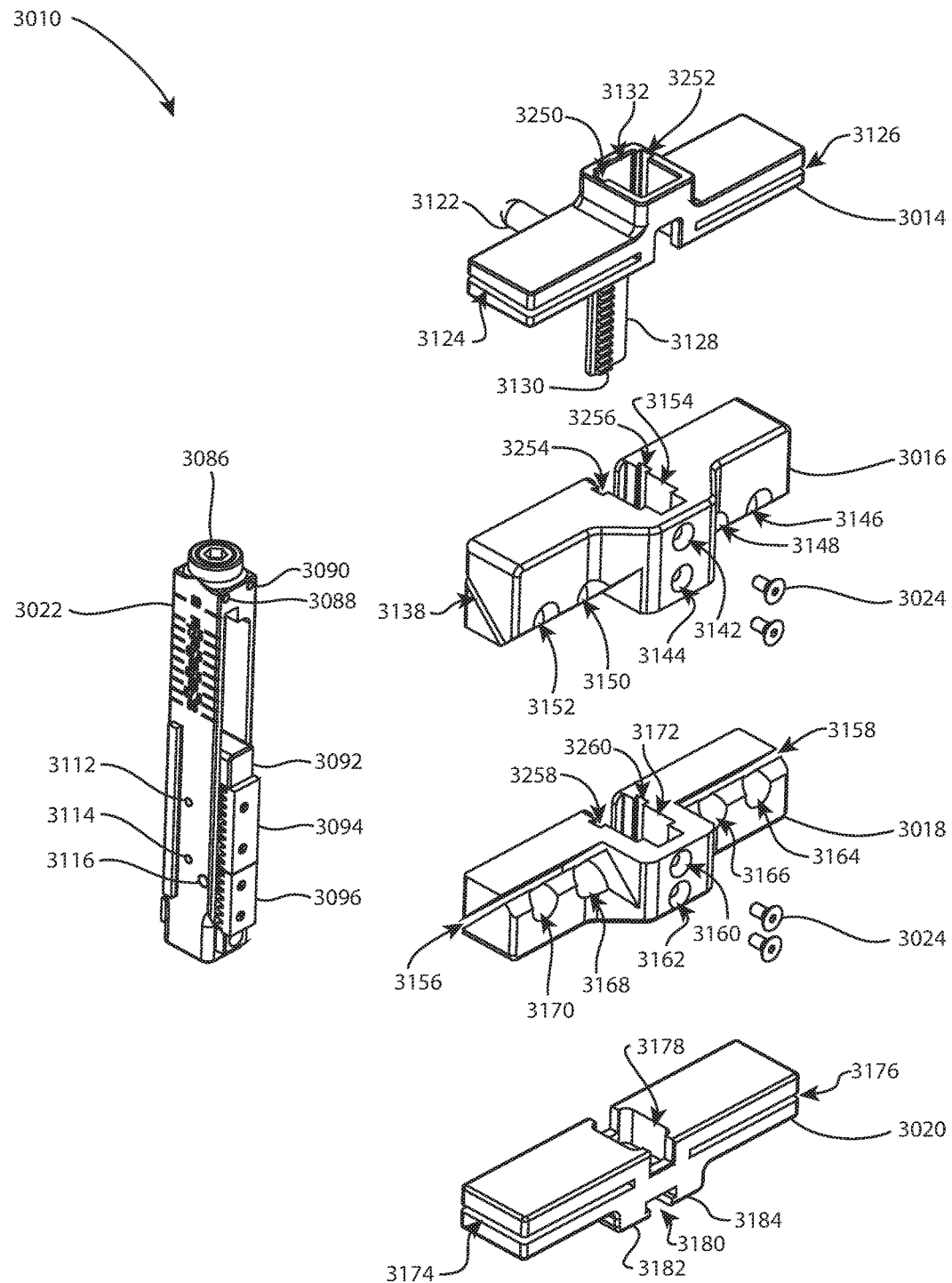
Figure 139E:
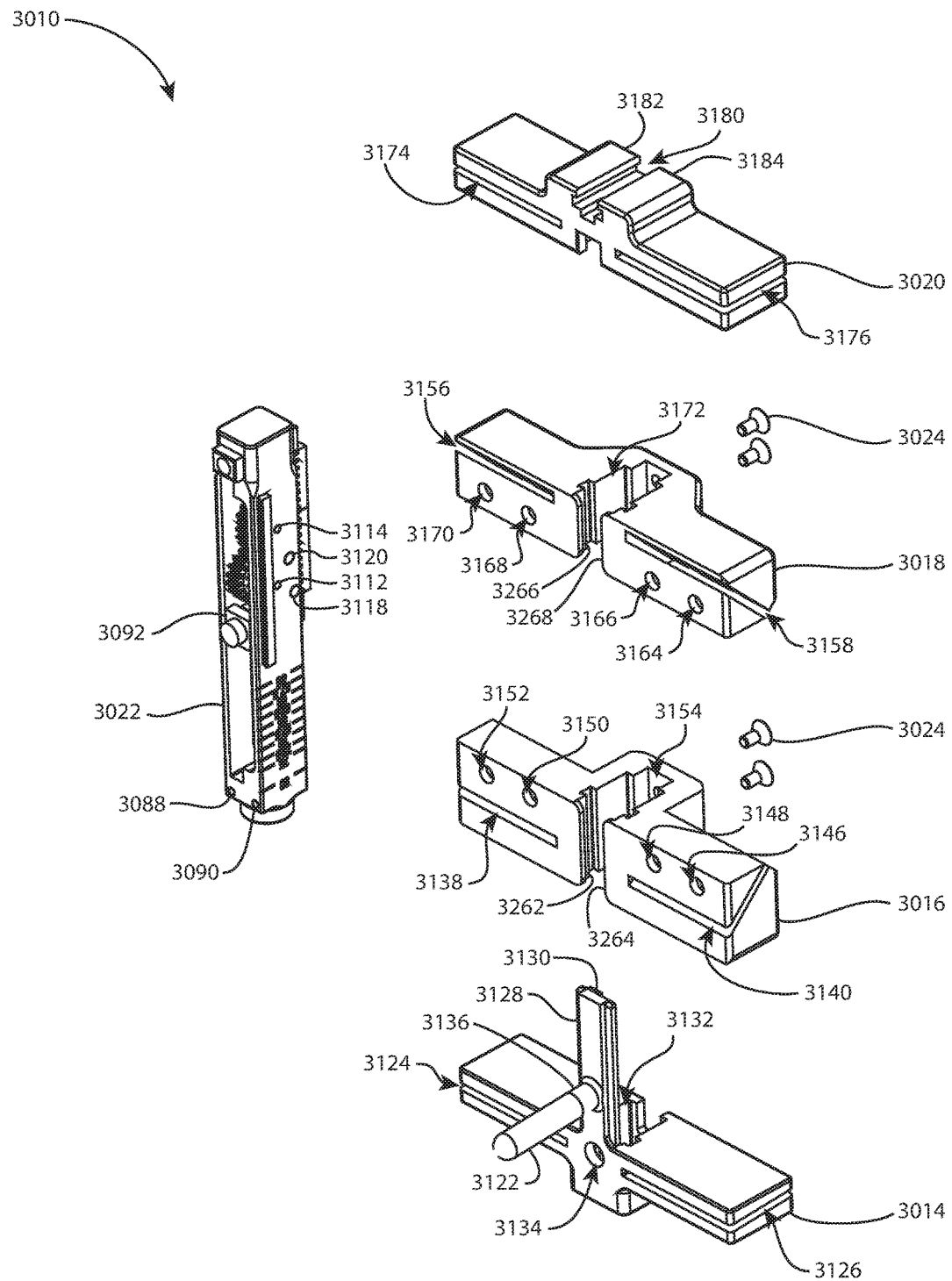
Figure 140A:
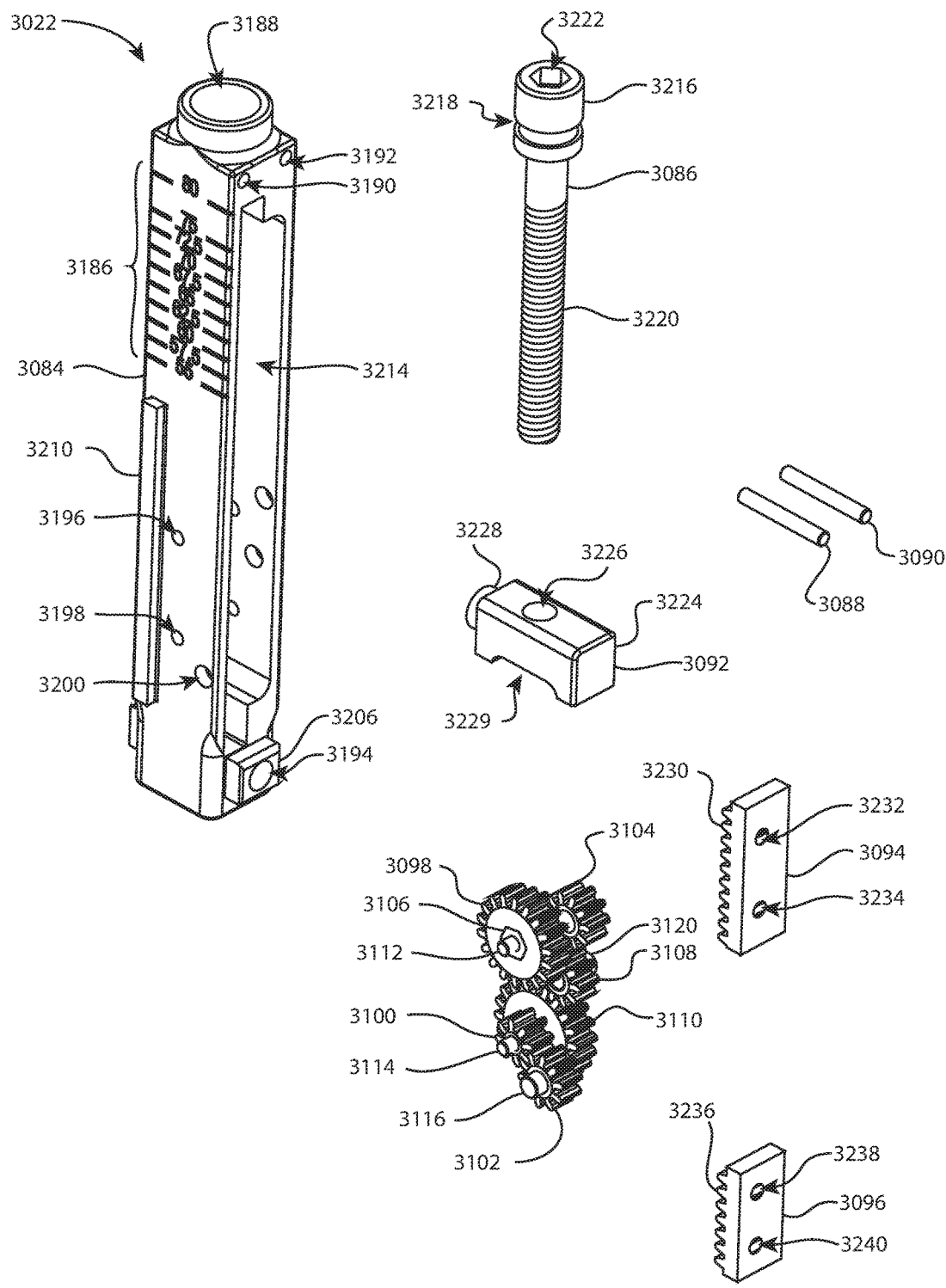
Figure 140B:
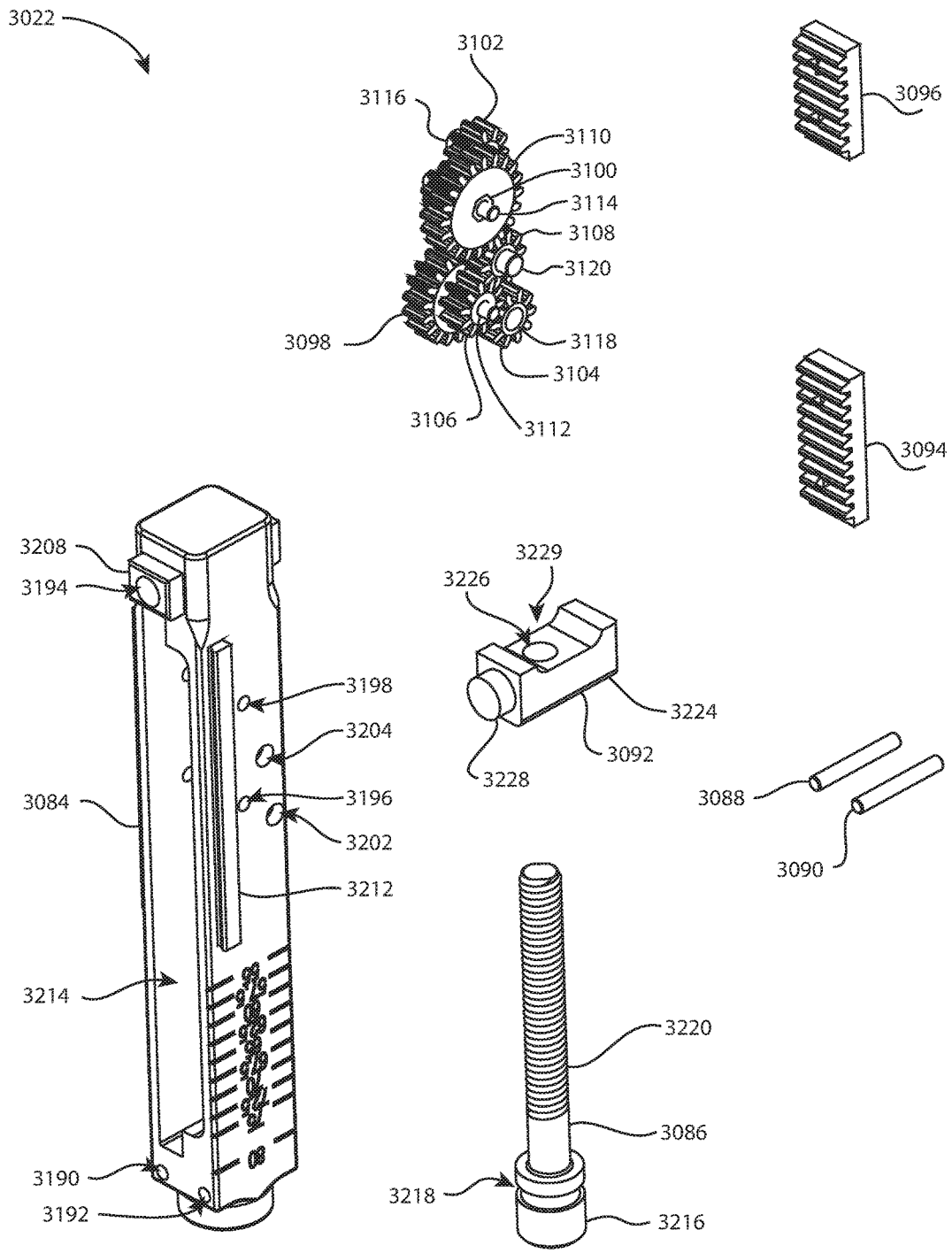
Figure 141A:
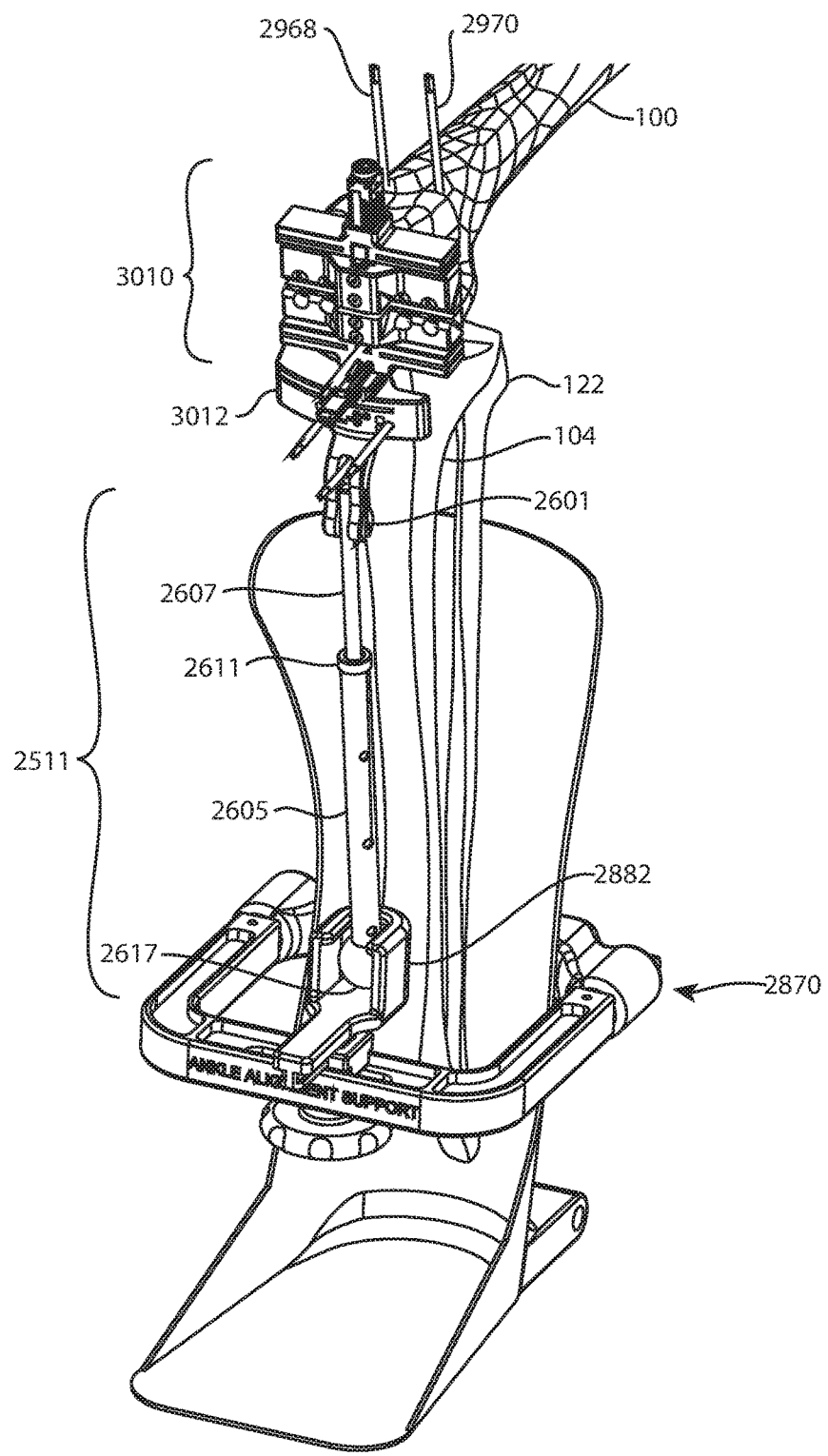
Figure 141B:
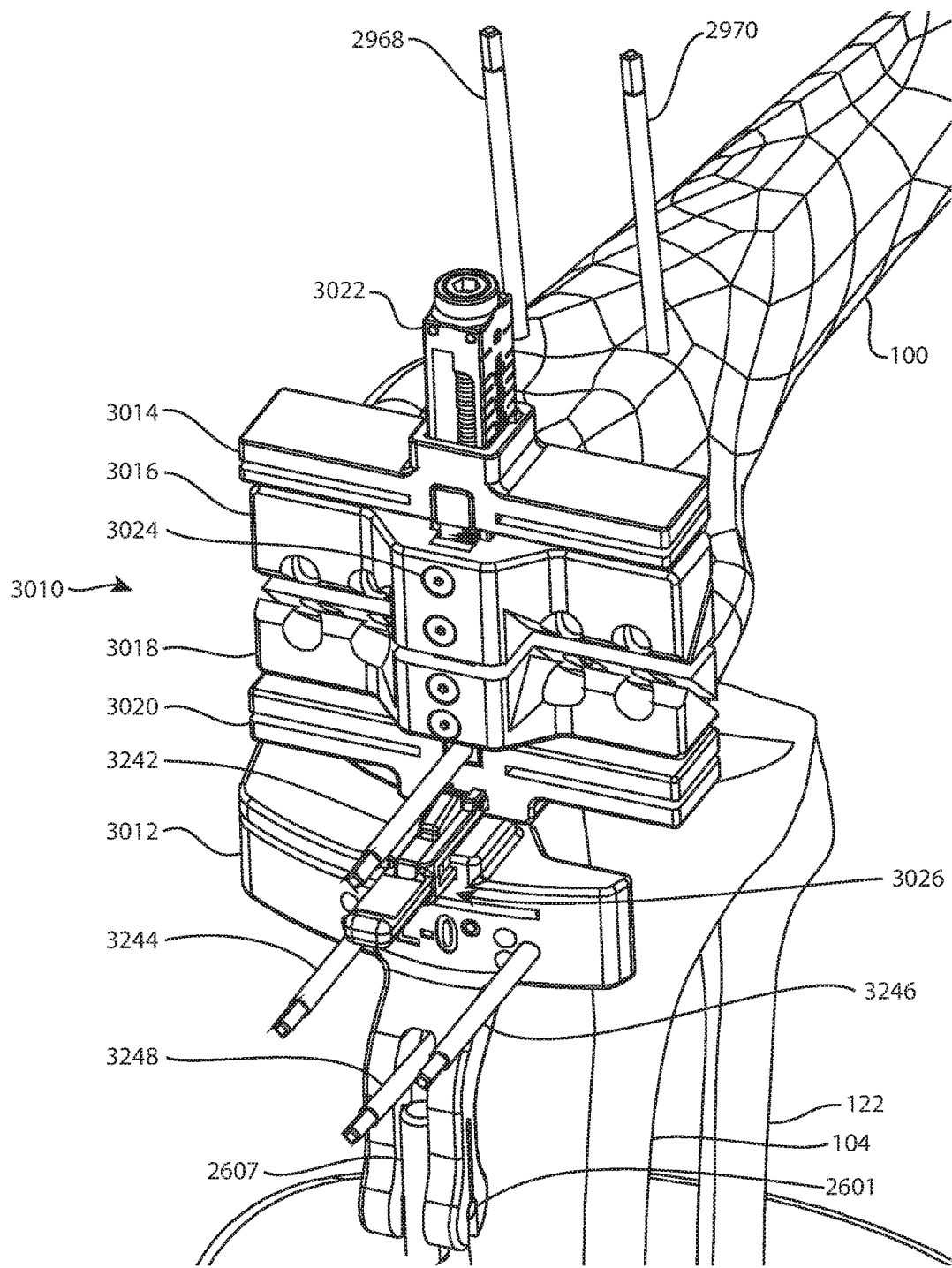
Figure 141C:
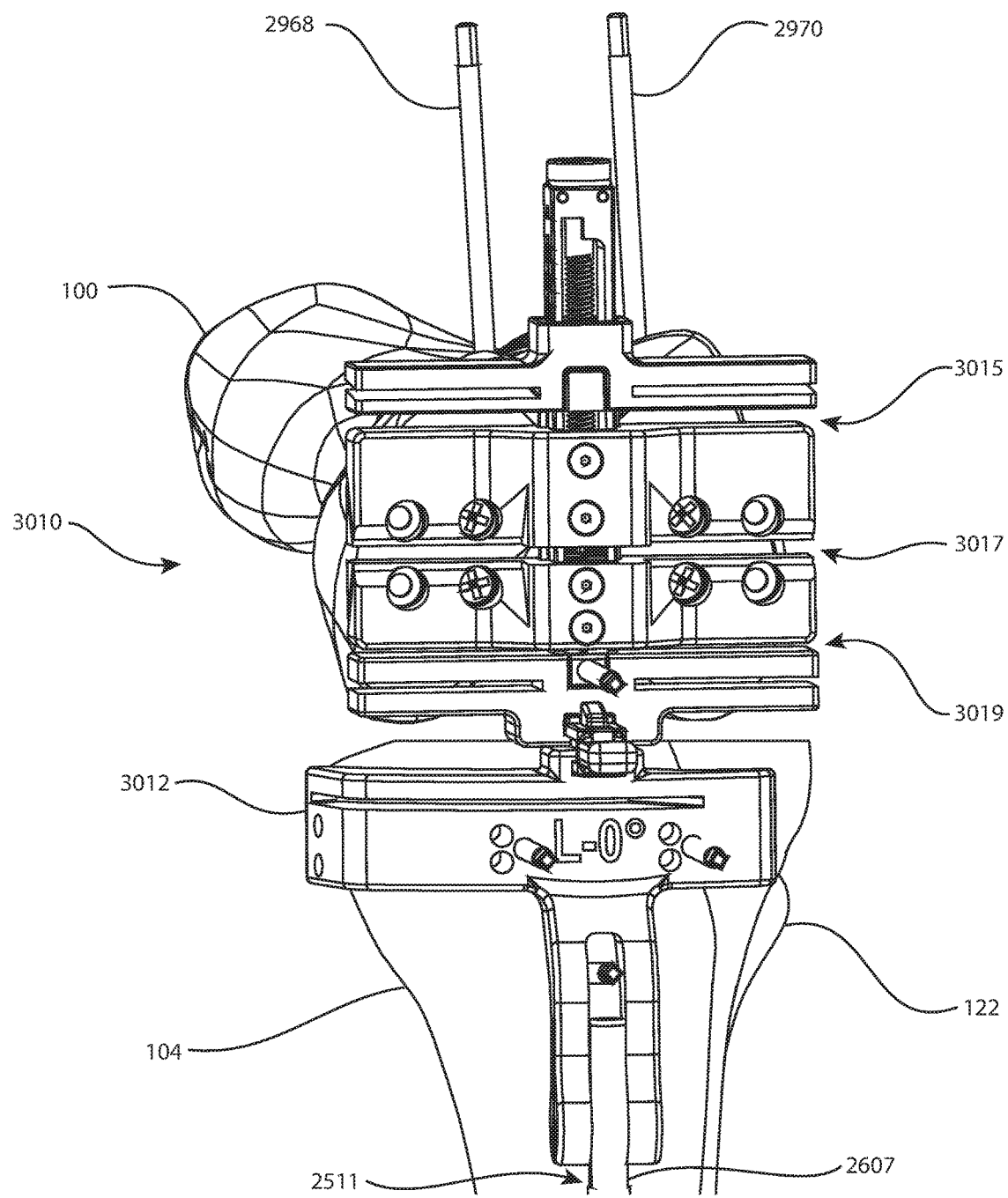
Figure 141D:
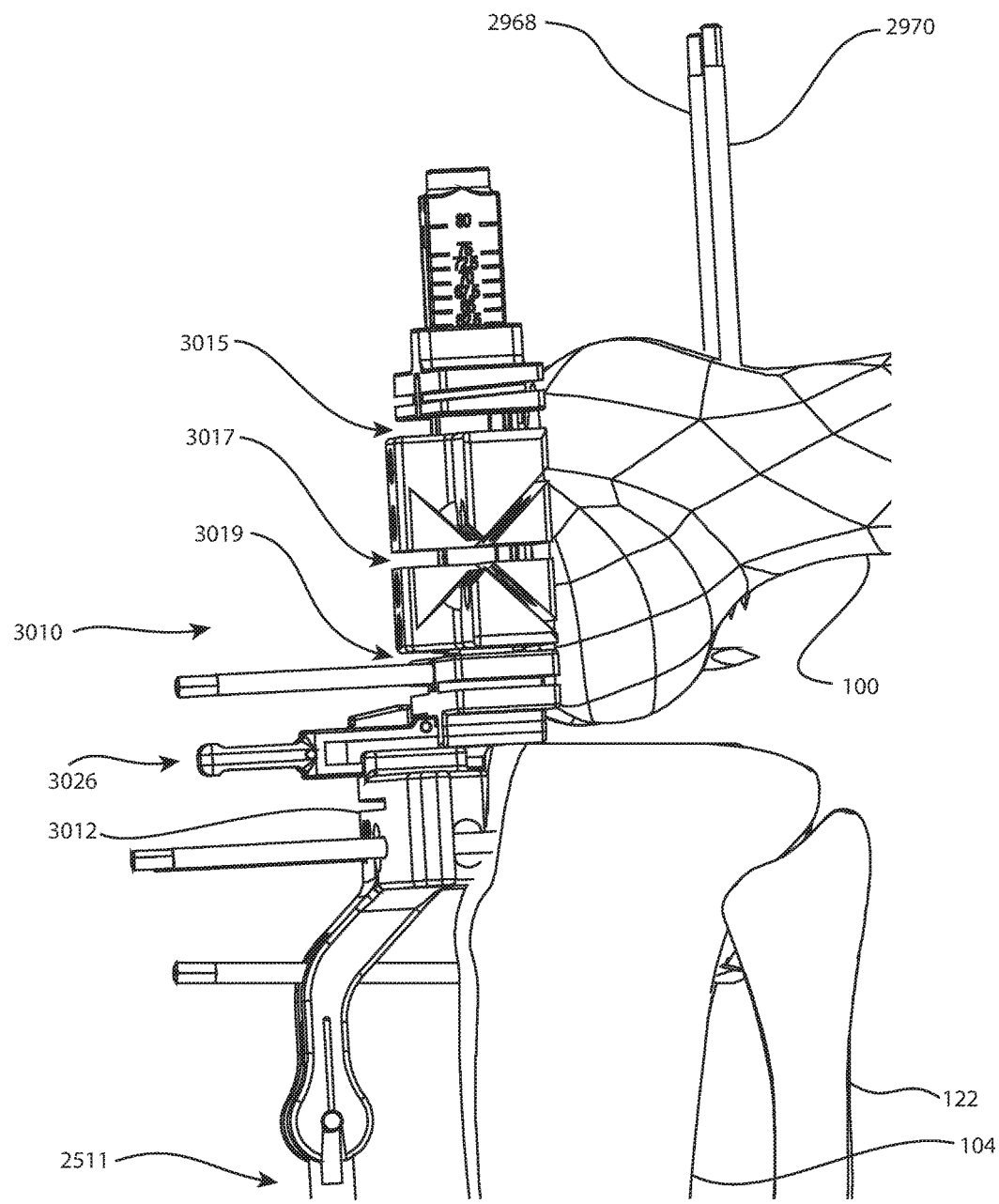
Figure 142:
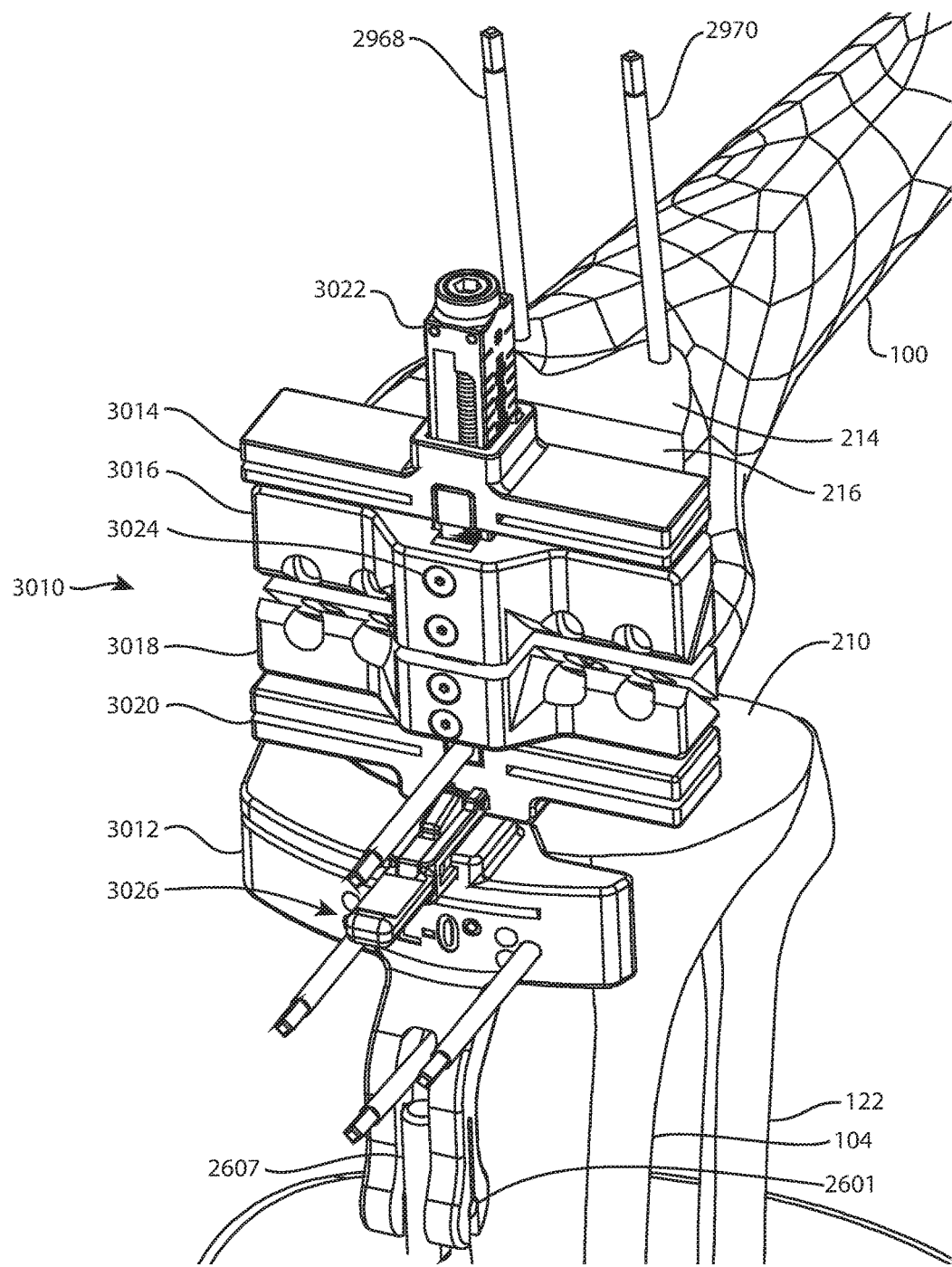
Figure 143:
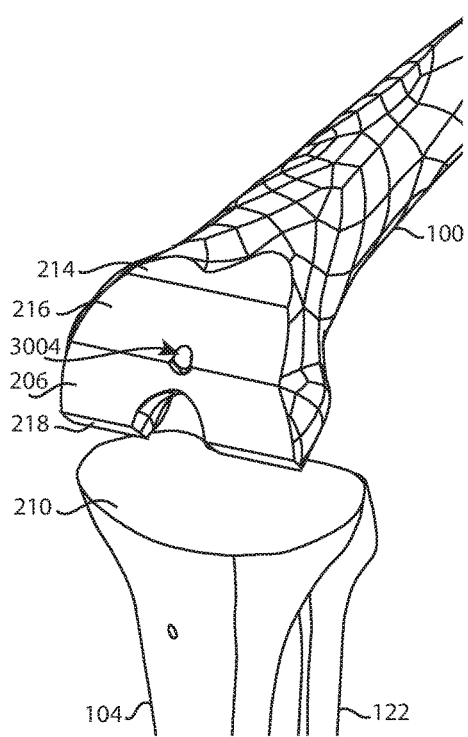
Figure 144:
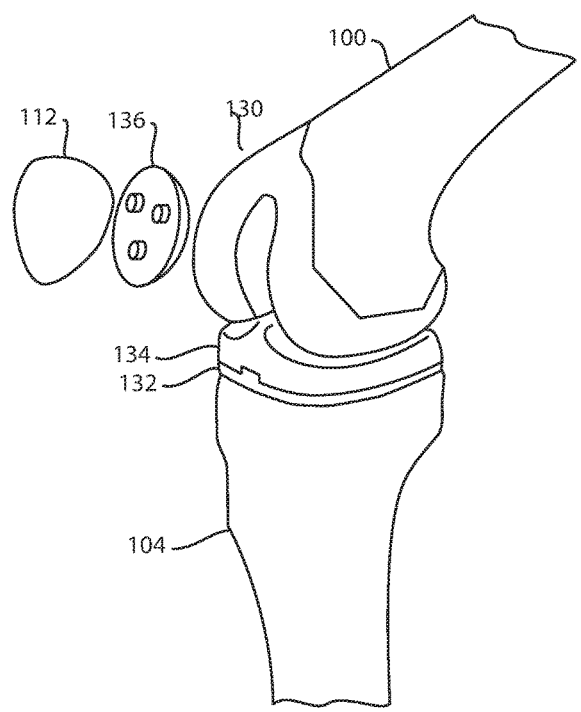
Figure 145:
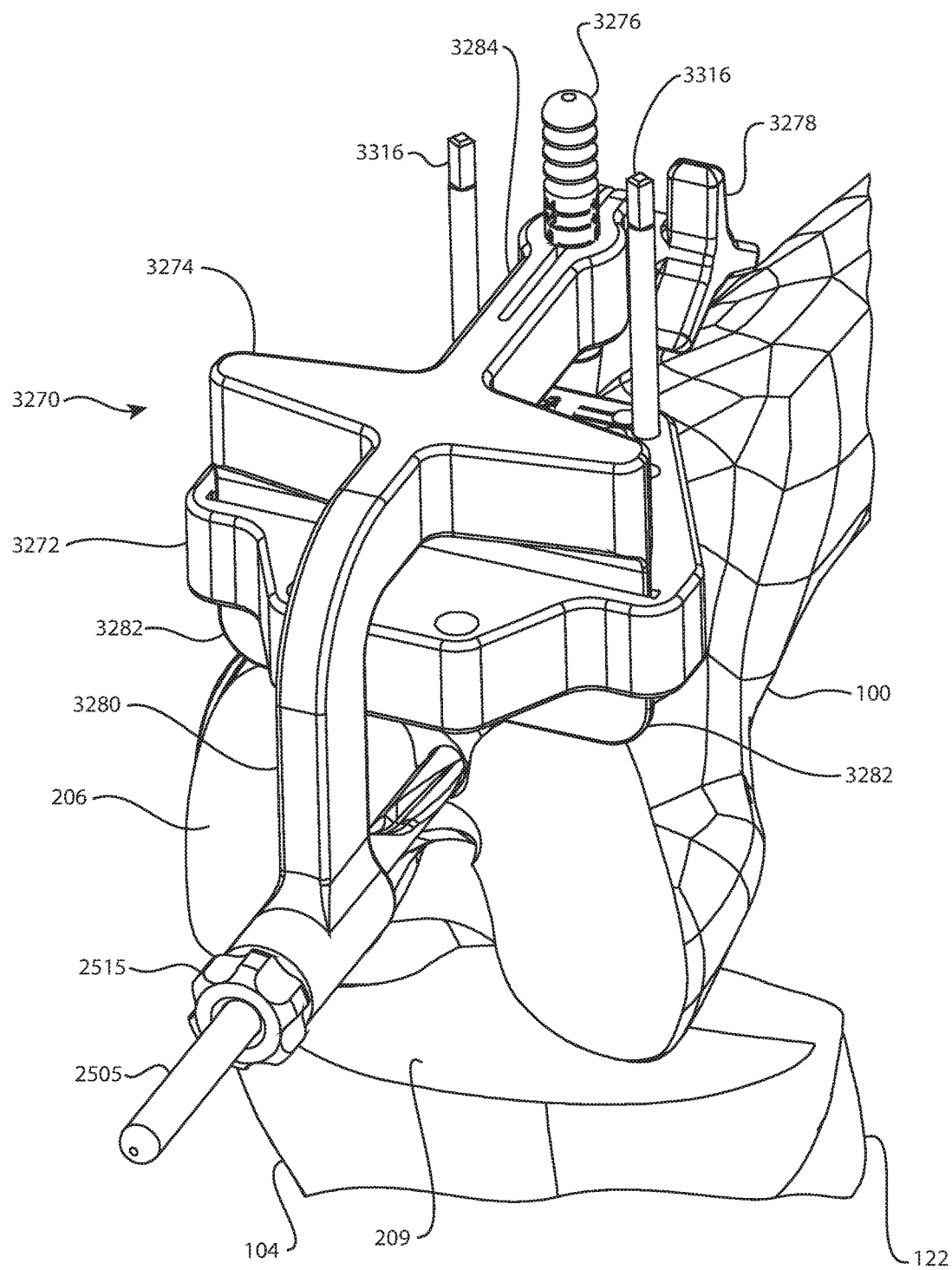
Figure 146A:
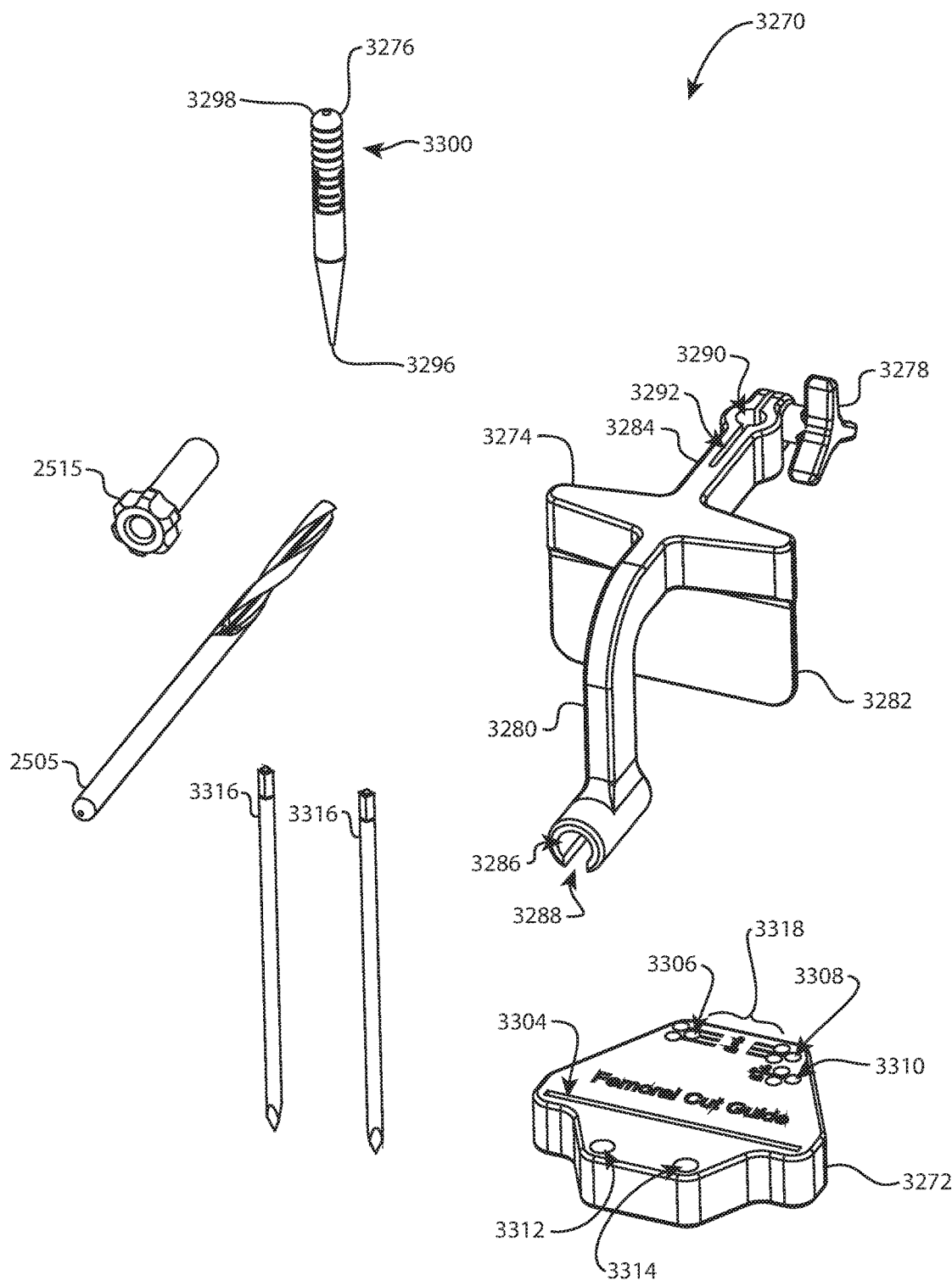
Figure 146B:
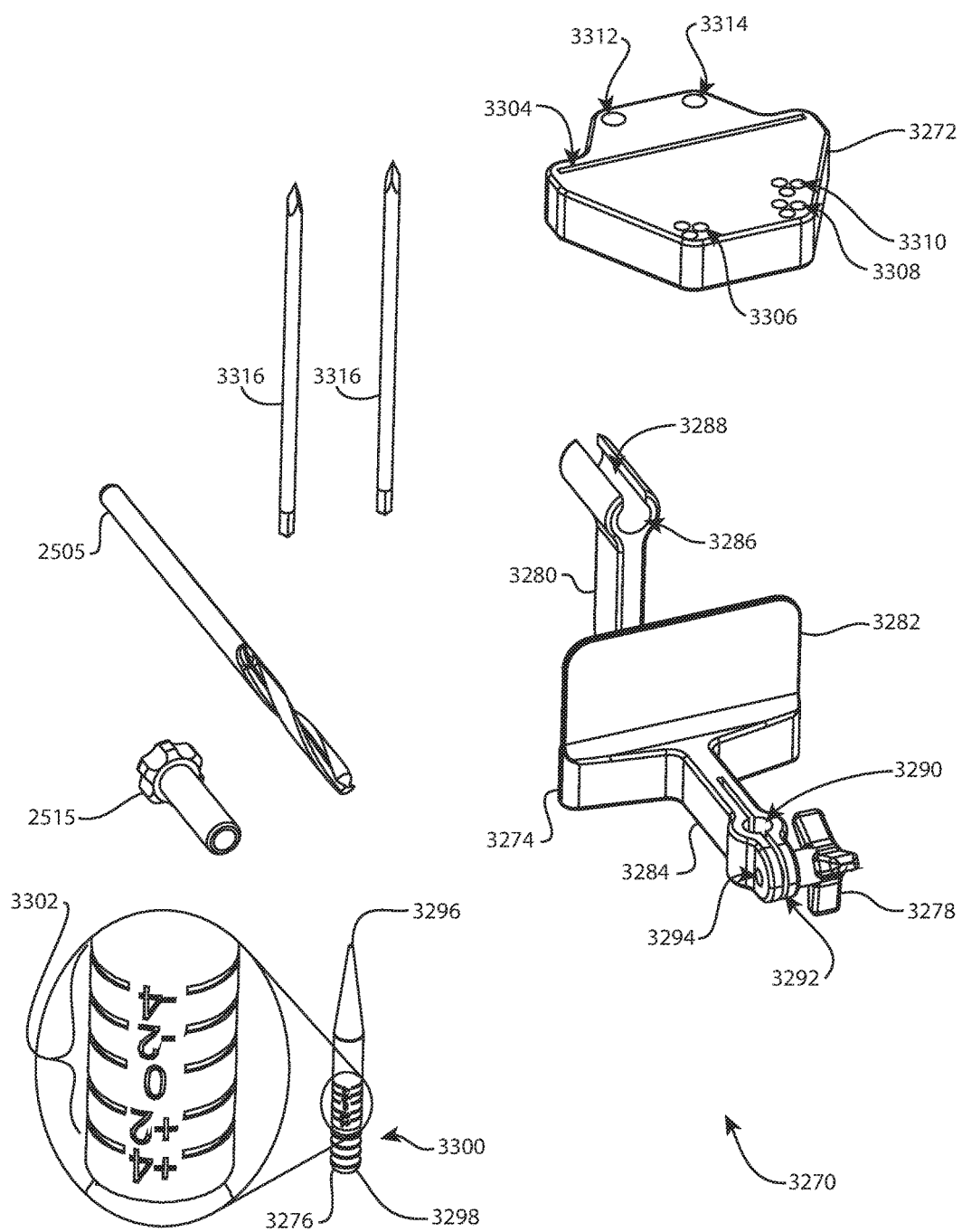

107 with bone pins inserted through the distal femoral cut guide assembly into the distal femur;

FIG. 110 is a perspective view of the femur, tibia, fibula, tibial pin, distal femoral cut guide assembly, a portion of the femoral extension rod assembly, and related bone pins of FIG. 109 after removing the femoral pin and making a distal femoral resection;

FIG. 111A is a perspective view of the femur, tibia, fibula, tibial pin, distal femoral cut guide assembly, a portion of the femoral extension rod assembly, and related bone pins of FIG. 110 with a distal femoral cut block assembly of the distal femoral cut guide assembly removed; and FIG. 111B is a lateral view of the femur, distal femoral cut guide assembly, a portion of the femoral extension rod assembly, and related bone pins of FIG. 111A;

FIG. 112 is a perspective view of the femur, tibia, fibula, tibial pin, distal femoral cut guide assembly, a portion of the femoral extension rod assembly, and related bone pins of FIG. 111A with a chamfer cut guide coupled to a femoral pin block of the distal femoral cut guide assembly;

FIG. 113 is a perspective view of the chamfer cut guide of FIG. 112;

FIG. 114 is a perspective view of the femur, tibia, fibula, tibial pin, distal femoral cut guide assembly, a portion of the femoral extension rod assembly, related bone pins, and chamfer cut guide of FIG. 112 with bone pins inserted through the chamfer cut guide into the distal femur;

FIG. 115A is a perspective view of the femur, tibia, fibula, tibial pin, distal femoral cut guide assembly, a portion of the femoral extension rod assembly, related bone pins, chamfer cut guide, and related bone pins of FIG. 114 after making an anterior chamfer cut and a posterior chamfer cut; and FIG. 115B is a lateral view of the femur, tibia, fibula, distal femoral cut guide assembly, a portion of the femoral extension rod assembly, related bone pins, chamfer cut guide, and related bone pins of FIG. 115A with an implant trial coupled to the chamfer cut guide;

FIG. 116A is a perspective view of the femur, tibia, fibula, femoral pin, tibial pin, three in one cut guide assembly, tibial extension rod assembly, and pins of FIG. 105 with a distal femoral cut guide coupled to the distal anterior femur and the three in one cut guide with bone pins; FIG. 116B is a perspective view of the distal femoral cut guide of FIG. 116A; and FIG. 116C is a side view of the distal femoral cut guide of FIG. 116A;

FIG. 117A is a perspective view of the femur, tibia, fibula, distal femoral cut guide, and pins of FIG. 116A after removing the femoral pin three in one cut guide assembly and tibial extension rod assembly and making a distal femoral resection; and FIG. 117B is a lateral view of the femur, tibia, fibula, distal femoral cut guide, and pins of FIG. 117A;

FIG. 118A is a perspective view of the femur, tibia, fibula, distal femoral cut guide, and pins of FIG. 117A with a chamfer cut guide coupled to the distal femur and the distal femoral cut guide with bone pins; and FIG. 118B is a lateral view of the femur, tibia, fibula, distal femoral cut guide, pins, and chamfer cut guide of FIG. 118A;

FIG. 119A is a perspective view of the femur, tibia, fibula, chamfer cut guide, and pins of FIG. 118A after making anterior and posterior chamfer cuts; and FIG. 119B is a lateral view of the femur, tibia, fibula, chamfer cut guide, and pins of FIG. 119A;

FIG. 120 is a perspective view of the femur, tibia, and fibula with the anterior, distal, and posterior femoral resections, the anterior and posterior femoral chamfer cuts, and the proximal tibial resection with all instruments removed;

FIG. 121 is a perspective view of a femur, tibia, and fibula with a foot receiver and a lower bar of a foot holder assembly;

FIG. 122 is a perspective view of the femur, tibia, fibula, foot receiver, and lower bar of FIG. 121 with a femoral support arm assembly;

FIG. 123A is a perspective view of the femur, tibia, fibula, foot receiver, lower bar, and femoral support arm assembly of FIG. 122 with a femoral head finder coupled to the femoral support arm assembly; and FIG. 123B is a top view of the femur, tibia, fibula, foot receiver, lower bar, femoral support arm assembly, and femoral head finder of FIG. 123A;

FIG. 124 is a perspective view of the femur, tibia, fibula, foot receiver, lower bar, femoral support arm assembly, and femoral head finder of FIG. 123A with a collar coupled to the femoral support arm assembly next to the femoral head finder;

FIG. 125 is a perspective view of the femur, tibia, fibula, foot receiver, lower bar, femoral support arm assembly, femoral head finder, and collar of FIG. 124 with a target clamp assembly coupled to the femoral support arm assembly next to the collar;

FIG. 126 is a perspective view of the femur, tibia, fibula, foot receiver, lower bar, femoral support arm assembly, collar, and target clamp assembly of FIG. 125 with a complete foot holder assembly including a bridge, target mounting block, dovetail lock, target, and thumbscrew coupled to the lower bar and the foot receiver;

FIG. 127 is a perspective view of the femur, tibia, fibula, foot holder assembly, femoral support arm assembly, collar, and target clamp assembly of FIG. 126 after making a provisional tibial resection;

FIG. 128A is a perspective view of the femur, tibia, fibula, foot holder assembly, femoral support arm assembly, collar, and target clamp assembly of FIG. 127 with a femoral pin guide assembly coupled to the anterior distal femur and the target clamp assembly via a femoral extension rod assembly; and FIG. 128B is a top view of the femur, tibia, fibula, foot holder assembly, femoral support arm assembly, collar, target clamp assembly, femoral pin guide assembly, and femoral extension rod assembly of FIG. 128A;

FIG. 129A is a perspective view of the femoral pin guide assembly of FIG. 128A; and FIG. 129B is another perspective view of the femoral pin guide assembly of FIG. 128A from a different direction;

FIG. 130 is a perspective view of the femur, tibia, fibula, femoral pin guide assembly, and a portion of the femoral extension rod assembly of FIG. 128A with femoral pins inserted through the femoral pin guide assembly into the distal femur;

FIG. 131 is a perspective view of the femur, tibia, fibula, femoral pin guide assembly, and a portion of the femoral extension rod assembly of FIG. 128A with a pin sleeve of the femoral pin guide assembly and one of the femoral pins removed;

FIG. 132 is a perspective view of the femur, tibia, fibula, and remaining femoral pin of FIG. 131 with the rest of the femoral pin guide assembly removed;

FIG. 133A is a perspective view of the femur, tibia, fibula, and femoral pin of FIG. 132 and the foot holder assembly of FIG. 126 with a knee angle guide coupled to the femoral pin; and FIG. 133B is a lateral view of the femur, tibia, fibula, femoral pin, foot holder assembly, and knee angle guide of FIG. 133A;

FIG. 134 is a perspective view of the femur, tibia, fibula, and femoral pin of FIG. 133A with the knee angle guide removed, with a distal femoral cut guide assembly coupled to the femur and the femoral pin;

FIG. 135A is an exploded perspective view of the femoral pin and distal femoral cut guide assembly of FIG. 134; and FIG. 135B is another exploded perspective view of the femoral pin and distal femoral cut guide assembly of FIG. 134 from a different direction;

FIG. 136 is a perspective view of the femur, tibia, fibula, and a portion of the distal femoral cut guide assembly of FIG. 134 after making a distal femoral resection and removing the femoral pin and an interlock and a distal plate of the distal femoral cut guide assembly;

FIG. 137A is a perspective view of the femur, tibia, and fibula of FIG. 136 and the foot holder assembly of FIG. 133A with a femoral four-in-one cut guide assembly coupled to the distal femur and a proximal tibial cut guide coupled to the proximal tibia and the foot holder assembly via a tibial extension rod assembly; FIG. 137B is an enlarged detail view of the femur, tibia, fibula, femoral four-in-one cut guide assembly, proximal tibial cut guide, and a portion of the tibial extension rod assembly of FIG. 137A; FIG. 137C is an anterior view of the femur, tibia, fibula, foot holder assembly, femoral four-in-one cut guide assembly, proximal tibial cut guide, and tibial extension rod assembly of FIG. 137A; and FIG. 137D is a lateral view of the femur, tibia, fibula, foot holder assembly, femoral four-in-one cut guide assembly, proximal tibial cut guide, and tibial extension rod assembly of FIG. 137A;

FIG. 138A is a perspective view of the femoral four-in-one cut guide assembly and the proximal tibial cut guide of FIG. 137A; FIG. 138B is another perspective view of the femoral four-in-one cut guide assembly and the proximal tibial cut guide of FIG. 137A from a different direction; FIG. 138C is an exploded perspective view of the femoral four-in-one cut guide assembly and the proximal tibial cut guide of FIG. 137A; and FIG. 138D is another exploded perspective view of the femoral four-in-one cut guide assembly and the proximal tibial cut guide of FIG. 137A from a different direction;

FIG. 139A is a front view of the femoral four in one cut guide assembly of FIG. 138A; FIG. 139B is a cross sectional view of the femoral four in one cut guide assembly of FIG. 139A, taken along section line 139B-139B of FIG. 139A; FIG. 139C is a cross sectional view of the femoral four in one cut guide assembly of FIG. 139A, taken along section line 139C-139C of FIG. 139A; FIG. 139D is an exploded perspective view of the femoral four-in-one cut guide assembly of FIG. 139A; and FIG. 139E is another exploded perspective view of the femoral four-in-one cut guide assembly of FIG. 139A from a different direction;

FIG. 140A is an exploded perspective view of a gear assembly of the femoral four in one cut guide assembly of FIG. 139A; and FIG. 140B is another exploded perspective view of the gear assembly of the femoral four in one cut guide assembly of FIG. 139A from a different direction;

FIG. 141A is a perspective view of the femur, tibia, fibula, foot holder assembly, femoral four-in-one cut guide assembly, proximal tibial cut guide, and tibial extension rod assembly of FIG. 17A with the femoral four-in-one cut guide assembly and proximal tibial cut guide adjusted to fit the femur and tibia, with bone pins inserted through the femoral four-in-one cut guide assembly into the femur, with bone pins inserted through the proximal tibial cut guide into the tibia; FIG. 141B is an enlarged detail view of the femur, tibia, fibula, foot holder assembly, femoral four-in-one cut guide assembly, proximal tibial cut guide, tibial extension rod assembly, and bone pins of FIG. 141A; FIG. 141C is an enlarged anterior detail view of the femur, tibia, fibula, foot holder assembly, femoral four-in-one cut guide assembly, proximal tibial cut guide, tibial extension rod assembly, and bone pins of FIG. 141A; and FIG. 141D is an enlarged lateral detail view of the femur, tibia, fibula, foot holder assembly, femoral four-in-one cut guide assembly, proximal tibial cut guide, tibial extension rod assembly, and bone pins of FIG. 141A;

FIG. 142 is a perspective view of the femur, tibia, fibula, femoral four-in-one cut guide assembly, proximal tibial cut guide, a portion of the tibial extension rod assembly, and bone pins of FIG. 141A after making anterior and posterior femoral resections, anterior and posterior chamfer cuts, and a proximal tibial resection;

FIG. 143 is a perspective view of the femur, tibia, and fibula with the anterior, distal, and posterior femoral resections, the anterior and posterior femoral chamfer cuts, and the proximal tibial resection with the femoral four-in-one cut guide assembly, proximal tibial cut guide, tibial extension rod assembly, and bone pins removed;

FIG. 144 is an isometric view of a knee joint with implanted femoral component, tibial component, articular insert, and patellar component, the patellar component shown exploded from the patella for clarity;

FIG. 145 is a perspective view of a femur, tibia, and fibula with another femoral pin guide assembly and another distal femoral cut guide coupled to the distal femur; and FIG. 146A is an exploded perspective view of the femoral pin guide assembly and distal femoral cut guide of FIG. 145; and FIG. 146B is another exploded perspective view of the femoral pin guide assembly and distal femoral cut guide of FIG. 145 from a different direction.

DETAILED DESCRIPTION

Exemplary embodiments of the technology will be best understood by reference to the drawings, wherein like parts are designated by like numerals throughout. It will be readily understood that the components of the system, as generally described and illustrated in the figures herein, could be arranged and designed in a wide variety of different configurations. Thus, the following more detailed description of the embodiments of the apparatus, system, and method is not intended to limit the scope of the invention, as claimed in this or any other application claiming priority to this application, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A midsagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Standard terminology related to knee arthroplasty is employed in this specification. Varus means deviation of the distal part of the leg below the knee inward, resulting in a bowlegged appearance. Valgus means deviation of the distal part of the leg below the knee outward, resulting in a knock-kneed appearance.

ABBREVIATIONS AND NOMENCLATURE

TKAI Total Knee Arthroplasty Instruments, Instrumentation
I Instruments, Instrumentation, or the like
AL Alignment
Fe Femur, Femoral, or Femur-related
Ti Tibia, Tibial, or Tibia-related
EG Extension Gap
FG Flexion Gap
FR Femoral Rotation
TS Tibial Slope
PS Posterior Stabilized
CR Cruciate Retaining
Kn Knee
AIS Anterior Iliac Spine
FeHe Femoral Head
IM Intramedullary
EM Extramedullary
DAFe Distal Anterior Femur Traditional TKAI utilizes IM I to determine proper distal femur saw cut alignment, and EM I to align the saw cut for the proximal tibia. Therefore it is acceptable to prepare the distal femur separate from the proximal tibia. There exists no conjoined effort to cut the distal femur and the proximal tibia as the single lower extremity body part which constitutes the knee joint.

This contemporary instrumentation process violates the principles established by Insall in the 1970s. (Insall, John N. Surgery of the Knee. New York: Churchill Livingstone, 1984. Pages 631-365. Entire book incorporated by reference in its entirety.) Popular TKAI teaches this inexact IM I process because it is simpler to teach, understand and utilize by most surgeons. This contradiction is best illustrated by examining the long time relationship of Zimmer, Inc. and one of its premier consultants, Dr. Bob Booth (Philadelphia). Dr. Booth successfully and famously performs exact TKAI utilizing his mentor's (Dr. Insall's) principles. However, Zimmer does not commercialize Dr. Booth's instruments and techniques because the technique proves too technically difficult for most surgeons.

This disclosure teaches bony and soft tissue preparation of the knee joint utilizing instruments and techniques consistent with proven TKAI principles.

Technique

A longitudinal incision 150 is made from proximal to distal with its mid point over the anterior knee. A medial arthrotomy is performed in standard fashion. The patella 112 is everted and dislocated laterally as the knee is flexed to 90 degrees. The medial and lateral supporting ligaments of the knee are balanced as needed.

The proximal tibia 106 is resected at a right angle to the long axis of the tibia 104, removing approximately 6 mm to 10 mm of bone (in traditional fashion utilizing a tibial cut guide referencing the anterior tibial spine). However, this may be a provisional resection that removes 3 mm to 5 mm of bone to increase the working space inside the knee joint.

The lower extremity (and knee) is now positioned in full extension (0 degrees flexion). The full extension of the knee relaxes the extensor mechanism. The suprapatellar fat pad 116 is elevated from the anterior distal femur 102 with a small periosteal elevator 154 (elevating the fat layer from the anterior femur only—leaving the fat pad attached medial and lateral on the femur).

An instrument is now inserted, from distal to proximal, externally along the distal anterior femoral cortex under the suprapatellar fat pad 116. This instrument somewhat resembles a bone plate, having a (longitudinal) distal to proximal length longer than its medial to lateral length (width). This instrument is referred to as a base 10. Rising from the distal end of this unattached plate, residing on the anterior cortex of the distal femur 102, is an element containing a series of stacked directional holes 14, 16, 18 which align themselves with each axis of each hole pointing (proximal) toward the head 118 of the femur 100. The axis of each of these directional holes is 5 degrees valgus to the distal anterior femoral cortical plate or base 10, previously described. This 5 degree divergence angle varies in absolute direction (relative to mid line of the body) depending upon right or left knee undergoing this surgery.

In a design, a "hinged" rod is attached, through two of the longitudinal stacked holes so as to align the direction of this rod in the direction of the head 118 of the femur. The "hinged" rod is referred to as an alignment rod 156. The proximal end of the rod, once deployed, will be positioned over the mid portion of the head 118 of the femur, and preferably directly over the center 120 of the femoral head 118. This important reference point is determined to be 1) two finger breadths medial to the anterior superior iliac spine or, much better, 2) determined by fluoroscopy, radiographs, C-arm, or the like.

The significance of this reference rod 156 is 1) its attachment as part of the femoral "plate" or base 10 residing on the anterior surface of the distal femur. The medial/lateral position of the proximal end of the rod can be changed by simply and minimally moving the proximal end of the femoral "plate" medially (thus increasing the valgus of the distal femoral cut) or laterally (increasing the varus) to the midline of the distal anterior femoral cortex. Preferably, the distal end of the rod 156 is attached to the base 10 so that the rod passes directly over the medial/lateral center of the distal femur, and the proximal end of the rod 156 is moved medial/lateral until the rod passes directly over the center 120 of the femoral head 118.

Once alignment is obtained, 2 screws are driven into slots in the distal end of the femoral "plate" or base 10, in order to secure alignment. These 2 screws may be placed outside of the cutting path for the anterior femoral resection 214 so that the cut can occur without hitting the screws.

A parallel handle 21 is attached to the distal femur cortical "plate" which attaches these two parallel elements distally (but not proximally), and is anterior and separate to the soft tissues of the distal thigh. This parallel "plate" handle 21 permits compression to be applied to the distal femur cortical "plate" or base 10 by the surgeon in order to prevent movement (medial or lateral) of the plate from the desired alignment position (with respect to femoral head 118). Small, sharp "cleats" may be included on the bone-facing surface of the base 10 to increase friction contact of the "plate" to the distal anterior femoral bone.

Once femoral alignment is secured, the "hinged" rod is moved from (proximal) reference to the hip, to distal reference of the lower extremity, i.e. the anterior tibial spine or crest, ankle, and/or second toe of the foot. This mechanical connection of 1) alignment of the femur 100 to the 2) alignment of the tibia 104—through rotation of the "hinged" rod 156 from proximal extremity to distal extremity (while the knee remains unmoved and in full extension) permits direct alignment of the proximal extremity (femur 100) with the distal extremity (leg or tibia 104) along the mechanical axis 202 of the leg.

Now, the ankle/foot region of the lower extremity can simply be moved (lateral or medial) under the distal end of the "hinged" rod 156 to align the entire lower extremity (hip, knee, ankle) in an exact straight line along the mechanical axis 202 of the leg.

The "hinge" aspect of the rod 156 permits proximal alignment referencing the femoral head 118 without being adversely affected by obesity (the rod angles superiorly over a large mid section without compromising alignment with the femoral head 118).

The "hinged" rod 156 now rotated distally and placed exactly parallel with the lower extremity (through an articulation at the hinge point) (referencing the plane of the distal anterior femoral cortex), can allow proper attention and calibration for the (final) angle of cut for the proximal tibial cut (previously rough cut).

This means that the desired posterior slope of the tibial cut can now be referenced off of the exact alignment of the entire length of the lower extremity, through reference to the distal anterior femoral cortex making the distally positioned "hinged" rod parallel to the distal anterior femoral cortex by a short extension of the deployed "hinged" rod extending proximally parallel to the femoral cortex and finally reaching distally until referencing the ankle or 2nd toe of the foot.

Cutting guides for the distal femur and (simultaneously) proximal tibia are hung from the deployed "hinged rod" 156. While the "hinged" rod is overlying the entire tibia 104, the knee joint is distracted until the collateral ligaments of the knee are "very" taut (knee still in full extension) and the center of the ankle is under the distal rod 156. Once properly and fully distracted and aligned, a four point drill guide (attached at a right angle from the "hinged" rod) is positioned anterior to the knee joint.

The midpoint of this four point drill guide is positioned at the natural joint line. Now, each of the four points of the drill guide (positioned about 20+mm apart—equal to the sum width [thickness] of the intended tibial and femoral prostheses—in extension) are utilized to drill holes (2 each and [all] parallel) in the distal femur and the proximal tibia. Extended, shouldered studs are now placed in each of the drill holes in anticipation of saw guides being positioned by matching receiving holes in the cut plates (one for the distal femur and the other for the proximal tibia).

The distraction device is relaxed and removed from the knee. The cut guides are placed over the shouldered studs. The knee is now flexed (the "hinged" rod elevated and drawn proximally over the femur) and each of the two cuts are now made, aligned and properly angled (proximal tibia) by the two cut guides—femur and tibia.

The "hinged rod" attachment to the riser (on the femoral "plate") is now advanced distally by extension through the two stacked holes in the riser, so to match the end of the cut femur. The knee is flexed to 90 degrees. The "hinged" rod is now deployed distally and allowed to flex to 90 degrees at its riser hinge. At 90 degrees flexion the rod will now cross the cut surface of the femur and parallel the anterior spine of the tibia.

To adjust for femoral rotation, a technique is now employed. The "hinged" rod is made parallel to Whiteside's line (middle of anterior and distal femur extending through middle of cut surface of femur [from the bottom of the trochlear groove to the top of the intercondylar notch (trochlear notch), at right angles to the epicondylar axis, which is a line between the most prominent points of the medial and lateral epicondyles, or a line connecting the lateral epicondylar prominence and the medial sulcus of the medial epicondyle]), and then the femur adjusted on the tibia so that Whiteside's line and the anterior spine of the tibia are in perfect alignment.

A multi-cut guide is now deployed with a right angle rod attachment within the femoral anterior cortex "plate". This rod extension attached to the top of the multi-cut femoral guide will permit (for the first time) perfect reference to cutting the anterior and distal femur—by allowing the anterior cut slot to aim directly, proximal, to the base of the femoral "plate". The guide will allow anterior and posterior adjustment of up to 2 mm to allow surgeons to (mildly) notch the femur, or even rise anterior to the anterior cortex—the choice is made by the surgeon depending on his interest in the sight of the posterior femoral cut (more or less bone posteriorly).

As discussed in the above paragraphs, femoral rotation is adjusted relative to Whiteside's line and the tibial cut (right angle to it) and then the multi-cut guide is pinned to the distal femur, and all chamfer cuts and anterior and posterior cuts are thus made, directly related to and reference to, the companion member of the knee joint.

Instruments

Base 10 (datum) (FIG. 1) includes trunnion 12 and screw holes 14, 16, 18.

The base 10 may be modified so that one (lateral, medial, or posterior) side of the base registers on an anatomic ridge or other structure or detail of the distal anterior femur. More than one (lateral, medial, or posterior) side of the base may be modified to register on anatomic structures or details of the distal anterior femur. The anatomic structures or details may be protruding features, such as ridges, or recessed features, such as sulci, fossae, grooves, or other depressed features.

Drill guide assembly 20 (FIGS. 2-3) includes handle 21, socket end 22, drill guide 24, handle 26, and tube 28.

Figure 6:
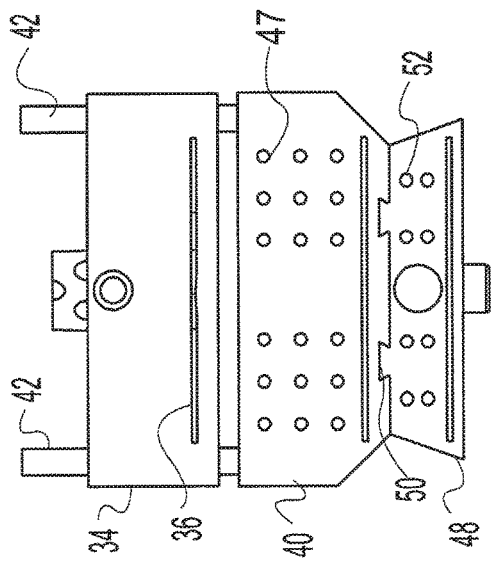
FIG. 6 is a front view of the assembly of FIG. 4.
Figure 4:
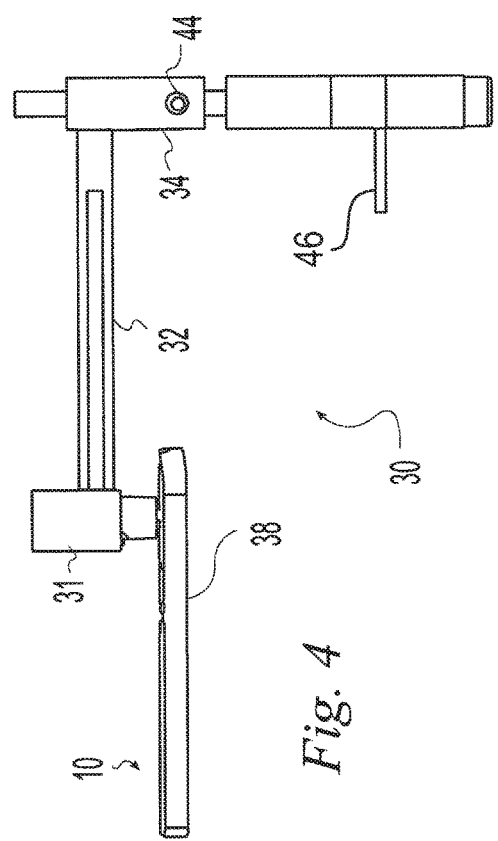
FIG. 4 is a side view of the base of FIG. 1 assembled with a cut guide assembly.
Figure 5:
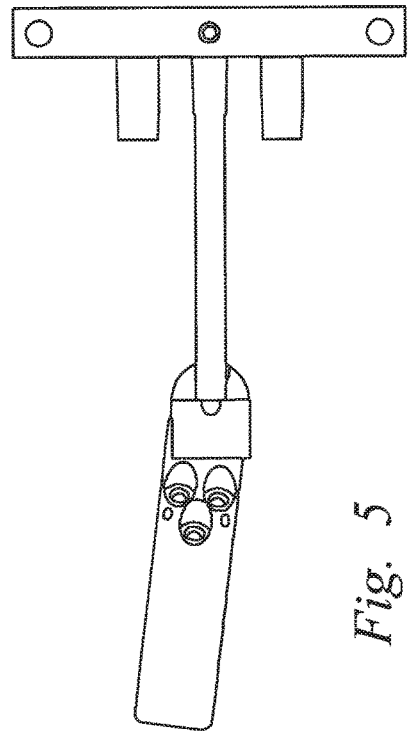
FIG. 5 is a top view of the assembly of FIG. 4.

Cut guide assembly 30 (FIGS. 4-6) includes pivot block 31, arm 32, and anterior femoral cut guide 34. The anterior femoral cut guide 34 includes cut slot 36 aligned with posterior surface 38 of base 10 so that anterior femoral resection 214 is flush with the distal anterior femoral cortical surface on which the base is mounted. This means that the posterior surface 38, cut slot 36, and the anterior femoral resection 214 all lie in a common plane. The cut guide assembly 30 also includes posterior femoral cut guide 40; linked to anterior femoral cut guide 34; adjustable on rails 42 for A/P distance; locked with set screws 44; sizes may be etched on rails and/or size may be set with feeler gauges and the actual implant and/or with calipers; The posterior femoral cut guide 40 may include optional posterior condylar abutment tabs 46 or optional pin/screw fixation holes 47. The cut guide assembly 30 also includes proximal tibial cut guide 48, which mounts to the posterior femoral cut guide 40 and may be available in various sizes to match measured flexion gap. The proximal tibial cut guide 48 may mount to the posterior femoral cut guide 40 via dovetail engagement 50, with an optional locking screw. The proximal tibial cut guide 48 may include optional pin/screw fixation holes 52.

Anatomy

Figure 7:
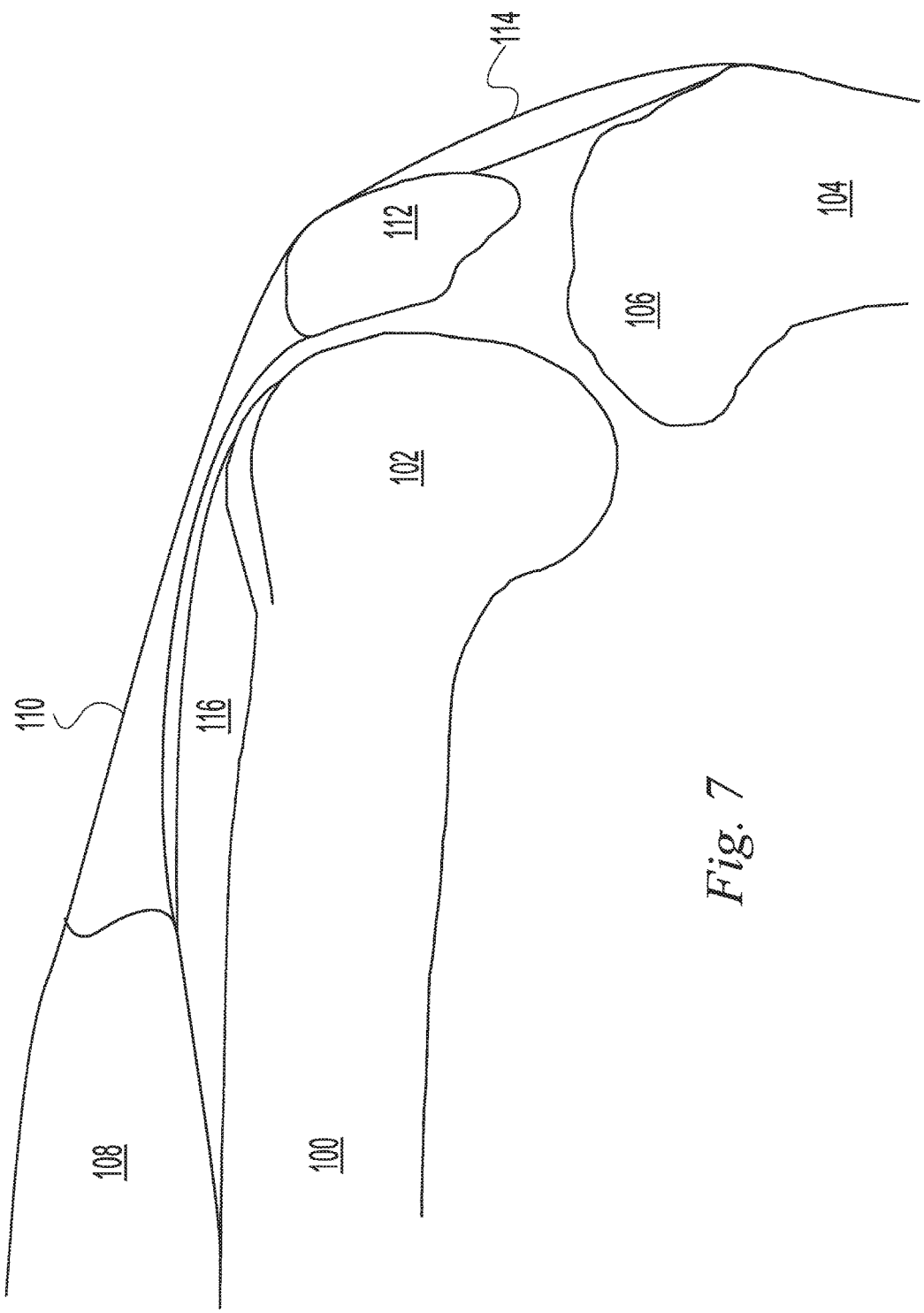
FIG. 7 is a side view of certain anatomical structures of the human knee in cross section.

FIG. 7: femur 100, distal femur 102, tibia 104, proximal tibia 106, quadriceps muscle 108, patellar ligament 110, patella 112, patellar tendon 114, and suprapatellar fat pad 116. FIG. 8: femoral head 118 and center 120 of the femoral head 118.

Figures 18, 19:
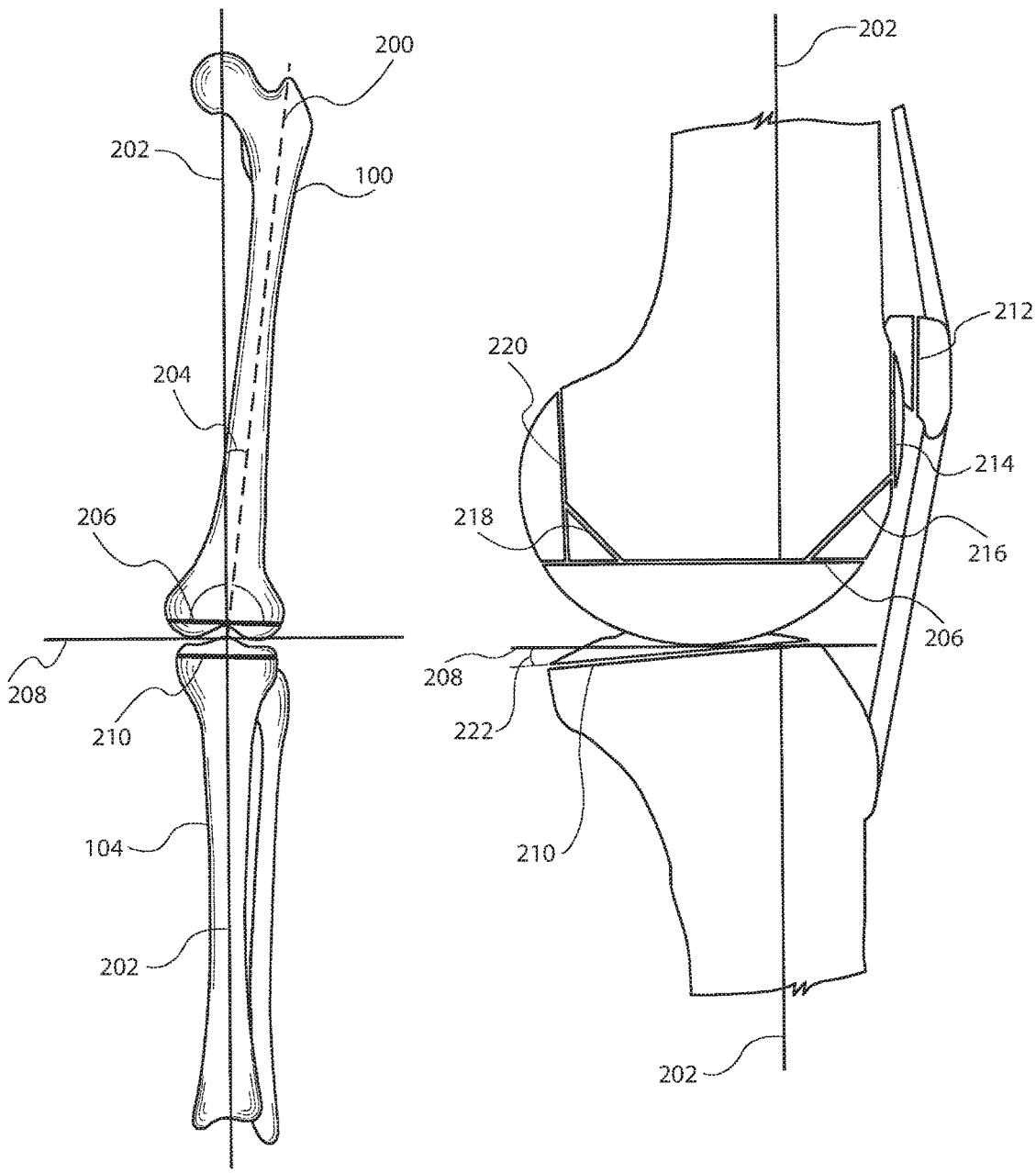
FIG. 18 is a front view of certain anatomical landmarks and geometry of the human knee and leg.
FIG. 19 is a side view of certain anatomical landmarks and geometry of the human knee.

FIG. 18: femoral shaft axis 200, mechanical axis 202 of the leg, angle 204 between femoral shaft axis 200 and mechanical axis 202 of the leg, distal femoral resection 206, knee joint line 208, proximal tibial resection 210.

FIG. 19: patellar resection 212, anterior femoral resection 214, anterior femoral chamfer cut 216, posterior femoral chamfer cut 218, posterior femoral resection 220, angle 222 between knee joint line 208 and proximal tibial resection 210.

Figure 20:
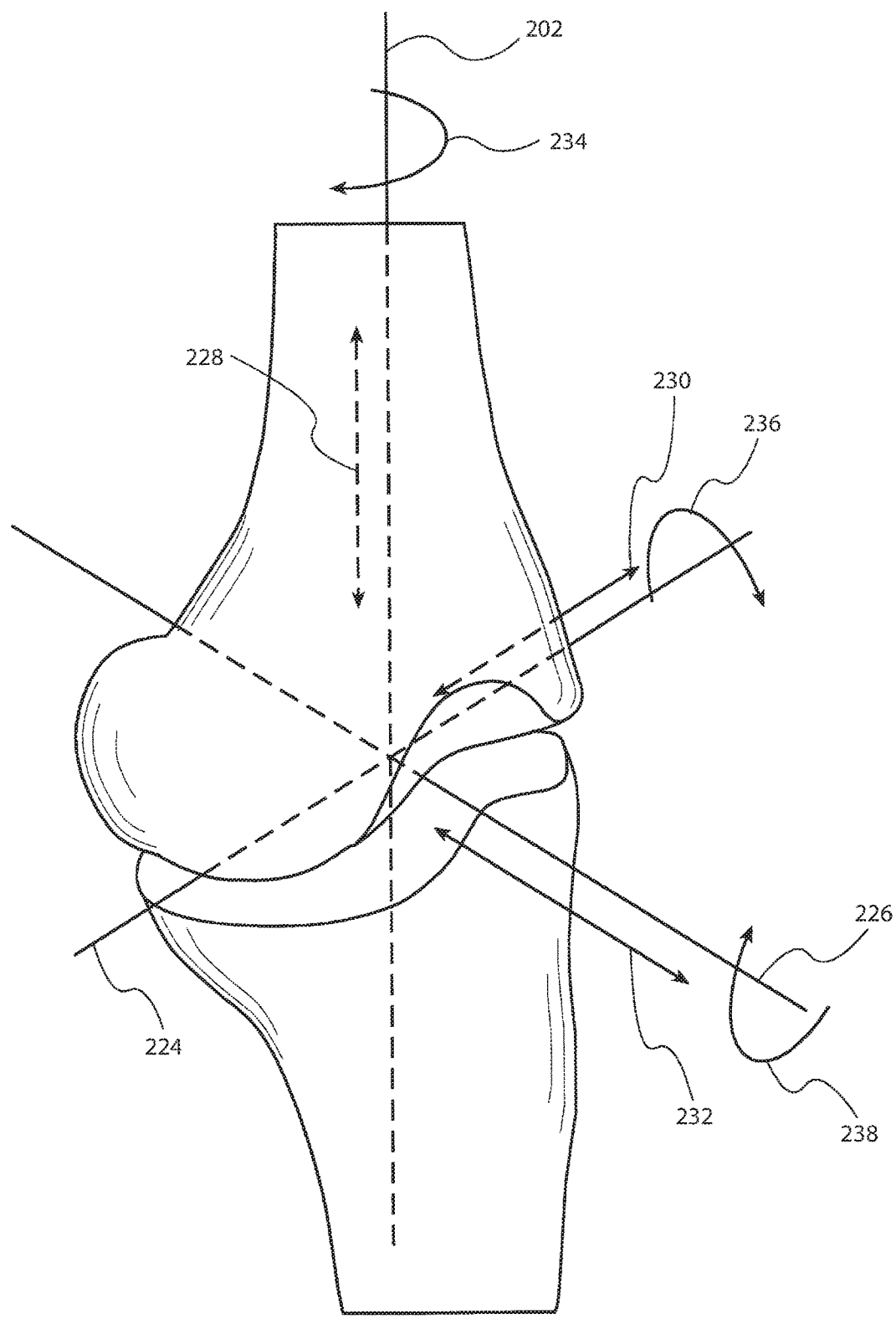
FIG. 20 is a perspective view of the femur and tibia of the human knee.

FIG. 20: transverse axis 224 of the knee (may also be the axis about which the knee flexes and extends), anterior-posterior axis 226 of the knee (may also be the axis about which the knee goes into varus and valgus), superior-inferior translation 228 along the mechanical axis 202 of the leg, medial-lateral translation 230 along the transverse axis 224 of the knee, anterior-posterior translation 232 along the anterior-posterior axis 226 of the knee, axial rotation 234 about the mechanical axis 202 of the leg, rotation 236 about the transverse axis 224 of the knee (also known as flexion and extension), rotation 238 about the anterior-posterior axis 226 of the knee (also known as varus-valgus rotation).

Method

Figure 10:
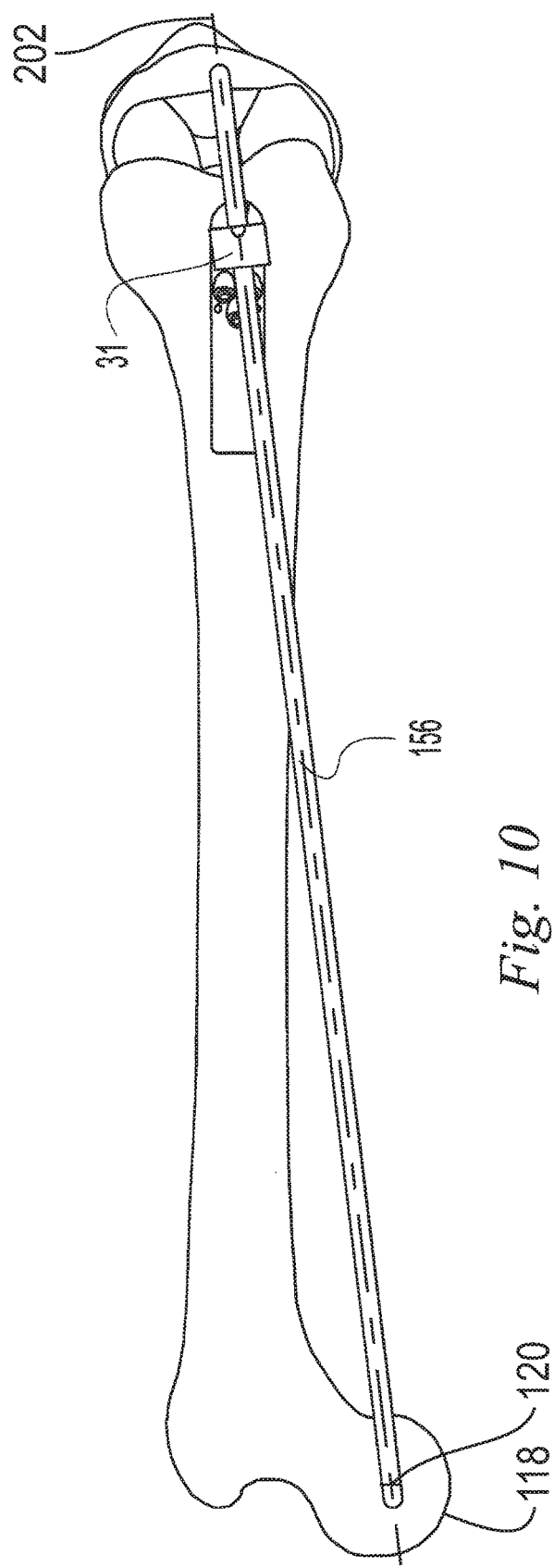
FIG. 10 is a top view of a step in a surgical procedure, aligning a femoral extension rod over the center of the femoral head and the medial/lateral center of the distal femur to establish a mechanical axis of the leg.

Mounting the base 10 to the distal anterior femoral cortex (FIGS. 8-10) may include the steps of making an incision 150, everting the patella 112, resecting the distal margin 152 of the fat pad 116, blunt dissection such as with an elevator 154 under the fat pad along the midline of the femoral shaft, inserting the base 10 under fat pad 116 with the base 10 aligned with the femoral shaft and centered in the medial/lateral width of the distal femur (epicondylar width), using drill guide 20 to drill two holes through base 10 into femur 100, drilling proximal hole through muscle and fat pad, tapping if desired/necessary, and anchoring base to femur with screws.

Aligning the pivot block 31 with the mechanical axis 202 of the leg (FIG. 10) may include the steps of using the alignment rod 156 and locking the pivot block 31. With the pivot block 31 unlocked so that it is free to rotate, the alignment rod 156 is positioned over the femoral head 118 and moved medial/lateral until the rod passes directly over the femoral head center 120. The pivot block 31 is then locked to prevent any further medial/lateral rotation. However, the alignment rod 156 is still free to swing between proximal and distal positions.

Figure 11:
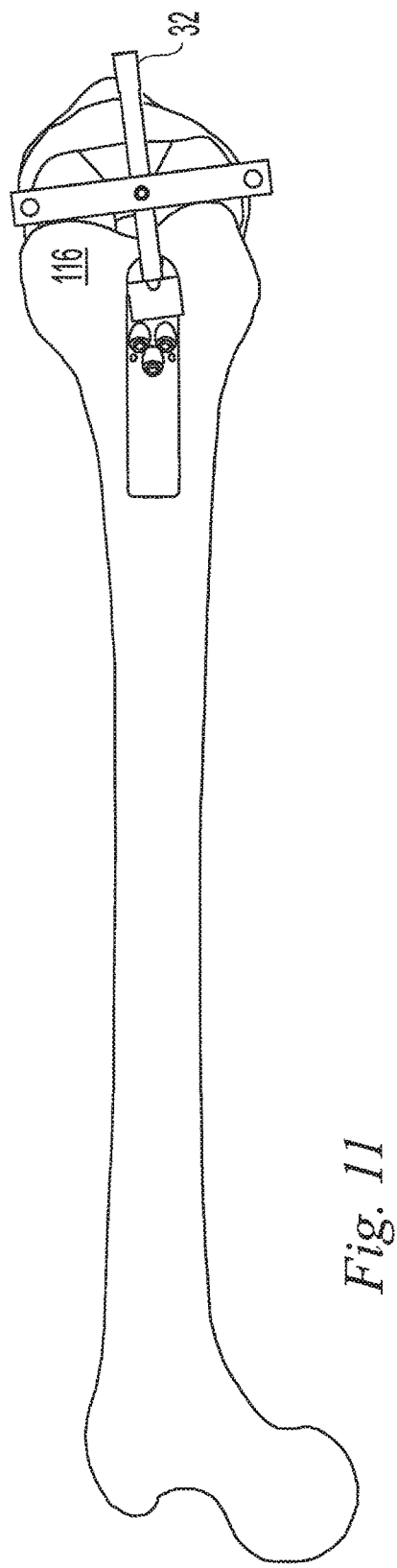
FIG. 11 is a top view of a step in a surgical procedure, aligning a femoral cut guide to the mechanical axis of the leg.
Figure 12:
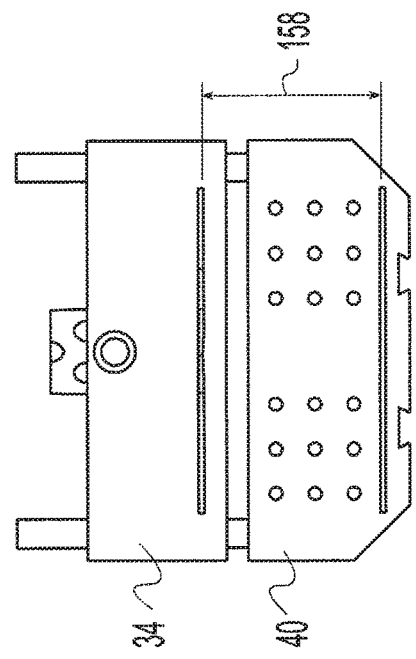
FIG. 12 is a front view of the cut guide assembly of FIG. 4 configured for making femoral cuts.
Figure 13:
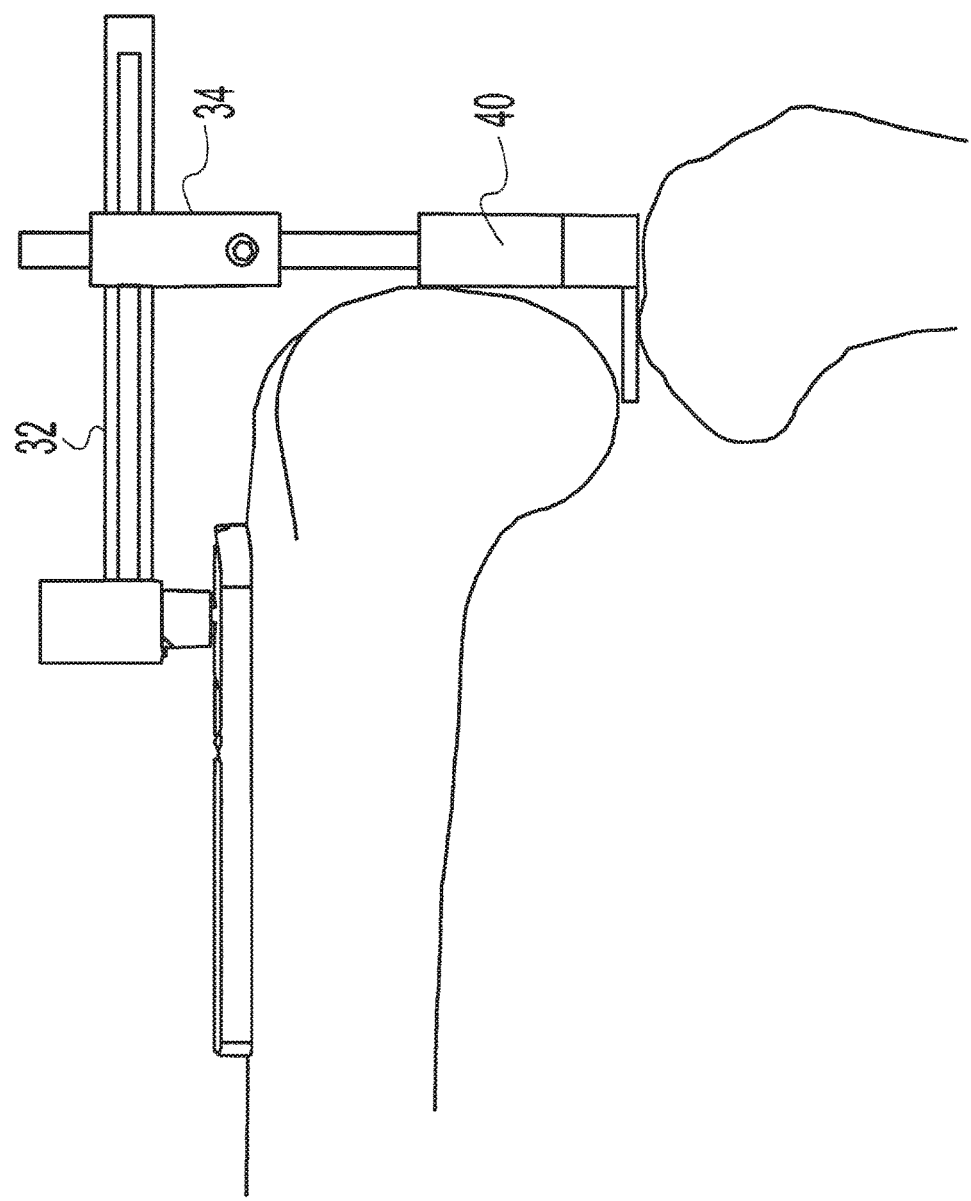
FIG. 13 is a side view of the surgical step of FIG. 11.
Figure 14:
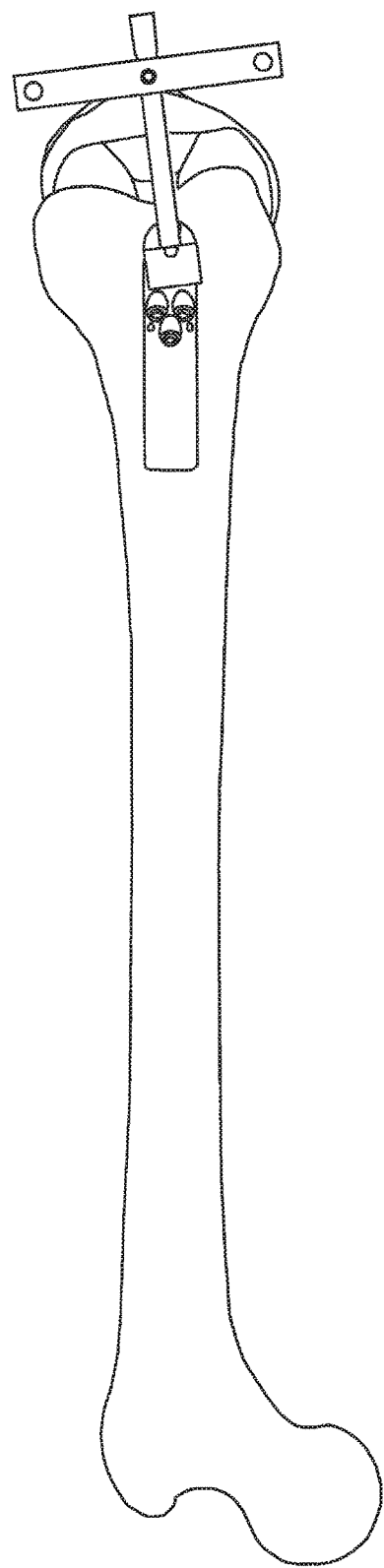
FIG. 14 is a top view of a step in a surgical procedure, aligning a tibial cut guide to the anterior tibia.
Figure 15:
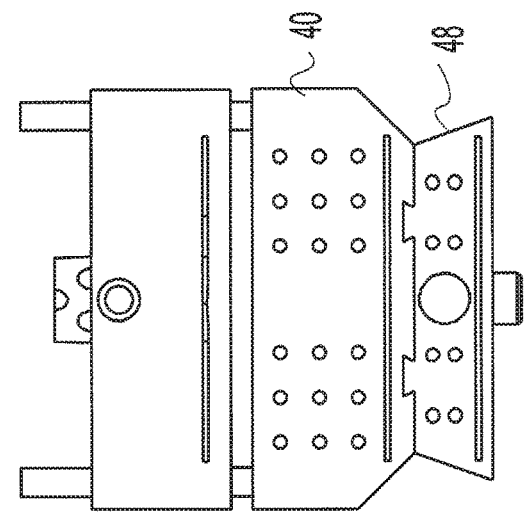
FIG. 15 is a front view of the cut guide assembly of FIG. 4 configured for making a tibial cut.

Making the femoral cuts (FIGS. 11-13) may include the steps of adjusting the femoral cut guides 34, 40 to match A/P femoral dimension 158 of templated femur size, flexing knee to 90 degrees, mounting arm 32 and femoral cut guides 34, 40 to pivot block 31, sliding cut guides into contact with distal femur, optionally adding pins or screws to secure posterior cut block to femur, and making anterior and posterior femoral cuts, e.g. with a powered oscillating saw or other cutting tool.

Figure 16:
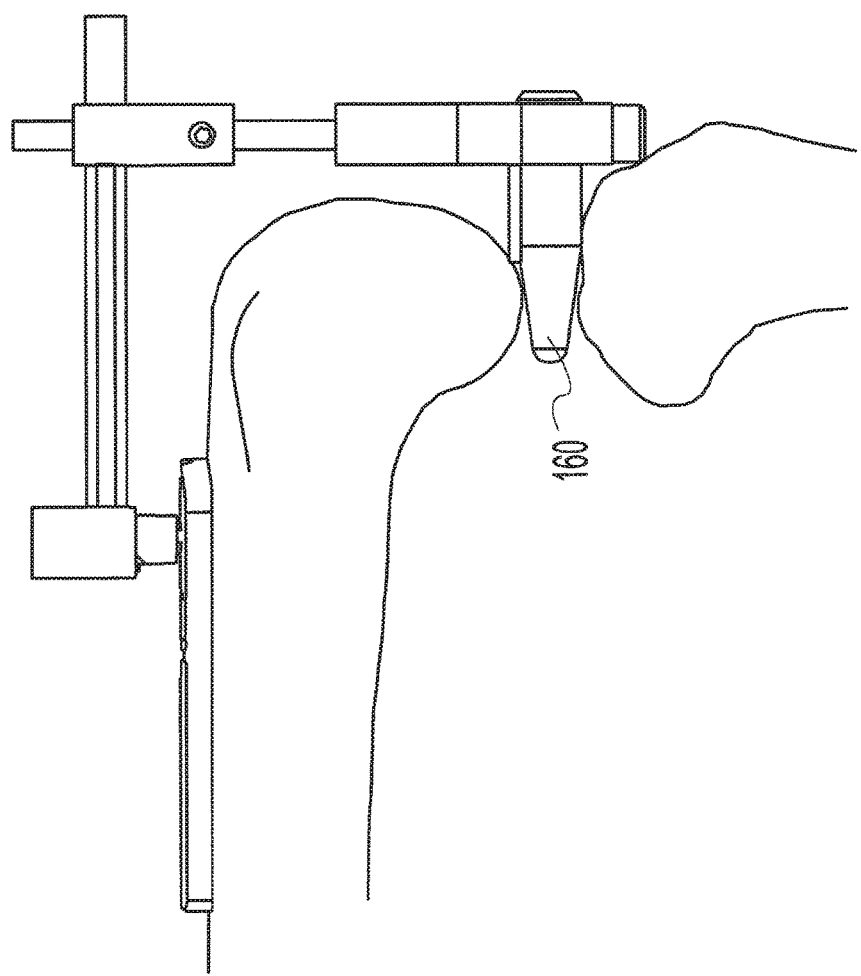
FIG. 16 is a side view of the surgical step of FIG. 14 illustrating the use of a joint distraction member.

Making the tibial cut (FIGS. 14-17) may include the steps of determining flexion gap with spacers (as is known in the art) to produce desired tension in flexion, selecting proximal tibial cut guide 48 to match measured gap, sliding femoral cut guides 34, 40 away from femur, mounting proximal tibial cut guide 48 to posterior femoral cut guide 40, sliding cut guides 40, 48 into contact with proximal tibia, tensioning joint (wedge 160 FIG. 16 or screw 162 through arm 32 FIG. 17), optionally adding pins or screws to secure proximal tibial cut block to tibia, and making proximal tibial cut.

Adjustments and remaining cuts may be made as known in the art, for example flexion and extension gap adjustments via soft tissue release or recutting bone, marginal osteophyte removal, distal femoral cut, and chamfer cuts.

Referring to FIGS. 21A-23B, another instrument system 300 is shown. This instrument system 300 is designed so that bone pins may be placed in the distal femur 102 and proximal tibia 106 while the knee joint is in full extension and maximally distracted, while referencing the distal anterior femoral cortex, and while the leg (femoral head center 120, distal femur 102, proximal tibia 106, and ankle/second toe/anterior tibial spine or crest) is properly aligned with the mechanical axis 202 of the leg. The bone pins serve as mounting fixtures for subsequent instruments, such as cut guides. The system 300 includes apparatus for referencing Whiteside's line while the distal femoral condyles are intact, before any femoral resection occurs, and locking this reference into the apparatus to guide later surgical steps. This design has advantages for, and may be used for, many types of knee arthroplasty, such as bicompartmental or bicondylar knee arthroplasty where the prosthetic components replace and extend across the medial and lateral compartments (with or without a prosthetic patellar component), or unicompartmental or unicondylar knee arthroplasty where the prosthetic components replace the medial or lateral compartment or a single condyle. This design may also be advantageous when replacing the medial and lateral compartments with independent medial and lateral unicompartmental prosthetic components, for example, to spare the anterior cruciate ligament (ACL).

The instrument system 300 may include a base 302, a femoral riser 304 (also known as a handle), a femoral extension rod 306, a tapered plug assembly 308, a tibial-femoral pin guide 310, a tibial riser 312, and a tibial extension rod 313. The instrument system 300 is shown with five tapered plug assemblies 308 (FIG. 21B) and a three-piece telescoping tibial extension rod 313 including a tibial outer extension rod 314, a first tibial inner extension rod 316, and a second tibial inner extension rod 318. The instrument system 300 may also include additional components as described below for FIGS. 21A-46.

Referring to FIGS. 24A-25B, the femoral riser 304, or handle, may be rigidly coupled to the base 302 in one or more orientations. FIGS. 24A-25B illustrate an arrangement in which the femoral riser 304 may be coupled to the base 302 in two orientations. The base 302 includes two slots 344, 346 recessed in a top surface 348 of the base. An acute angle 345 is formed between the slots 344, 346. The magnitude of the angle 345 may be related to the angle 204 between the femoral shaft axis 200, represented by a longitudinal axis 301 of the base 302, and the mechanical axis 202 of the leg (FIG. 18), represented by a longitudinal axis 311 of the femoral riser 304. In the illustrated example, angle 345 may be two times angle 204. The femoral riser 304 includes a ridge 350, or tab, which is received in one of the slots 344, 346 when the femoral riser 304 is coupled to the base 302. The base 302 also includes three holes 352, 354, 356 which are arranged adjacent to the ends of the slots 344, 346. In this example, three holes are sufficient since the slots intersect on the base 302; four holes would be more appropriate if the slots did not intersect on the base 302, and in general the number of holes varies according to the number and arrangement of slots on the base. The femoral riser 304 includes two holes 358, 360 which are arranged adjacent to the ends of the ridge 350. When the ridge 350 is inserted in slot 344, a fastener may be inserted through holes 358, 352, and another fastener may be inserted through holes 360, 356. When the ridge 350 is inserted in slot 346, a fastener may be inserted through holes 358, 352, and another fastener may be inserted through holes 360, 354.

Figures 21A, 21B:
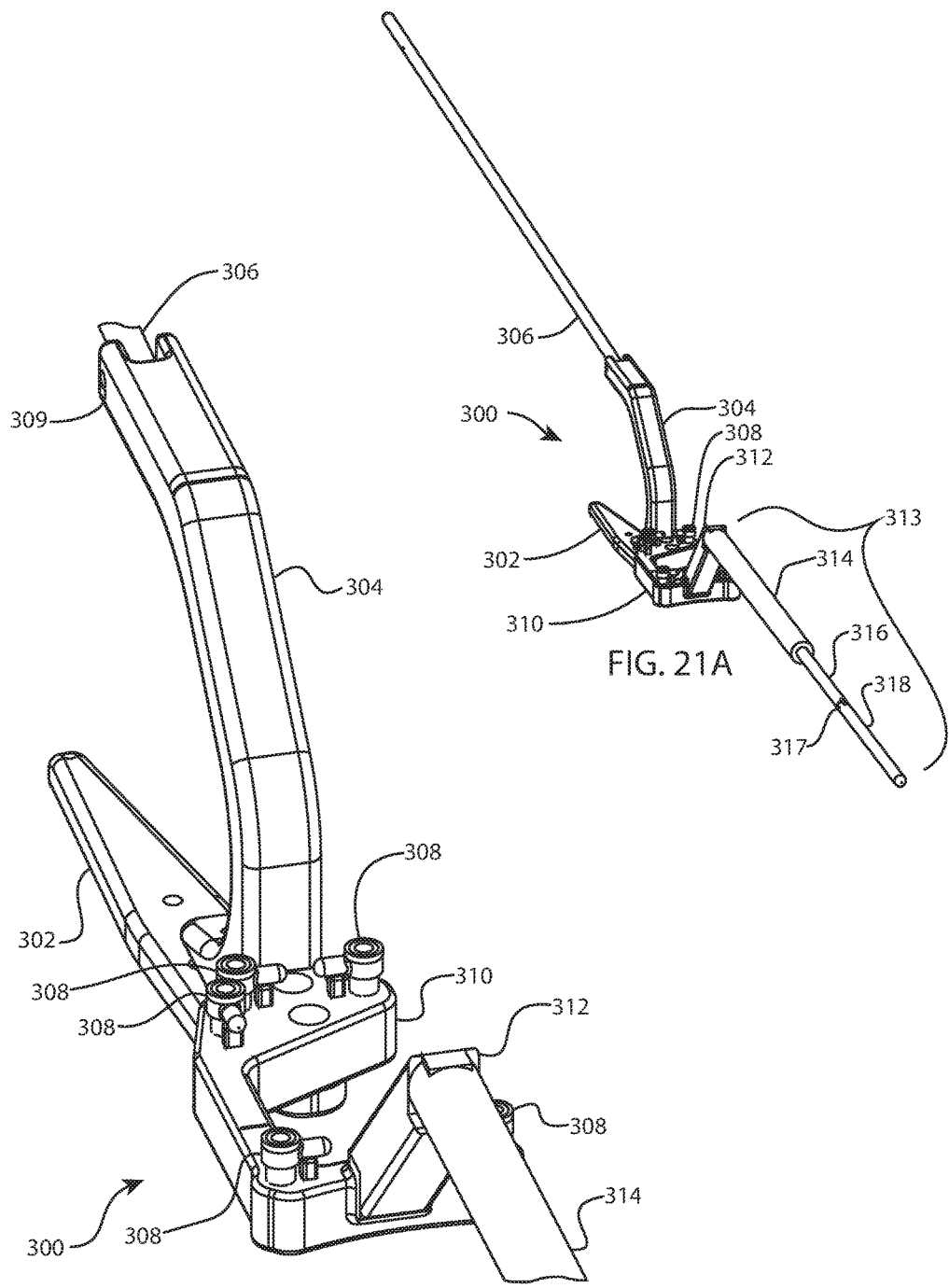
FIG. 21A is a perspective view of another instrument system.
FIG. 21B is an enlarged detail view of a portion of the instrument system of FIG. 21A.
Figure 22A:
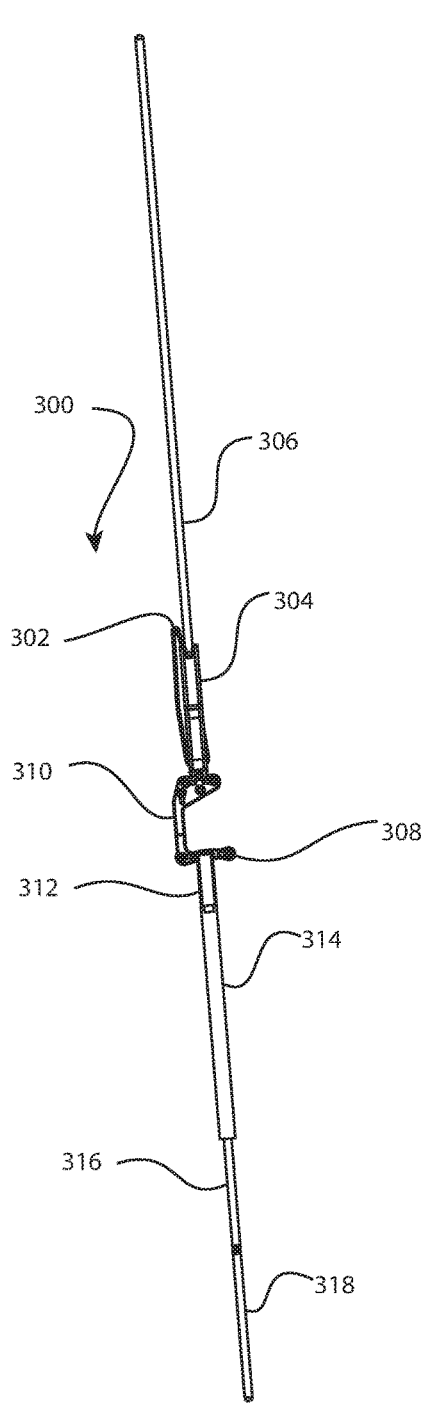
FIG. 22A is a top view of the instrument system of FIG. 21A.
Figure 22B:
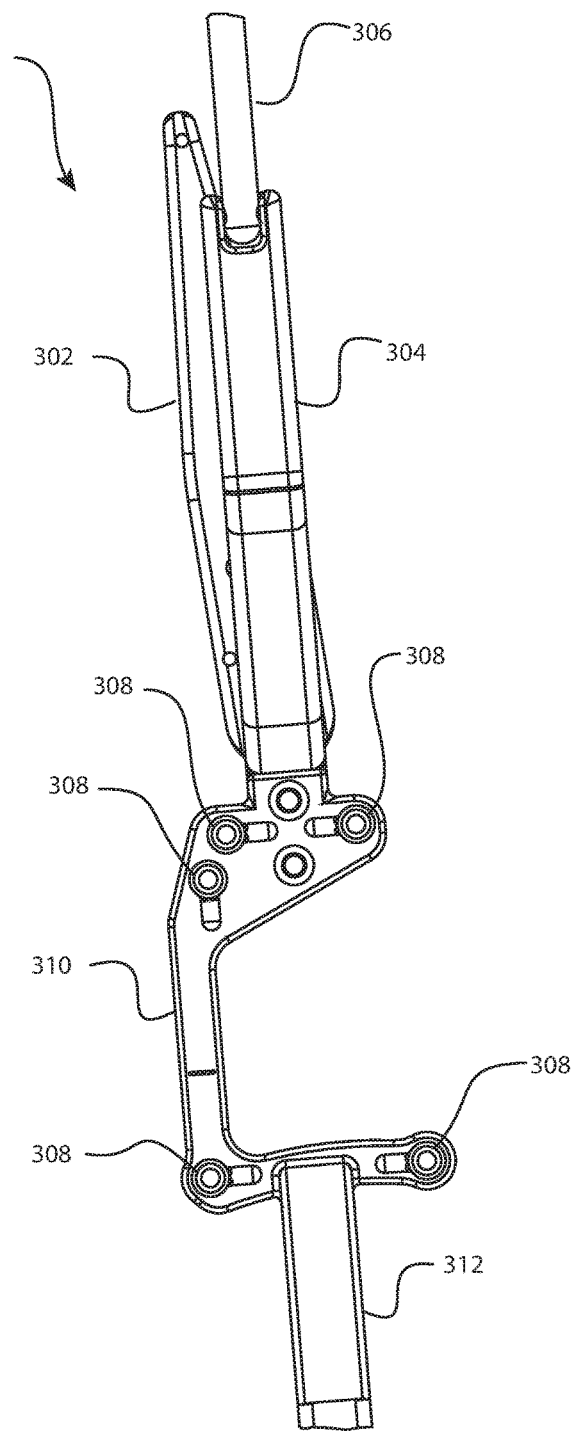
FIG. 22B is an enlarged detail view of a portion of the instrument system of FIG. 22A.

Referring to FIGS. 25A-26B, the femoral extension rod 306 may be pivotally coupled, or hinged, to the femoral riser 304 by a pin, screw, or other fastener through holes 305, 307. Hinge 309 is shown in FIGS. 21B and 23B. The femoral extension rod 306 may remain coupled to the femoral riser 304 in service. In use, the femoral extension rod 306 is free to pivot about the hinge 309 to adjust to the patient's anatomy. The femoral extension rod 306 pivots in an anterior-posterior direction which is generally parallel to the sagittal plane. The femoral extension rod 306 is constrained against pivoting in a medial-lateral direction which is generally parallel to the coronal plane.

Referring to FIGS. 25A, 25B, 28A, and 28B, the tibial-femoral pin guide 310 may be rigidly coupled to the femoral riser 304 by engaging a tab 362 of the femoral riser 304 (FIG. 25A) in a slot 364 of the tibial-femoral pin guide 310 (FIG. 28B) and inserting fasteners through holes 366, 370 and holes 368, 372. Alternatively, the tibial-femoral pin guide 310 may be coupled to the femoral riser 304 by engaging the tab 362 in the slot 364 without using fasteners.

Figure 27A:
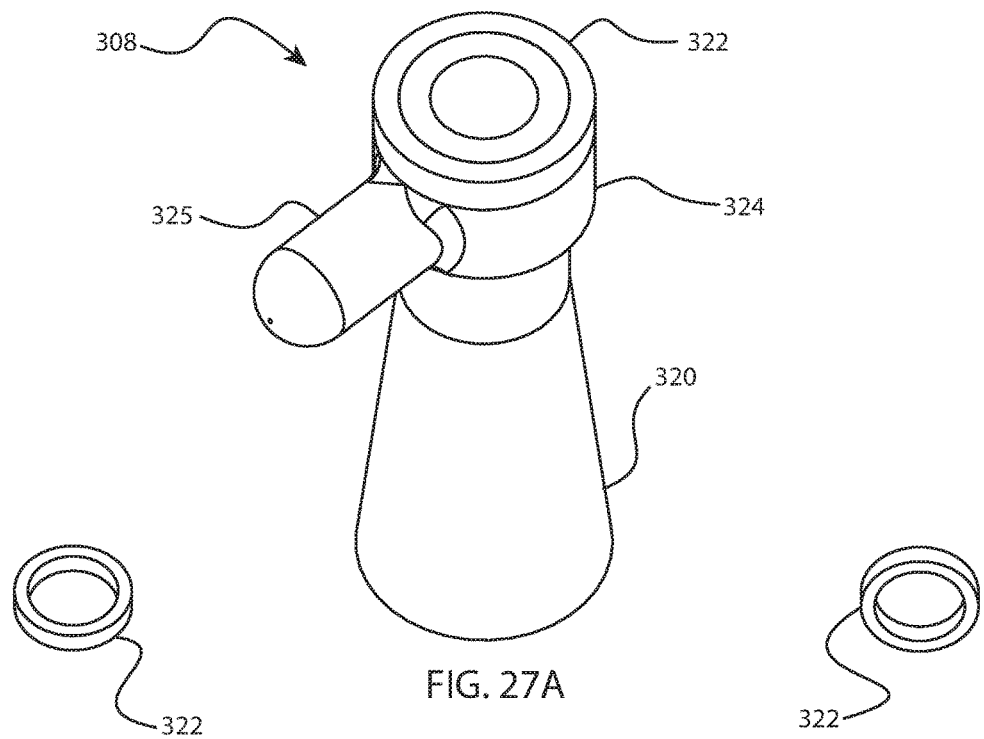
FIG. 27A is a perspective view of a tapered plug assembly of the instrument system of FIG. 21A.
Figure 27B:
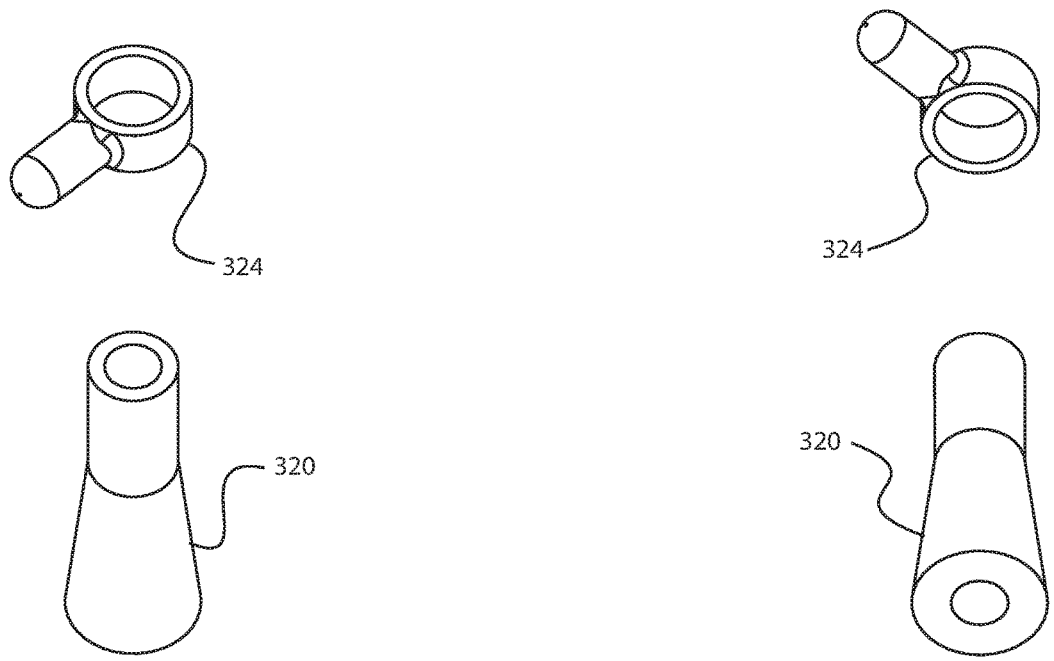
FIG. 27B is an exploded perspective view of the tapered plug assembly of FIG. 27A.
Figure 27C:
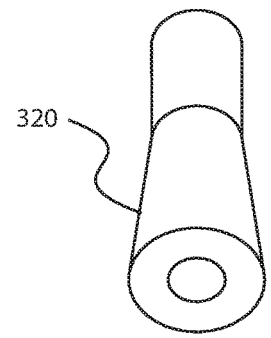
FIG. 27C is another exploded perspective view of the tapered plug assembly of FIG. 27A from a different direction.

Referring to FIGS. 27A-27C, the tapered plug assembly 308 may include a tapered plug 320, a cap 322, and a lock 324. The tapered plug assembly 308 may closely encircle the bone pin with minimal clearance, just enough clearance to permit the bone pin to be rotationally driven through the tapered plug assembly 308 while permitting little to no angular deviation of the bone pin. In an alternate embodiment, the tapered plug assembly 308 may move between a closed configuration and an open configuration. In the closed configuration, the tapered plug assembly 308 may fit closely around the bone pin. In the open configuration, the tapered plug assembly may fit loosely around the bone pin. The inside diameter through the tapered plug assembly 308 may be larger in the open configuration than in the closed configuration.

Referring to FIGS. 27A-28B, each tapered plug assembly 308 is received in a hole 374 of the tibial-femoral pin guide 310 so that the wide end of the tapered plug 320 is in the hole 374, the narrow end of the tapered plug 320 extends beside a boss 376 of the tibial-femoral pin guide 310, and an arm 325 of the lock 324 is adjacent to the boss 376. The hole 374 may have an internal taper corresponding to the external taper of the tapered plug 320. The tapered plug assembly 308 may be captive to the tibial-femoral pin guide 310 in service. When the arm 325 is over the boss 376 (FIGS. 21B, 22B) in a locked configuration, the tapered plug assembly 308 is held in tight engagement in the hole 374; when the arm 325 is rotated away from the boss 376 in an unlocked configuration, the tapered plug assembly 308 is free to drop down so as to fit more loosely in the hole 374. In the alternate embodiment, when the arm 325 is over the boss 376, the tapered plug assembly 308 is in the closed configuration; when the arm 325 is rotated away from the boss 376, the tapered plug assembly 308 is in the open configuration. The locked or closed configurations of the tapered plug assembly 308 provide precise, close-fitting holes while the bone pins are being driven, so that the pins are accurately positioned, mutually parallel to each other, and all perpendicular to the mechanical axis 202 of the leg. The unlocked or open configurations of the tapered plug assembly 308 provide a looser fit after the bone pins have been driven, so that the tibial-femoral pin guide 310 can be removed more easily. The unlocked configuration provides a looser fit between the hole 374 and the tapered plug 320, while the open configuration provides a looser fit between the tapered plug 320 and the bone pin.

Referring to FIGS. 28A-29B, the tibial riser 312 may be rigidly coupled to the tibial-femoral pin guide 310 by inserting boss 378 of the tibial-femoral pin guide 310 into notch 380 of the tibial riser 312 and inserting a fastener through holes 382, 384. Alternately, the tibial riser 312 may be permanently rigidly coupled to the tibial-femoral pin guide.

Referring to FIGS. 29A-30B, the tibial outer extension rod 314 may be permanently rigidly coupled to the tibial riser 312 by welding tabs 386 of the tibial outer extension rod 314 to a corresponding fitting 388 of the tibial riser 312. Any tibial extension rod may be coupled to the tibial riser 312 in the same way. Alternately, tibial outer extension rod 314 may be removably or hingedly coupled to the tibial riser 312.

Referring to FIGS. 30A-31B, the first tibial inner extension rod 316 may be telescopically coupled to the tibial outer extension rod 314 by inserting the first tibial inner extension rod 316 into a central longitudinal hole 390 of the tibial outer extension rod 314 and inserting a fastener through a slot 392 of the tibial outer extension rod 314 and into a hole 394 of the first tibial inner extension rod 316, so that the tibial inner extension rod 316 is slidable within, and captive to, the tibial outer extension rod 314. The fastener may be removable so that the first tibial inner extension rod 316 may be removed from the tibial outer extension rod 314.

Figure 23A:
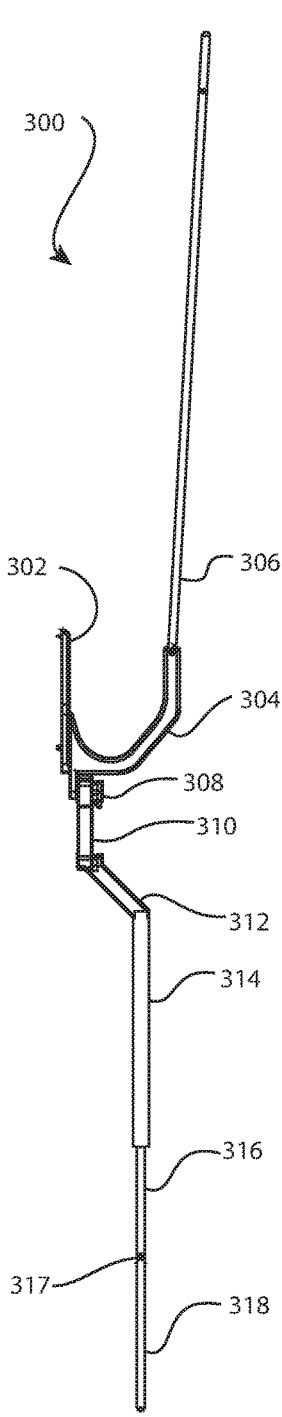
FIG. 23A is a side view of the instrument system of FIG. 21A.
Figure 23B:
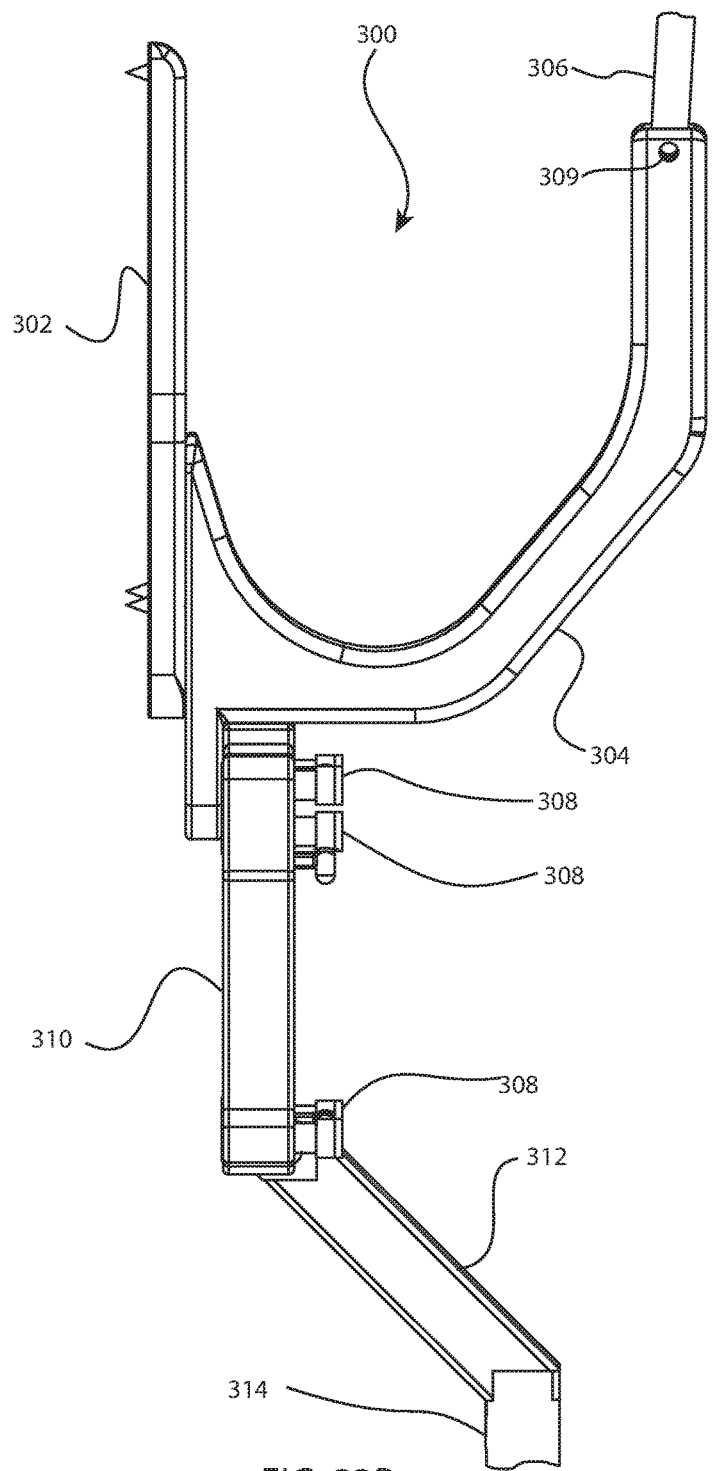
FIG. 23B is an enlarged detail view of a portion of the instrument system of FIG. 23A.
Figure 24A:
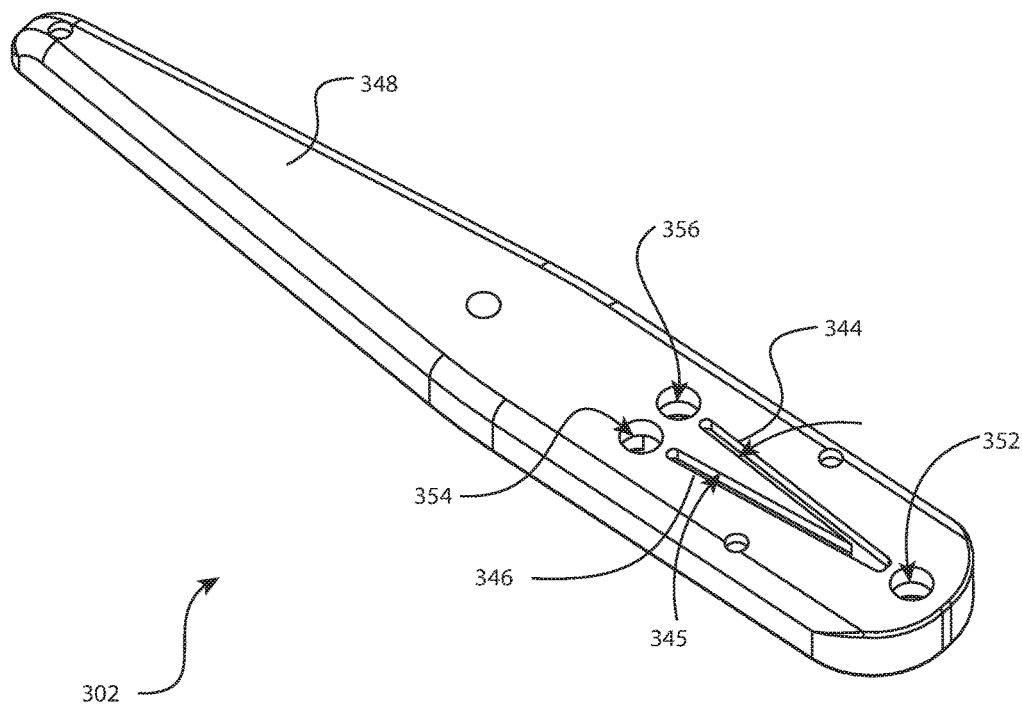
FIG. 24A is a perspective view of a base of the instrument system of FIG. 21A.
Figure 24B:
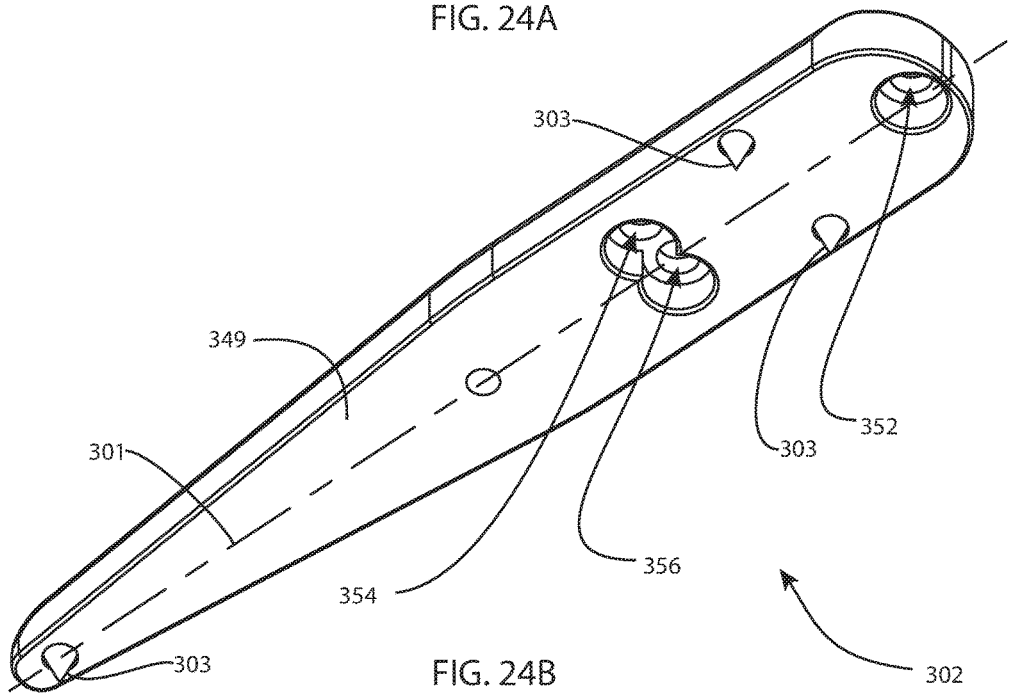
FIG. 24B is another perspective view of the base of FIG. 24A from a different direction.
Figure 25A:
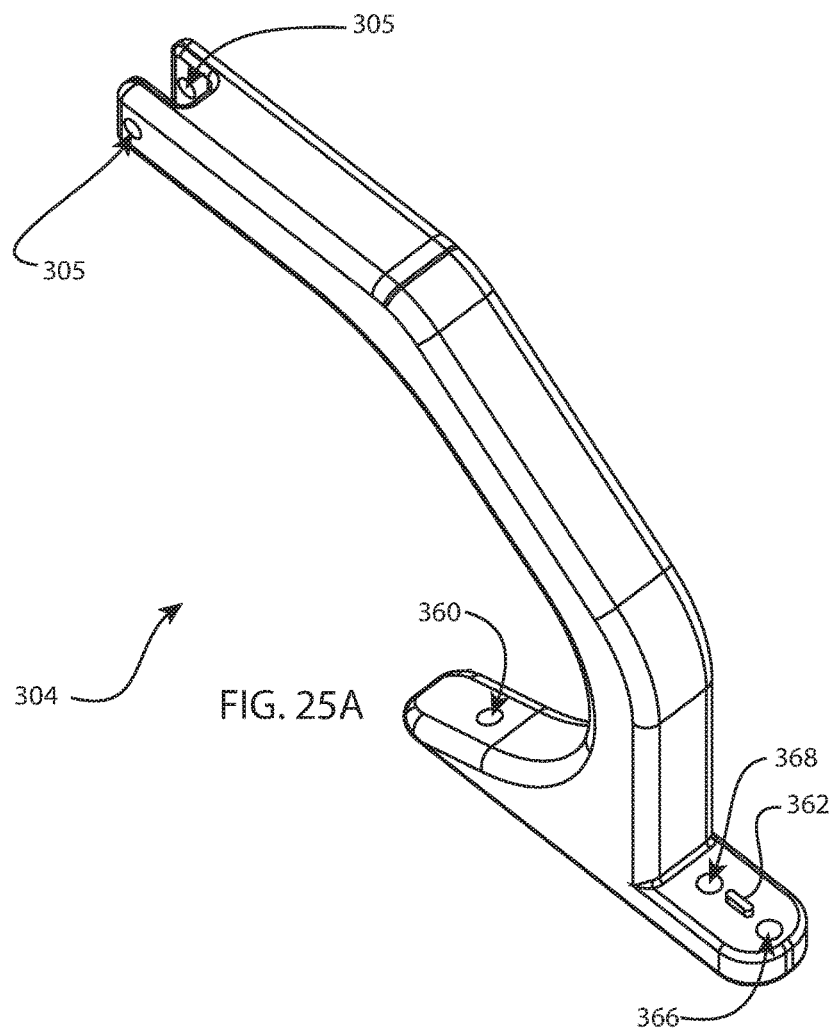
FIG. 25A is a perspective view of a femoral riser, or handle, of the instrument system of FIG. 21A.
Figure 25B:
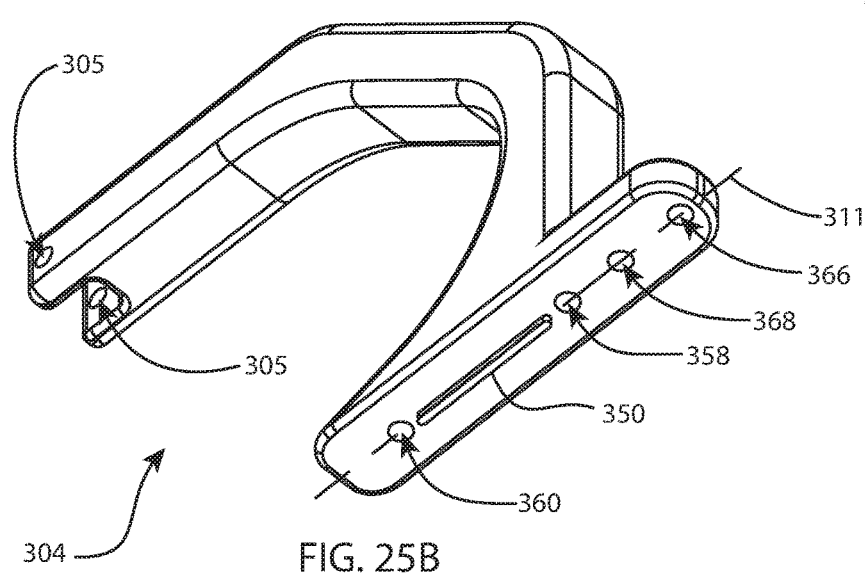
FIG. 25B is another perspective view of the femoral riser of FIG. 25A from a different direction.

Referring to FIGS. 31A-32B, second tibial inner extension rod 318 may be pivotally coupled to the first tibial inner extension rod 316 by inserting a fastener through holes 396, 398 to form a hinge 317 (FIGS. 21A and 23A). The second tibial inner extension rod 318 may remain coupled to the first tibial inner extension rod 316 in service. In use, the second tibial inner extension rod 318 is free to pivot about the hinge 317 to adjust to the patient's anatomy.

Prior to use, the base 302 and the femoral riser 304, with femoral extension rod 306, may be rigidly coupled together in an orientation appropriate to the surgical conditions, i.e., in a left orientation for a left knee, or in a particular angular orientation based upon pre-operative planning. Tapered plug assemblies 308 may be installed in the holes 374 of the tibial-femoral pin guide 310, and moved to the locked or closed configuration. The tibial riser 312, with tibial extension rod(s) 313, 314, 316, 318, may be rigidly coupled to the tibial-femoral pin guide 310. The tibial-femoral pin guide 310, with attached tibial riser 312 and tibial extension rod(s), may be rigidly coupled to the femoral riser 304.

Alternatively, the base 302, femoral riser 304, and femoral extension rod 306 may be coupled together as a femoral assembly, and the tibial-femoral pin guide 310, tapered plug assemblies 308 (locked or closed), tibial riser 312, and tibial extension rod(s) 313, 314, 316, 318 may be coupled together as a tibial assembly. Users may find that the femoral assembly is easier to manipulate without the tibial assembly attached, particularly when insinuating the base 302 between the suprapatellar fat pad 116 and the anterior distal femoral cortex. Users may prefer to couple the tibial assembly to the femoral assembly immediately before distracting the knee joint and aligning the tibia.

The base 302 may be inserted under the suprapatellar fat pad 116 and against the distal anterior femoral cortex in the manner described previously. The femoral riser 304 may rest against or within the trochlear groove. The femoral extension rod 306 may rest against the anterior aspect of the patient's thigh and hip. The proximal free end of the femoral extension rod 306 may be shifted medial-lateral until the femoral extension rod 306 passes over the center 120 of the femoral head 118. Proper alignment is achieved when the distal end of the femoral extension rod 306, base 302, and femoral riser 304 are centered in the medial/lateral width of the distal femur 102 while at the same time the proximal end of the femoral extension rod 306 passes over the femoral head center 120.

Shown later in this application, a target may be used in conjunction with the femoral extension rod 306 to precisely and objectively locate the center 120 of the femoral head 118. A target may be positioned over the anterior aspect of the patient's hip and/or over the center 120 of the femoral head 118 with fluoroscopic, radiographic, or C-arm imaging. Later, when the femoral extension rod 306 is positioned along the patient's thigh, the proximal free end of the rod 306 may be positioned relative to the target. The target may be a fork or "goal post," a ring, a reticle, "cross hairs," or the like, mounted to the free end of an adjustable arm whose base is stationary. In this application, a target may be "over the center of the femoral head" even if the target is actually superior or inferior to the femoral head, so long as the femoral extension rod passes over the center of the femoral head when the rod is aimed at the target. Alternatively, the proximal free end of the femoral extension rod 306 may be positioned relative to the anterior iliac crest.

Once the proximal free end of the femoral extension rod 306 is positioned over the center 120 of the femoral head 118, the base 302 may be pressed firmly against the distal anterior femoral cortex. An assistant may press down against the proximal portion of the femoral riser 304 with their palm. Optional spikes 303 (FIG. 24B) or other frictional elements may be included on the bone-facing side 349 of the base 302 to further stabilize the base against the bone. At this point, the base 302, the femoral riser 304, and the femoral extension rod 306 are aligned with the mechanical axis 202 of the leg (at least where it extends through the femur).

Certain ligaments may be at least partially released, or cut, at this stage or at another time in the procedure. For example, one or both of the cruciate ligaments may be cut at this stage in accordance with the design of the implants which will be used. One or both of the collateral ligaments may be released. At this stage, a provisional proximal tibial resection of about 3 mm to 5 mm to 6 mm (within surgical tolerances) may be made. The provisional proximal tibial resection increases the joint space so that a distractor, spreader, or other instrument may more easily fit between the distal femur and proximal (resected) tibia during a subsequent distraction step, and so that the knee joint (and lower limb) is more mobile during a subsequent lower limb positioning step. The provisional proximal tibial resection may also protect the posterior cruciate ligament (PCL) when a cruciate-retaining (CR) (or cruciate-sparing, CS) implant system is used.

The lower leg may now be distracted to the extent permitted by the existing ligamentous structures of the knee. A distractor, spreader, or other instrument may be used in the knee joint space to provide mechanical advantage. The distractor may indicate the applied distraction force. Alternatively, an assistant may manually distract the lower limb. As the distraction force is applied, the lower limb may be moved medial-lateral to align it with the distal free end of the tibial extension rod—in the example shown, the distal free end of extension rod 318. The alignment of the proximal free end of the femoral extension rod 306 may be monitored at this stage to ensure that it remains aligned over the center 120 of the femoral head 118 as the lower leg is brought into alignment with the distal free end of the tibial extension rod 318. The lower leg is properly aligned when the proximal end of the tibial extension rod 313 is centered in the medial/lateral width of the proximal tibia 106 and the distal free end of the tibial extension rod 318 is centered over the ankle and/or the second toe of the foot. This establishes the desired tibial varus/valgus rotation.

Once the knee joint is fully distracted, the proximal free end of the femoral extension rod 306 is positioned over the center 120 of the femoral head 118, the distal femur 102 and proximal tibia 106 are centered with respect to the femoral and tibial extension rods 306, 313, and the lower leg is aligned with the distal free end of the tibial extension rod 318, bone pins may be driven through the tapered plug assemblies 308 and the tibial-femoral pin guide 310. In the example shown, up to three pins may be driven into the distal femur 102, and up to two pins may be driven into the proximal tibia 106. All of the pins are parallel to each other and perpendicular to the mechanical axis 202 of the leg.

After the bone pins are driven, the tapered plug assemblies 308 may be moved to the unlocked or open configuration to provide a looser fit so that the tibial-femoral pin guide 310 can be removed more easily. The tibial-femoral pin guide 310 may be uncoupled from the femoral riser 304 and removed from the surgical site, along with the tapered plug assemblies 308, the tibial riser 312, and the tibial extension rods 313, 314, 316, 318. The base 302 may then be pulled distally out from under the suprapatellar fat pad 116, along with the femoral riser 304 and the femoral extension rod 306. Only the bone pins remain in the distal femur 102 and proximal tibia 106.

Referring to FIGS. 35-41B, a femoral base block assembly 330 may be included in the instrument system 300. The femoral base block assembly 330 may include a femoral base block 332, a translation bar 334, a knob 336, a top component 338, a bottom component 340, and a socket 342. The translation bar 334 includes two parallel shafts 335, 337 which slide within holes 339, 341, respectively, of the femoral base block 332.

The femoral base block 332 of the assembly 330 may be placed over the femoral bone pins after the rest of the components of system 300 have been removed and before any resections are made (other than the provisional tibial resection mentioned above). The femoral base block 332 may be oriented so that a tab 333 (FIG. 36B) contacts the distal anterior femoral cortex in or immediately adjacent to the former location of the distal portion of the base 302 (i.e., near the former location of hole 352). The tab 333 therefore contacts the distal anterior femoral cortex in the same plane as the base 302, providing direct referencing for a subsequent anterior femoral resection 214. A short shaft or rod (not shown) may be coupled in the socket 342 so that the short shaft extends posteriorly in the intercondylar notch (trochlear notch). The knee may be flexed to facilitate access and visualization of the intercondylar notch. The short shaft, socket 342, bottom component 340, top component 338, and knob 336 may be rotated about a post 400 of the translation bar 334 to align the short shaft with Whiteside's line. The short shaft may be locked in alignment with Whiteside's line, for example by tightening the knob 336, top component 338, bottom component 340, socket 342, or with a locking element (not shown). The femoral base block assembly 330 may then be removed from the femoral pins and the short shaft may be removed from the socket 342.

Figure 33A:
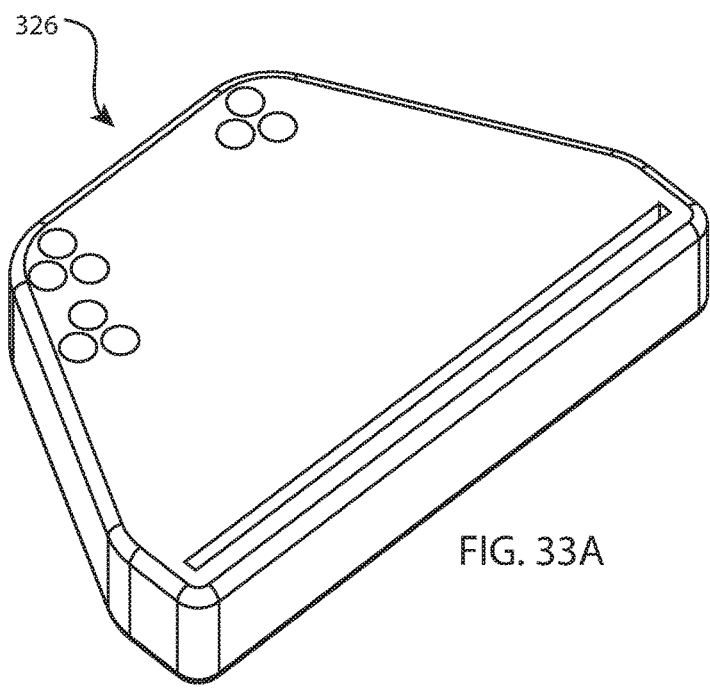
FIG. 33A is a perspective view of a femoral cut guide of the instrument system of FIG. 21A.
Figure 33B:
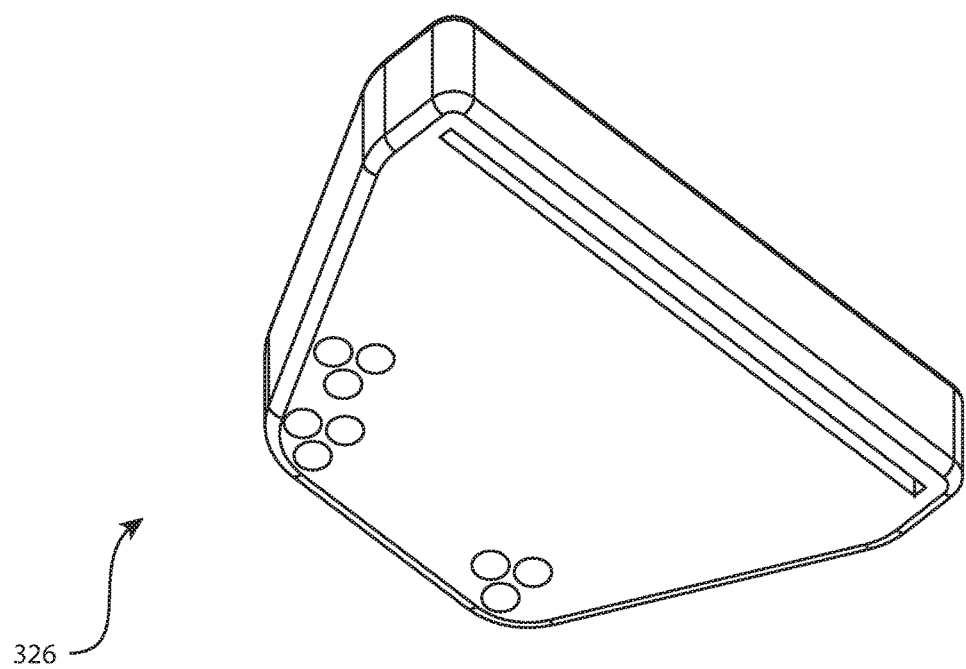
FIG. 33B is another perspective view of the femoral cut guide of FIG. 33A from a different direction.

Referring to FIGS. 33A-33B, a femoral cut guide 326 may be included in the instrument system 300. The femoral cut guide 326 may be placed over the femoral pins, and a saw used through the femoral cut guide to make a distal femoral resection 206.

The femoral base block 332 of the assembly 330 may be replaced over the femoral pins, and a femoral cutting block or four-in-one cut guide 750 (FIGS. 61A and 61B) may be coupled to the socket 342 so that the four-in-one cut guide rests against the distal femur in proper alignment with Whiteside's line due to the pre-set rotational position of the knob 336, top component 338, bottom component 340, and socket 342. The four-in-one cut guide 750 may guide multiple femoral cuts, such as the anterior femoral resection 214, the anterior femoral chamfer cut 216, the posterior femoral resection 220, and the posterior femoral chamfer cut 218. The anterior femoral resection 214 may be precisely aligned with the distal anterior femoral cortex as a result of the base 302 directly referencing the distal anterior femoral cortex and the femoral base block assembly 330 suspending the four-in-one cut guide 750 with its anterior resection slot 756 at the same level. The tab 333 of the femoral base block 332 contacts the distal anterior femoral cortex as did the base 302 to provide accurate positioning of the anterior resection slot of the femoral cutting block coupled to the femoral base block assembly 330.

Figure 34A:
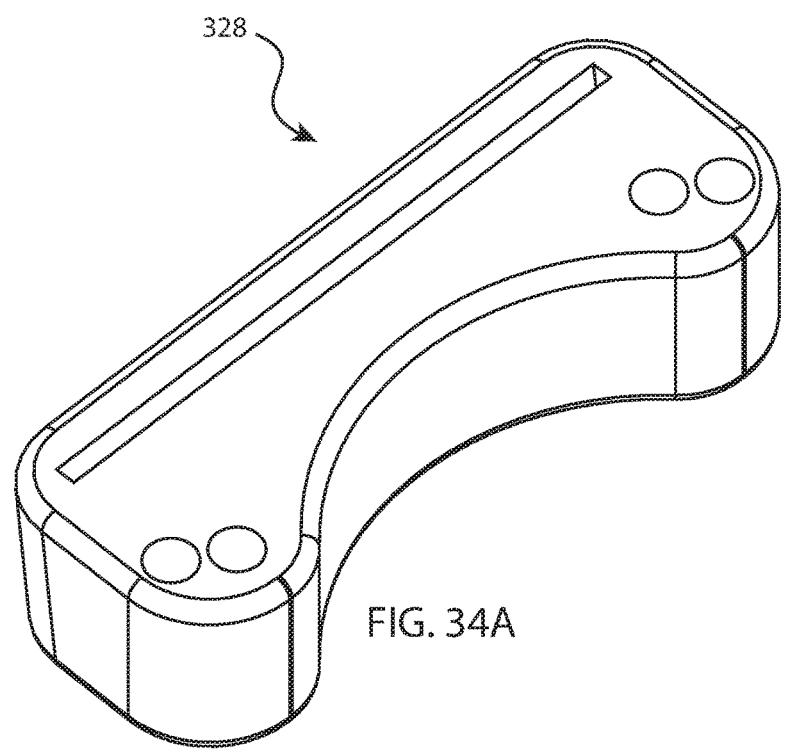
FIG. 34A is a perspective view of a tibial cut guide of the instrument system of FIG. 21A.
Figure 34B:
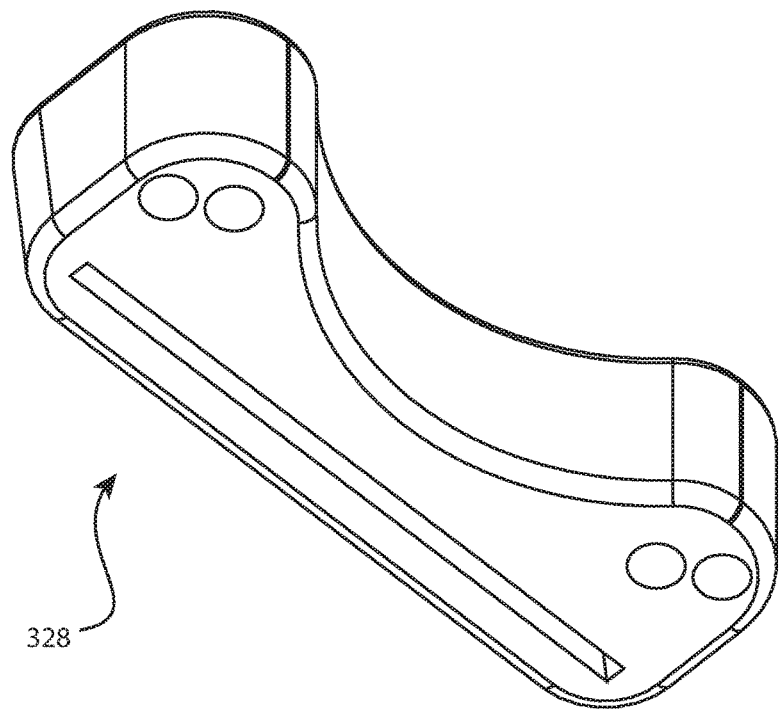
FIG. 34B is another perspective view of the tibial cut guide of FIG. 34A from a different direction.

Referring to FIGS. 34A-34B, a tibial cut guide 328 may be included in the instrument system 300. The tibial cut guide 328 may be placed over the tibial pins, and a saw used through the tibial cut guide to make a proximal tibial resection 210. The proximal tibial resection 210 may be made at the same time as, or immediately after, the distal femoral resection 206; it may also be made after all femoral resections are complete. The tibial cut guide 328 may be designed to produce a tibial resection 210 that is perpendicular to the mechanical axis 202 of the leg, which may be referred to as a zero degree resection. The tibial cut guide 328 may be designed to produce a tibial resection 210 that forms an angle other than 90 degrees with the mechanical axis. For example, the tibial cut guide 328 may produce a tibial resection 210 that slopes posteriorly and inferiorly. A sloping tibial resection 210 may be referred to by its angle relative to a perpendicular resection. For example, a six degree tibial resection slopes from anterior-superior to posterior-inferior, making a six degree angle with a theoretical perpendicular resection. Multiple posterior resection angles are contemplated herein, for example, zero degrees and six degrees.

Figure 35:
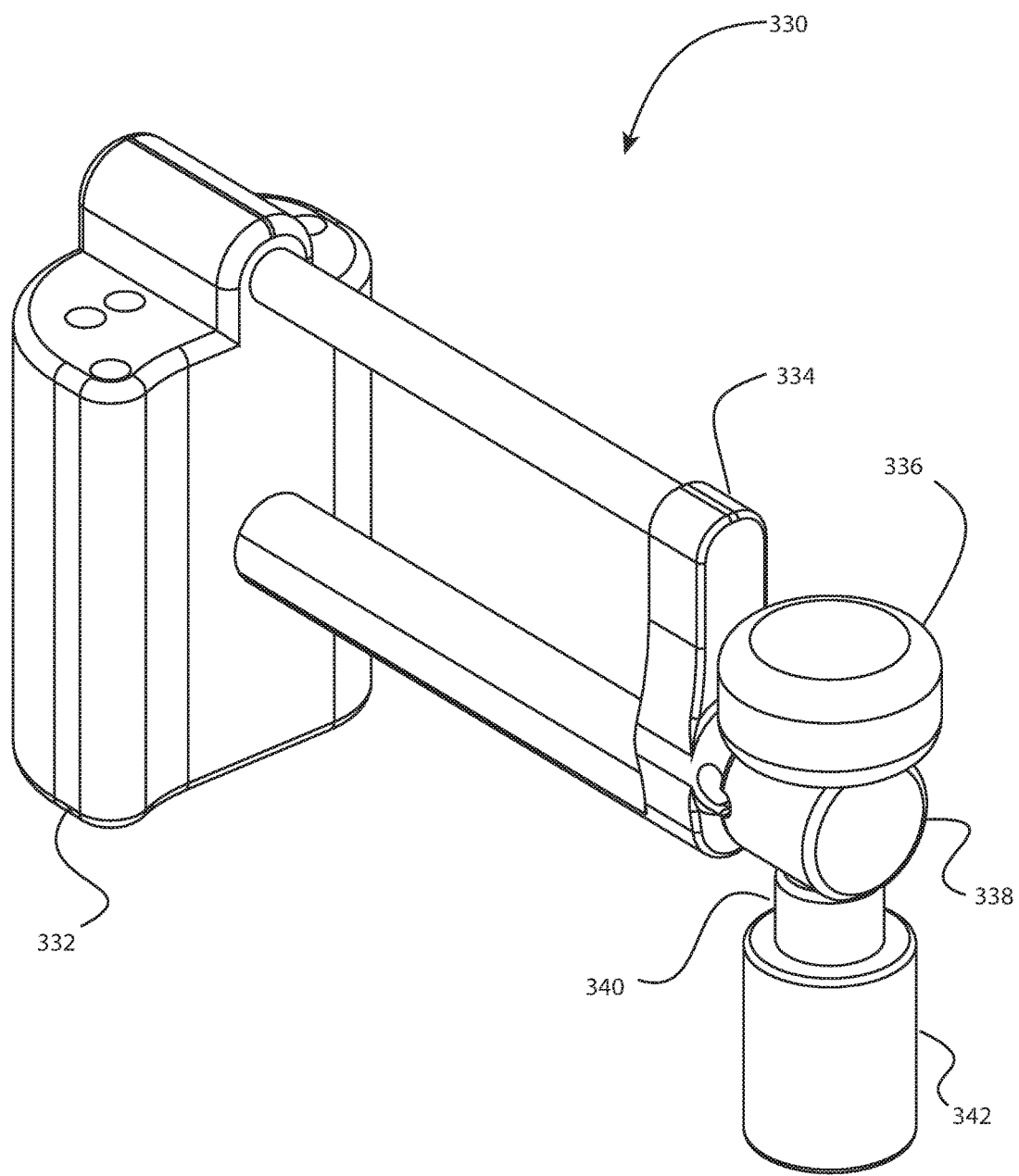
FIG. 35 is a perspective view of a femoral base block assembly.
Figures 36A, 36B:
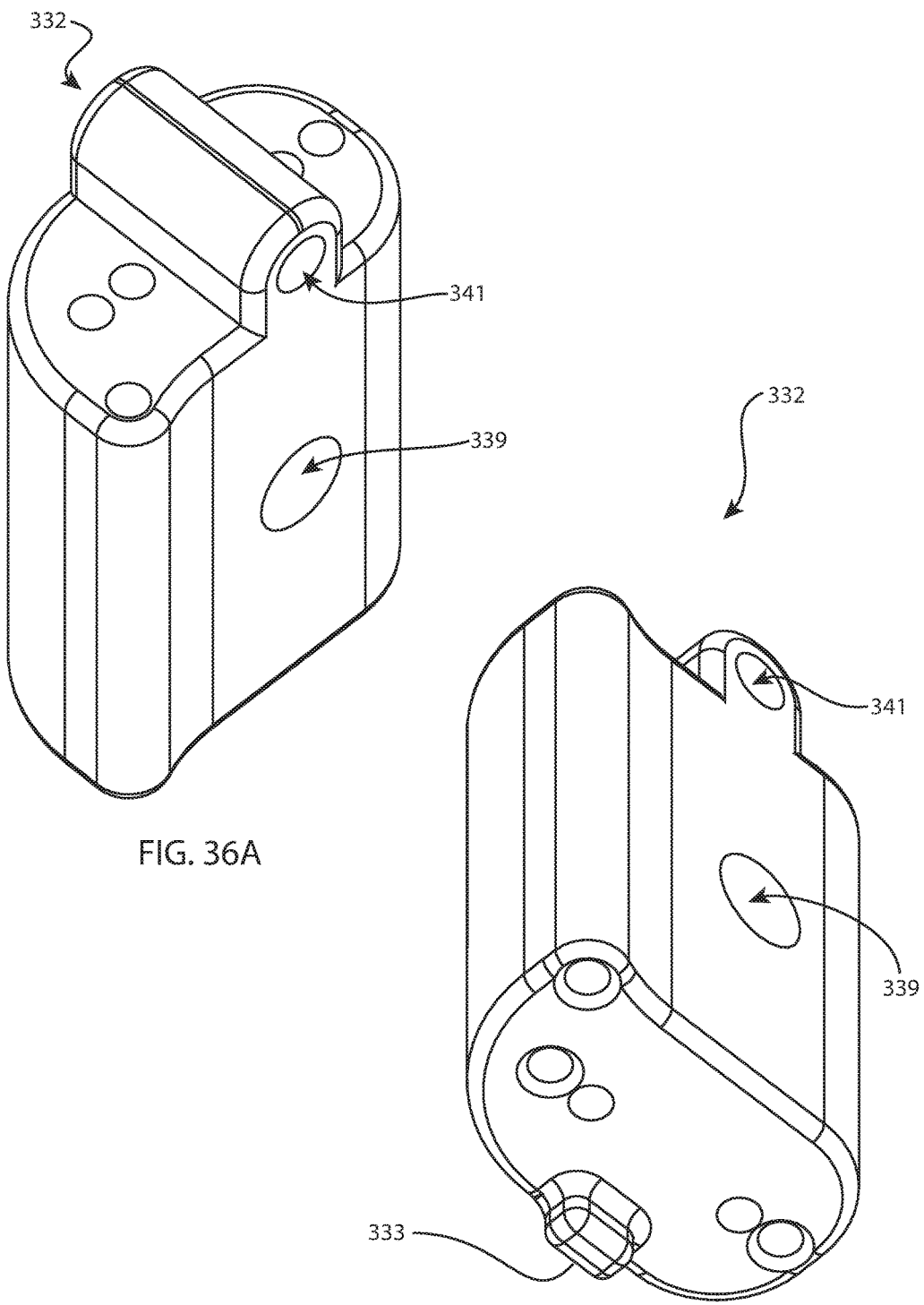
FIG. 36A is a perspective view of a femoral base block of the instrument system of FIG. 35.
FIG. 36B is another perspective view of the femoral base block of FIG. 36A from a different direction.
Figure 37:
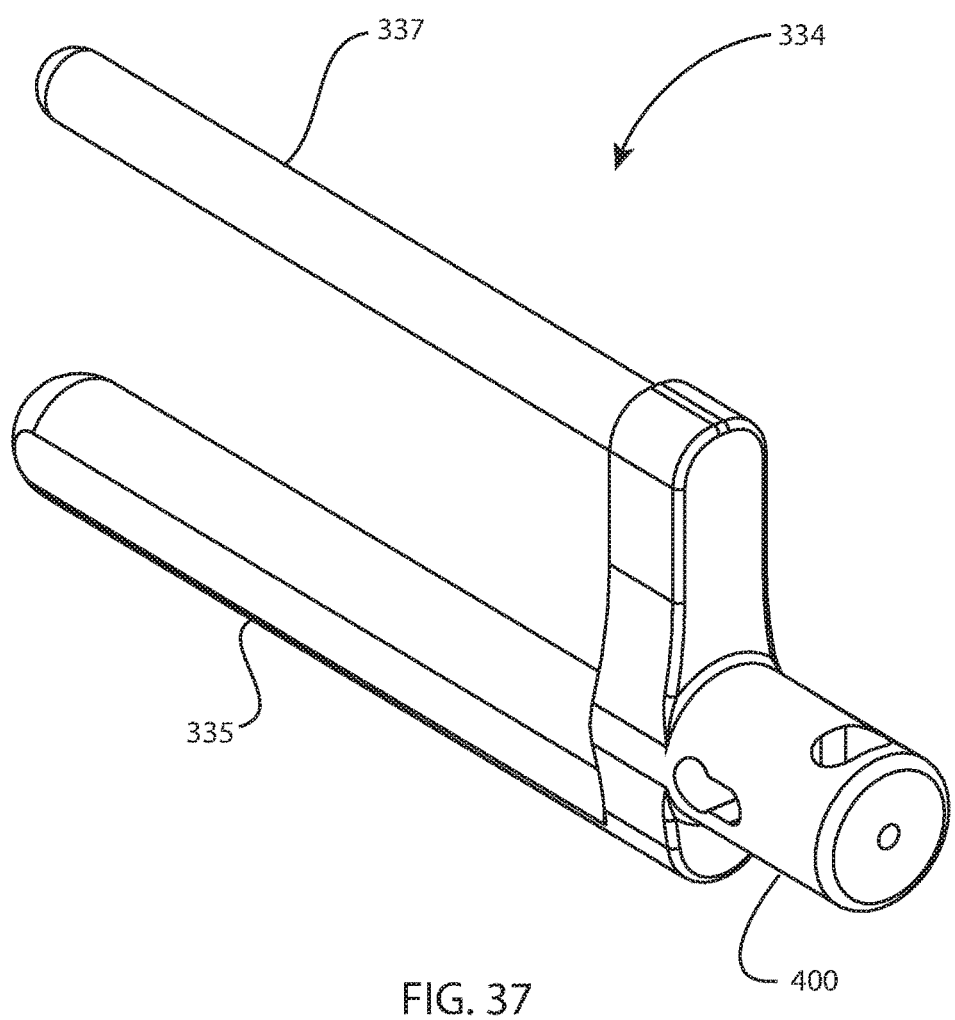
FIG. 37 is a perspective view of a translation bar of the femoral base block assembly of FIG. 35.
Figure 40A:
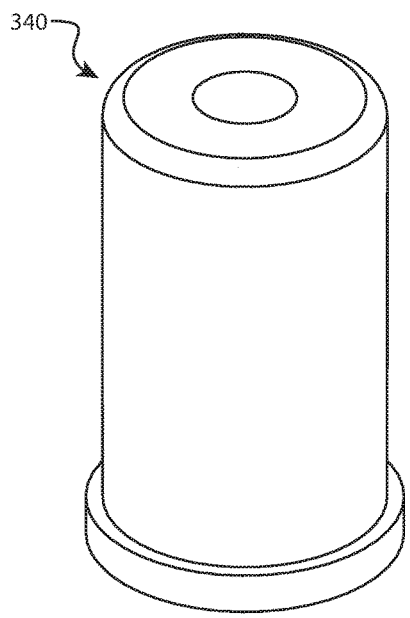
FIG. 40A is a perspective view of a bottom component of the femoral base block assembly of FIG. 35.
Figure 40B:
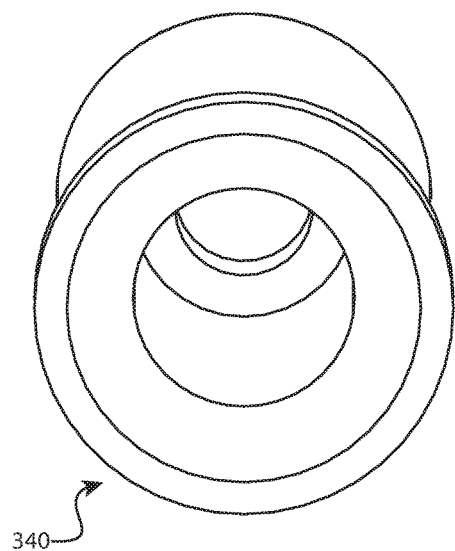
FIG. 40B is another perspective view of the bottom component of FIG. 40A from a different direction.
Figure 41A:
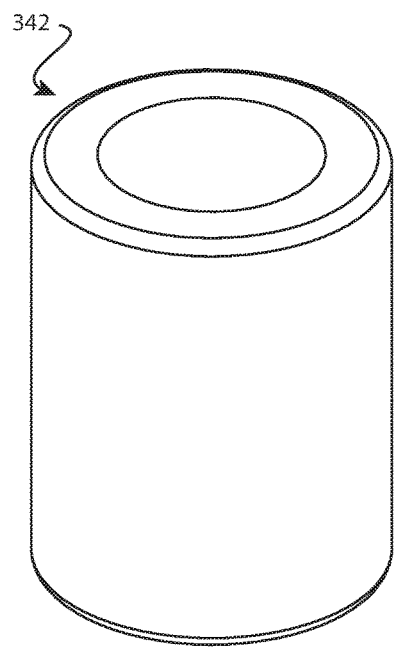
FIG. 41A is a perspective view of a socket of the femoral base block assembly of FIG. 35.
Figure 41B:
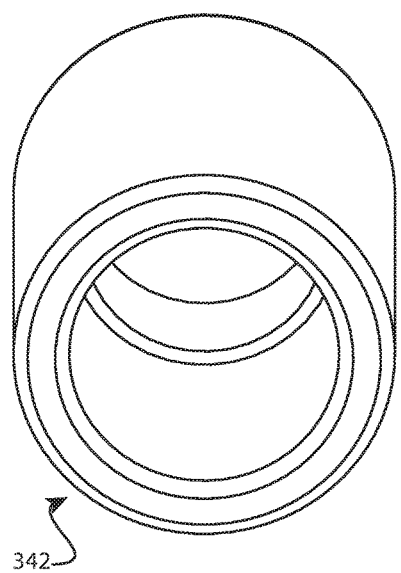
FIG. 41B is another perspective view of the socket of FIG. 41A from a different direction.
Figure 43A:
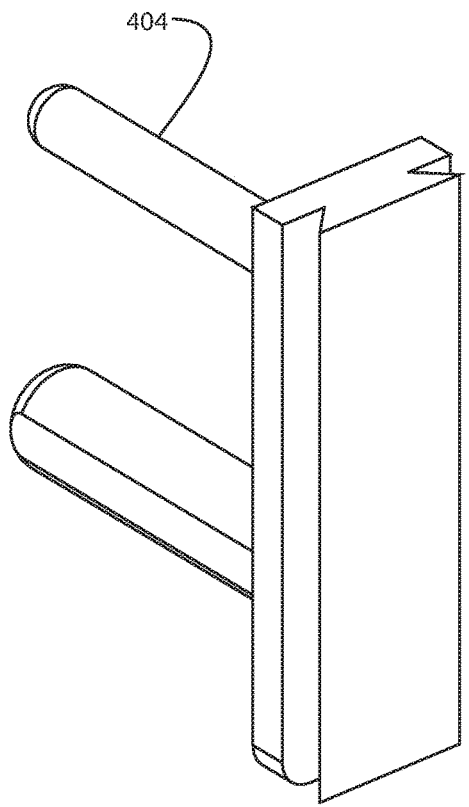
FIG. 43A is a perspective view of the translation bar of FIG. 42A.
Figure 43B:
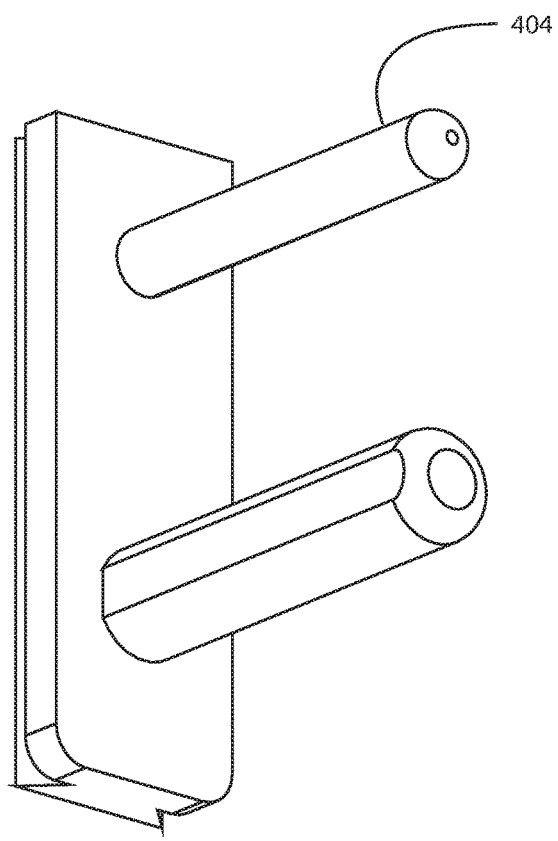
FIG. 43B is another perspective view of the translation bar of FIG. 43A from a different direction.
Figure 44A:
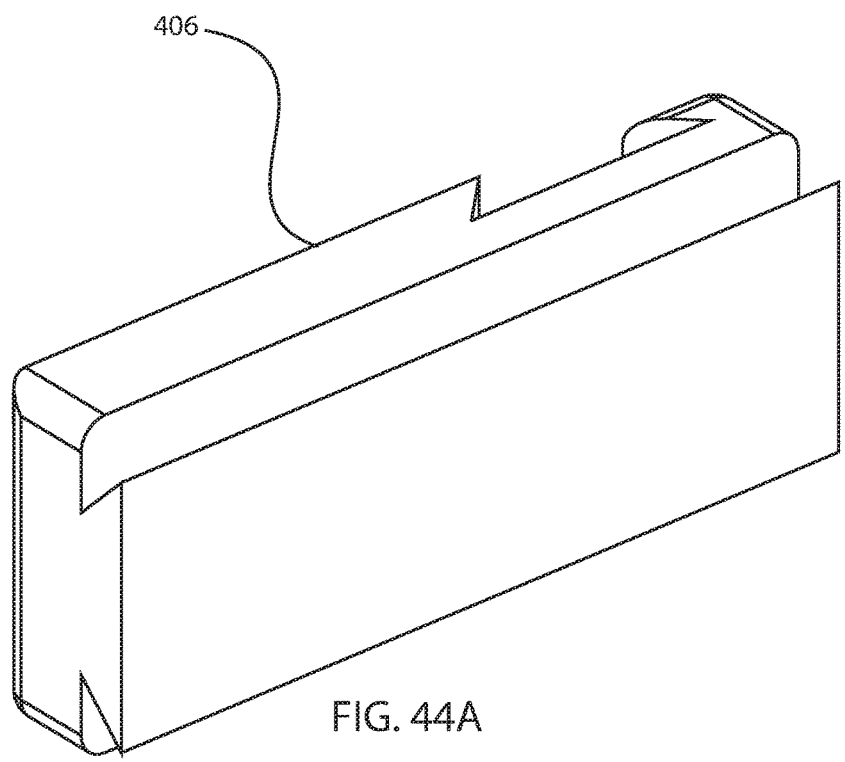
FIG. 44A is a perspective view of the slide of FIG. 42A.
Figure 44B:
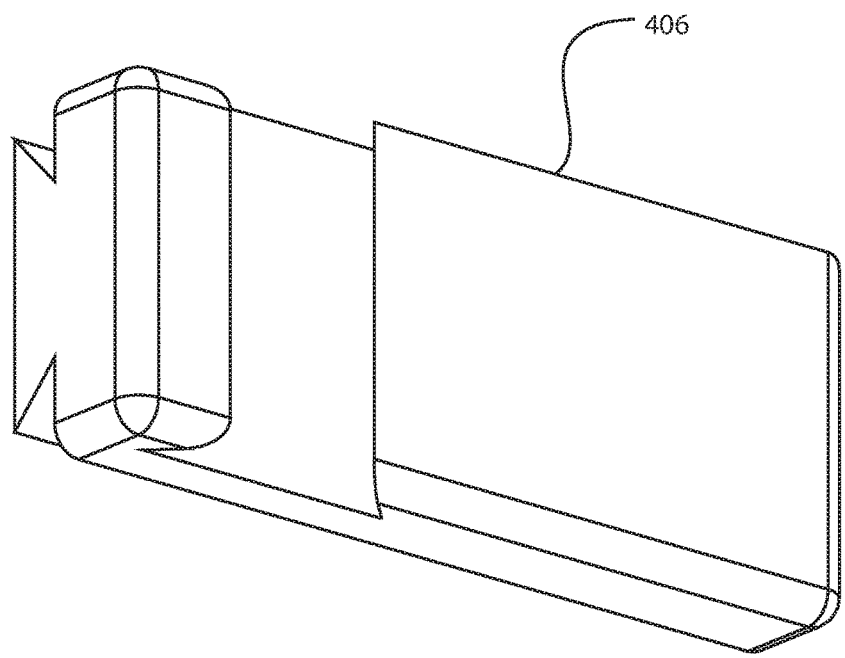
FIG. 44B is another perspective view of the slide of FIG. 44A from a different direction.
Figure 45A:
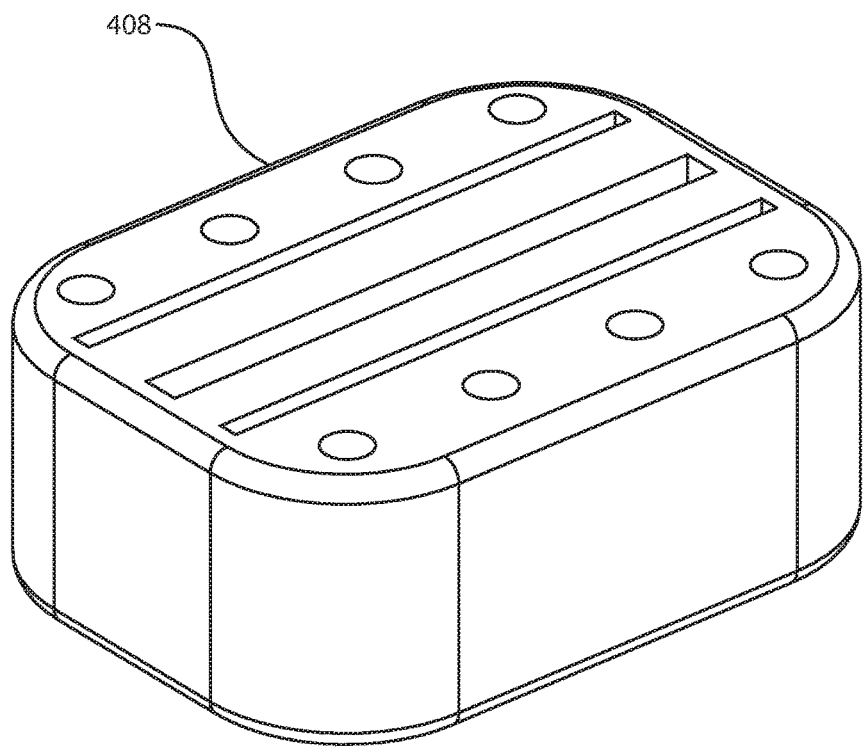
FIG. 45A is a perspective view of the cut guide of FIG. 42A.
Figure 45B:
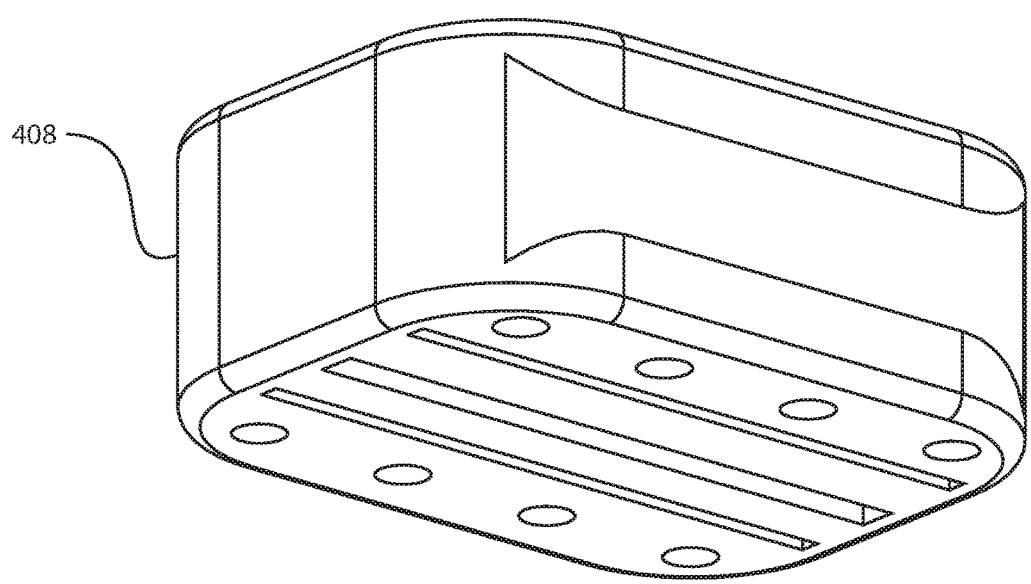
FIG. 45B is another perspective view of the cut guide of FIG. 45A from a different direction.
Figure 46:
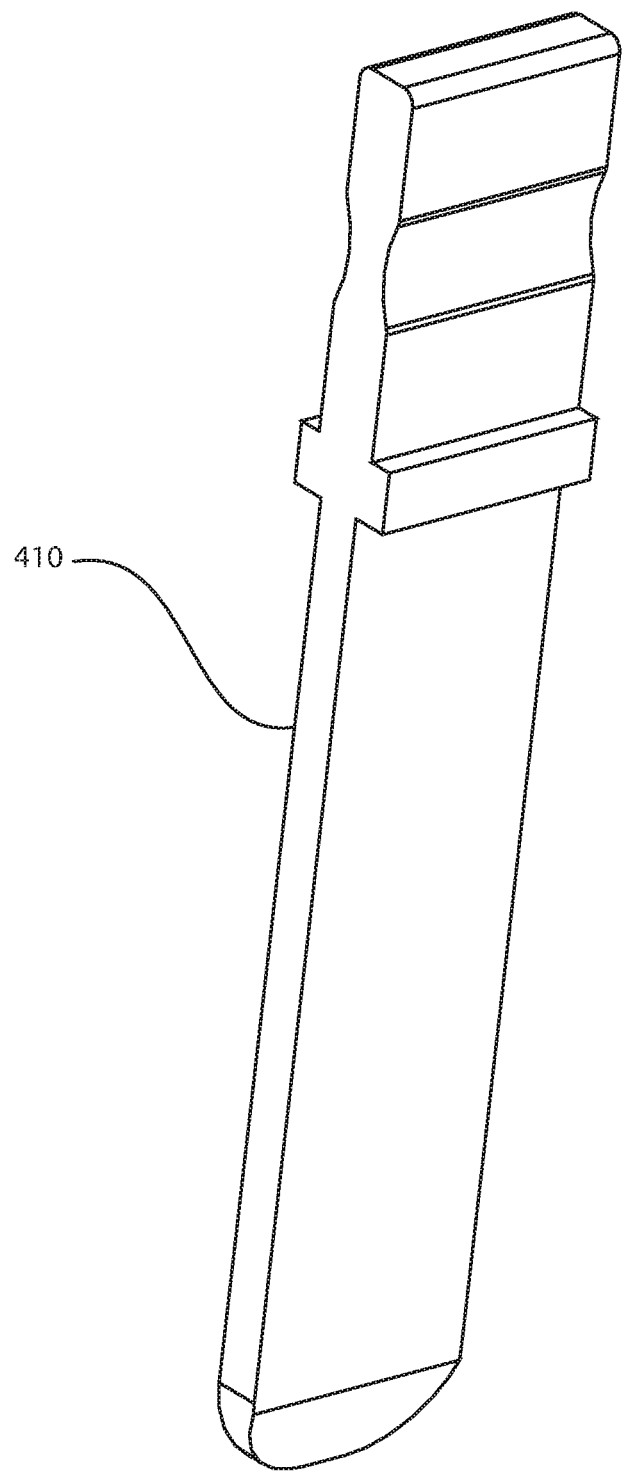
FIG. 46 is a perspective view of the condyle probe of FIG. 42A.

Referring to FIGS. 42A-46, another translation bar 404, a slide 406, a cut guide 408, and a condyle probe 410 may all be substituted into the femoral base block assembly 330 of FIG. 35 instead of the translation bar 334, knob 336, top component 338, bottom component 340, and socket 342. The translation bar 404, slide 406, cut guide 408, and condyle probe 410 may be referred to collectively as an alternate translation/cut guide assembly 402. The alternate translation/cut guide assembly 402 may be applicable to bicompartmental or bicondylar knee arthroplasty, or unicompartmental or unicondylar knee arthroplasty. The alternate translation/cut guide assembly 402 may be particularly applicable to unicompartmental or unicondylar knee arthroplasty due to the X-Y translation provided by the double dovetail slide design, which provides anterior-posterior and medial-lateral sliding adjustment in addition to the superior-inferior sliding adjustment provided by the translation bar 404. The cut guide 408 includes slots for distal femoral and proximal tibial cuts. The condyle probe 410 may be used to center the cut guide 408 across the joint space.

Referring to FIGS. 47A-49B, yet another instrument system 500 is shown. This instrument system is designed to be used while the knee joint is in full extension and maximally distracted, while referencing the distal anterior femoral cortex, and while the leg is properly aligned with the mechanical axis 202 of the leg. The femoral head center 120, distal femur 102, proximal tibia 106, and ankle/second toe/anterior tibial crest or spine are all simultaneously aligned with the mechanical axis 202. The system 500 includes apparatus for referencing Whiteside's line while the distal femoral condyles are intact, before any femoral resection occurs, and locking this reference into the apparatus to guide later surgical steps.

The instrument system 500 is illustrated with a combination of components that is similar to those depicted in FIGS. 21A and 21B for instrument system 300. The instrument system 500 may include a base 502, a femoral riser 504 (also known as a handle), a femoral extension rod 506, a tibial connection block 508, and a tibial pin guide 510. The instrument system 500 may also include a tibial riser 509 like tibial riser 312, and a tibial extension rod 511 like tibial extension rod 313, alignment rod 156, femoral extension rod 306, or femoral extension rod 506. The illustrated tibial extension rod 511 is identical to the femoral extension rod 506. The instrument system 500 may also include additional components as described below for FIGS. 47A-68B. At least the femoral riser 504, tibial connection block 508, tibial pin guide 510, and, if present, tibial riser 509 may be disposable components molded from polymer materials.

Figures 50A, 50B:
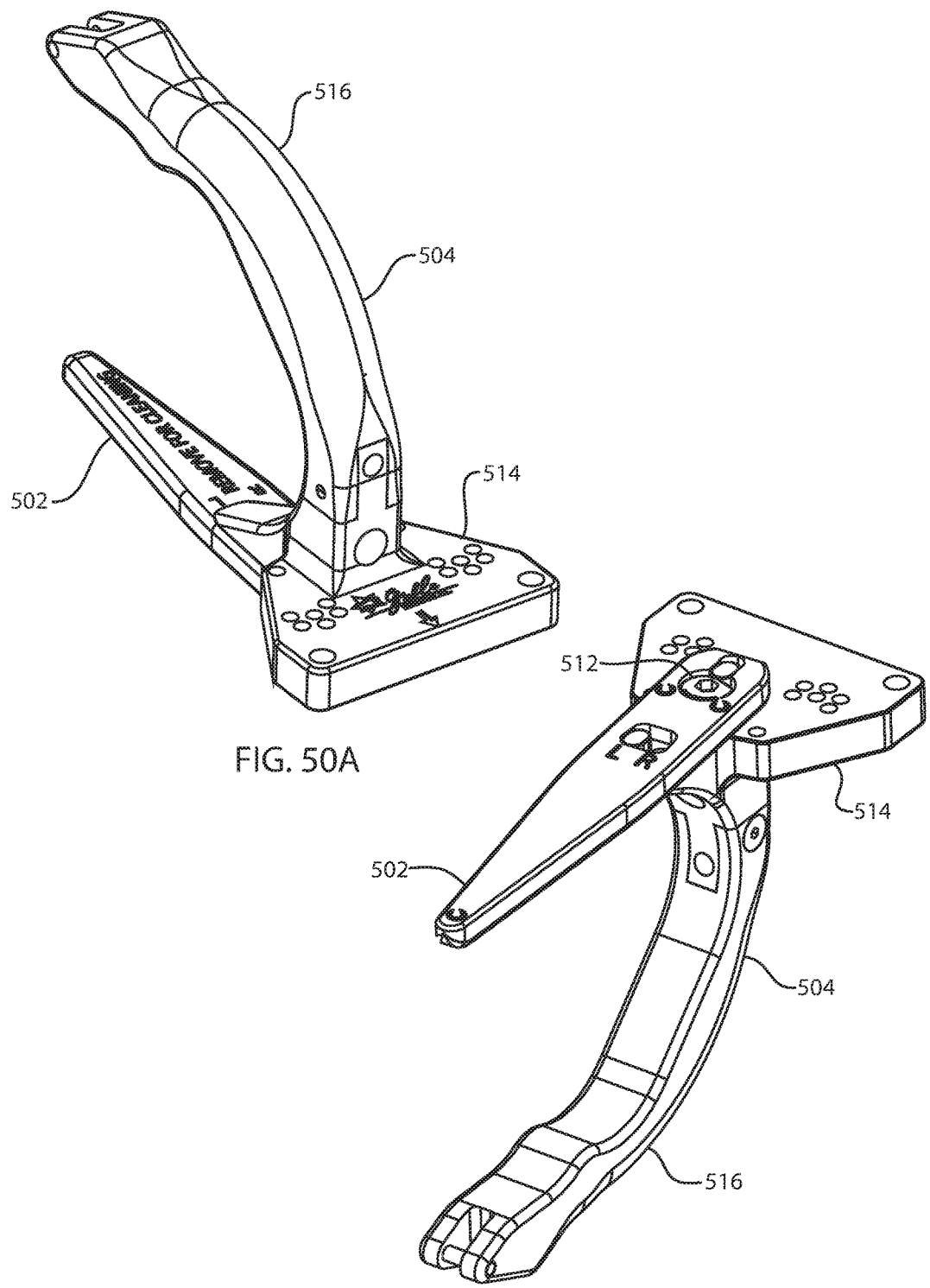
FIG. 50A is a perspective view of a base and a femoral riser assembly of the instrument system of FIG. 47A.
FIG. 50B is another perspective view of the base and femoral riser assembly of FIG. 50A from a different direction.

Referring to FIGS. 50A and 50B, the femoral riser 504 is shown coupled to the base 502. A cam 512 is visible coupled to the base 502 in FIG. 50B. The femoral riser 504 may include a femoral pin guide 514 and a handle 516. The femoral pin guide 514 and handle 516 may be rigidly coupled together in a releasable or permanent manner. The femoral pin guide 514 and handle 516 may be fabricated as a unitary part. The coupled femoral riser 504 and base 502 may be analogous to the coupled femoral riser 304, base 302, and a portion of the tibial-femoral pin guide 310.

Referring to FIGS. 51A and 51B, the base 502 is an elongated plate with a bone contacting surface 518 and an opposite top surface 520. The base 502 has a distal portion 522 and a proximal portion 524 which tapers to a proximal tip which is narrower than the distal portion. A longitudinal axis 503 extends along the length of the base 502 between the distal and proximal portions 522, 524; only a portion of the axis 503 is shown in FIG. 51B for clarity. The base 502 includes a hole 526 through the distal portion 522. A pocket 528 is recessed into the bone contacting surface 518 around the hole 526. The pocket 528 may be described as a counterbore around the hole 526. The base 302 includes three oblong holes 530, 532, 534 recessed into the top surface 520. Each hole 530, 532, 534 includes a shelf 536 on at least one side wall. The shelves 536 are illustrated on the distal side walls of the holes 530, 532, 534 but may be on the proximal side walls or elsewhere instead. The base 502 may include one or more frictional elements, such as spikes 538 protruding from the bone contacting surface 518.

Referring to FIGS. 51C and 51D, the cam 512 includes a body 540 and a spindle 542 that protrudes from the body. The body 540 has a non-circular cross-sectional profile around the spindle 542 so that as the cam 512 turns about the spindle, the body can exert (or release) a side force against another object. Thus the body 540 has a locking portion 546 and an unlocking portion 548 which may be generally opposite the locking portion, or at least circumferentially spaced apart from the locking portion. The locking portion 546 extends radially farther from the spindle 542 than the unlocking portion 548 does. The body 540 may include a resilient portion 550, which may be between the locking portion 546 and the unlocking portion 548, or may be associated with the locking portion 546 as illustrated. The resilient portion 550 is characterized by a slot 552 which enables the resilient portion to flex under load. The spindle 542 is cylindrical and is narrower than the body 540. A torque socket 544 is recessed into the body 540 opposite the spindle 542, and concentric with the spindle. The torque socket 544 is illustrated as a hex socket, although a square, cruciate, hexalobular, or other non-circular shape could be substituted.

The cam 512 is coupled to the base 502 by inserting the spindle 542 into the hole 526 and inserting the body 540 into the pocket 528. The cam 512 may be captive to the base 502, at least during use. The cam 512 may be removable from the base 502.

Figure 52A:
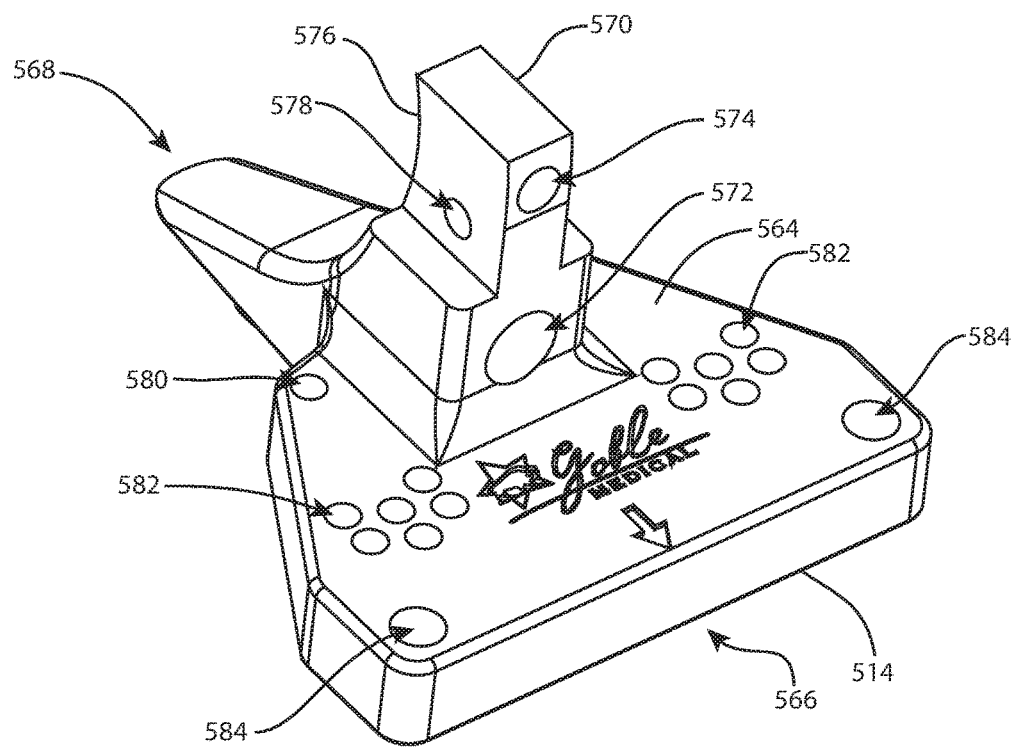
FIG. 52A is a perspective view of a femoral pin guide of the femoral riser assembly of FIG. 50A.
Figure 52B:
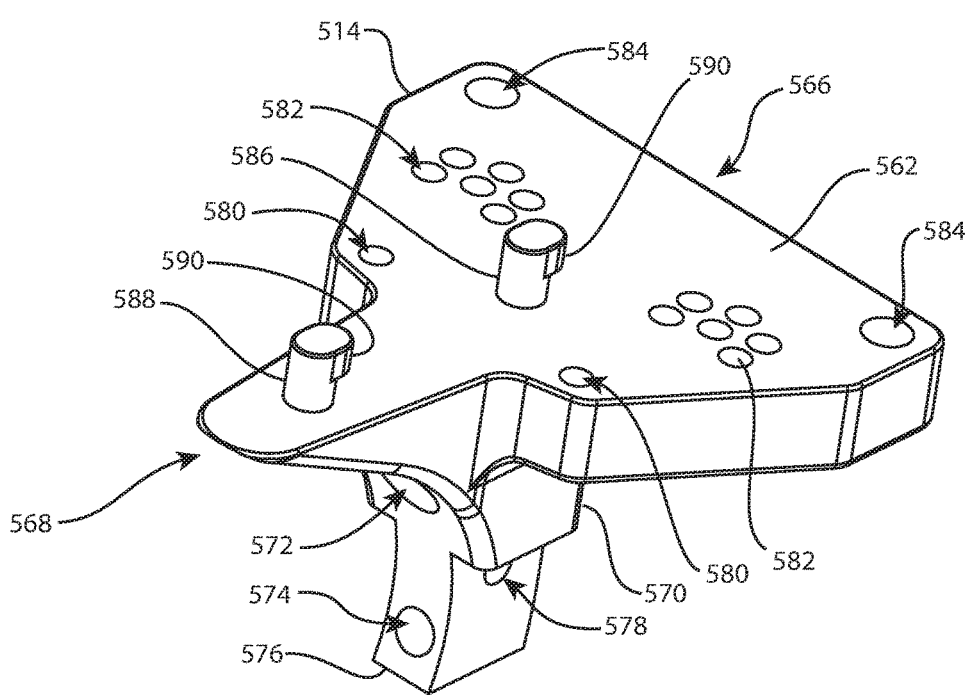
FIG. 52B is another perspective view of the femoral pin guide of FIG. 52A from a different direction.

Referring to FIGS. 52A and 52B, the femoral pin guide 514 is a roughly triangular plate with a bone facing surface 562 and an opposite top surface 564. The femoral pin guide 514 has a distal portion 566 and a proximal portion 568 which tapers to a proximal tip which is narrower than the distal portion. A stalk 570 protrudes from the top surface 564. A first hole 572 extends through the stalk 570 in a proximal-distal direction and a second, smaller diameter, hole 574 extends through the stalk parallel to the first hole 572 and farther from the top surface 564. The stalk 570 terminates in a narrow tab 576 which has a hole 578 that is transverse to the holes 572, 574. The femoral pin guide 514 is illustrated with several holes 580, 582 which receive bone pins. Two proximal holes 580 are shown and twelve distal holes 582 are shown, although any number of holes may be provided. The left and right holes 580 converge together as they approach the bone facing surface 562. The left group and the right group of holes 582 also converge together as they approach the bone facing surface 562. This is best appreciated in FIGS. 73 and 77. The left group and the right group of holes 582 may include individual holes 582 that are spaced apart widely enough in the medial-lateral direction that all five femoral resections 206, 214, 216, 218, 220 may be cut, and a femoral trial component coupled to the resected distal femur, while the base 502 and femoral pin guide 514 remain secured to the femur 100. These widely spaced holes 582 may be located outboard of the mounting holes 584 so that bone pins driven through the widely spaced holes 582 penetrate the epicondyles. Briefly referring to FIGS. 52A and 80A, a first widely spaced hole 582 may be medial to the medial mounting hole 584 and a second widely spaced hole 582 may be lateral to the lateral mounting hole 584, "medial" and "lateral" used with reference to the patient's body. The femoral pin guide 514 may be widened to support the widely spaced holes 582. Advantageously, this detail enables the knee joint, with trial components, to be taken through a range of motion with the femoral pin guide 514 secured to the femur 100. Femoral alignment to the mechanical axis 202 of the leg is thus preserved until the knee is proven to function satisfactorily with trial components. The femoral pin guide 514 includes two mounting holes 584 in the distal medial and lateral corners. A hole (not shown) may be present centered between the mounting holes 584. The femoral pin guide 514 includes a first post 586 and a second post 588 protruding from the bone facing surface 562. Each post 586, 588 includes an oblong tab 590 on at least one side of the free end of the post. The tabs 590 are shown on the distal sides of the posts 586, 588 but may be on the proximal sides or elsewhere instead to match the oblong holes 530, 532, 534 of the base 502. The femoral pin guide 514 may be analogous to a proximal portion of the tibial-femoral pin guide 310.

Referring to FIGS. 53A and 53B, the handle 516 is an elongated curved part with a distal portion 592 and a proximal portion 594. The distal portion 592 includes a slot 596. A hole 598 extends through the handle 516 across the slot 596. The proximal portion 594 includes a slot 600. A hole 602 extends through the handle 516 across the slot 600.

Figure 48A:
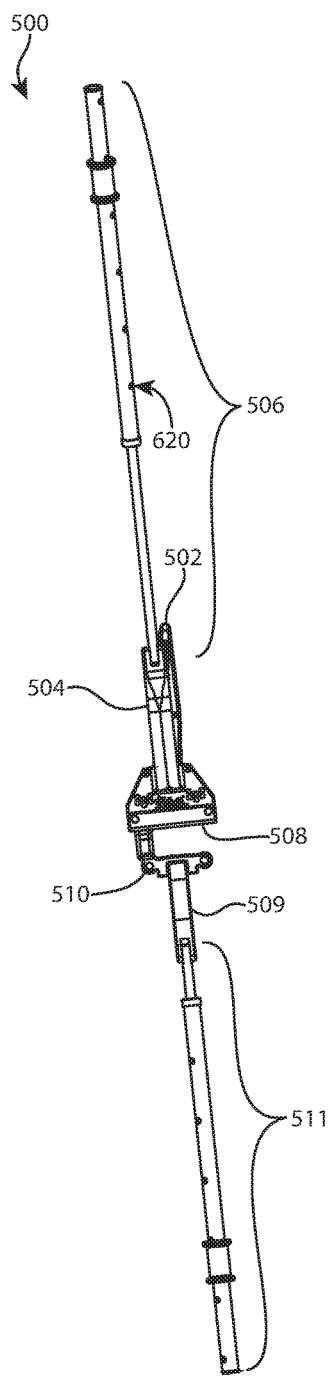
FIG. 48A is a top view of the instrument system of FIG. 47A.
Figure 48B:
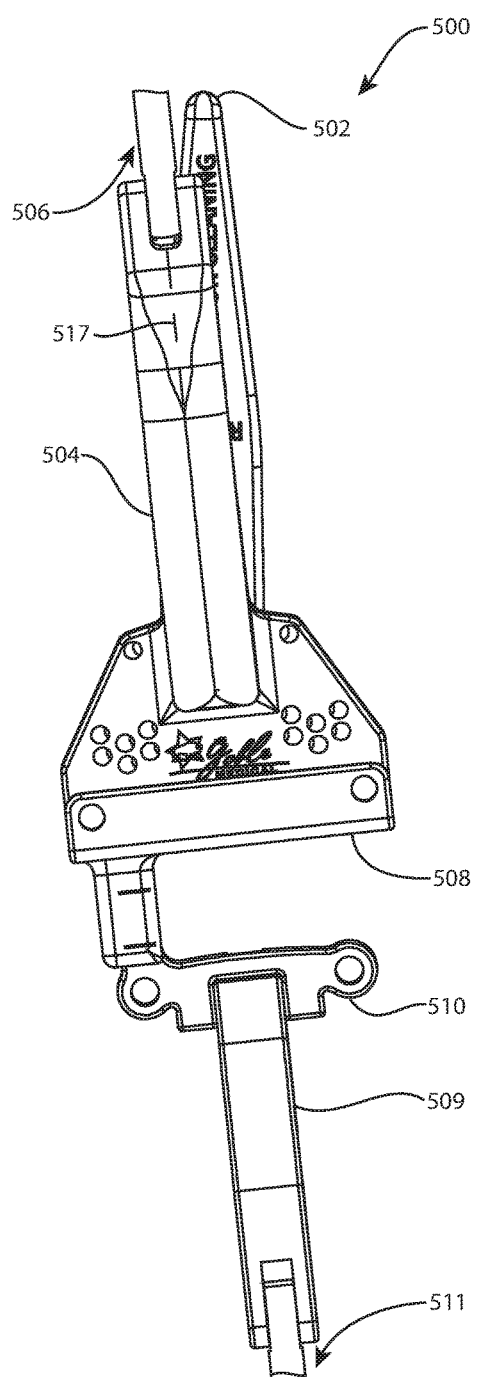
FIG. 48B is an enlarged detail view of a portion of the instrument system of FIG. 48A.

The handle 516 is coupled to the femoral pin guide 514 by inserting the tab 576 into the slot 596 so that the proximal portion 568 and the proximal portion 594 extend in the same direction, aligning the hole 598 with the hole 578, and inserting a fastener through the holes 598, 578. Referring briefly to FIGS. 48B and 80B, the handle 516 extends along the mechanical axis 202 of the leg in use, at least in an anterior view. Therefore, the handle 516 may be said to have a longitudinal axis 517 that extends in a proximal-distal direction.

The femoral riser 504 may be rigidly coupled to the base 502 in one or more orientations. In the example shown, the femoral riser 504 may be coupled to the base 502 in two orientations corresponding to a left or right knee with a fixed angle 204. The first post 586 is received in oblong hole 530 and the second post 588 is received in oblong hole 532 or oblong hole 534. Then the cam 512 may be rotated within the pocket 528 until the resilient portion 550 contacts the first post 586, pushing the tabs 590 to engage the shelves 536 to lock the base 502 to the femoral riser 504. Additional orientations may be provided by providing additional oblong holes, like holes 532, 534, to receive the second post 588. For example, an array of four oblong holes may be provided to provide a choice of left or right knee and small or large angle 204 between the mechanical axis 202, represented by the axis 517 of the handle 516, and the femoral shaft axis 200, represented by the axis 503 of the base 502. It is contemplated that the angle 204 may be adjustable between 4 degrees and 7 degrees by providing an array of oblong holes to receive the second post 588. Briefly referring to FIGS. 49B and 77, when the femoral riser 504 is coupled to the base 502, the bone facing surface 562 of the femoral pin guide 514 is spaced apart anteriorly with respect to the bone contacting surface 518 of the base. This spacing is advantageous because it complements the natural anatomy of the intact distal femur by avoiding contact with the anterior aspects of the femoral condyles, and also because it provides room to make the anterior femoral resection 214 and anterior femoral chamfer cut 216 with the base 502 and femoral riser 504 coupled to the femur 100.

Figure 49A:
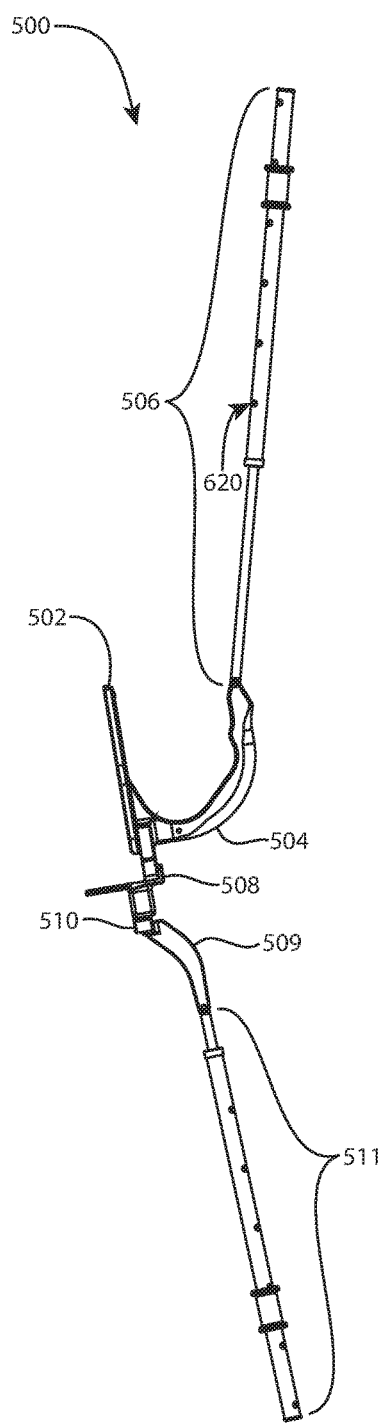
FIG. 49A is a side view of the instrument system of FIG. 47A.
Figure 54A:
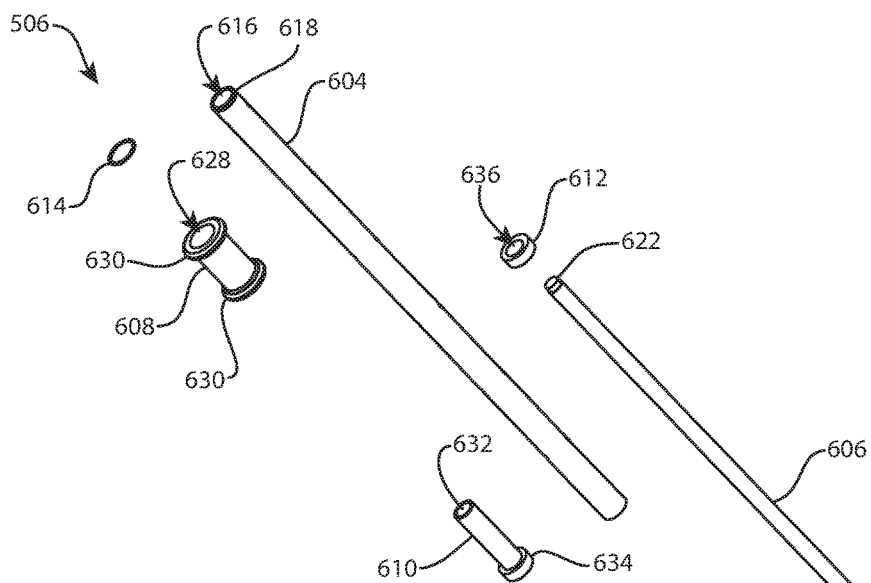
FIG. 54A is an exploded perspective view of a femoral extension rod assembly of the instrument system of FIG. 47A.
Figure 54B:
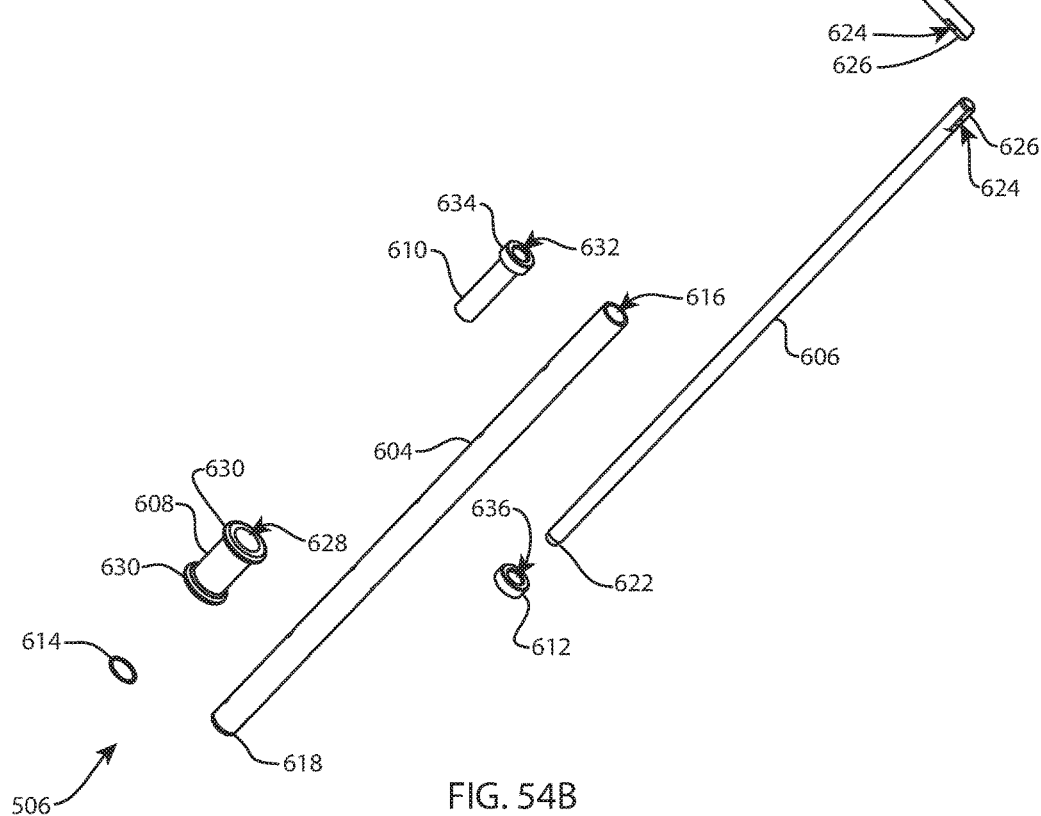
FIG. 54B is another exploded perspective view of the femoral extension rod assembly of FIG. 54A from a different direction.

Referring to FIGS. 54A and 54B, the femoral extension rod 506 may be a telescopic assembly including an outer extension rod 604, an inner extension rod 606, a spool 608, a sleeve 610, a ring 612, and a retaining ring 614. The femoral extension rod 506 may alternately be a fixed length rod like femoral extension rod 306. The outer extension rod 604 is a tubular part with a central longitudinal hole 616 and an external groove 618 around one end. One or more ports 620 may pierce the outer extension rod 604. The ports 620 are best seen in FIGS. 48A and 49A. The inner extension rod 606 is a cylindrical rod with an external groove 622 around one end and a transverse hole 624 through an opposite end. The inner extension rod 606 may include flats 626 on both sides around the hole 624. The spool 608 is a tubular part with a central longitudinal hole 628 and an external flange 630 projecting outwardly around each end. The sleeve 610 is a tubular part with a central longitudinal hole 632 and an external flange 634 projecting outwardly around one end. The ring 612 has a central hole 636.

The femoral extension rod 506 may be assembled as follows. The ring 612 is permanently fixed to the groove 622 of the inner extension rod 606. The ring 612 and inner extension rod 606 slide into the outer extension rod 604 so that the ring 612 is pointed toward the same end of the assembly as the groove 618 of the outer extension rod 604. The inner extension rod 606 slides into the sleeve 610, and the sleeve slides into the outer extension rod 604 so that the flange 634 abuts the end of the outer extension rod 604 opposite the groove 618. The sleeve 610 is fixed to the outer extension rod 604. The ring 612 is too large to pass through the sleeve 610. The spool 608 slides over the outer extension rod 604. The retaining ring 614 rests in the groove 618 of the outer extension rod. The retaining ring 614 and the flange 634 are each too large to pass through the spool 608.

Figures 47A, 47B:
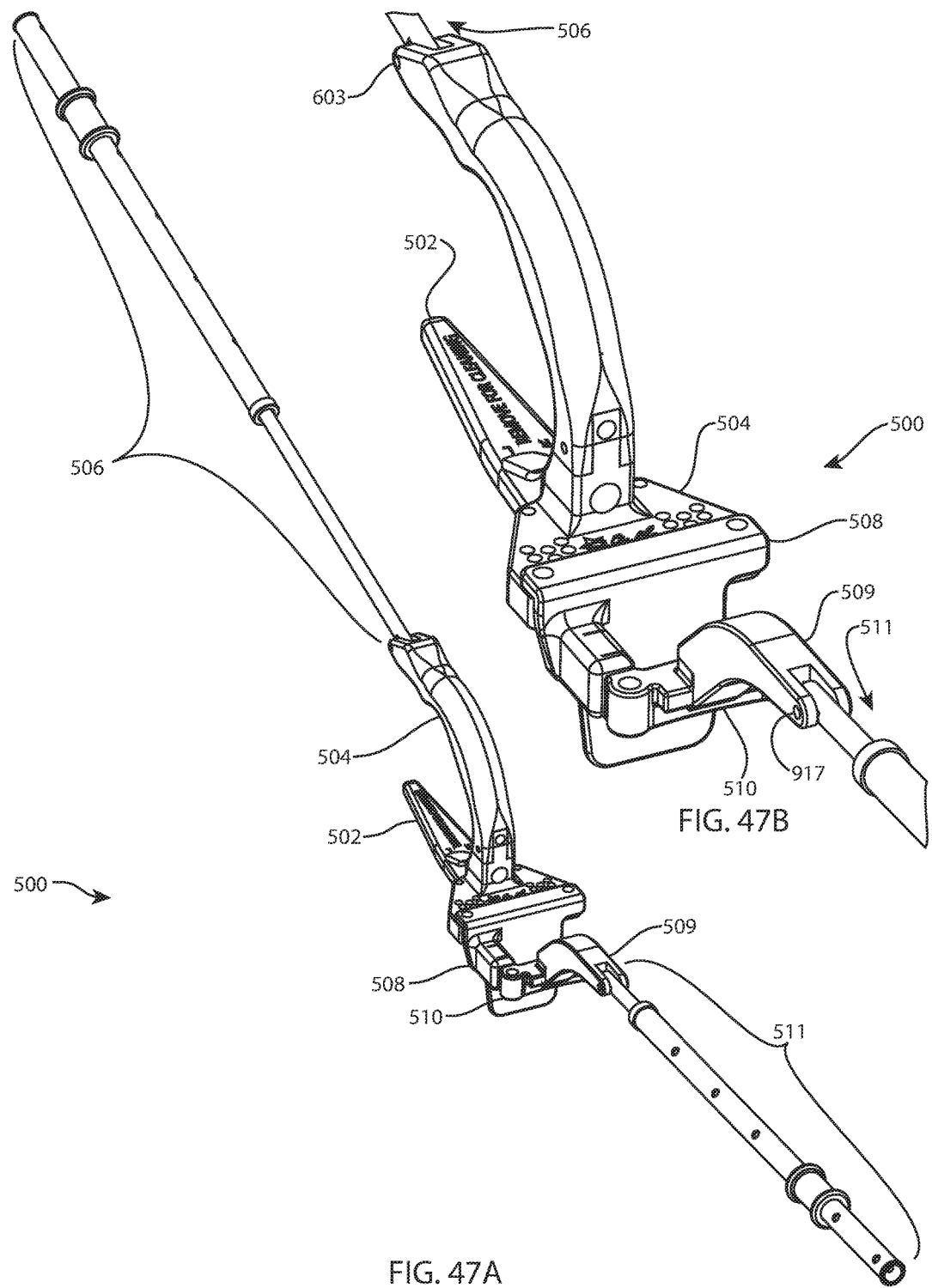
FIG. 47A is a perspective view of yet another instrument system, showing an assembly of components similar to those shown in FIG. 21A.
FIG. 47B is an enlarged detail view of a portion of the instrument system of FIG. 47A.
Figure 49B:
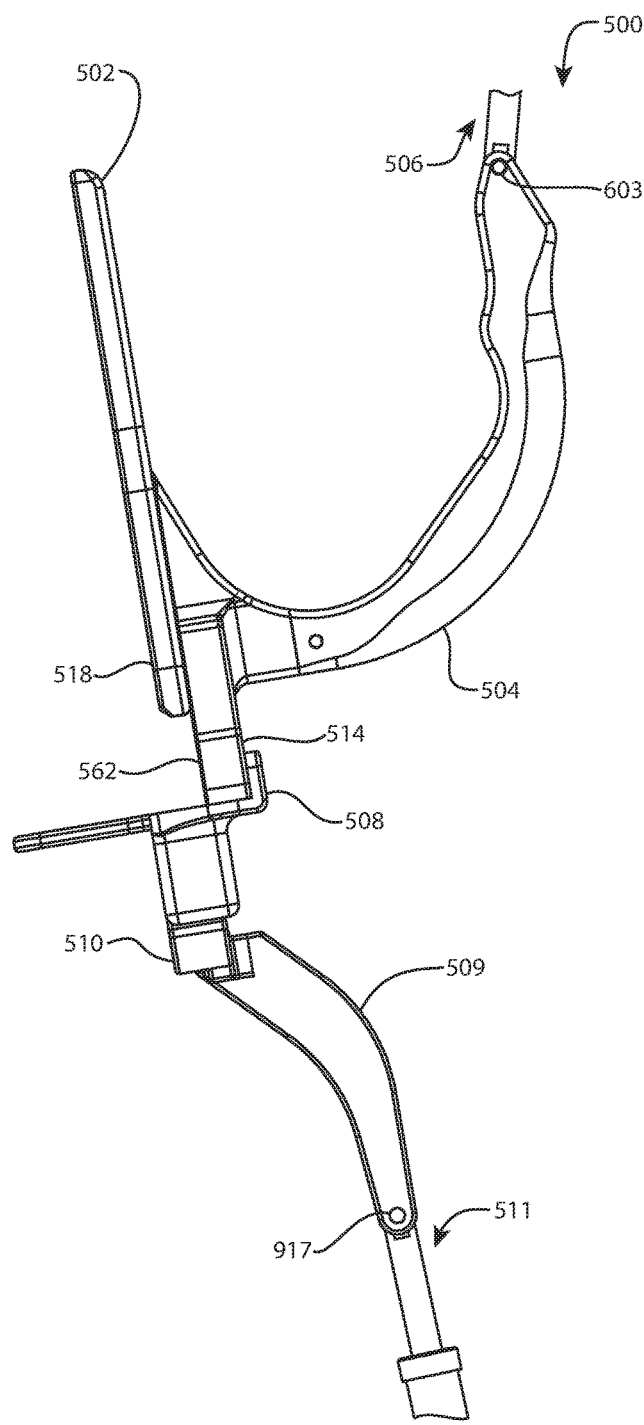
FIG. 49B is an enlarged detail view of a portion of the instrument system of FIG. 49A.

The assembled femoral extension rod 506 may be coupled to the handle 516 by inserting the end of the inner extension rod 606 with the hole 624 into the slot 600, aligning the hole 602 with the hole 624, and inserting a fastener through the holes 602, 624 to form a hinge 603 (FIGS. 47B and 49B). The femoral extension rod 506 is free to pivot about the hinge 603. In use, the femoral extension rod 506 pivots in an anterior-posterior direction which is generally parallel to the sagittal plane. The femoral extension rod 506 is constrained against pivoting in a medial-lateral direction which is generally parallel to the coronal plane. The outer extension rod 604 is free to slide (telescope) along the inner extension rod 606 at least until the ring 612 abuts the sleeve 610, and the spool 608 is free to slide along the outer extension rod at least between the flange 634 and the retaining ring 614. However, the spool 608 is captive to the outer extension rod 604, which is captive to the inner extension rod 606. The end of the inner extension rod 606 with the hole 624 is the distal end of the femoral extension rod 506, and the end of the outer extension rod 604 with the retaining ring 614 is the proximal end of the femoral extension rod.

Figure 55A:
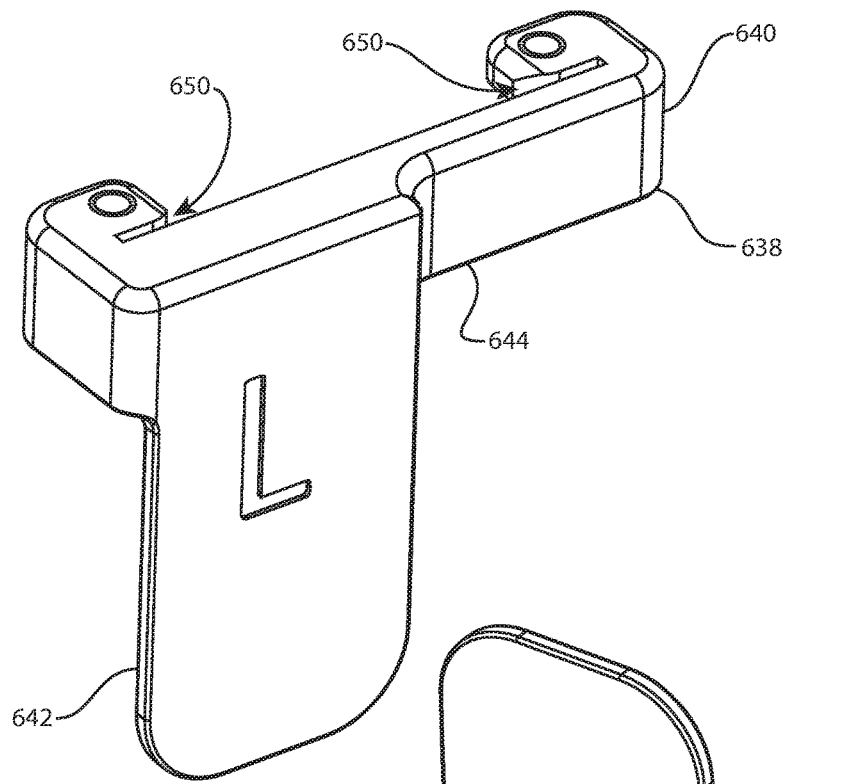
FIG. 55A is a perspective view of a distal femoral condyle block for use with the instrument system of FIG. 47A.
Figure 55B:
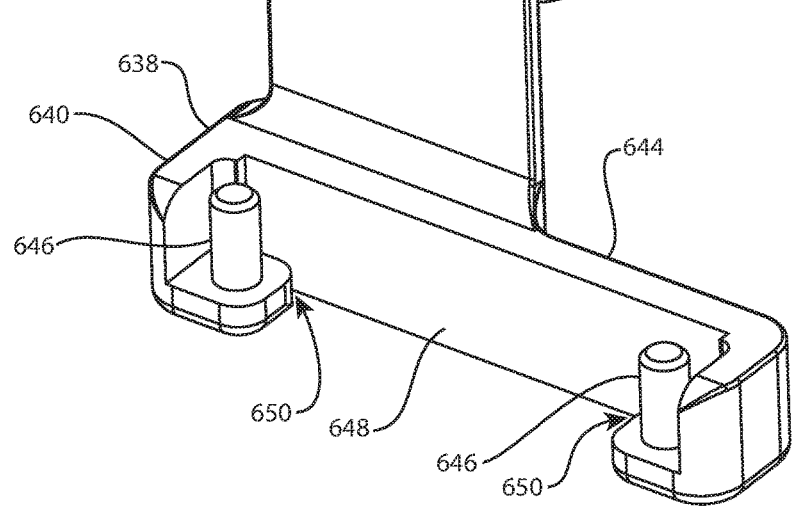
FIG. 55B is another perspective view of the distal femoral condyle block of FIG. 55A from a different direction.

Referring to FIGS. 55A and 55B, a distal femoral condyle block 638 includes a mounting portion 640 and a paddle 642. The mounting portion 640 includes a bar 644 with a peg 646 extending from each end of the bar. The pegs 646 are parallel, and in this example they are separate pins which are coupled to the bar 644. However, the pegs 646 may be integrally formed with the bar 644. The bar 644 includes a planar cut guide surface 648 which faces the pegs 646 and which may extend into one or more slots 650 beside the pegs. The cut guide surface 648 may be entirely enclosed within a single slot 650 rather than having an open middle portion as shown. The slot(s) 650 may be referred to as saw slots or cut guide slots. The paddle 642 in this example is a generally rectangular flat plate which is integrally formed with the bar 644 and extends from the bar 644 in the same direction as the pegs 646. The illustrated distal femoral condyle block 638 is for a left knee, hence the paddle 642 is positioned to rest on a distal medial femoral condyle in use.

The distal femoral condyle block 638 releasably couples to the femoral riser 504. The pegs 646 fit into the mounting holes 584 so that the cut guide surface 648 faces the distal portion 566. There is room to pass a saw blade between the cut guide surface 648 and the distal portion 566 to make a distal femoral resection 206; thus a saw slot or cut guide slot is formed between these features. The distal femoral condyle block 638 may function as a distal femoral cut guide.

The illustrated distal femoral condyle block 638 is designed so that the proximal surface of the paddle 642 is 9 mm from the distal surface of the distal portion 566 when the distal femoral condyle block 638 is coupled to the femoral riser 504, and so that the cutting slot is formed between the cut guide surface 648 and the distal surface of the distal portion 566. However, there are situations where it may be desirable to take more than 9 mm of bone from the distal femoral condyles, for example in patients with flexion contracture where only the extension gap requires adjustment so that the knee can be brought to full extension. Flexion contracture may only be appreciated after an initial 9 mm distal femoral resection 206 has been made and the knee joint has been taken through a range of motion with trial components. The system 500, as well as the other systems disclosed herein, may be adapted to provide multiple locations (cutting slot positions) for the distal femoral resection 206. The distal femoral condyle block 638 may be designed so that the proximal surface of the paddle 642 is more than 9 mm from the distal surface of the distal portion 566 when the distal femoral condyle block 638 is coupled to the femoral riser 504. Dimensions between 11 mm and 17 mm are contemplated. This positions the distal surface of the distal portion 566 sufficiently proximal to the distal medial femoral condyle so that the distal femoral resection 206 may be adjusted (re-cut) to take 2 mm, up to 8 mm, more bone from the distal femoral condyles, from an initial distal femoral resection 206 that is 9 mm proximal to the distal medial femoral condyle. The distal femoral condyle block 638 may be designed with multiple discrete cutting slots, the distal-most cutting slot including the cut guide surface 648 spaced 9 mm from the proximal surface of the paddle 642, and the more proximal cutting slots incrementally spaced, for example 2 mm apart; or the distal femoral condyle block 638 may include a movable cutting slot that can be adjusted in the proximal-distal direction to remove 9 mm to 17 mm of bone from the distal femoral condyles; or a set of distal femoral condyle blocks 638 may be provided, each with a different distal femoral resection depth; or the distal femoral condyle block 638 may be used only to initially position the base 502 and the femoral riser 504, and one or more separate distal femoral cut blocks (not shown) may be provided, that releasably couple to the femoral riser 504 in the same way as the distal femoral condyle block 638. Of course the 17 mm example dimension may be larger or smaller as a matter of design choice. This paragraph further supports the advantages of keeping the base 502 and the femoral pin guide 514 secured to the femur 100 while the knee joint is taken through a range of motion with trial components. The distal femoral resection 206 may be adjusted (re-cut) in alignment with the mechanical axis 202 of the leg.

Figure 72A:
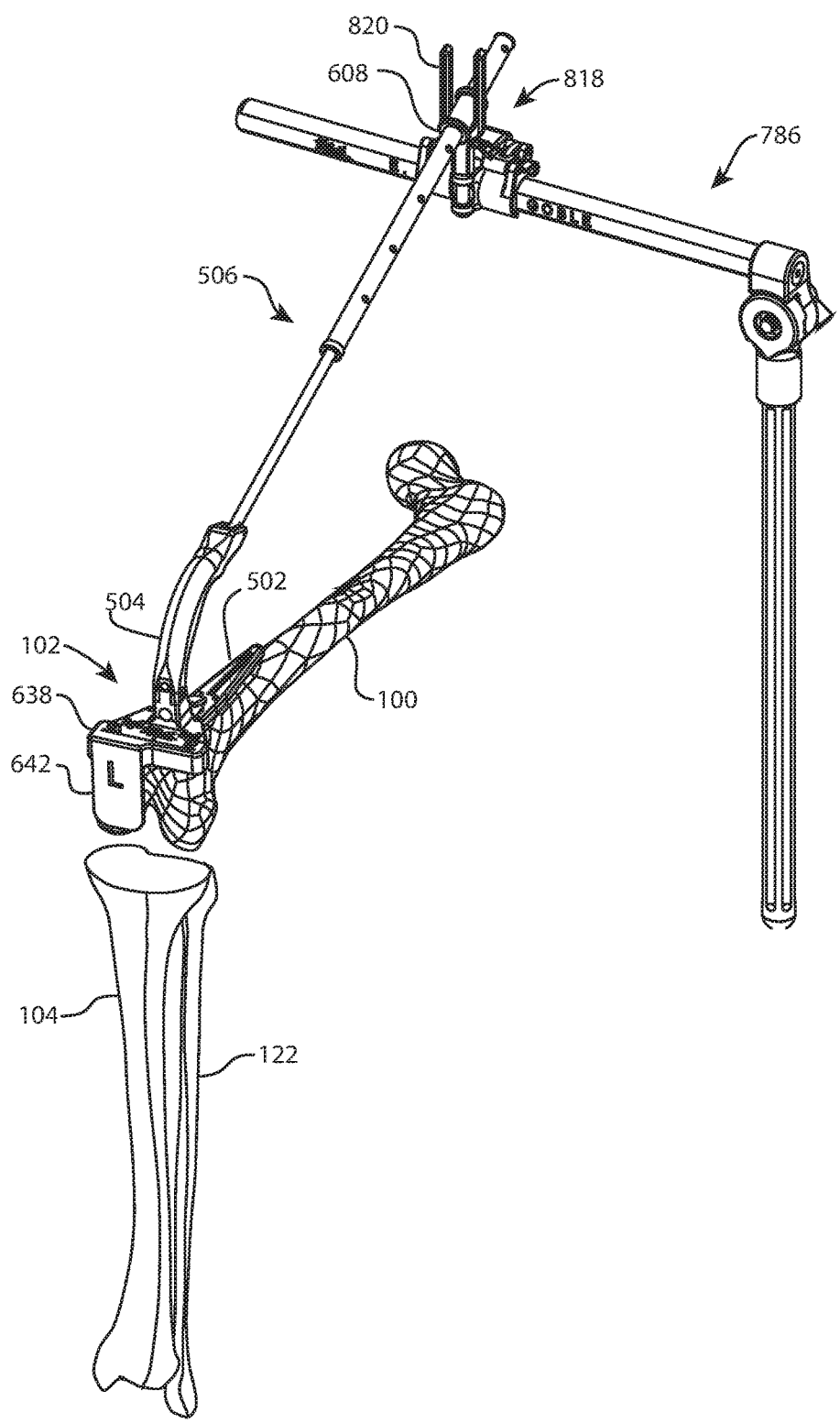
FIG. 72A is a perspective view of the femur, tibia, fibula, femoral support arm assembly, and target clamp assembly of FIG. 71, after positioning the base of FIG. 47A on the anterior distal femur, extending the femoral extension rod assembly of FIG. 47A through the target of the target clamp assembly, and coupling the distal femoral condyle block of FIG. 55A to the femoral riser assembly.
Figure 72B:
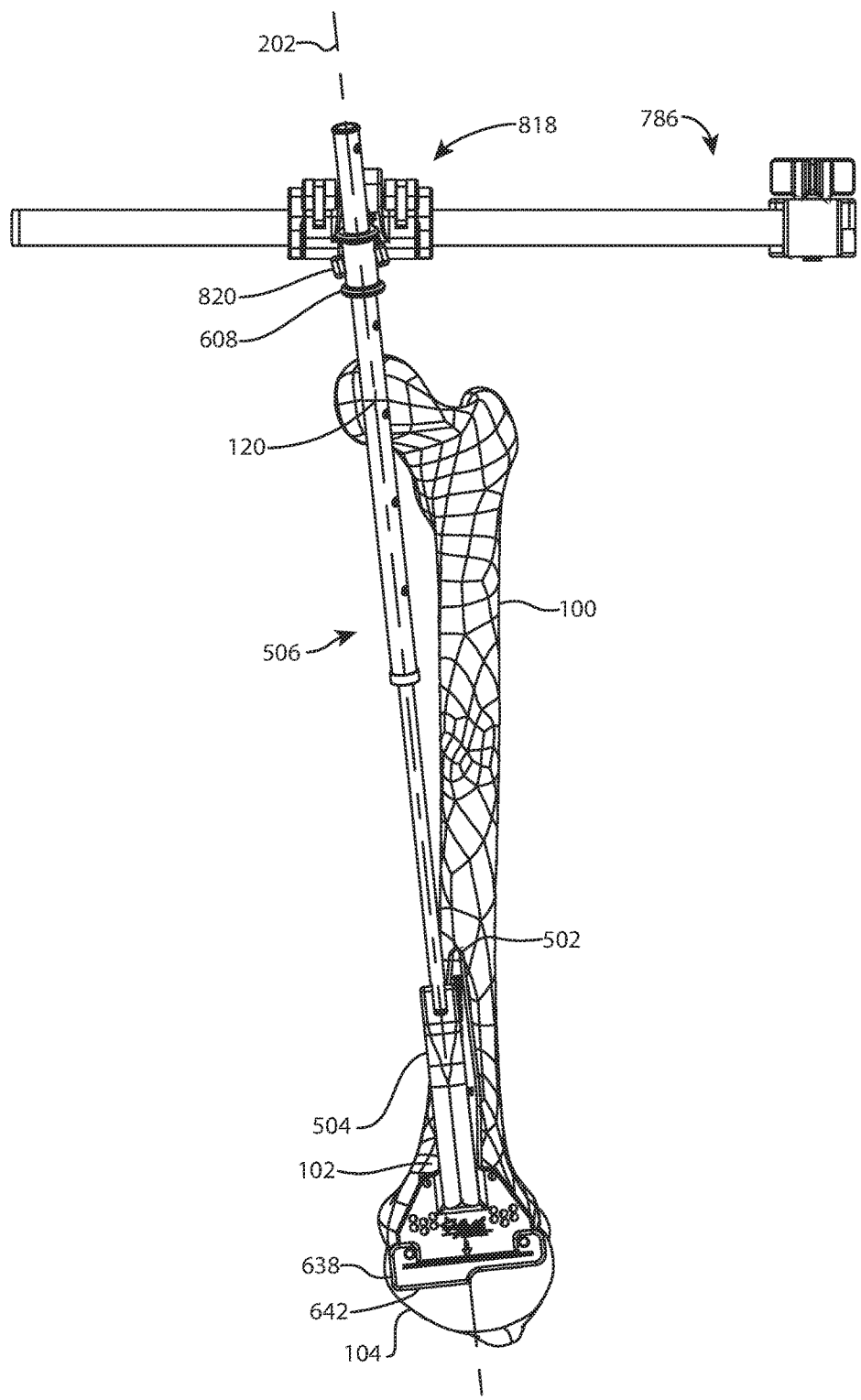
FIG. 72B is a top view of the femur, tibia, fibula, femoral support arm assembly, target clamp assembly, base, femoral riser assembly, distal femoral condyle block, and femoral extension rod assembly of FIG. 72A.
Figure 73:
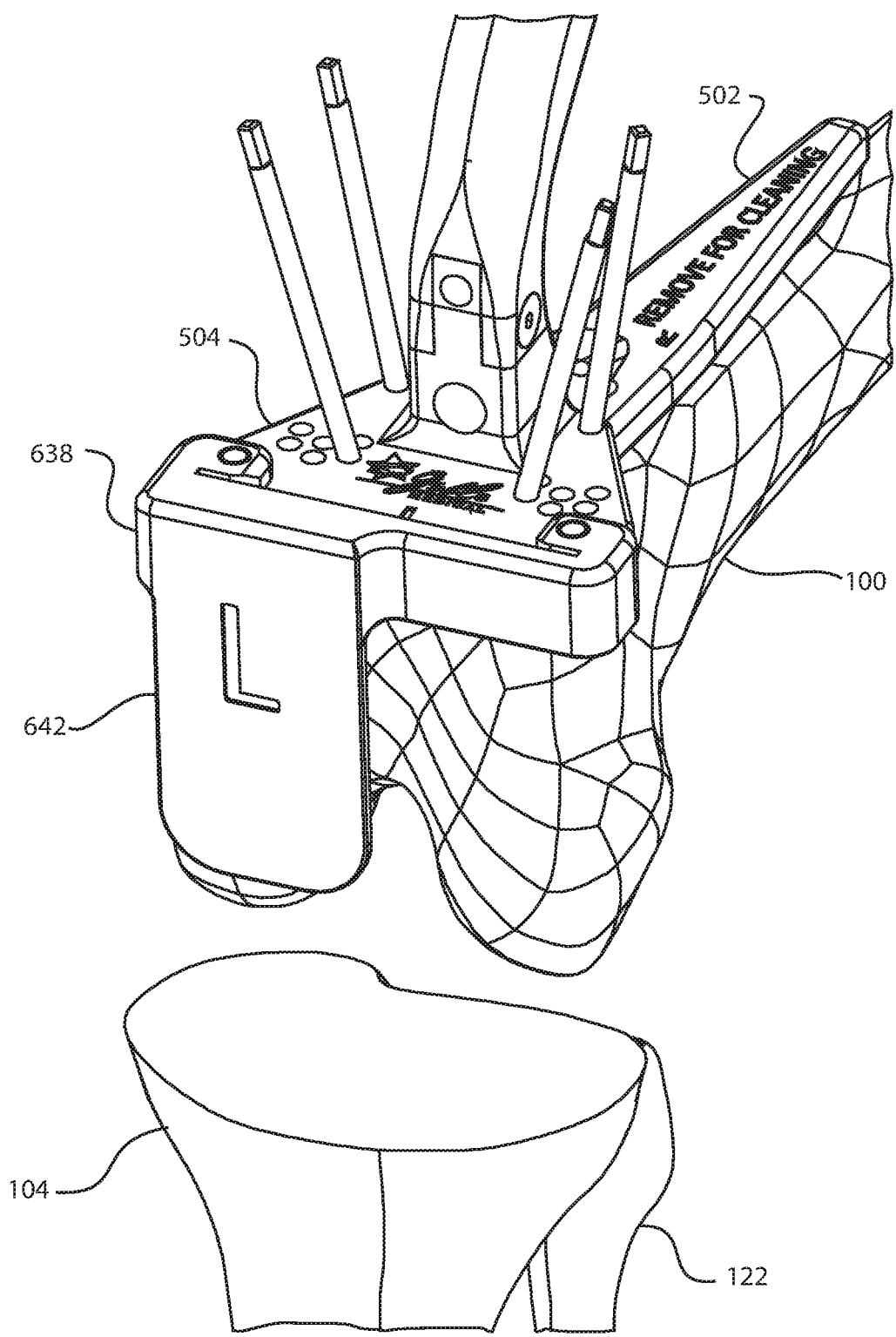
FIG. 73 is a perspective view of the femur, tibia, fibula, base, femoral riser assembly, and distal femoral condyle block of FIG. 72A, after fixing the femoral riser assembly to the anterior distal femur with pins.
Figure 75:
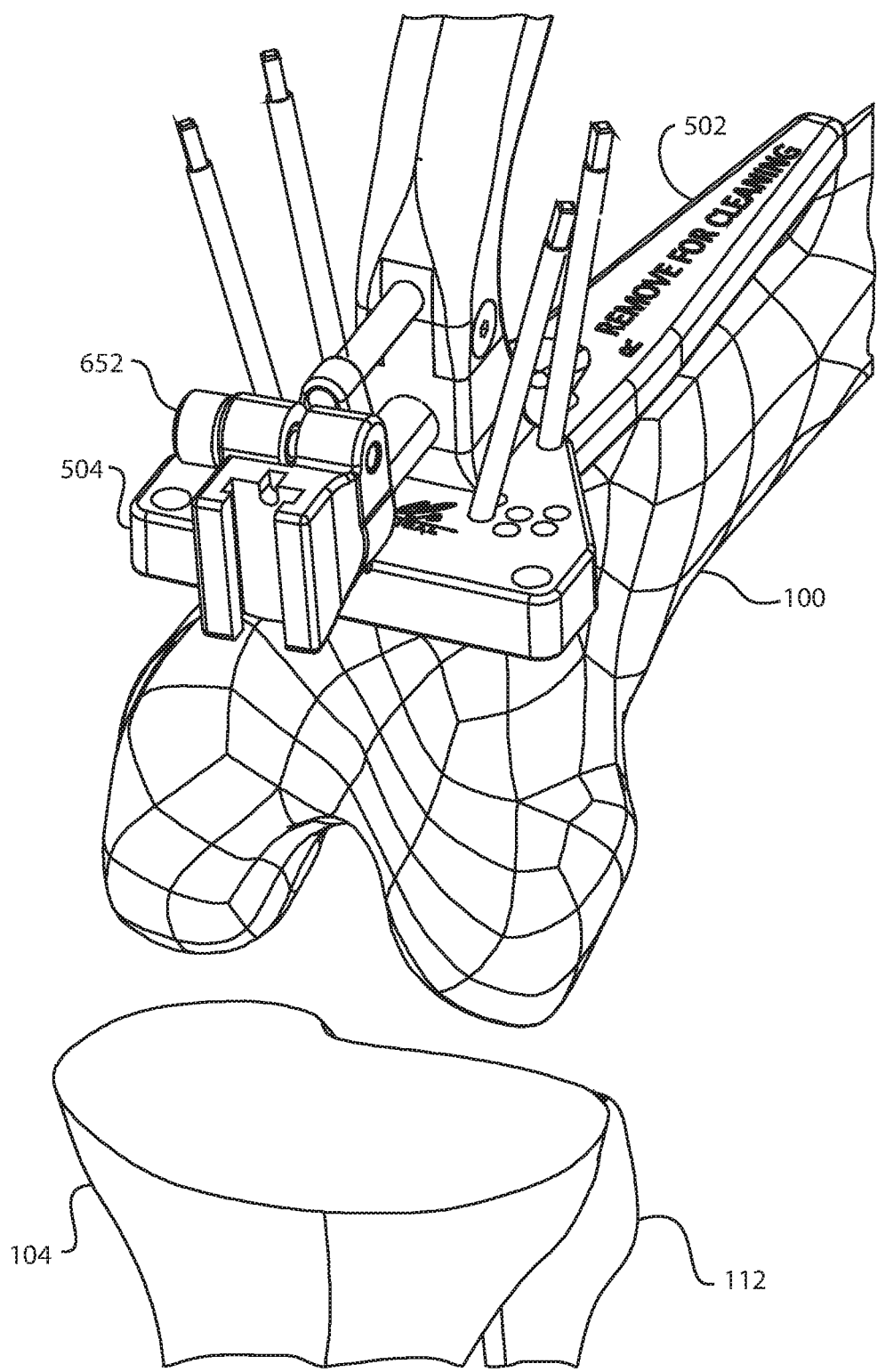
FIG. 75 is a perspective view of the femur, tibia, fibula, base, and femoral riser assembly of FIG. 74, after attaching the angle block assembly of FIG. 56A.
Figure 76:
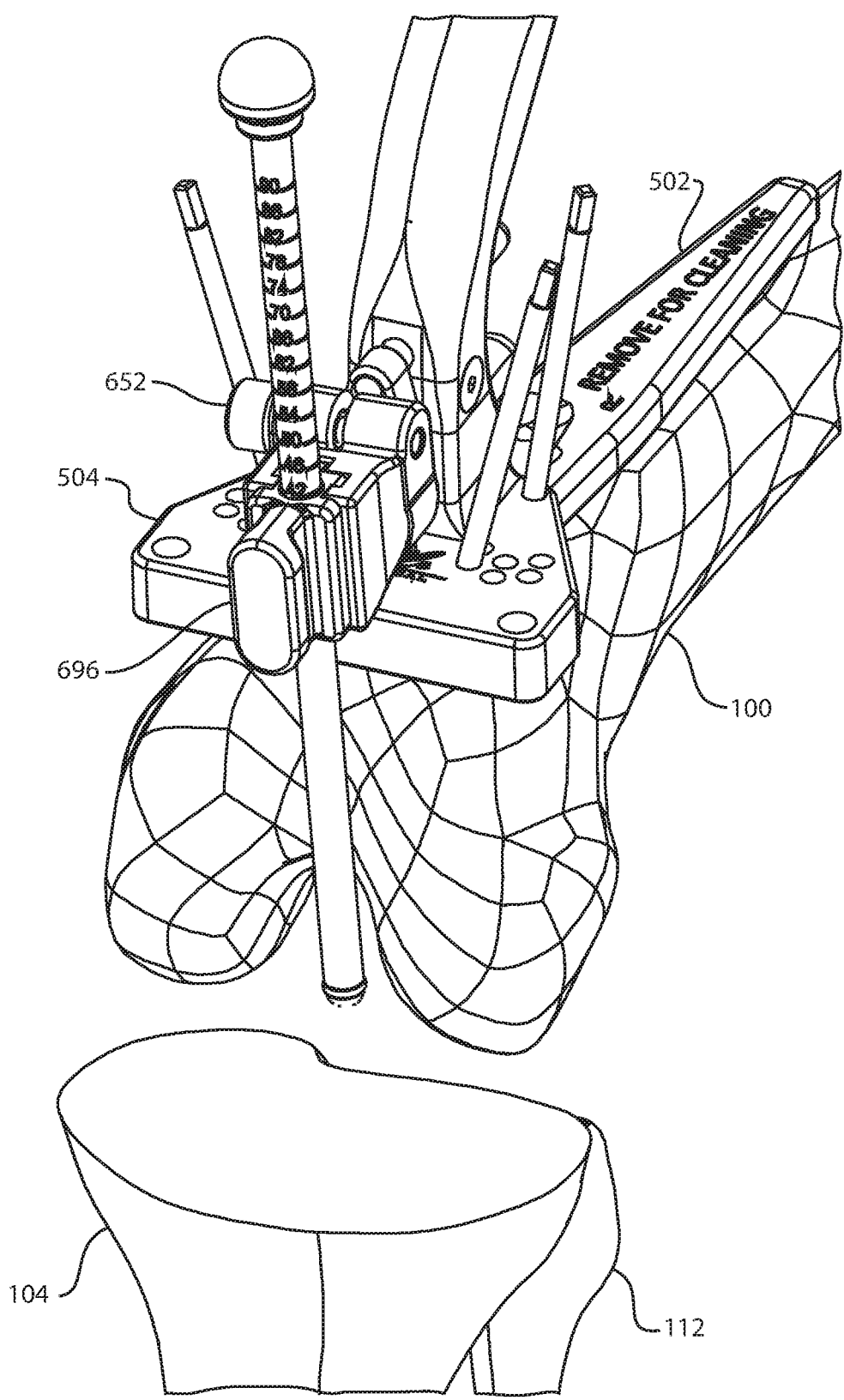
FIG. 76 is a perspective view of the femur, tibia, fibula, base, femoral riser assembly, and angle block assembly of FIG. 75, after coupling the Whiteside's line gage assembly of FIG. 58A to the angle block assembly.
Figure 77:
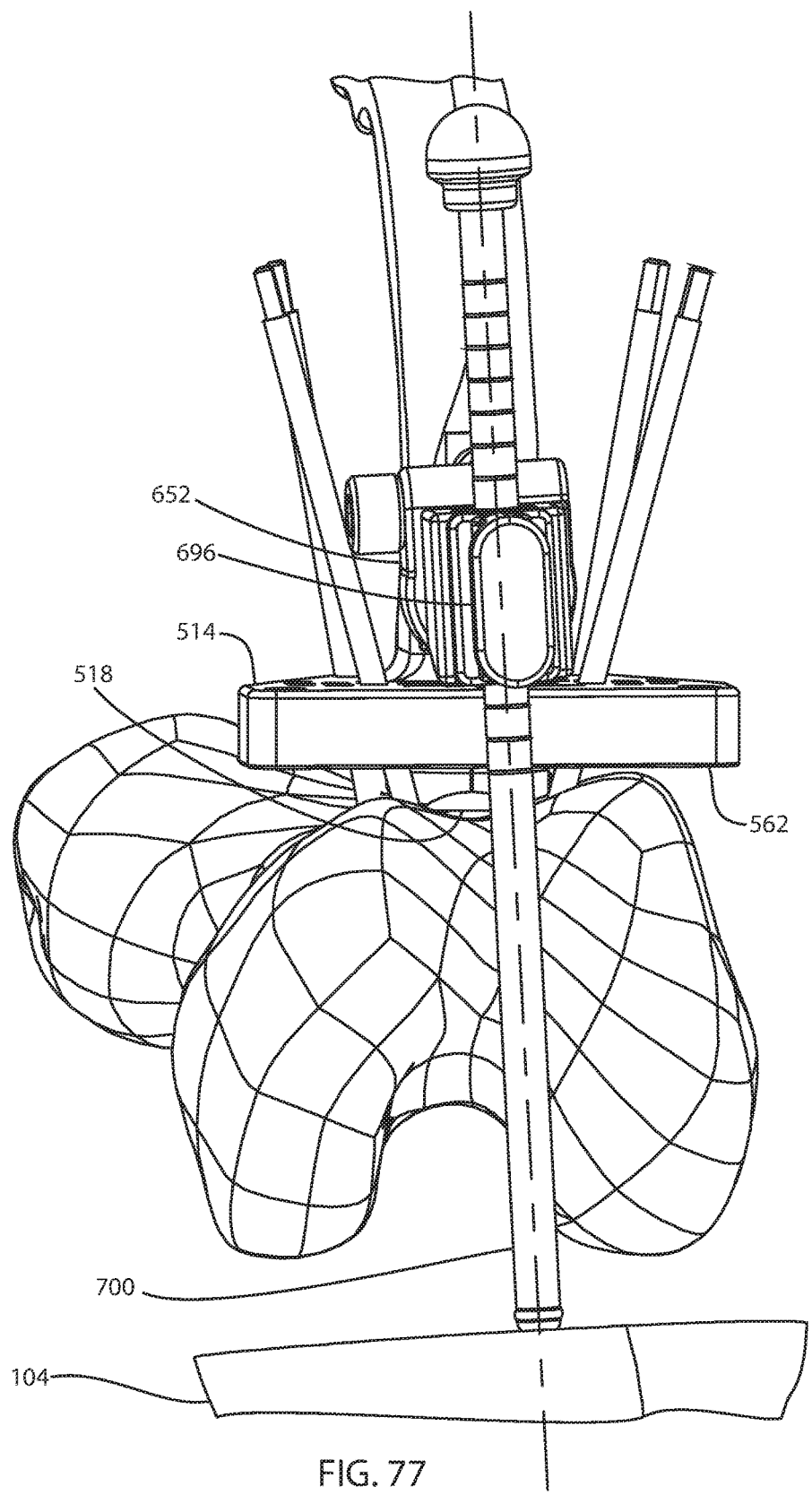
FIG. 77 is a distal view of the femur, tibia, base, femoral riser assembly, angle block assembly, and Whiteside's line gage assembly of FIG. 76, after locking the Whiteside's line gage assembly in an orientation parallel to Whiteside's line.

The illustrated distal femoral condyle block 638 is designed with the mounting portion 640 extending across the full width of the femoral pin guide 514 (FIG. 72B) and the paddle 642 extending across the full width of the distal medial condyle (FIGS. 72A and 73). However, the distal femoral condyle block 638 may be designed with a narrower mounting portion 640, and optionally a narrower paddle 642, so that the distal femoral condyle block 638 may be used simultaneously with the Whiteside's angle gage assembly 696 described below. Referring briefly to FIGS. 75-77, the narrower mounting portion 640 may couple to the distal medial portion of the femoral riser 504. The paddle 642 would still rest against the distal aspect of the medial femoral condyle.

The distal femoral condyle block 638 may be designed to couple to the angle block assembly 652 described next, for example, to the dovetail channel 668; or to the Whiteside's angle gage assembly 696, for example, to the distal dove tail rail 706. Advantageously, this allows the distal femoral condyle block 638 to slide proximally and distally with respect to the femur 100.

Figure 56A:
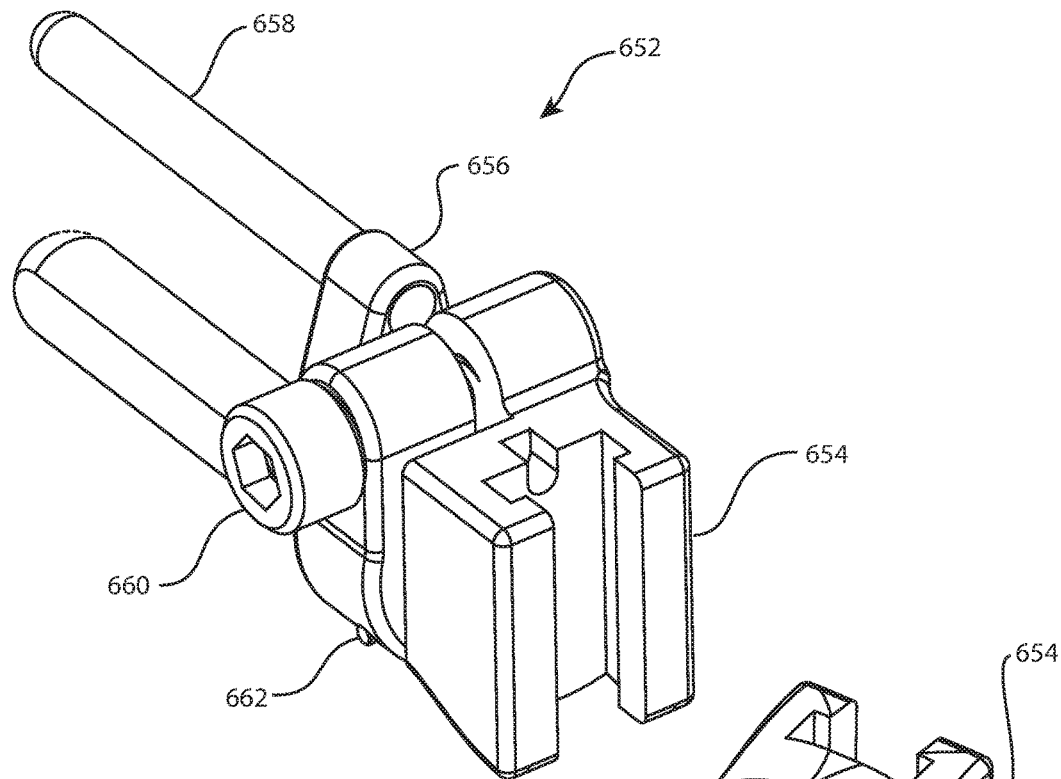
FIG. 56A is a perspective view of an angle block assembly for use with the instrument system of FIG. 47A.
Figure 56B:
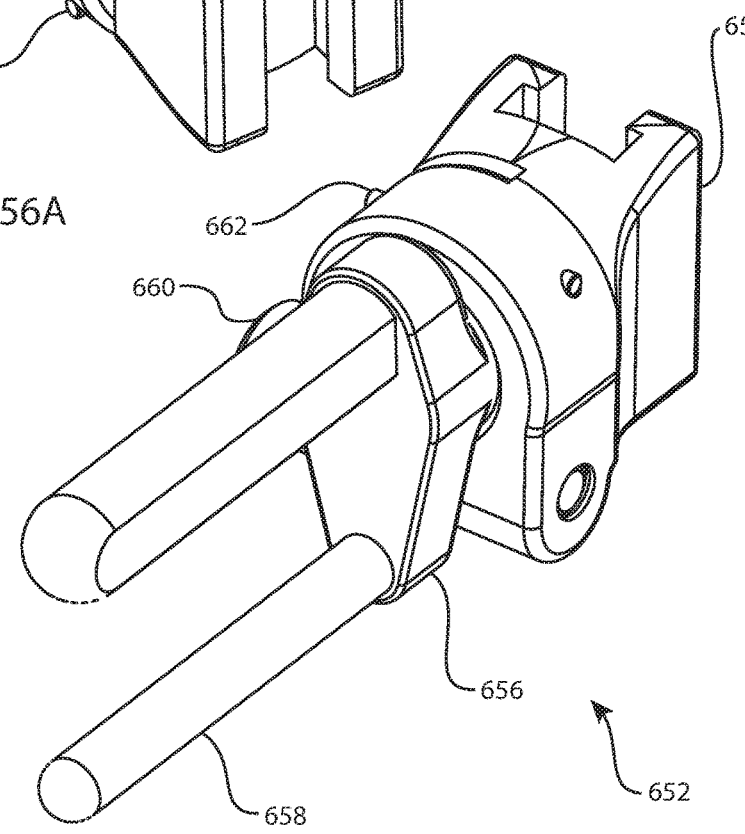
FIG. 56B is another perspective view of the angle block assembly of FIG. 56A from a different direction.

Referring to FIGS. 56A and 56B, an angle block assembly 652 includes an angle block 654, a translation bar 656, a translation pin 658, a bolt 660, and a dowel pin 662. Referring to FIG. 35, the angle block assembly 652 is analogous to the femoral base block assembly 330.

Figure 57A:
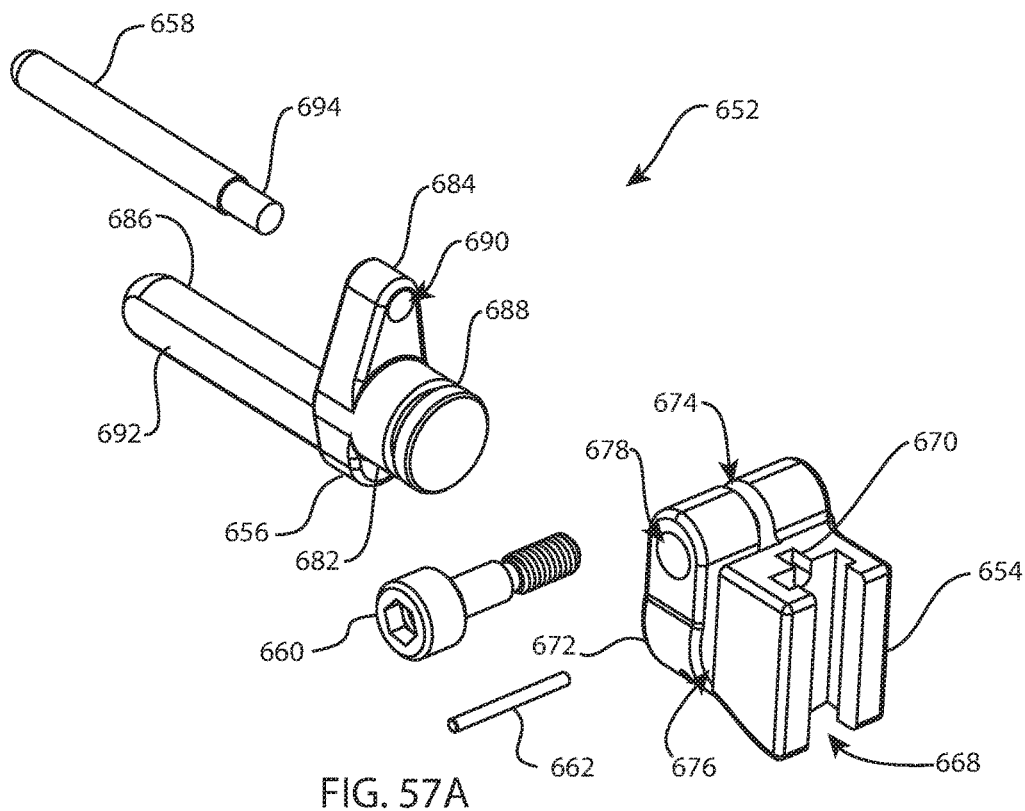
FIG. 57A is an exploded perspective view of the angle block assembly of FIG. 456A.
Figure 57B:
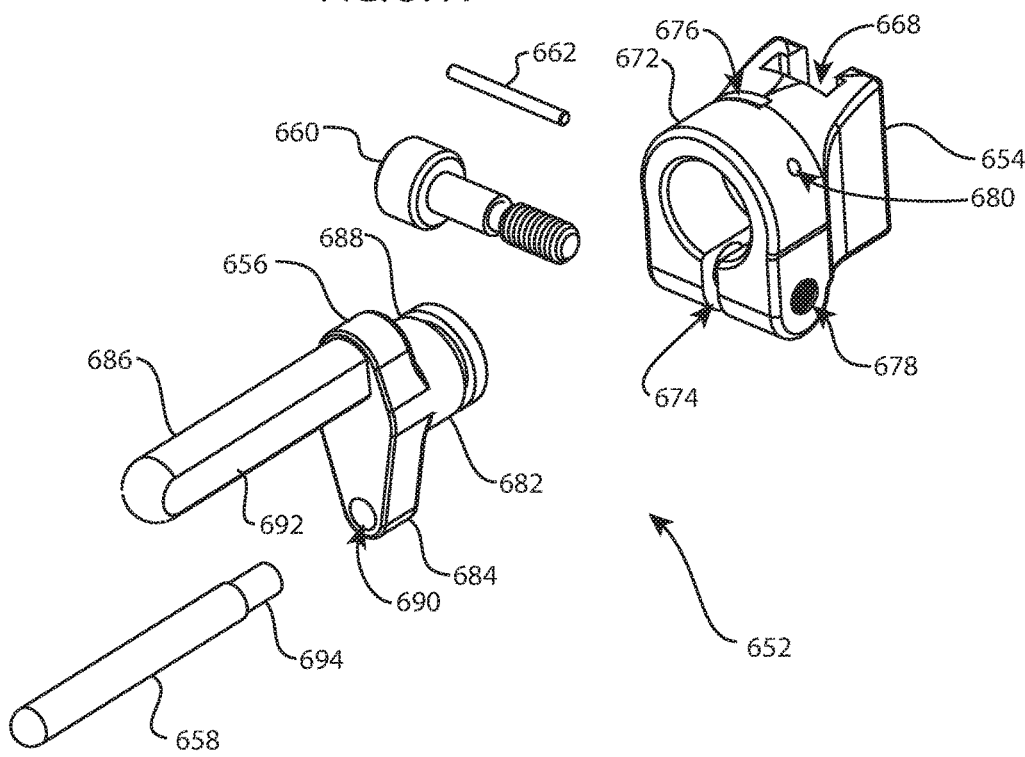
FIG. 57B is another exploded perspective view of the angle block assembly of FIG. 57A from a different direction.

Referring to FIGS. 57A and 57B, the angle block 654 includes a dovetail channel 668 with a notch 670 at one end (the upper or anterior end, in use). The angle block 654 also includes an integral clamp ring 672 opposite the dovetail channel 668. The clamp ring includes a slit 674 that extends through a side of the clamp ring, and a slot 676 that extends between the clamp ring 672 and the dovetail channel 668 along part of the width of the angle block 654. The slit 674 and the slot 676 intersect so that the clamp ring 672 has appropriate flexibility for clamping. A hole 678 extends through the clamp ring 672 across the slit 674. Another hole 680 extends through the clamp ring opposite the slit 674.

The translation bar 656 includes a post 682, a body 684, and a pin 686. These parts may be integrally formed as shown, or separate parts coupled together. The post 682 includes an exterior circumferential groove 688. The body may include one or two holes 690; one hole 690 is illustrated. Bilateral flats 692 may extend along opposite sides of the pin 686.

The translation pin 658 is a cylindrical part with a rounded end and an opposite end having a reduced diameter 694 compared to the rest of the part.

The angle block assembly 652 may be assembled as follows. The hole 690 receives the reduced diameter 694 end of the translation pin 658. The translation pin 658 may be permanently fixed in the hole 690. The clamp ring 672 receives the post 682. The hole 680 and the groove 688 receive the dowel pin 662 to retain the translation bar 656 to the angle block 654 while permitting the translation bar 656 to rotate about the post 682 when the clamp ring 672 is loosened. The hole 678 receives the bolt 660 which is used to tighten and loosen the clamp ring 672.

The angle block assembly 652 may be coupled to the femoral riser 504. The hole 572 receives the pin 686 and the hole 574 receives the pin 658 so that the translation bar 656, with attached translation pin 658, is constrained to slide straight in and out of the femoral riser 504. In use, the pins 686, 658 extend proximally and the dovetail channel 668 faces distally.

Figure 58A:
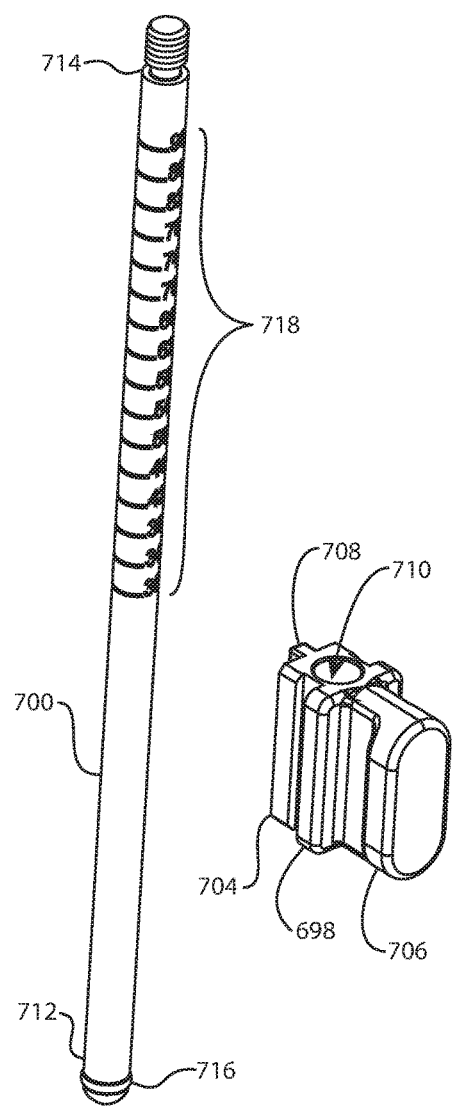
FIG. 58A is an exploded perspective view of a Whiteside's angle gage assembly for use with the angle block assembly of FIG. 56A.
Figure 58B:
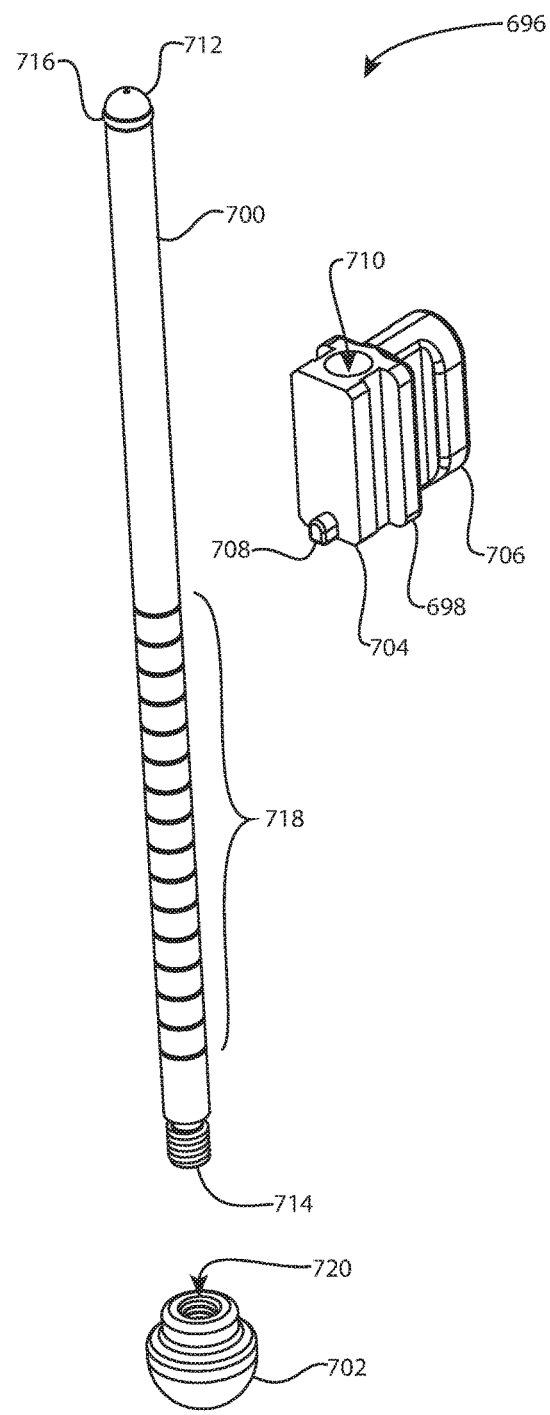
FIG. 58B is another exploded perspective view of the Whiteside's angle gage assembly of FIG. 58A from a different direction.

Referring to FIGS. 58A and 58B, a Whiteside's angle gage assembly 696 includes a body 698, a shaft 700, and a cap 702. The body 698 includes a proximal dovetail rail 704 and a distal dovetail rail 706. A tab 708 extends from one end of the proximal dovetail rail 704 (the upper or anterior end, in use). A hole 710 extends through the body 698. The dovetail rails 704, 706 and the hole 710 are all parallel. The shaft 700 is a cylindrical part with a rounded end 712 and an opposite end 714 terminating in a threaded portion. The rounded end 712 includes an external flange 716. Indicia 718 may be provided on the shaft 700, such as a millimeter or inch scale, or a scale relating to available implant sizes. The cap 702 includes a threaded socket 720 in one end.

The Whiteside's angle gage assembly 696 may be assembled as follows. The shaft 700 is inserted into the hole 710 so that the threaded end 714 protrudes next to the tab 708. The end 714 is threaded into the threaded socket 720.

The Whiteside's angle gage assembly 696 may be coupled to the angle block assembly 652 by sliding the proximal dovetail rail 704 into the dovetail channel 668 until the tab 708 is fully seated in the notch 670. With the clamp ring 672 loosened, the shaft 700 may be adjusted to align parallel with Whiteside's line of an intact distal femur 102. The clamp ring 672 may be tightened by turning the bolt 660 to lock the angle block 654 relative to the translation bar 656, thus saving the angle of the Whiteside's line for future use. More specifically, the dovetail channel 668 is locked parallel to the Whiteside's line. The indicia 718 may be read at this time, for example the anterior-posterior femoral dimension or femoral implant size.

Figures 59A, 59B:
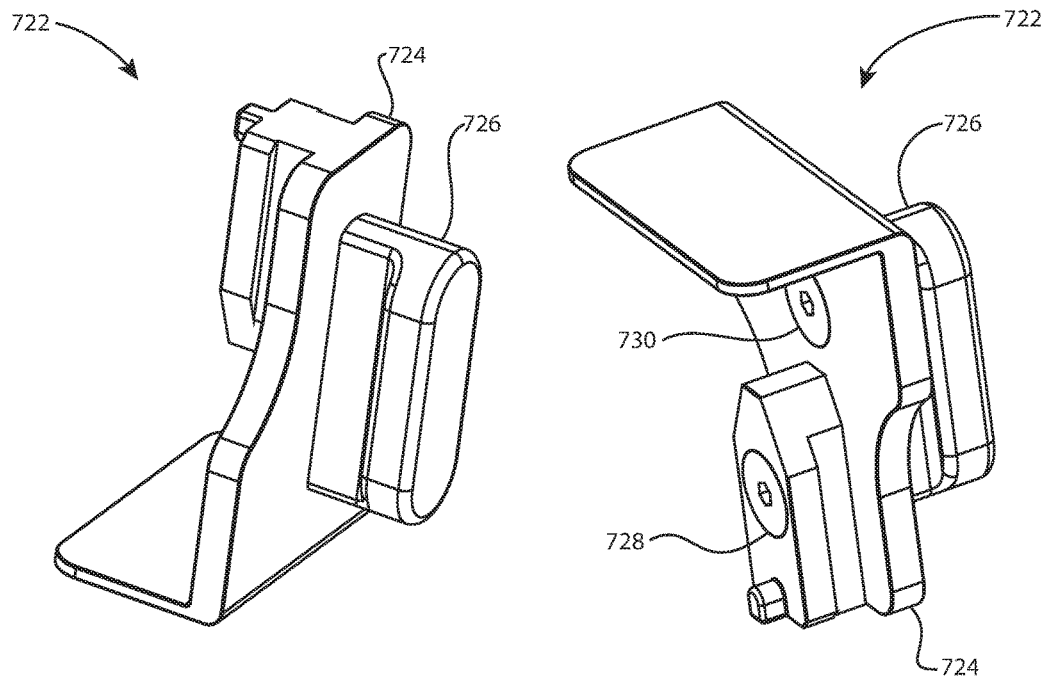
FIG. 59A is a perspective view of a cut guide mounting block assembly for use with the angle block assembly of FIG. 56A.
FIG. 59B is another perspective view of the cut guide mounting block assembly of FIG. 59A from a different direction.

Referring to FIGS. 59A and 59B, a cut guide mounting block assembly 722 includes a mounting block 724, a distal dovetail rail 726, a first screw 728, and a second screw 730.

Figure 60:
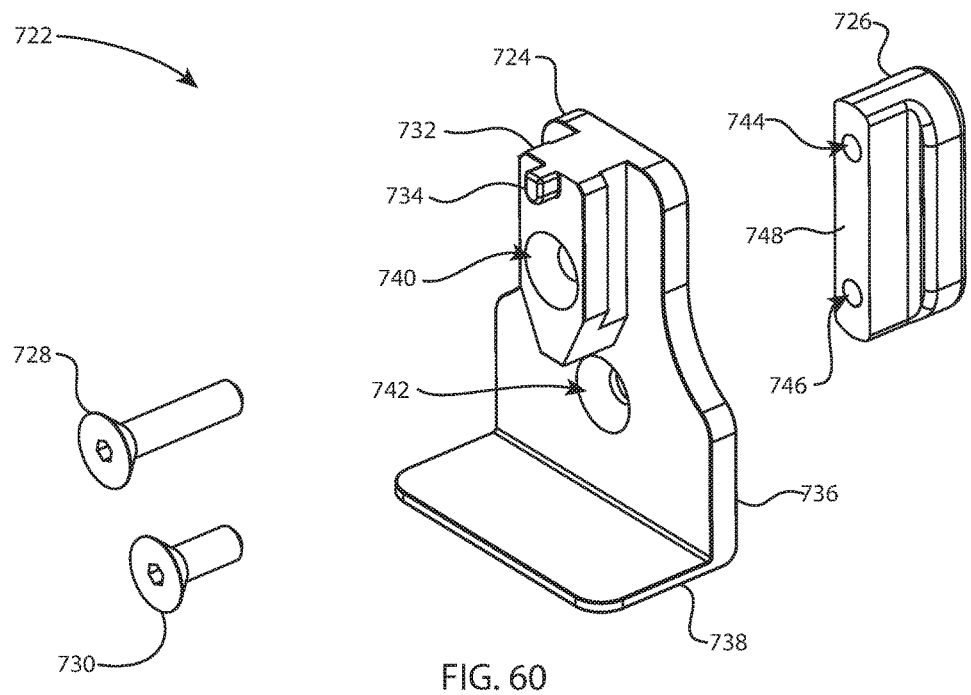
FIG. 60 is an exploded perspective view of the cut guide mounting block assembly of FIG. 59A.

Referring to FIG. 60, the mounting block 724 includes a proximal dovetail rail 732. A tab 734 extends from one end of the proximal dovetail rail 732 (the upper or anterior end, in use). A first plate 736 extends parallel to the proximal dovetail rail 732; in use, the first plate extends in the anterior-posterior and medial-lateral directions. A second plate 738 extends perpendicular to the first plate 736; in use, the second plate extends in the proximal-distal and medial-lateral directions. The proximal dovetail rail 732, first plate 736, and second plate 738 may be integrally formed as shown, or may be separate parts coupled together. A first hole 740 extends in the proximal-distal direction through the proximal dovetail rail 732. A second hole 742 extends parallel to the first hole 740 through the first plate 736.

The distal dovetail rail 726 includes a first hole 744 and a second hole 746. The holes 744, 746 are parallel and extend in the proximal-distal direction into a proximal surface 748 of the distal dovetail rail 726.

The cut guide mounting block assembly 722 may be assembled as follows. The proximal surface 748 of the distal dovetail rail 726 is placed against the distal aspect of the first plate 736. The holes 740, 744 are aligned and the holes 742, 746 are aligned. The first screw 728 is inserted through the hole 740 and threaded into the hole 744. The second screw 730 is inserted through the hole 742 and threaded into the hole 746.

The cut guide mounting block assembly 722 may be coupled to the angle block assembly 652 by sliding the proximal dovetail rail 732 into the dovetail channel 668 until the tab 734 is fully seated in the notch 670.

Figure 61A:
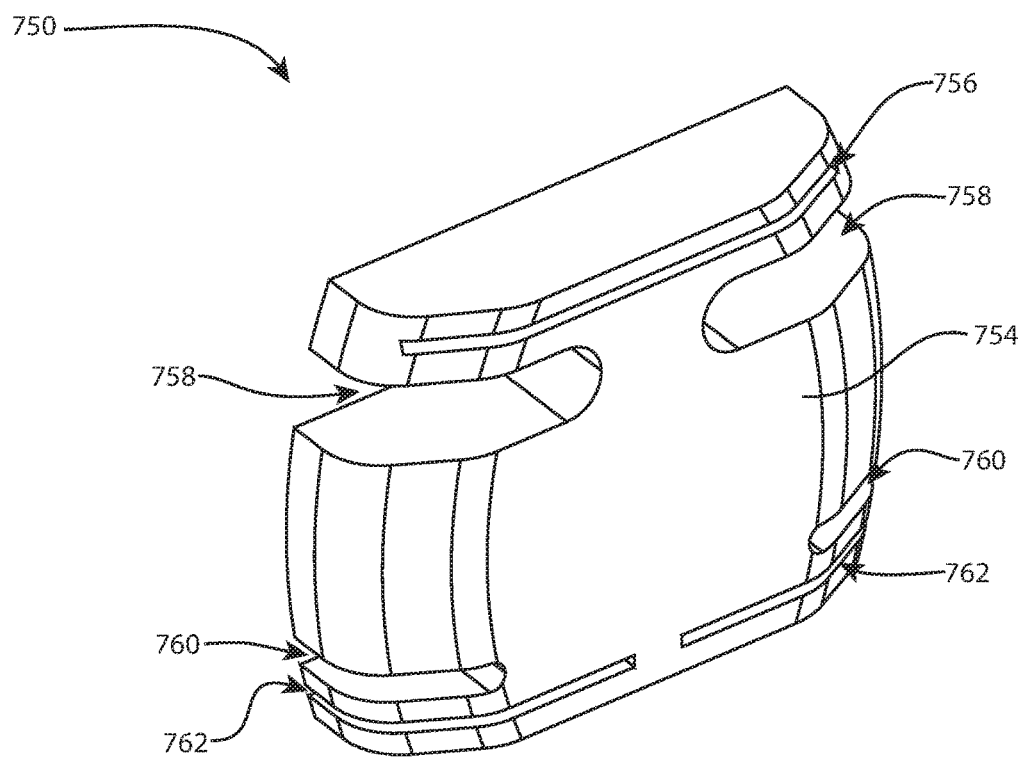
FIG. 61A is a perspective view of a four-in-one cut guide for use with the cut guide mounting block assembly of FIG. 59A.
Figure 61B:
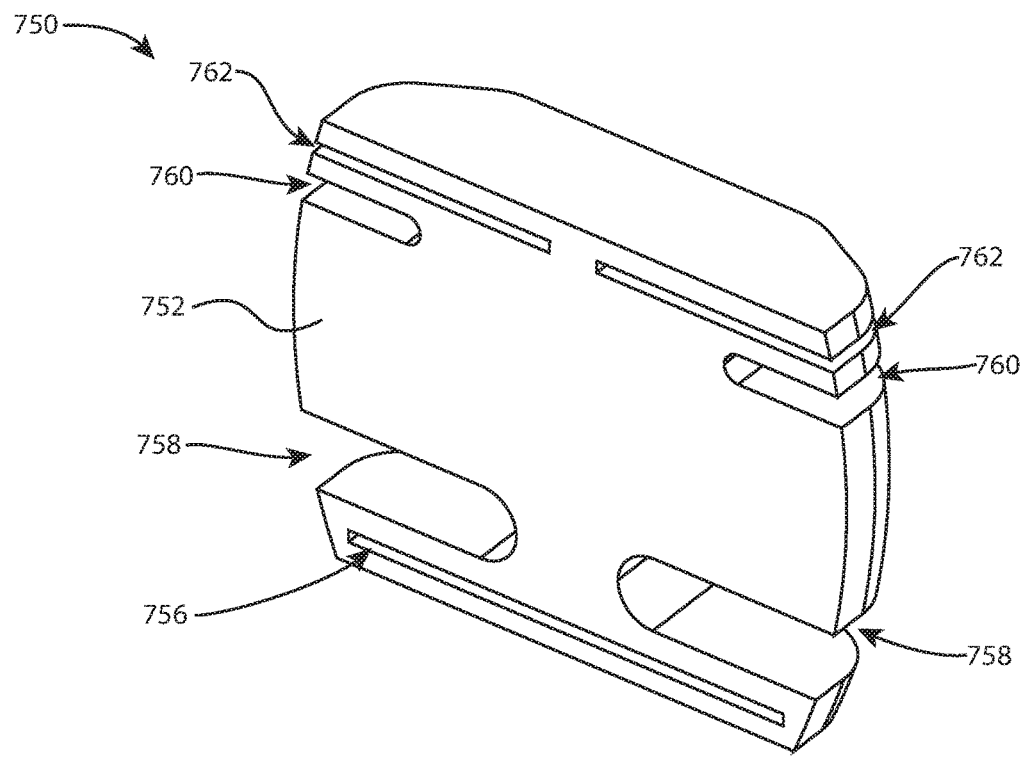
FIG. 61B is another perspective view of the four-in-one cut guide of FIG. 61A from a different direction.

Referring to FIGS. 61A and 61B, a four-in-one cut guide 750 is a generally rectangular plate with a proximal surface 752, an opposite distal surface 754, a first slot 756, a second slot 758, a third slot 760, and a fourth slot 762. Bilateral slots 758, bilateral slots 760, and bilateral slots 762 are shown. The slots 756, 762 may be the same width and may be narrower than the slots 758, 760. There may be just enough room to pass a saw blade through the slot 756 or the slot 762 to make an anterior femoral resection 214 or a posterior femoral resection 220, respectively. The slots 756, 762 may be said to define cutting paths of the saw blade acting through the slots. The slots 756, 762 may be referred to as saw slots or cut guide slots. The slot 760 may be narrower than the slot 758.

The four-in-one cut guide 750 may be coupled to the cut guide mounting block assembly 722 by inserting the second plate 738 through the slot 756 from distal to proximal.

Figure 62A:
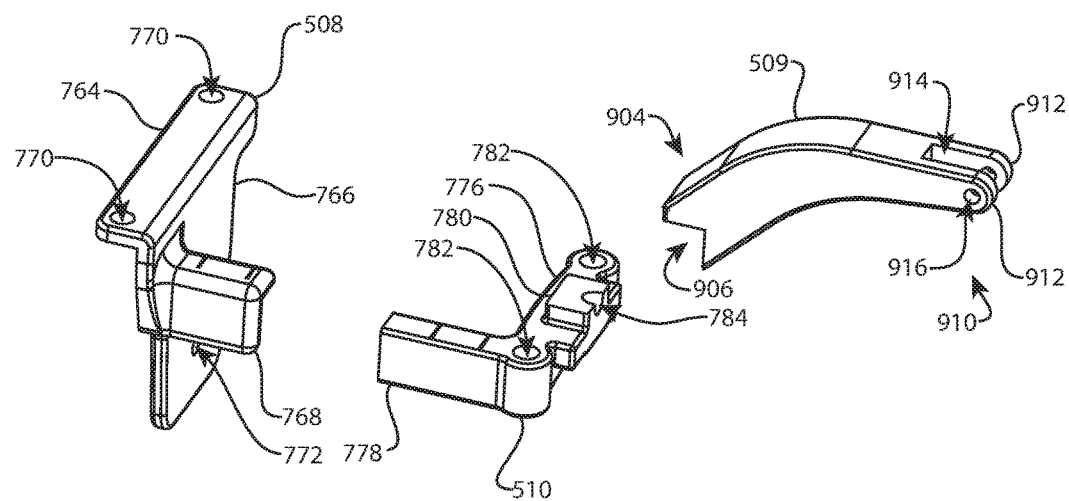
FIG. 62A is an exploded perspective view of a tibial connection block, a tibial pin guide, and a tibial riser of the instrument system of FIG. 47A.
Figure 62B:
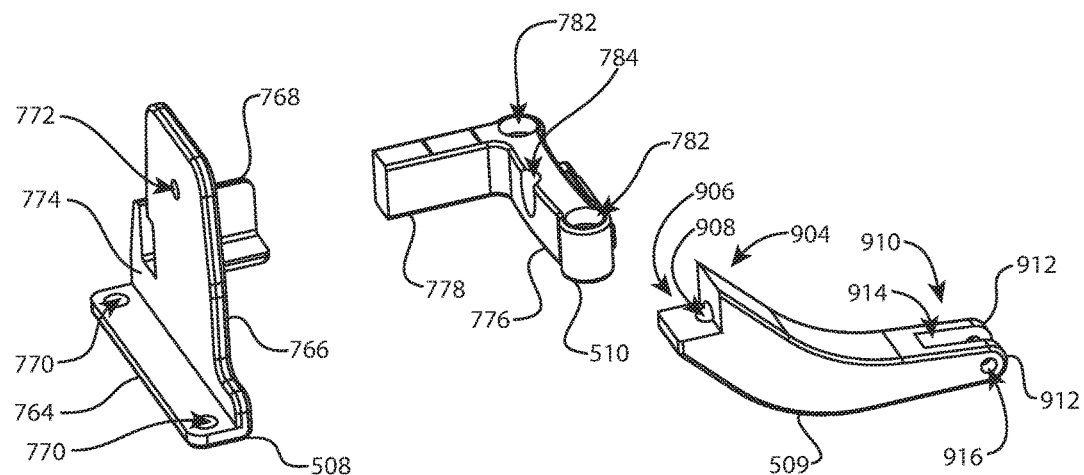
FIG. 62B is another exploded perspective view of the tibial connection block, pin guide, and riser of FIG. 62A from a different direction.
Figure 63A:
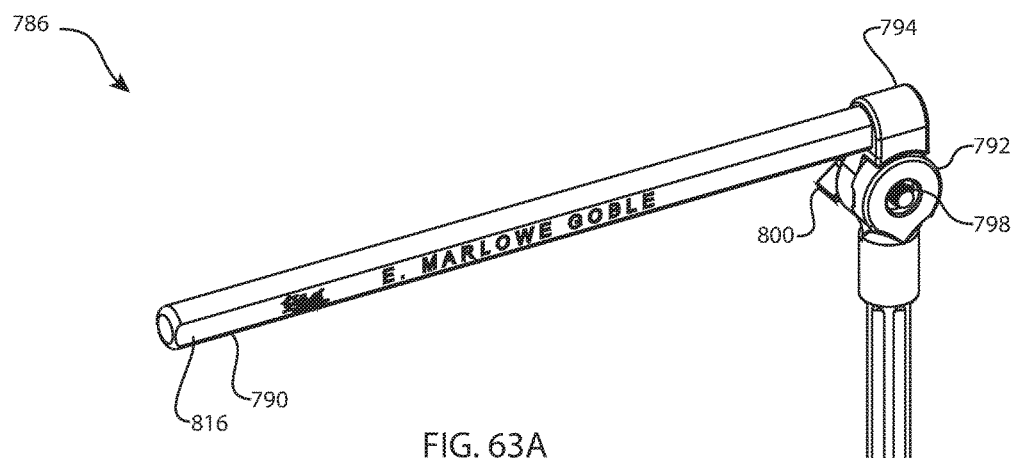
FIG. 63A is a perspective view of a femoral support arm assembly for use with the instrument system of FIG. 47A.
Figure 63B:
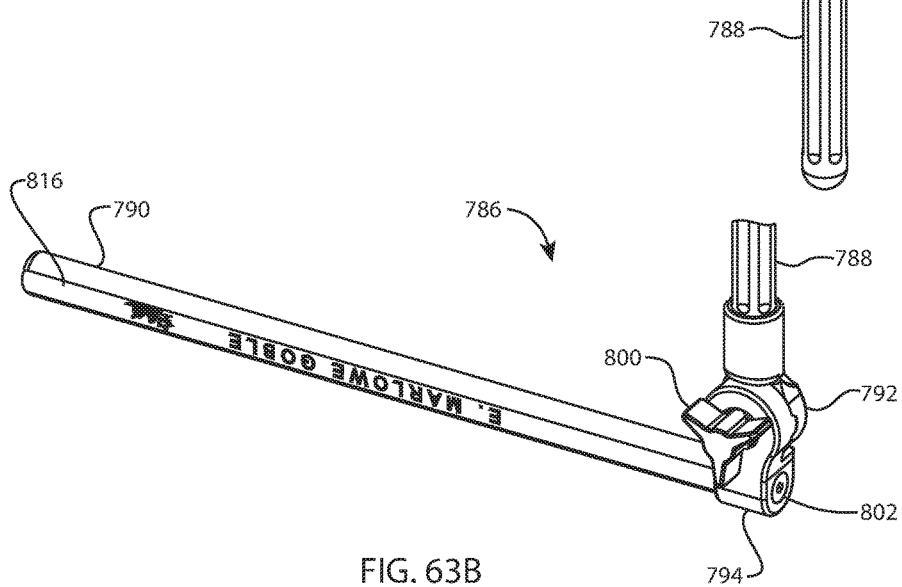
FIG. 63B is another perspective view of the femoral support arm assembly of FIG. 63A from a different direction.
Figure 64A:
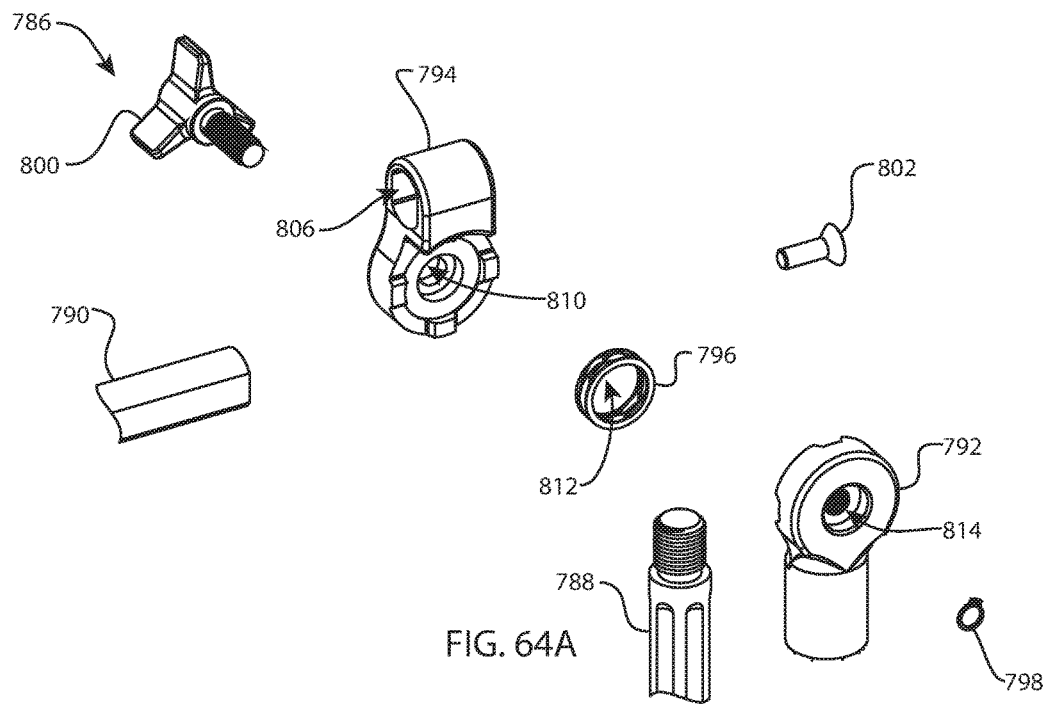
FIG. 64A is an exploded perspective view of the femoral support arm assembly of FIG. 63A.
Figure 64B:
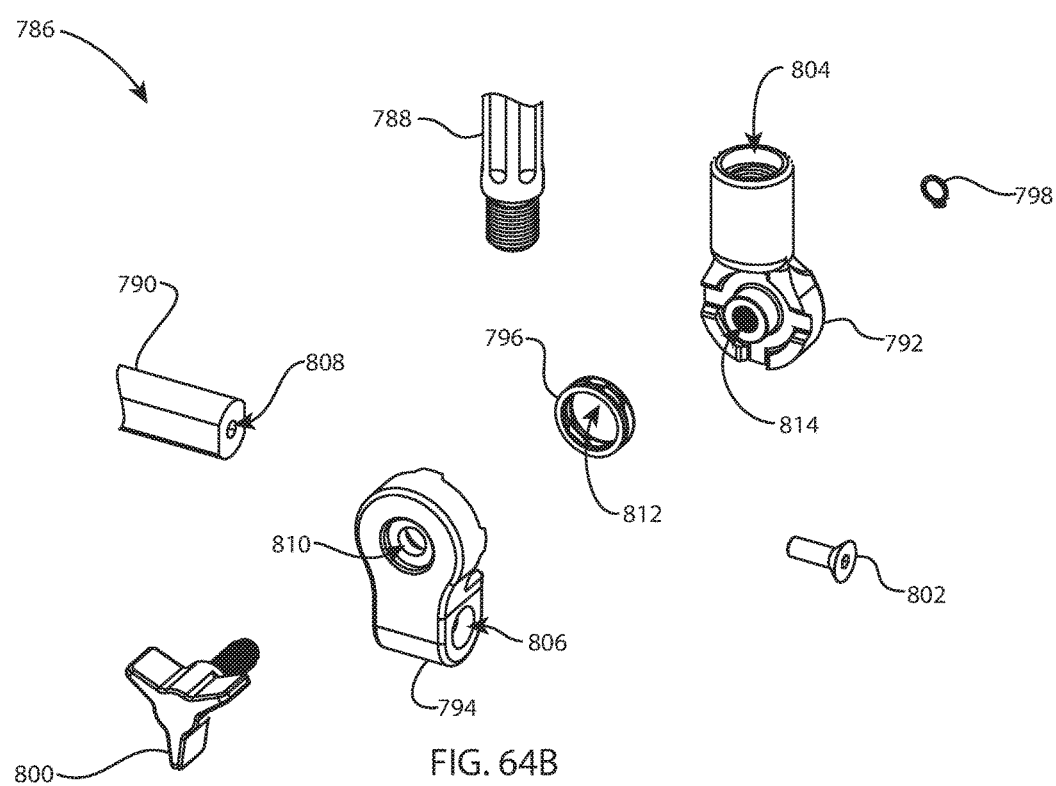
FIG. 64B is another exploded perspective view of the femoral support arm assembly of FIG. 64A from a different direction.
Figure 65A:
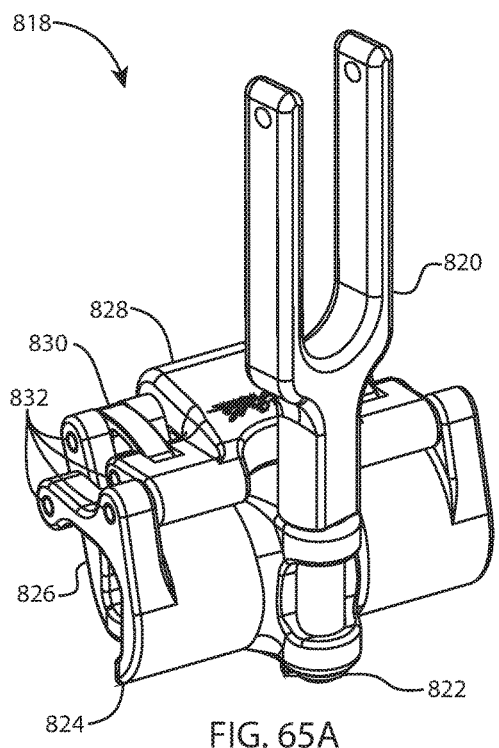
FIG. 65A is a perspective view of a target clamp assembly for use with the femoral support arm assembly of FIG. 63A.
Figure 65B:
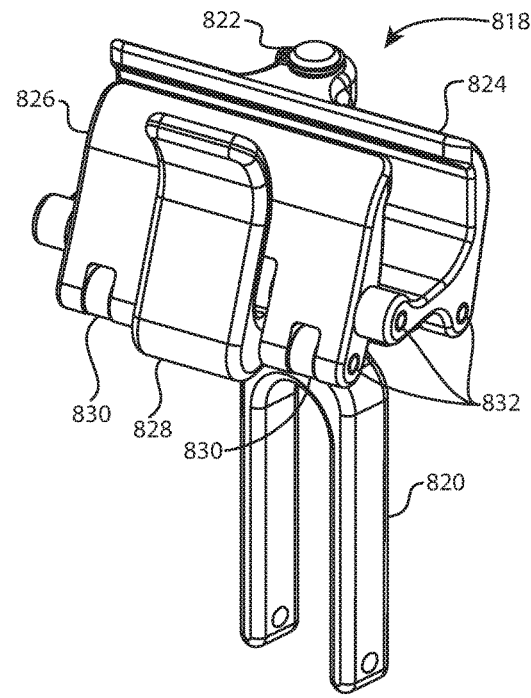
FIG. 65B is another perspective view of the target clamp assembly of FIG. 65A from a different direction.
Figure 65C:
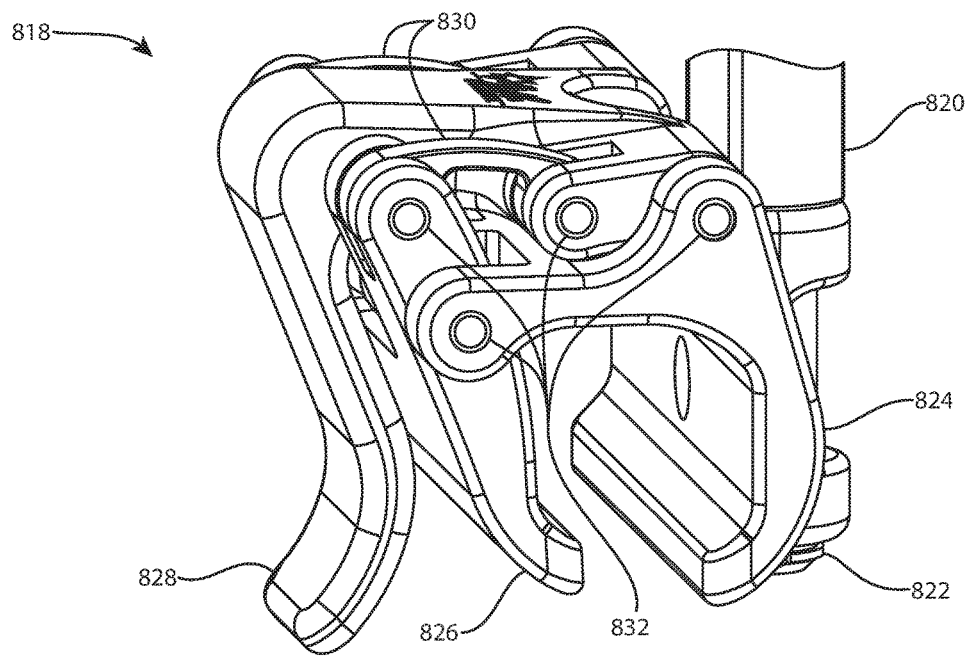
FIG. 65C is yet another perspective view of the target clamp assembly of FIG. 65A from another different direction.
Figure 67A:
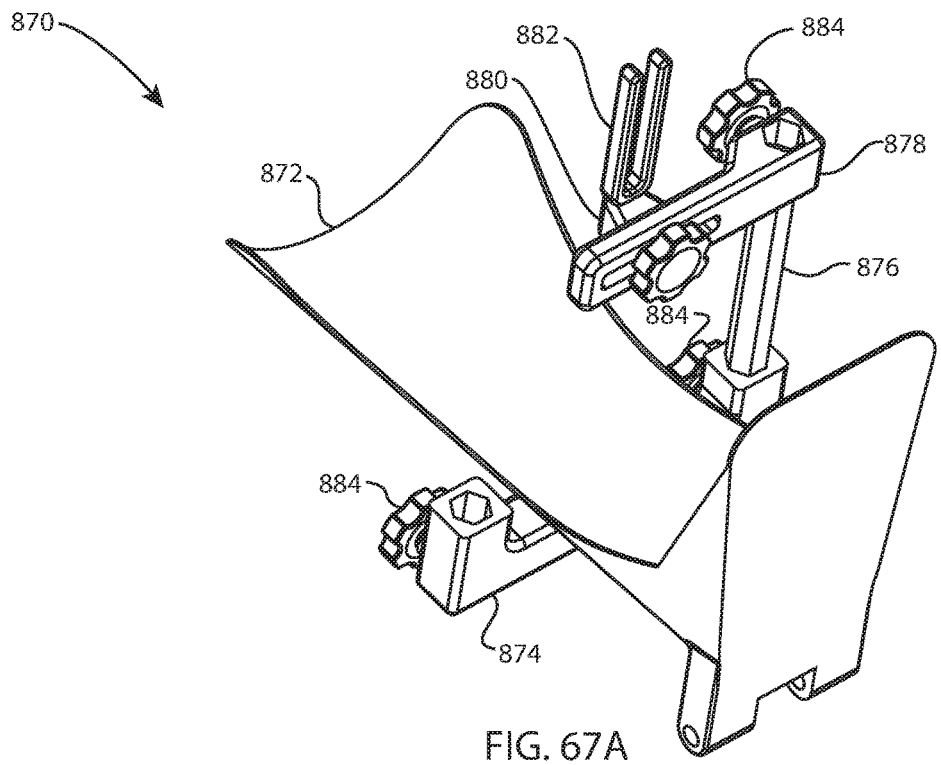
FIG. 67A is a perspective view of a foot holder assembly for use with the instrument system of FIG. 47A.
Figure 67B:
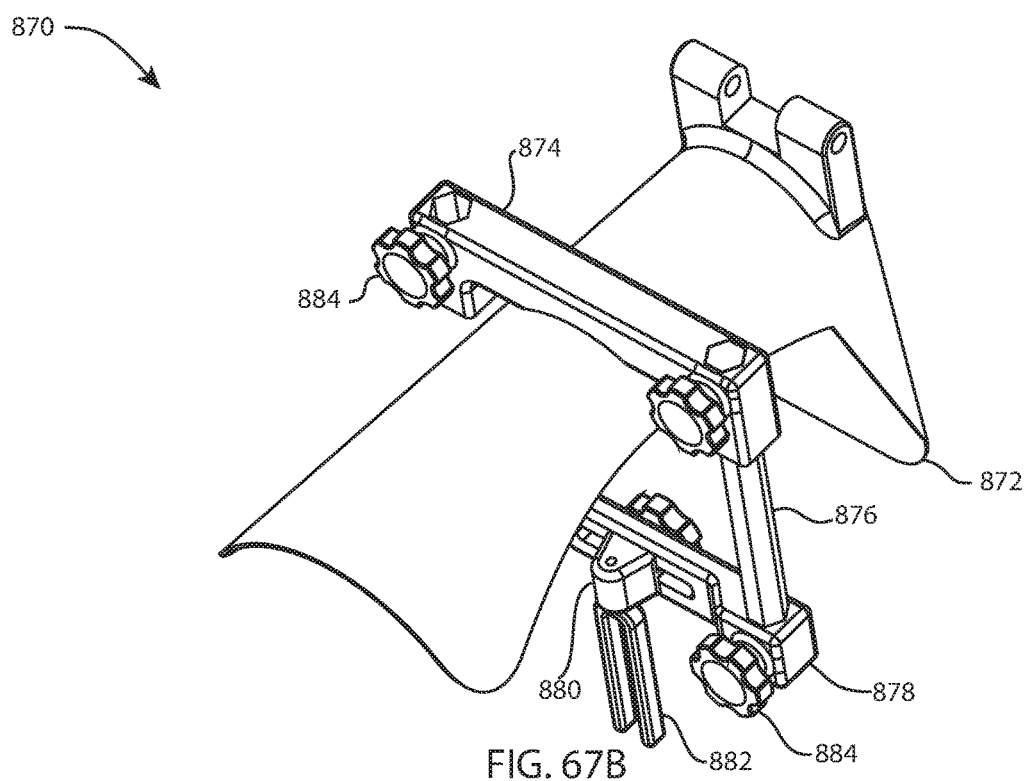
FIG. 67B is another perspective view of the foot holder assembly of FIG. 67A from a different direction.
Figure 68A:
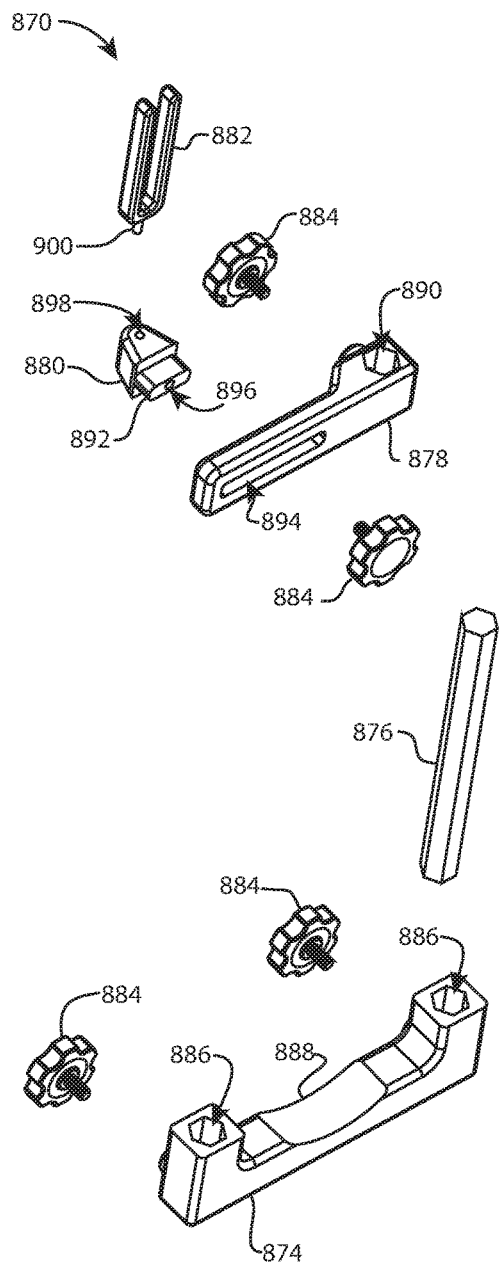
FIG. 68A is an exploded perspective view of the foot holder assembly of FIG. 67A, the foot holder omitted for clarity.
Figure 68B:
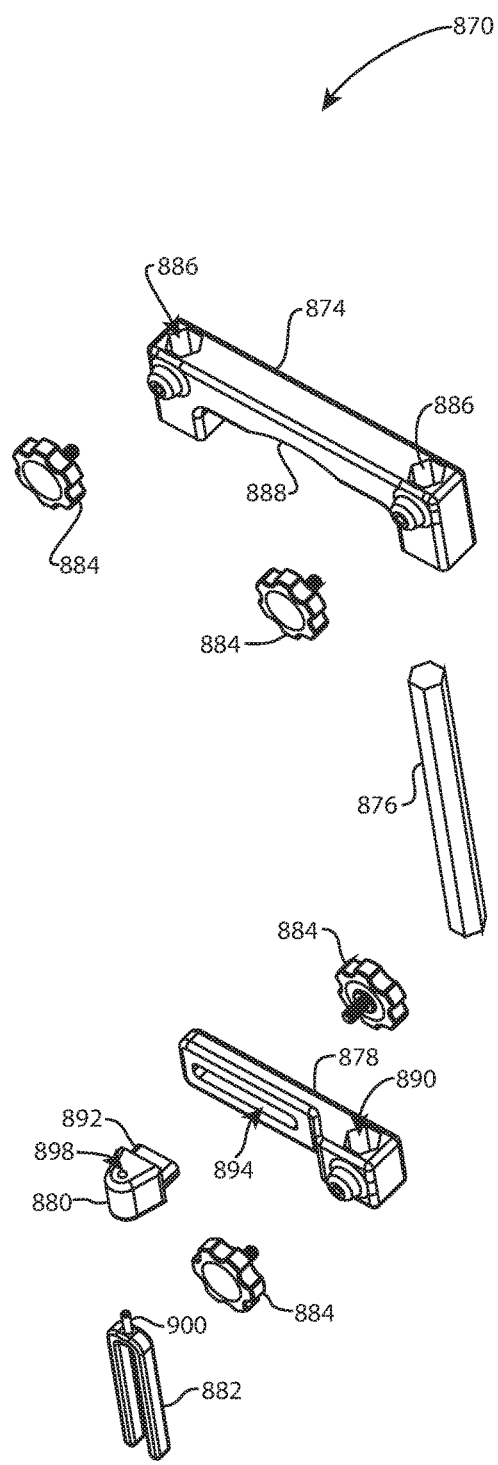
FIG. 68B is another exploded perspective view of the foot holder assembly of FIG. 68A from a different direction.

Referring to FIGS. 62A and 62B, the tibial connection block 508 includes a mounting plate 764, a second plate 766, and a distal protrusion 768. In use, the mounting plate 764 extends in the proximal-distal and medial-lateral directions. The second plate 766 extends perpendicular to the mounting plate 764 in the anterior-posterior and medial-lateral directions. The distal protrusion 768 extends distally from the second plate 766, and is adjacent to a medial or lateral side of the second plate. The mounting plate 764, second plate 766, and distal protrusion 768 may be integrally formed as shown, or may be separate parts coupled together. The distal protrusion 768 may form a right angle channel as shown, or may include a socket that opens distally, for example a square socket. Bilateral holes 770 extend in the anterior-posterior direction through the mounting plate 764. These holes 770 receive the same pegs 646 described previously for the distal femoral condyle block 638 (FIGS. 55A and 55B). Alternately, the pegs may be integrally formed with the mounting plate 764. A hole 772 extends in the proximal-distal direction through the second plate 766. This hole 772 may receive and stabilize a distractor jaw tip. The second plate 766 includes a proximal surface 774. The tibial connection block 508 may be analogous to a middle portion of the tibial-femoral pin guide 310.

The tibial connection block 508 releasably couples to the femoral riser 504. The pegs 646 fit into the mounting holes 584 so that the proximal surface 774 faces the distal portion 566.

The tibial pin guide 510 includes a bar 776, a proximal protrusion 778, and a distal boss 780. In use, the bar 776 extends in the medial-lateral direction, the proximal protrusion 778 extends proximally from one end of the bar 776, and the distal boss 780 extends distally from the center of the bar 776. The bar 776, proximal protrusion 778, and distal boss 780 may be integrally formed as shown, or may be separate parts coupled together. Bilateral holes 782 extend in the anterior-posterior direction through the bar 776. These holes 782 receive bone pins. A slanting hole 784 extends through the distal boss 780 from postero-proximal to antero-distal. The distal boss 780 is analogous to the boss 378 of the tibial-femoral pin guide 310 (FIGS. 28A-28B and the hole 784 is analogous to the hole 382.

Figure 28A:
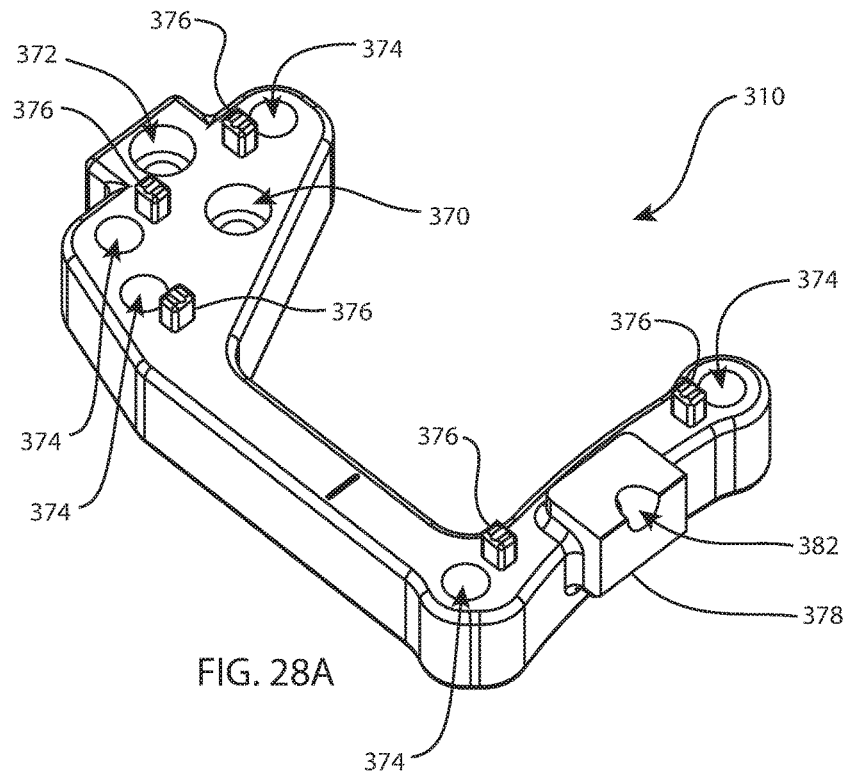
FIG. 28A is a perspective view of a tibial-femoral pin guide of the instrument system of FIG. 21A.
Figure 28B:
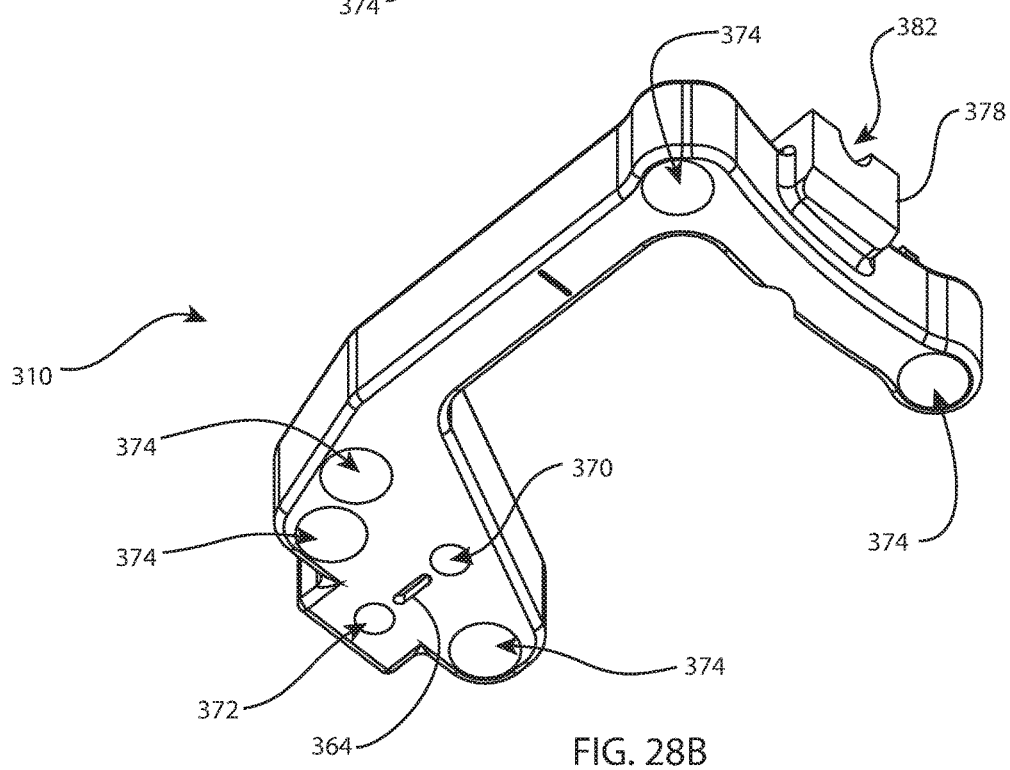
FIG. 28B is another perspective view of the tibial-femoral pin guide of FIG. 28A from a different direction.
Figure 29A:
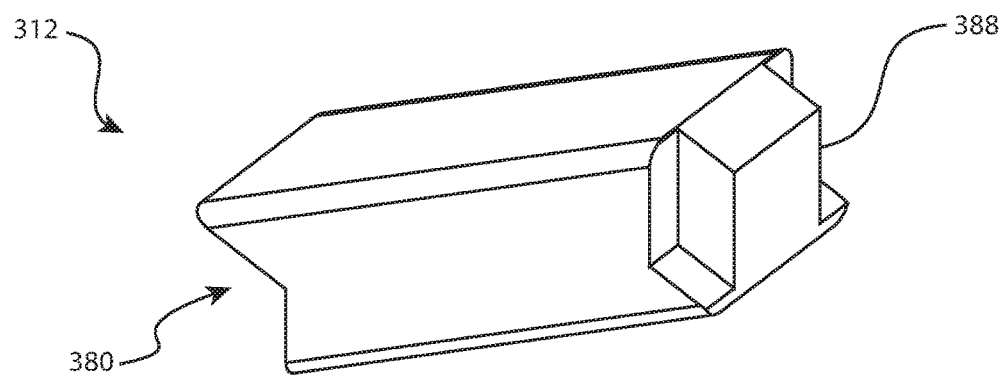
FIG. 29A is a perspective view of a tibial riser of the instrument system of FIG. 21A.
Figure 29B:
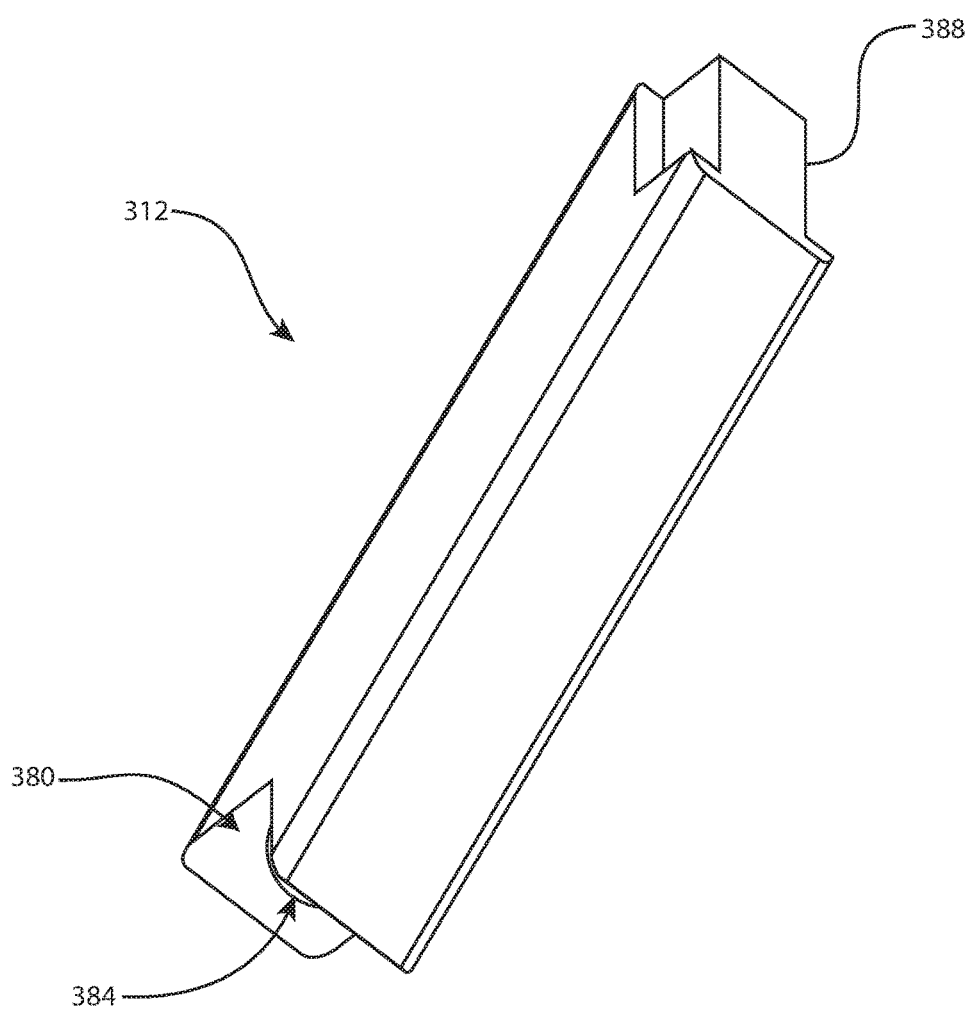
FIG. 29B is another perspective view of the tibial riser of FIG. 29A from a different direction.
Figure 31A:
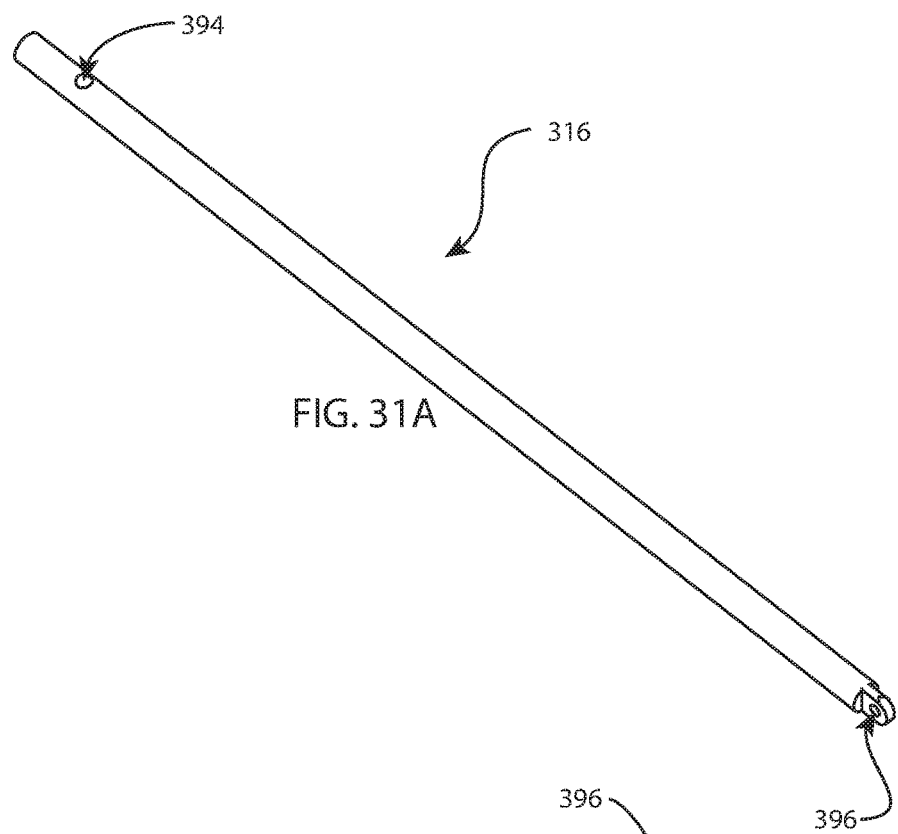
FIG. 31A is a perspective view of a first tibial inner extension rod of the instrument system of FIG. 21A.
Figure 31B:
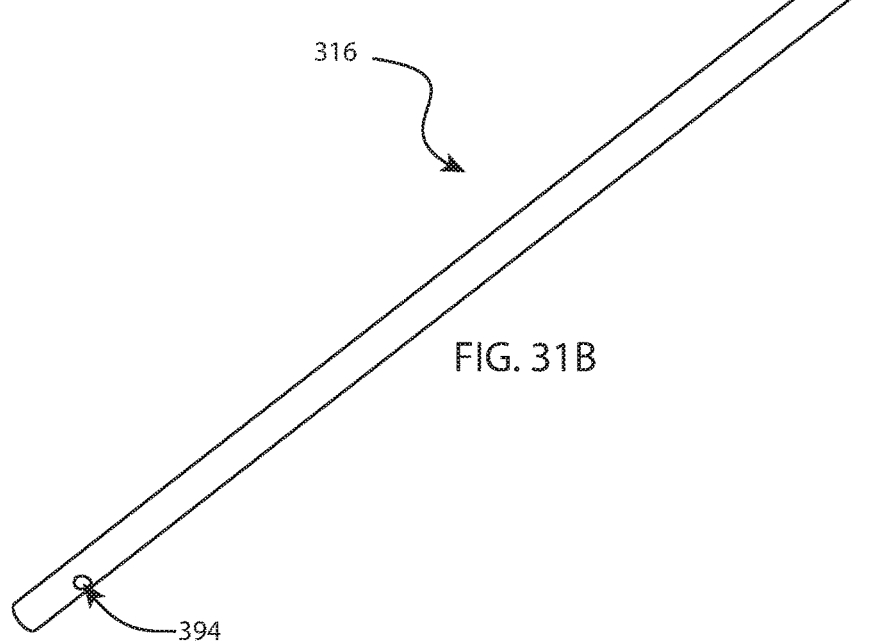
FIG. 31B is another perspective view of the first tibial inner extension rod of FIG. 31A from a different direction.
Figure 32A:
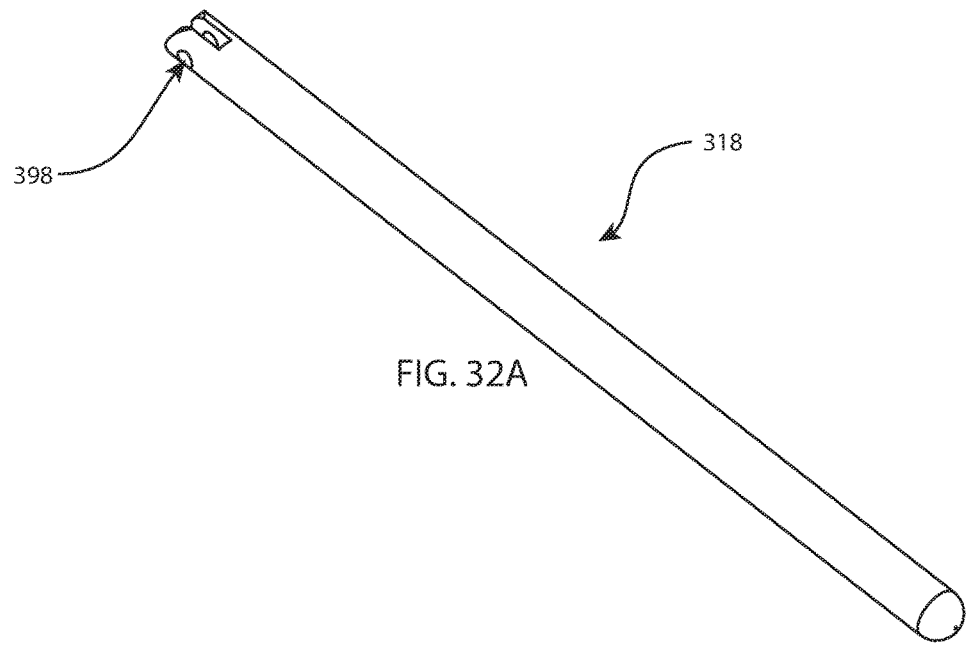
FIG. 32A is a perspective view of a second tibial inner extension rod of the instrument system of FIG. 21A.
Figure 32B:
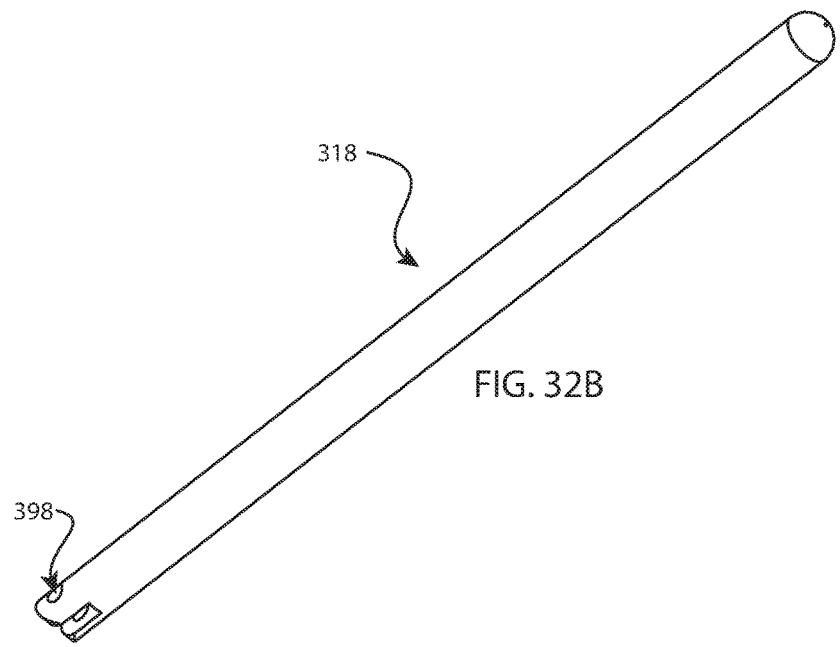
FIG. 32B is another perspective view of the second tibial inner extension rod of FIG. 32A from a different direction.

The tibial pin guide 510 may be coupled to the tibial connection block 508 by inserting the proximal protrusion 778 in the distal protrusion 768. Not shown, a fastener may extend through a slot in the distal protrusion and into a socket, such as a threaded hole, in the proximal protrusion so that the tibial pin guide 510 is lockably slidable in the proximal-distal direction relative to the tibial connection block 508. Referring to FIGS. 28A and 28B, the coupled tibial pin guide 510 and tibial connection block 508 may be analogous to the tibial-femoral pin guide 310.

The tibial pin guide 510 may be designed to couple to the angle block assembly 652 instead of the tibial connection block 508. The tibial pin guide 510 may be modified to include a dovetail rail, like the proximal dovetail rail 704 of the Whiteside's angle gage assembly 696 (FIGS. 58A and 58B), which couples to the dovetail channel 668 of the angle block assembly 652 (FIGS. 57A and 57B).

The tibial riser 509 includes a proximal end 904 with a notch 906 that is complementary to the distal boss 780 of the tibial pin guide 510 and a slanting hole 908 that extends into the first end 904 from postero-proximal to antero-distal. The tibial riser 509 includes a distal end 910 that is divided into two arms 912 separated by a slot 914. A transverse hole 916 extends through the arms 912 and across the slot 914.

The tibial riser 509 may be coupled to the tibial pin guide by abutting the distal boss 780 in the notch 906 so that holes 784, 908 are aligned, and inserting a fastener through the holes. Alternately, the tibial riser 509 and the tibial pin guide 510 may be integrally formed as a single part. The tibial pin guide 510 may be coupled to the tibial riser 312 (FIGS. 29A and 29B) (with attached tibial extension rod 313) by inserting distal boss 780 into notch 380 and inserting a fastener through holes 784, 384. Alternately, the tibial riser 312 may be permanently rigidly coupled to the tibial pin guide 510.

The tibial extension rod 511 may be identical to the femoral extension rod 506 (FIGS. 54A and 54B), and is shown this way in this application. More specifically, the illustrated tibial extension rod 511 includes the outer extension rod 604, the inner extension rod 606, the spool 608, the sleeve 610, the ring 612, and the retaining ring 614, which are assembled and function as described previously for the femoral extension rod 506.

The assembled tibial extension rod 511 may be coupled to the tibial riser 509 by inserting the end of the inner extension rod 606 with the hole 624 into the slot 914, aligning the hole 602 with the hole 916, and inserting a fastener through the holes 602, 916 to form a hinge 917 (FIGS. 47B and 49B). The tibial extension rod 511 is free to pivot about the hinge 917. In use, the tibial extension rod 511 pivots in an anterior-posterior direction which is generally parallel to the sagittal plane. The tibial extension rod 511 is constrained against pivoting in a medial-lateral direction which is generally parallel to the coronal plane. The end of the inner extension rod 606 with the hole 624 is the proximal end of the tibial extension rod 511, and the end of the outer extension rod 604 with the retaining ring 614 is the distal end of the tibial extension rod 511.

Referring to FIGS. 63A-64B, a femoral support arm assembly 786 includes a post 788, a bar 790, a first clamp body 792, a second clamp body 794, a spring 796, a retaining ring 798, a thumbscrew 800, and a screw 802. The post 788 threads into a socket 804 of the first clamp body 792. The bar 790 is inserted into a socket 806 of the second clamp body 794 and the screw 802 is threaded into a hole 808 of the bar to fix the bar 790 in the socket 806. The spring 796 is sandwiched between the first and second clamp bodies 792, 794. The thumbscrew 800 is inserted through a hole 810 through the second clamp body 794 and a passageway 812 through the spring 796, and threaded into a hole 814 through the first clamp body 794. The retaining ring 798 fits around the threaded tip of the thumbscrew 800 to prevent unintentional disassembly of the thumbscrew 800, second clamp body 794, spring 796, and first clamp body 794. When the thumbscrew 800 is tightened, the bar 790 is held in a fixed orientation relative to the post 788. When the thumbscrew 800 is loosened, the bar 790 may be rotated relative to the post 788 about the threaded shaft of the thumbscrew. The post 788 may be clamped to an operating table. The bar 790 may include bilateral flats 816 that extend the length of the post 788. While the femoral support arm assembly 786 is presented in the context of supporting the target clamp assembly 818 discussed next, it also has utility as a tool holder in the immediate operative site, when outfitted with clamp-on tool holders.

Referring to FIGS. 86A and 86B, a femoral head finder 918 is a T-shaped part with a body 920 and a stem 922. The body 920 forms the crossbar of the T-shape and the stem 922 forms the upright of the T-shape. The body 920 includes a deep groove or channel 924 that extends along the length of the body 920 so that the body is open along its bottom side.

The femoral head finder 918 may be coupled to the bar 790 of the femoral support arm assembly 786; the bar 790 is received in the channel 924. Note that the channel 924 has flat interior sides that are complementary to the flats 816 of the bar 790 so that the femoral head finder 918 does not rotate about the bar 790.

Referring to FIGS. 87A and 87B, a collar 926 is a ring with a radial hole 928 through a side wall of the ring. The hole 928 may be threaded to receive a set screw (not shown). The collar 926 may be coupled to the bar 790; the bar 790 is received in the collar 926. The set screw may be tightened in the hole 928 to lock the collar 926 to the bar 790.

Referring to FIGS. 65A-66B, a target clamp assembly 818 includes a target 820, a retaining ring 822, a first clamp body 824, a second clamp body 826, a lever 828, a link 830, and a pin 832. The example shows two links 830 and eight pins 832. The target 820 includes a slot 834 formed between a pair of uprights 836. The target may be called a goalpost or tuning fork. A ring, reticle, cross hairs, or the like may substitute for the goalpost design. The link 830 is preferably compliant or elastic.

A hole 838 of the first clamp body 824 receives a post 840 of the target 820; the retaining ring 822 engages a circumferential external groove 842 around the tip of the post 836 to prevent unintended disassembly of the first clamp body 824 and the target 820. The lever 828 is positioned between arms 844 of the first clamp body 824 so that hole 846 aligns with hole 848. A pin 832 is inserted into holes 846, 848 from each side of the first clamp body 824. Links 830 are positioned in notches 850 of the lever 828 so that holes 852 align with holes 854. A pin 832 is inserted into holes 852, 854 from each side of the lever 828. The links 830 are positioned in notches 856 of the second clamp body 826 so that holes 858 align with holes 860. A pin 832 is inserted into holes 858, 860 from each side of the second clamp body 826. Tabs 862 of the second clamp body 826 are positioned in notches 864 of the first clamp body 824 so that holes 866 align with holes 868. A pin 832 is inserted into holes 866, 868 from each side of the first clamp body 824. Preferably, a width of the first clamp body 824, in the direction of the holes 846, 866, is equal to the length of the body 920 of the femoral head finder 918.

The target clamp assembly 818 couples to the bar 790 of the femoral support arm assembly 786. With the lever 828 lifted so that the first and second clamp bodies 824, 826 are open, the bar 790 is received between the first and second clamp bodies. The lever 828 is lowered to urge the first and second clamp bodies 824, 826 against the bar 790. The links 830 are preferably compliant, elastic, or resilient, and may function as extension springs in the target clamp assembly 818.

While the target clamp assembly 818 is shown with a captive target 820, alternative clamp assemblies are contemplated that have other functional structures besides the target 820, for example replacing the target with a universal receiver for various tools.

Referring to FIGS. 67A-68B, a foot holder assembly 870 includes a foot holder 872, a lower bar 874, a post 876, an upper bar 878, a target mounting block 880, a target 882, and a thumbscrew 884. Four thumbscrews are included in the example shown. The post 876 may be received in either one of the bilateral sockets 886 in the lower bar 874 and fixed in place with a thumbscrew. The foot holder 872, which may be called a boot, rests in a concave portion 888 of the lower bar 874, and may be coupled to the lower bar 874 temporarily or permanently. The lower bar 874 may be coupled to the foot holder 872 anywhere along the proximal-distal length of the foot holder. The post 876 is also received in a hole 890 in the upper bar 878 and fixed in place with a thumbscrew 884. The post 876, sockets 886, and hole 890 are all hexagonal in this example, although other non-circular or circular shapes are contemplated. The target mounting block 880 includes a tab 892 which is received in an elongated slot 894 through the upper bar 878. The tab 892 includes a hole 896 into which a thumbscrew 884 threads to fix the target mounting block 880 in place during use. The target mounting block 880 includes another hole 898 which receives a post 900 of the target. The upper bar 878, target mounting block 880, target 882, and associated thumbscrew 884 may be replaced by the bar 790 (FIGS. 63A-64B) and target clamp assembly 818. More than one lower bar 874 may be coupled to the foot holder 872 simultaneously, in which case each lower bar 874 may have an associated post 876, upper bar 878, target mounting block 880, target 882, and thumbscrews 884; or bar 790 and target clamp assembly 818.

Methods of using the instrument system 500 will now be described with reference to FIGS. 69-85.

Figure 69:
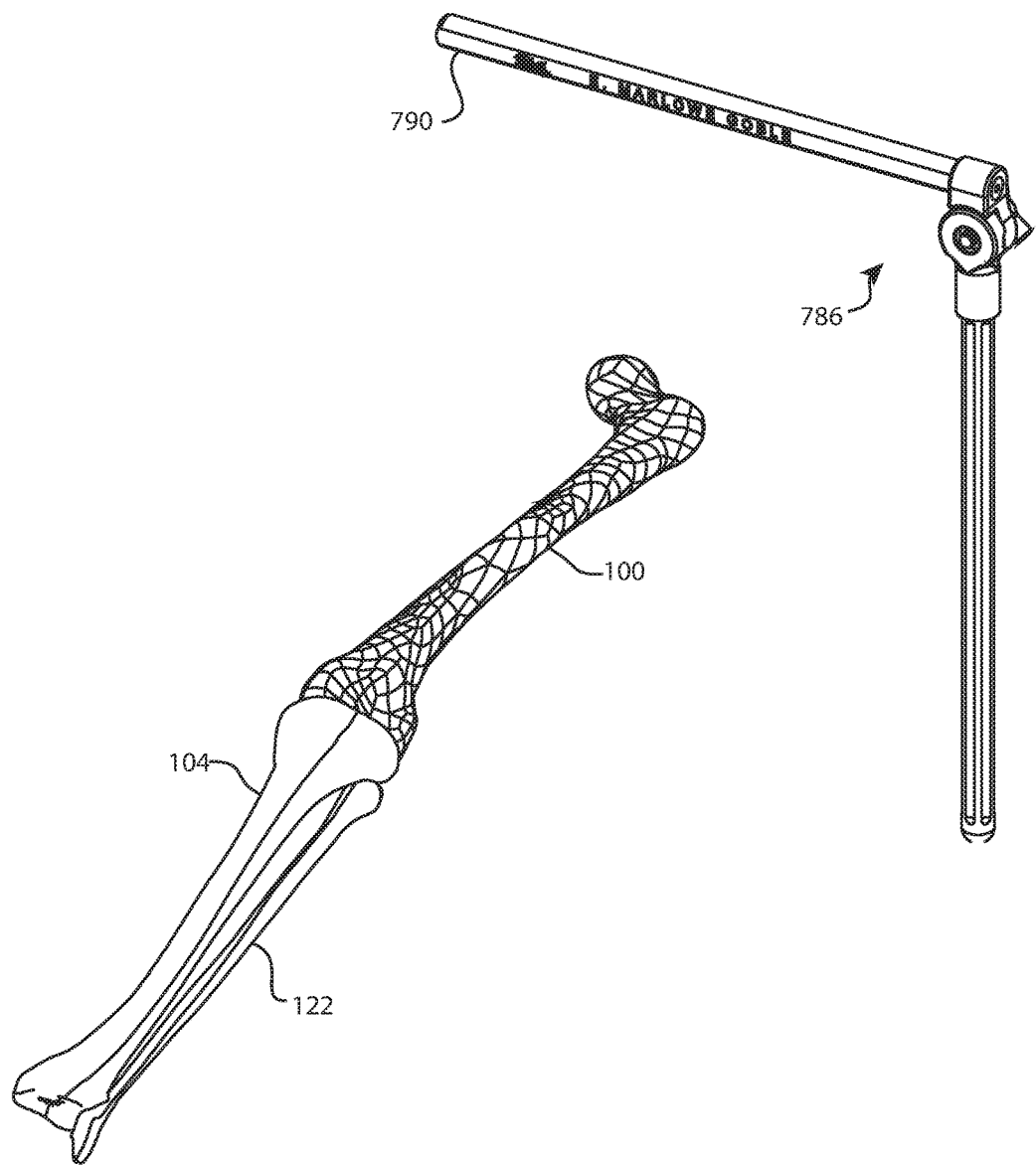
FIG. 69 is a perspective view of a femur, tibia, and fibula, showing the femoral support arm assembly of FIG. 63A.

Referring to FIG. 69, the femur 100, tibia 104, and fibula 122 are shown with the knee in full extension to represent a patient lying on an operating table during preparations for surgery. The femoral support arm assembly 786 is shown in position relative to the patient's leg, and may be clamped to the operating table in this position before being draped. The bar 790 extends horizontally over the patient's pelvis.

Figure 70:
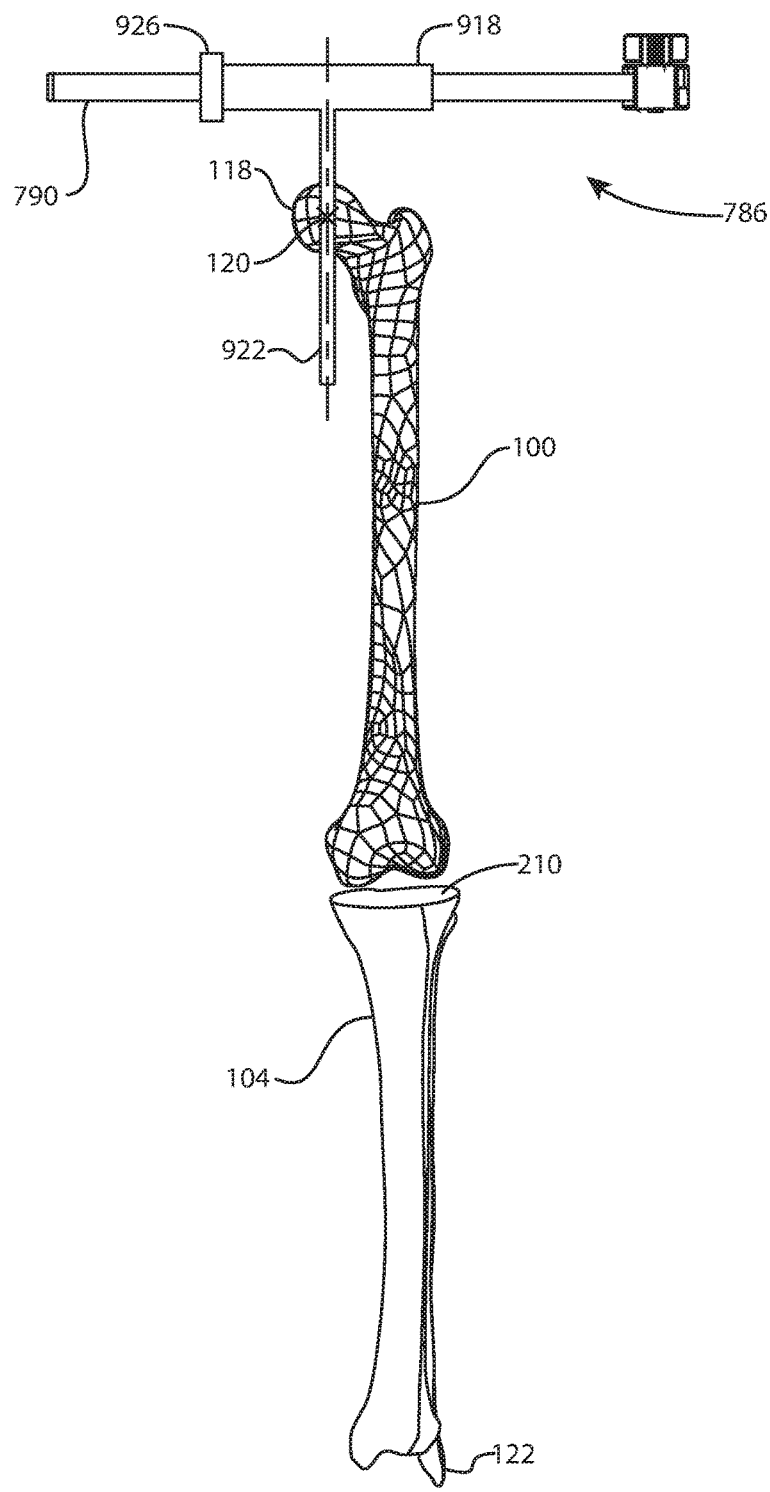
FIG. 70 is a perspective view of the femur, tibia, fibula, and femoral support arm assembly of FIG. 69 after performing a provisional proximal tibial resection.

Referring to FIG. 70, the femoral support arm assembly 786 may be positioned proximal (or distal) to the femoral head 118 so that the femoral head is exposed for radiographic or fluoroscopic imaging. Alternatively, the femoral support arm assembly 786 may be positioned directly over the center 120 of the femoral head 118, particularly if the bar 790 is radiolucent. The femoral head finder 918 has been coupled to the bar 790 and positioned along the bar so that the stem 922 extends over the center 120 of the femoral head 118. Radiographs, fluoroscopy, a C-arm, or other imaging may be used to verify that the stem 922 extends over the center 120 of the femoral head 118. The collar 926 has also been coupled to the bar 790 and positioned abutting the femoral head finder 918. After the stem 922 is positioned over the center 120 of the femoral head 118, the collar 926 may be locked to the bar 790. The femoral head finder 918 may then be removed from the bar 790. These steps shown in FIG. 70 are preferably performed before the patient is sterile draped and before the tourniquet is tightened. FIG. 70 also shows that a provisional tibial resection 210 has been made. The provisional tibial resection 210 may be made with the knee in full extension or in flexion. This step shown in FIG. 70 is performed after the patient is sterile draped and after the tourniquet is tightened.

Figure 71:
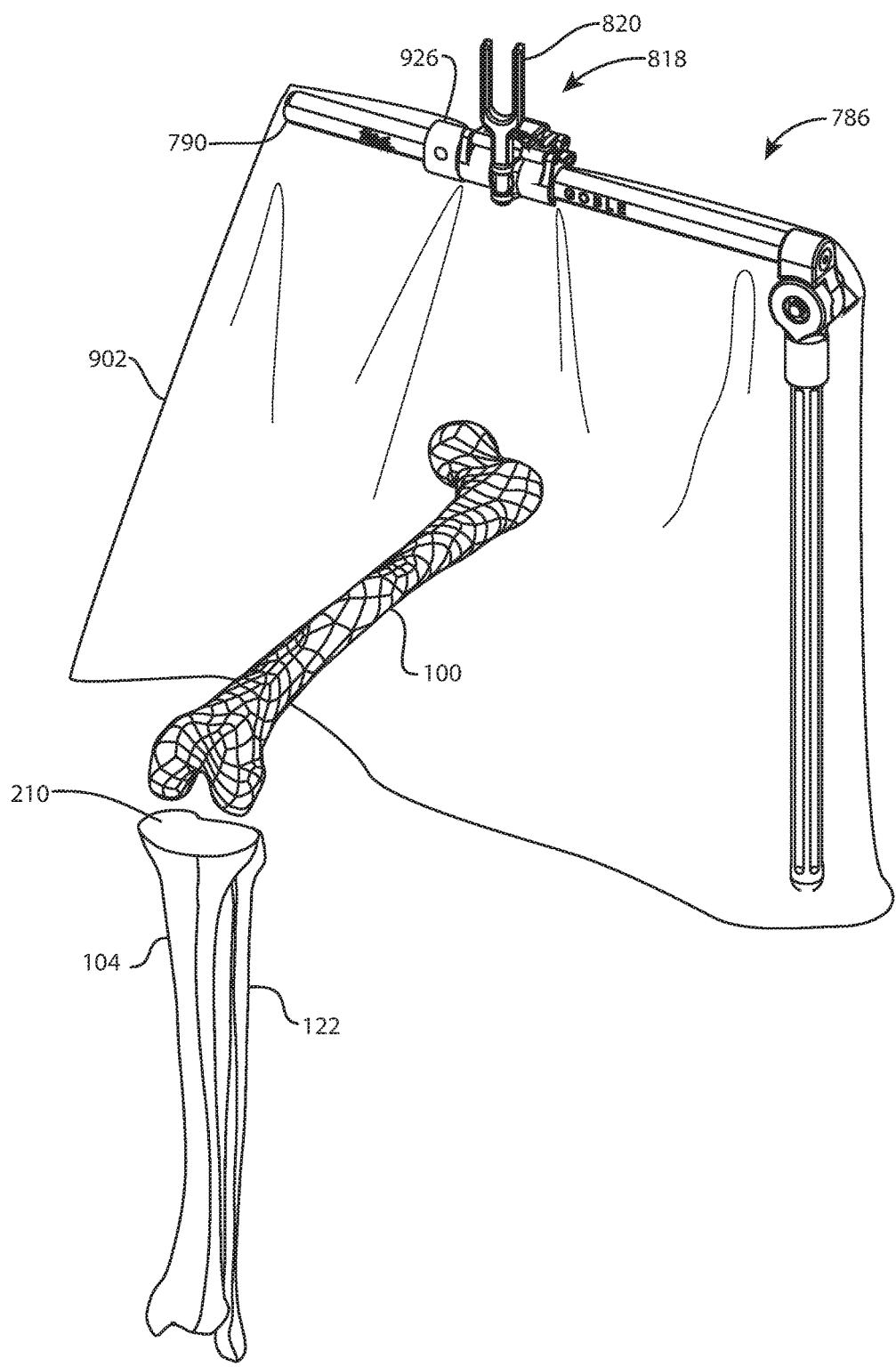
FIG. 71 is a perspective view of the femur, tibia, fibula, and femoral support arm assembly of FIG. 70, after coupling the target clamp assembly of FIG. 65A to the femoral support arm assembly.

Referring to FIG. 71, the target clamp assembly 818 has been coupled to the bar 790 of the femoral support arm assembly 786. Advantageously, this can occur after the femoral support arm assembly 786 has been covered with a drape 902, which is depicted as being sheer so that the femoral support arm assembly can be seen. The compliant, elastic, or resilient links 830 adjust to accommodate the thickness of the drape 902. The target 820 may be positioned proximal (or distal) to the femoral head 118, or directly over the center 120 of the femoral head, particularly if the target 820 is radiolucent. In this application, a target may be "over the center of the femoral head" even if the target is actually superior or inferior to the femoral head, so long as the femoral extension rod passes over the center of the femoral head when the femoral extension rod is aimed at the target. The target clamp assembly 818 has been coupled to the bar 790 directly adjacent to the collar 926. The bar 790 and the collar 926 are non-sterile and beneath the drape 902, while the target clamp assembly 818 is sterile and above the drape 902. This detail is noteworthy because the center 120 of the femoral head 118 may be objectively and precisely found in the non-sterile pre-operative phase, and transferred to the sterile operative phase by feeling the collar 926 through the sterile drape and positioning the target clamp assembly 818 next to the collar 926.

Referring to FIGS. 72A and 72B, the base 502 and femoral riser 504 have been coupled together for a left knee. The distal femoral condyle block 638 and the femoral extension rod 506 have been coupled to the femoral riser 504. The base 502 is being positioned against the anterior distal femur 102 and centered in the medial-lateral width of the distal femur 102, the paddle 642 is against the medial distal femoral condyle, and the femoral extension rod 506 is being aligned with the mechanical axis 202 of the leg (at least where it crosses the femur 100). The spool 608 is in the target 820.

Optionally, the angle block assembly 652 and the Whiteside's angle gage assembly 696 may be used during this step to assist in centering the femoral riser 504 and base 502 in the medial-lateral width of the distal femur 102, optionally using a narrow distal femoral condyle block 638, or a distal femoral condyle block that couples to the Whiteside's angle gage assembly 696. The angle block assembly 652 may be coupled to the femoral riser 504 and the Whiteside's angle gage assembly 696 may be coupled to the angle block assembly 652, with the shaft 700 of the Whiteside's angle gage assembly 696 extending within the intercondylar notch (trochlear notch), similar to the arrangement shown in FIG. 77, but without bone pins through the femoral pin guide 514. The base 502 may then be moved medial or lateral to center the shaft 700 in the intercondylar notch.

Optionally, a bone pin or screw may be driven into the distal femur 102 through a hole (not shown) that is centered between the mounting holes 584 of the femoral pin guide 514. The screw holds the femoral riser 504 and base 502 centered in the medial-lateral width of the distal femur 102 and serves as a pivot post about which the femoral riser 504, base 502, and the femoral extension rod 506 can rotate in the medial-lateral direction so that the femoral extension rod may be positioned over the center 120 of the femoral head 118.

Referring to FIG. 73, the femoral riser 504 has been pinned to the distal femur, along with the attached base 502 and femoral extension rod 506. The base 502 is under the suprapatellar fat pad 116 against the anterior distal femoral cortex and centered in the medial-lateral width of the distal femur 102, the paddle 642 is against the medial distal femoral condyle, and the femoral extension rod passes over the center 120 of the femoral head 118 and between the uprights 836 of the target 820. The bone pins extend into the distal femur in the metaphyseal, or metaphyseal equivalent, region as opposed to the diaphyseal or epiphyseal regions.

Depending upon bone quality and the configuration of any frictional elements protruding from the bone contacting surface 518 of the base 502, the bone contacting surface 518 may actually be spaced apart slightly from the anterior distal femoral cortex, rather than directly against the cortex. For example, in hard bone, the spikes 538 alone may bear against the cortex. In this situation, the three spikes 538 may be said to define a theoretical bone contacting plane. The theoretical bone contacting plane functions the same as the actual bone contacting surface 518, and is interchangeable with the actual bone contacting surface 518 in this specification.

Figure 74:
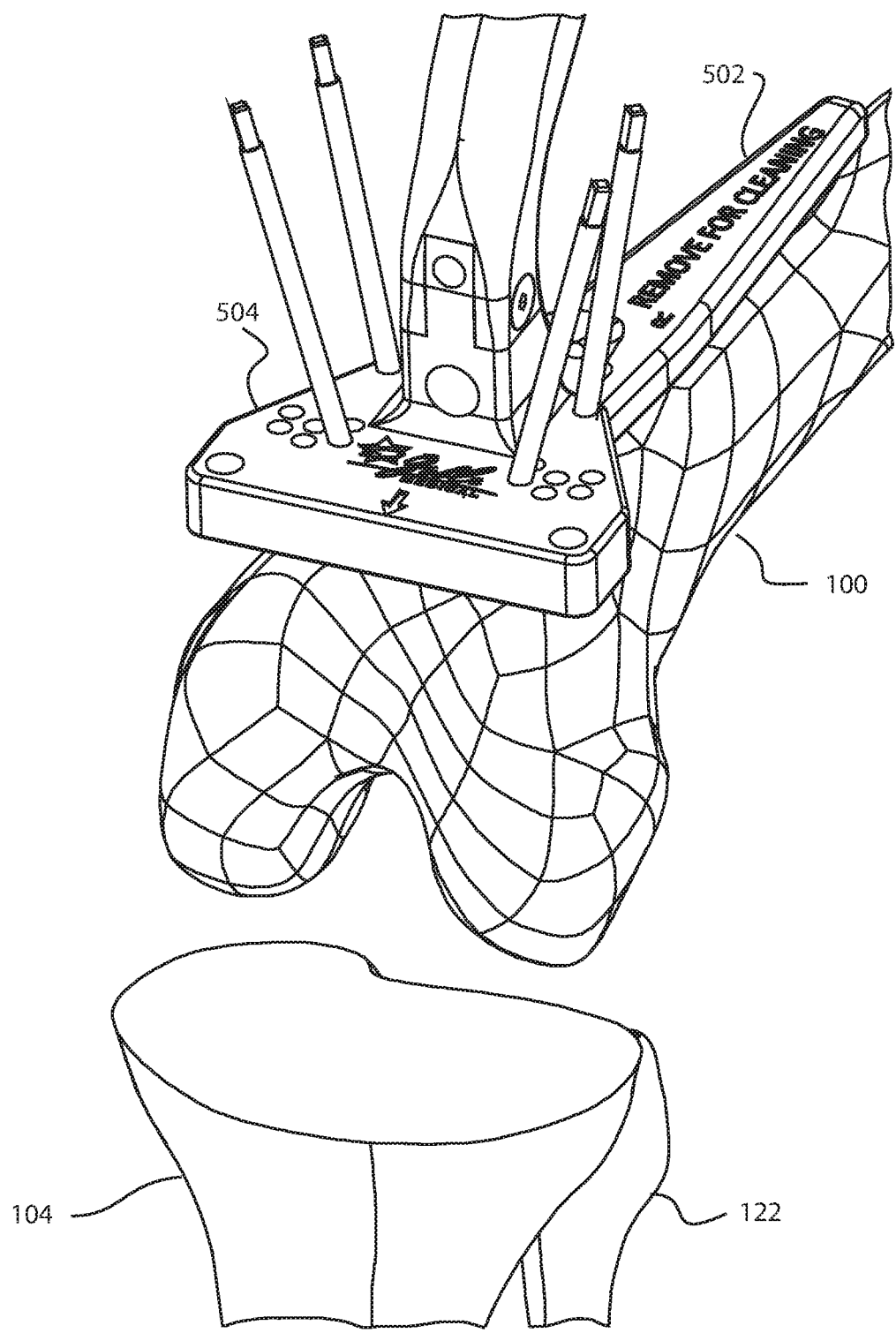
FIG. 74 is a perspective view of the femur, tibia, fibula, base, and femoral riser assembly of FIG. 73, after removing the distal femoral condyle block.

Referring to FIG. 74, the distal femoral condyle block 638 has been removed.

Referring to FIG. 75, the angle block assembly 652 has been coupled to the femoral riser 504. The clamp ring 672 has been loosened. The knee is shown in flexion in FIGS. 71-75, but may instead be in full extension during these steps.

Referring to FIG. 76, the Whiteside's angle gage assembly 696 has been coupled to the angle block assembly 652.

Referring to FIG. 77, the shaft 700 has been aligned with Whiteside's line and the clamp ring 672 has been tightened to save the orientation of the Whiteside's line in the angle block assembly 652. The knee is shown in flexion in FIGS. 76-77; this is preferable because it improves visibility of Whiteside's line.

Figure 78:
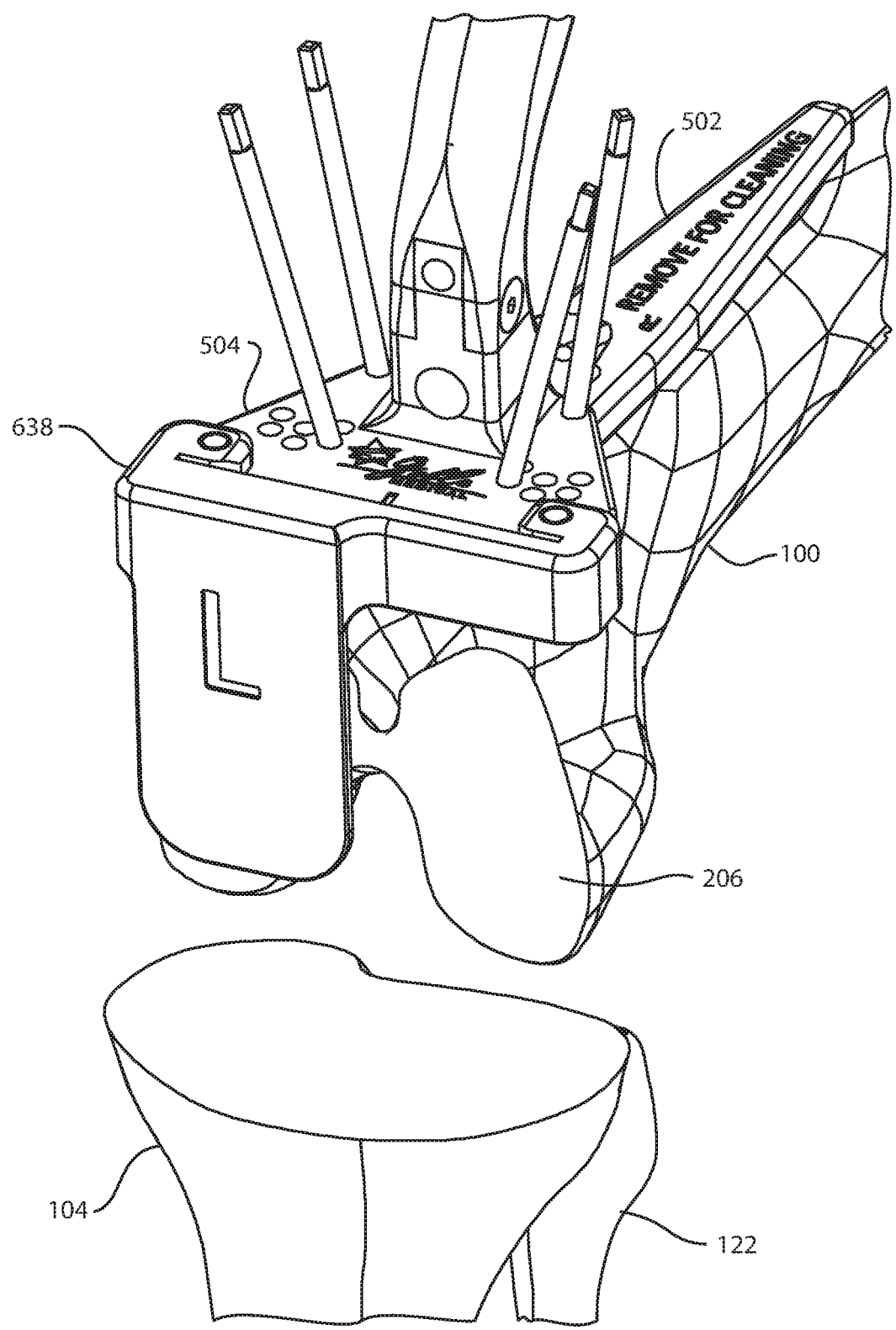
FIG. 78 is a perspective view of the femur, tibia, fibula, base, and femoral riser assembly of FIG. 77, after removing the Whiteside's line gage assembly and the angle block assembly, reattaching the distal femoral condyle block of FIG. 55A to the femoral riser assembly, and making a distal femoral resection guided by the distal femoral condyle block.

Referring to FIG. 78, the Whiteside's angle gage assembly 696 and the angle block assembly 652 have been removed from the femoral riser 504 and the distal femoral condyle block 638 has been replaced. A distal femoral resection 206 has been made, guided by the distal femoral condyle block 638. Preferably, the distal femoral resection 206 is made perpendicular to the mechanical axis 202 of the leg.

Figure 79:
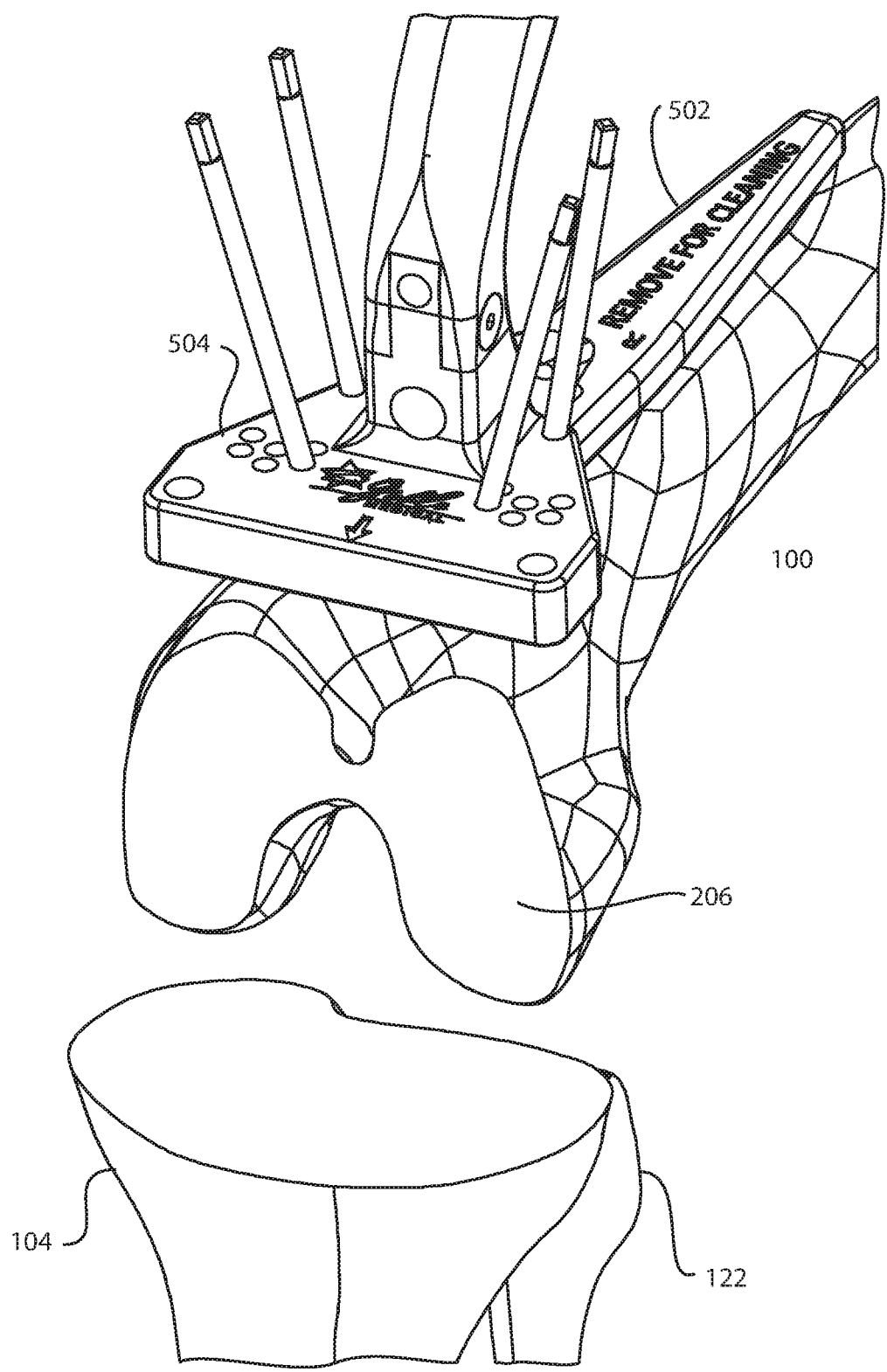
FIG. 79 is a perspective view of the femur, tibia, fibula, base, and femoral riser assembly of FIG. 78 after again removing the distal femoral condyle block.

Referring to FIG. 79, the distal femoral condyle block 638 has been removed again. The knee is shown in flexion in FIGS. 78-79, but may instead be in full extension during these steps.

Figure 80A:
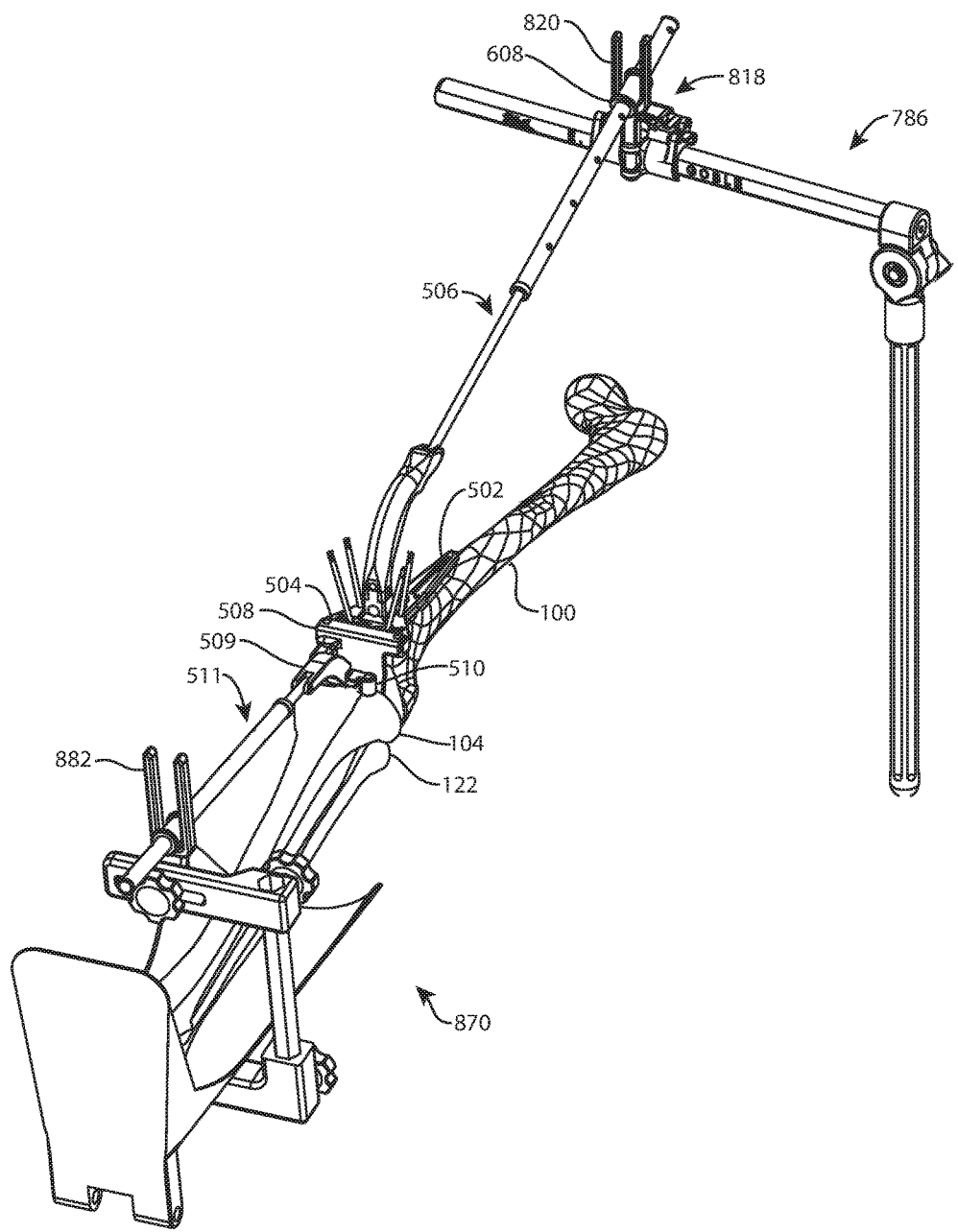
FIG. 80A is a perspective view of the femur, tibia, fibula, base, and femoral riser assembly of FIG. 79, after coupling the tibial connection block of FIG. 47A to the femoral riser assembly, coupling the tibial pin guide to the tibial connection block, placing the knee joint in full extension, and securing the foot in the foot holder assembly of FIG. 67A.
Figures 80B, 80C:
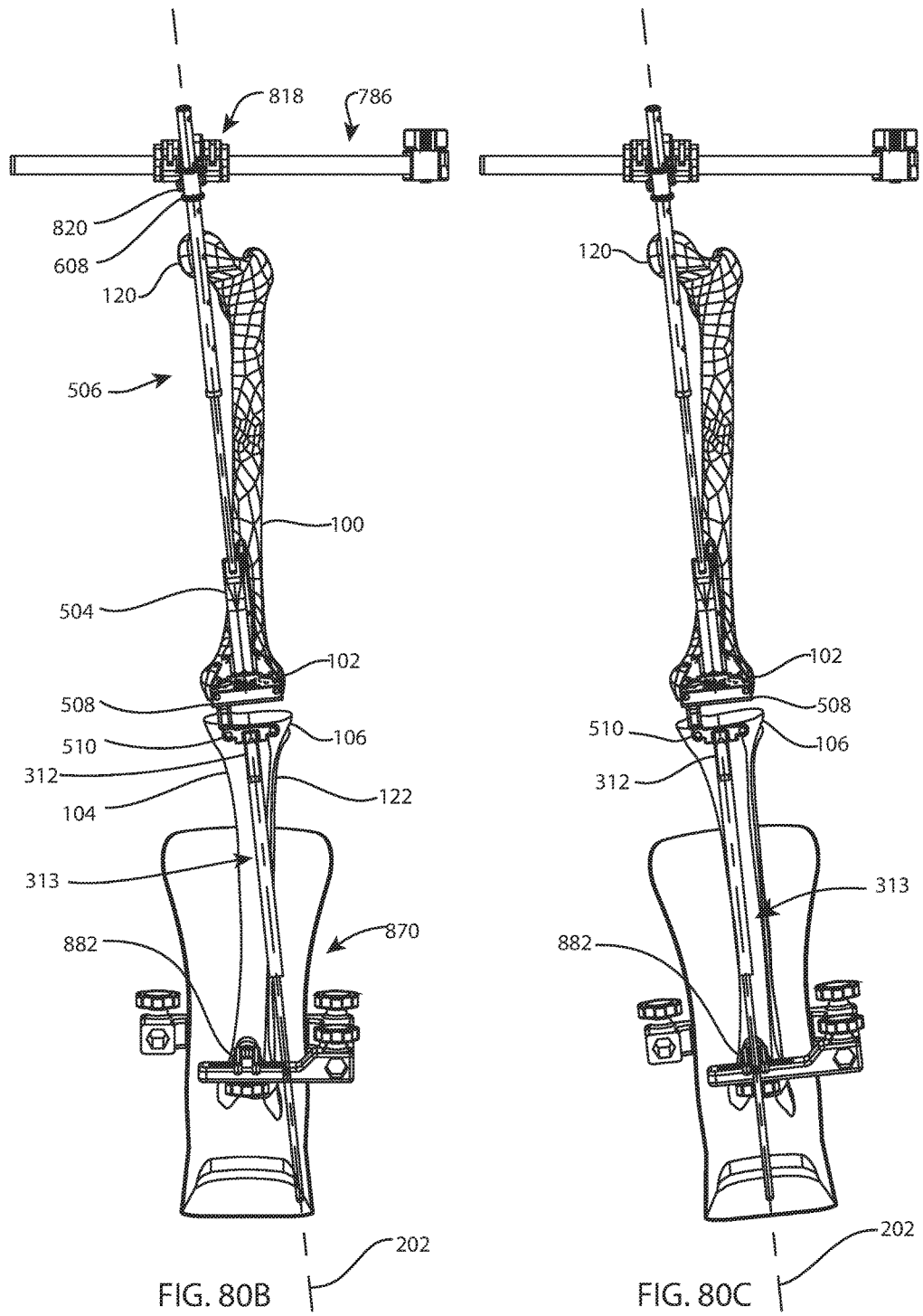
FIG. 80B is a top view of the femur, tibia, fibula, base, femoral riser assembly, tibial connection block, tibial pin guide, and foot holder assembly of FIG. 80A.
FIG. 80C is a top view of the femur, tibia, fibula, base, femoral riser assembly, tibial connection block, tibial pin guide, and foot holder assembly of FIG. 80B after aligning the tibia to the mechanical axis of the leg.

Referring to FIGS. 80A-B, the knee is in full extension, the foot has been secured within the foot holder assembly 870, the tibial connection block 508 has been coupled to the femoral riser 504, and the tibial pin guide 510 has been coupled to the tibial connection block 508 in preparation for the step of aligning the tibia to the mechanical axis 202 of the leg. In FIG. 80A, the tibial pin guide 510 is coupled to the tibial riser 509, which is coupled to the telescoping tibial extension rod 511. In FIG. 80B, the tibial pin guide 510 is shown in an alternate arrangement coupled to the tibial riser 312, which is coupled to the telescoping tibial extension rod 313. The proximal surface 774 of the tibial connection block 508 may be against the distal femoral resection 206. Other femoral resections 214, 216, 218, 220 may have been performed prior to this step. The foot holder assembly 870 is readily adaptable to hold the tibial target 882 over the anterior tibial crest or the tibial tuberosity, or any other location along the length of the tibia, ankle, or foot. Multiple tibial targets may be used, for example, one tibial target over the distal tibia/ankle and another tibial target over the tibial tuberosity.

As an alternative to a tibial target that is mounted to the foot holder assembly 870, a tibial target may be directly coupled to the tibia. For example, two bone pins may be placed in the proximal anterior tibia, one on either side of the tibial tuberosity, to serve as a proximal tibial target. The bone pins may be placed using a hand-held pin guide (not shown). The bone pins may be spaced apart so that the tibial riser 312 or 509 fits between the bone pins, is closely constrained by the bone pins to prevent medial-lateral translation, and is free to pivot in the medial-lateral direction so that the tibial extension rod 313 or 511 may be aimed at the distal tibial target.

Referring to FIGS. 80B and 80C, one can appreciate that the femoral extension rod 506 and the tibial extension rod 313 or 511 are collinear in an anterior view.

Referring to FIG. 80C, the tibial pin guide 510 is shown coupled to the tibial riser 312, which is coupled to the telescoping tibial extension rod 313. Alternately, the tibial pin guide 510 may be coupled to the tibial riser 509, which is coupled to the telescoping tibial extension rod 511. The tibia 104 has been aligned to the mechanical axis 202 of the leg so that the entire leg is aligned: femoral head center 120, distal femur 102, proximal tibia 106, and, in this example, the ankle. Preferably, the knee joint is distracted to the extent permitted by the existing ligamentous structures of the knee while the tibia 104 is aligned to the mechanical axis 202. Now parallel bone pins may be inserted through the holes 782 of the tibial pin guide 510 into the tibia 104 in preparation for further surgical steps involving the tibia 104. The tibial pin guide 510 may be removed from the tibia, leaving the parallel bone pins behind. A subsequent instrument may be coupled to the tibia by sliding the instrument over the parallel bone pins. For example, the tibial cut guide 328 of FIGS. 34A-34B may be placed over the tibial bone pins, and a saw used through the tibial cut guide to make a proximal tibial resection 210.

Figure 81:
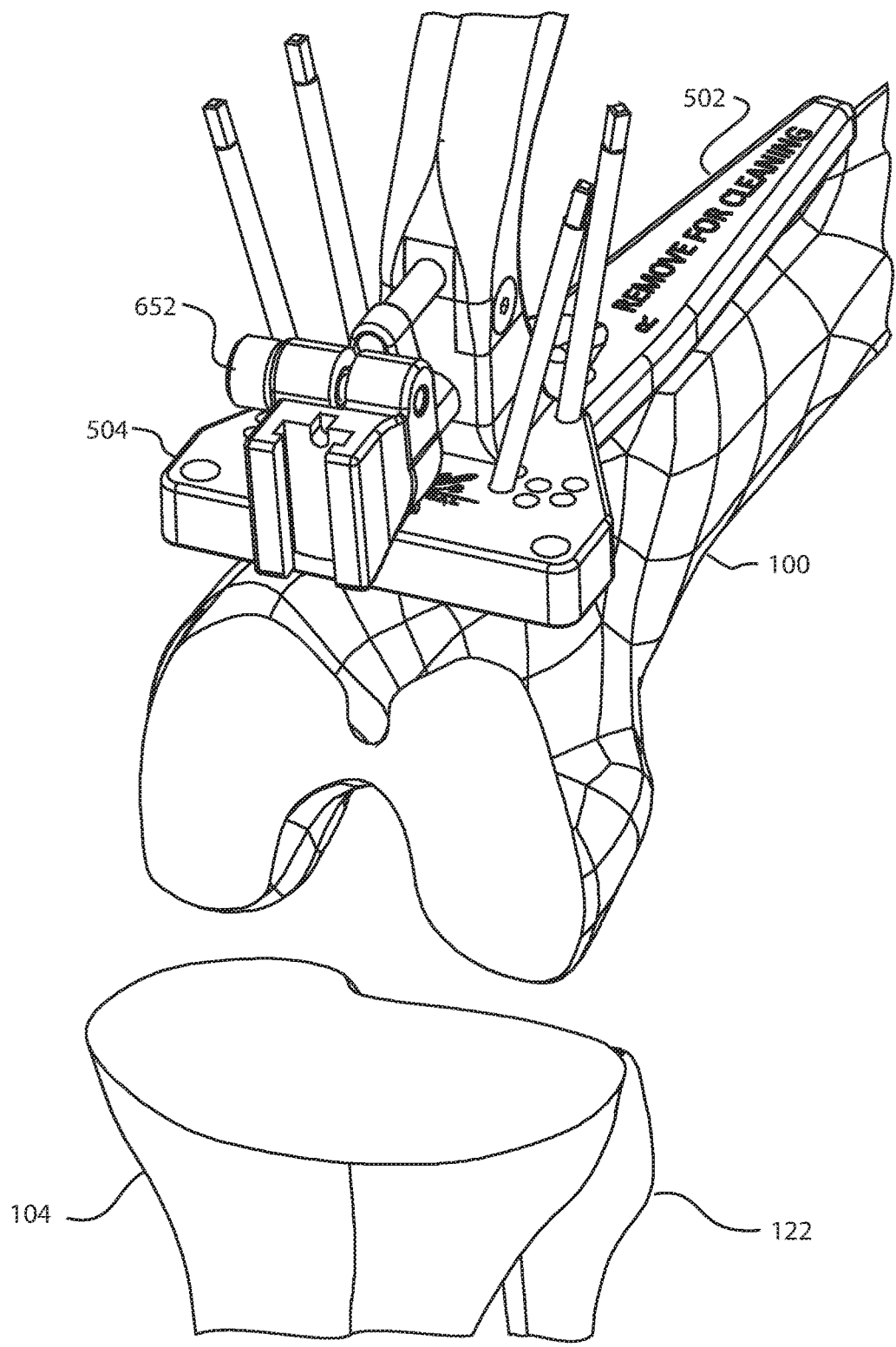
FIG. 81 is a perspective view of the femur, tibia, fibula, base, and femoral riser assembly of FIG. 80A, after removing the tibial connection block and tibial pin guide and reattaching the angle block assembly of FIG. 77 to the femoral riser assembly.

Referring to FIG. 81, the surgical procedure has turned to the femur 100. The angle block assembly 652 has been reattached to the femoral riser 504, and the clamp ring 672 remains tight, maintaining the alignment of Whiteside's line (FIG. 77) for the subsequent steps.

Figure 82:
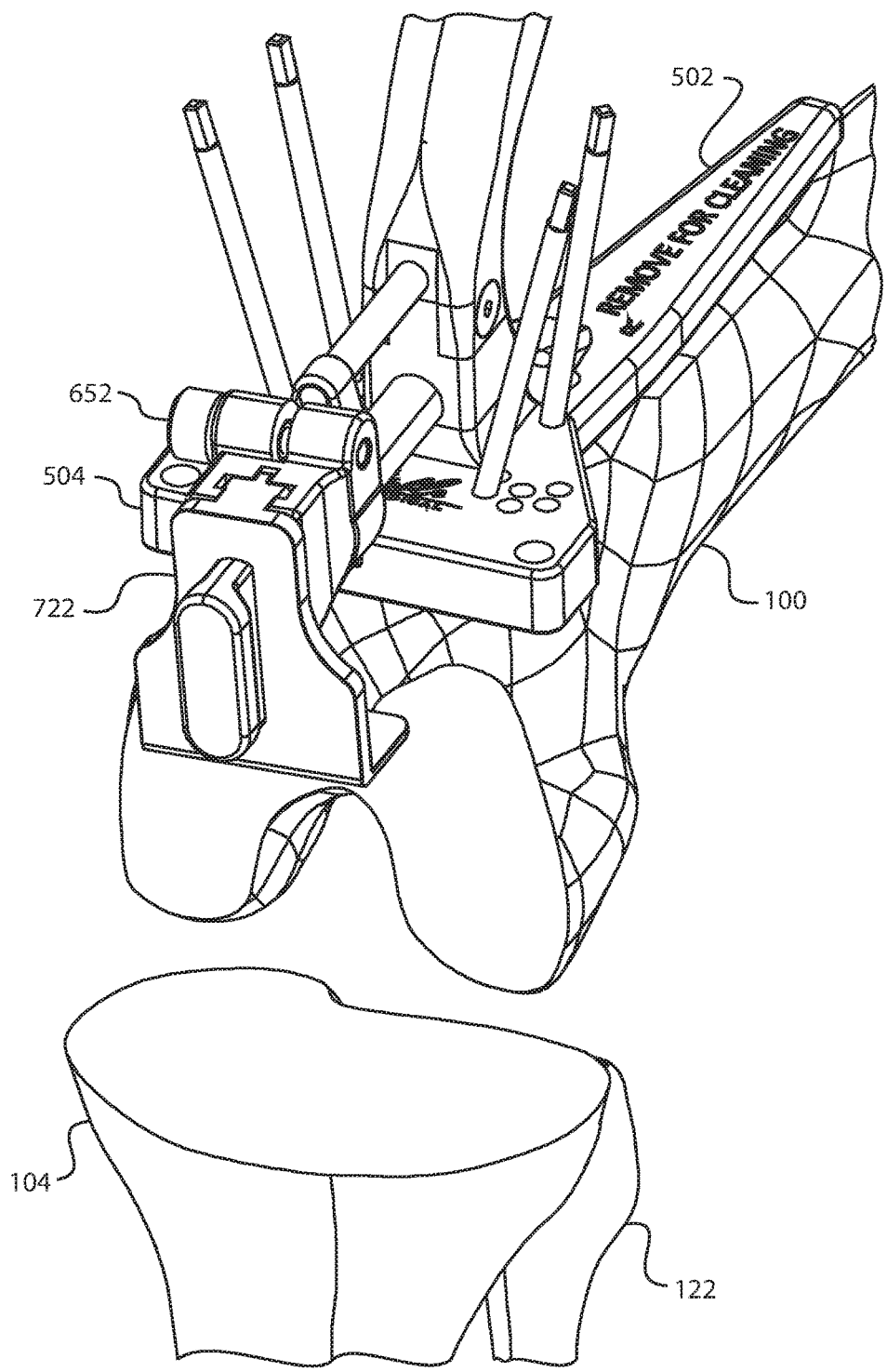
FIG. 82 is a perspective view of the femur, tibia, fibula, base, femoral riser assembly, and angle block assembly of FIG. 81, after coupling the cut guide mounting block assembly of FIG. 59A to the angle block assembly.

Referring to FIG. 82, the cut guide mounting block assembly 722 has been coupled to the angle block assembly 652.

Figure 83:
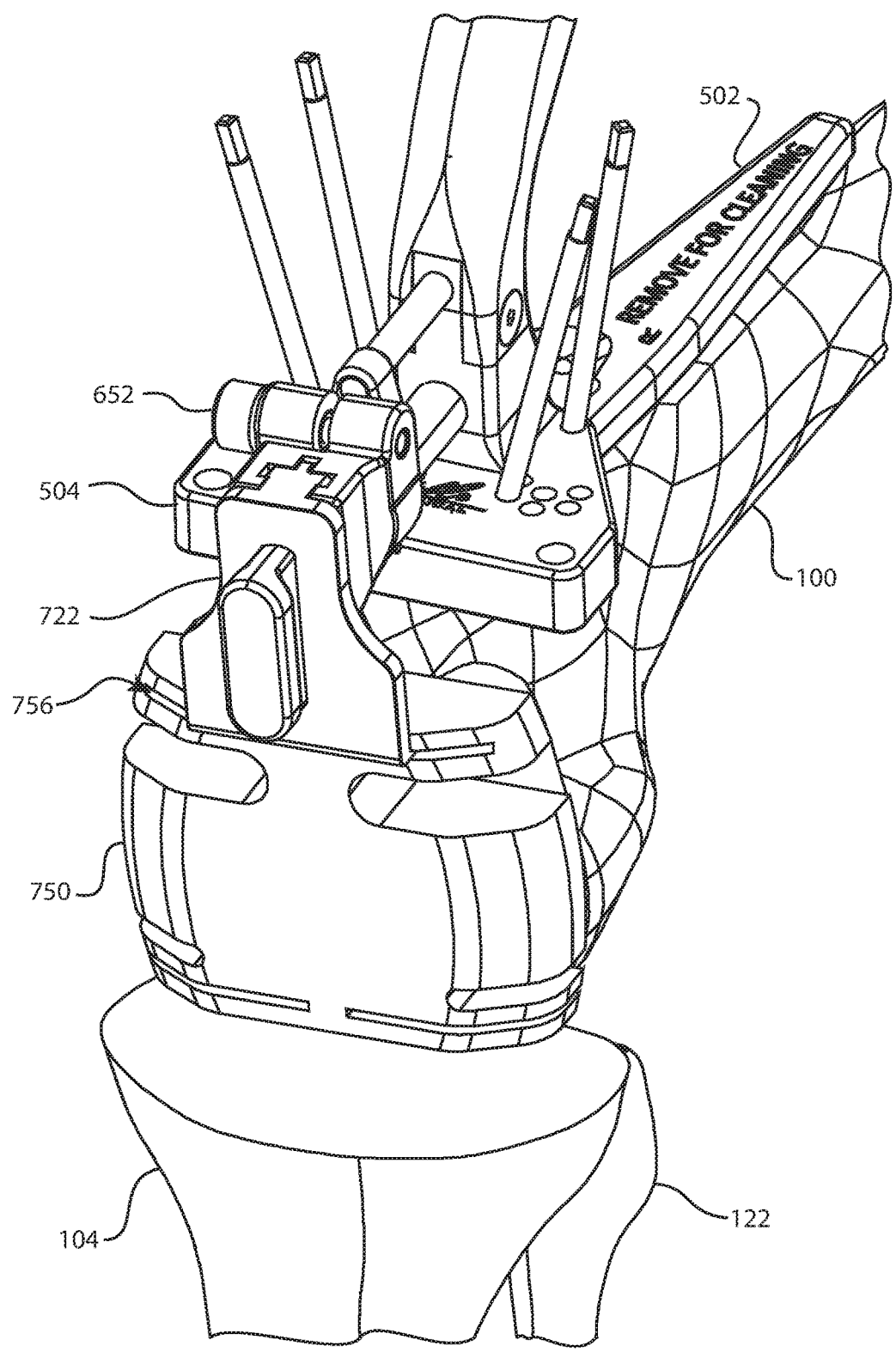
FIG. 83 is a perspective view of the femur, tibia, fibula, base, femoral riser assembly, angle block assembly, and cut guide mounting block assembly of FIG. 82, after coupling the four-in-one cut guide of FIG. 61A to the cut guide mounting block assembly.

Referring to FIG. 83, the four-in-one cut guide 750 has been coupled to the cut guide mounting block assembly 722.

Figure 84:
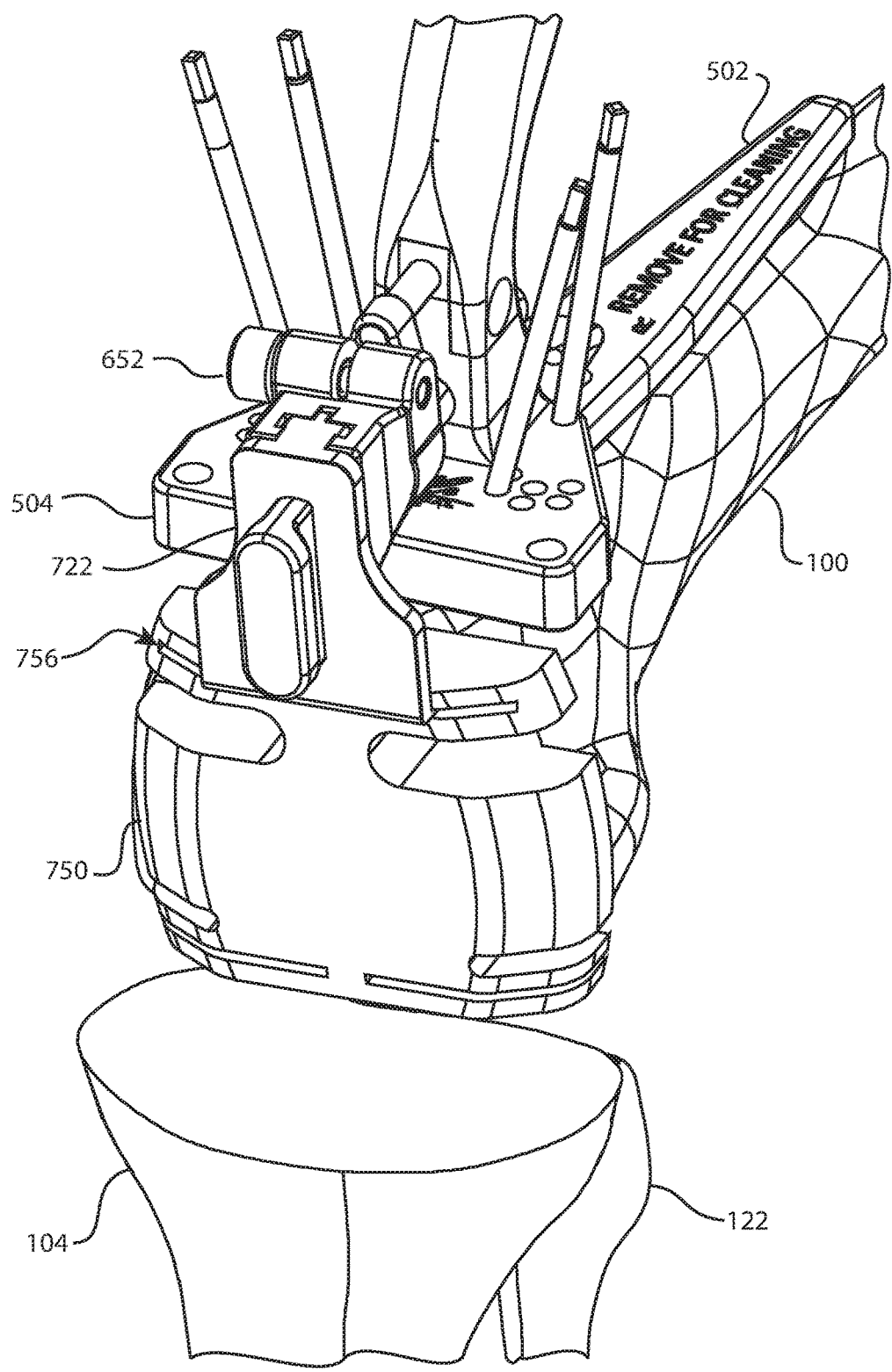
FIG. 84 is a perspective view of the femur, tibia, fibula, base, femoral riser assembly, angle block assembly, cut guide mounting block assembly, and four-in-one cut guide of FIG. 83 after aligning the four-in-one cut guide against the distal femoral resection.

Referring to FIG. 84, the four-in-one cut guide 750 has been aligned in the medial-lateral direction and positioned against the distal femoral resection 206. At this point, bone pins may be driven through medial and lateral holes (not shown) in the four-in-one cut guide 750 to secure the guide 750 to the distal femur.

Alternately, a drill bit or bone pin may be driven through a slot of the four-in-one cut guide 750 so that the drill extends in a proximal-distal direction, parallel to the bone contacting surface 518 of the base 502, at the level of the spikes 538. The drill bit or bone pin acts as a hanger for the four-in-one cut guide 750 while permitting rotational and side-to-side adjustment of the four-in-one cut guide. Rotational alignment may be provided by a block with an inclined plane, wherein the block is seated on the proximal tibial resection 210, wherein the four-in-one cut guide 750 rests on the inclined plane, wherein the plane is inclined in the medial-lateral direction and is higher under the lateral condyle. The plane may be 3 mm higher under the lateral condyle.

Figure 85:
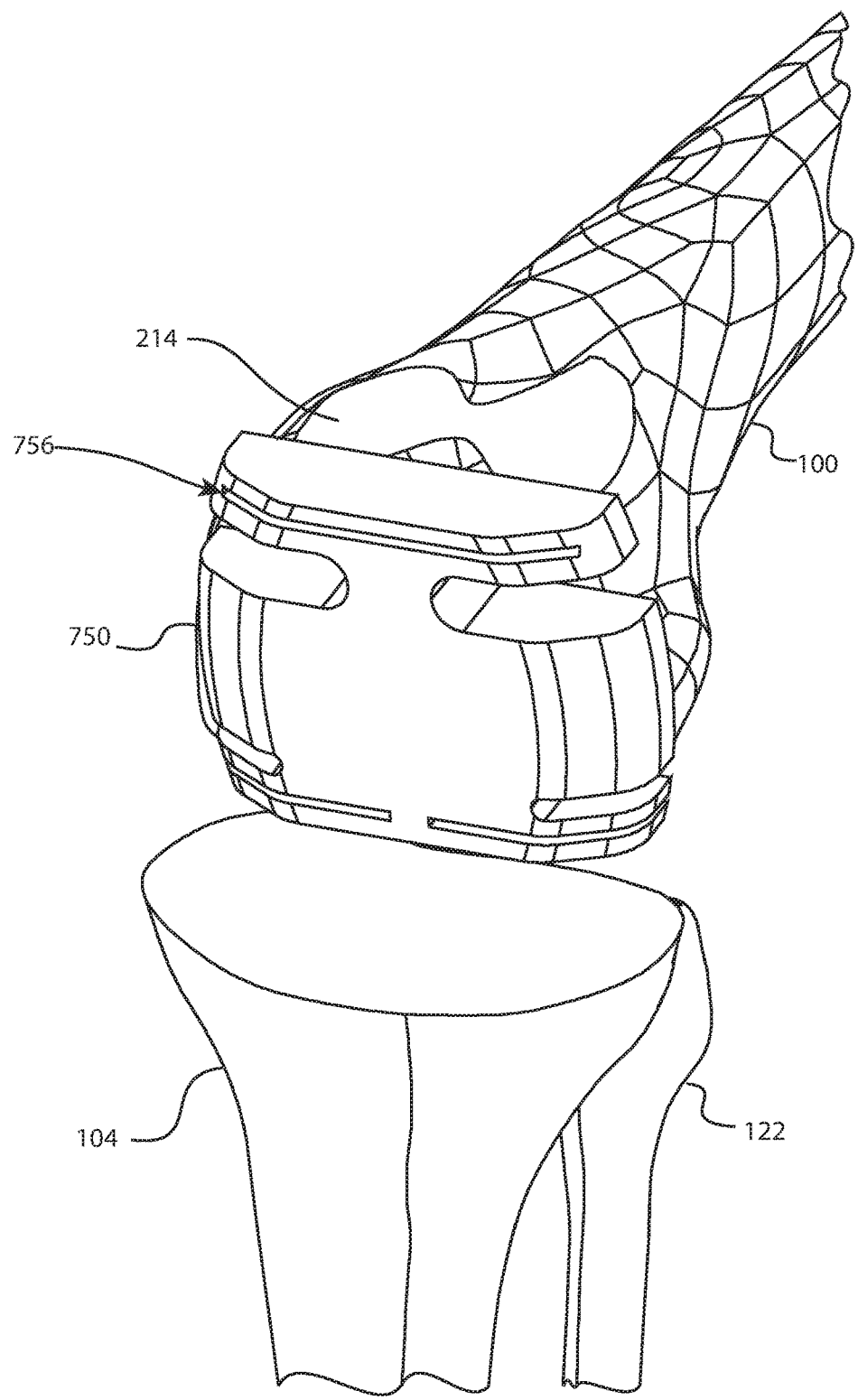
FIG. 85 is a perspective view of the femur, tibia, fibula, and four-in-one cut guide of FIG. 85, after fixing the four-in-one cut guide to the distal femoral resection, removing the base, femoral riser assembly, cut guide mounting block assembly, and angle block assembly, and making an anterior femoral resection guided by the four-in-one cut guide.

Referring to FIG. 85, the cut guide mounting block assembly 722, the angle block assembly 652, the femoral riser 504, and the base 502 have been removed from the femur 100, leaving only the four-in-one cut guide 750 secured to the femur. However, as explained above, preferably the femoral riser 504 and base 502 remain coupled to the femur 100 in this step. An anterior femoral resection 214 has been made through the slot 756. The anterior femoral resection 214 and the bone contacting surface 518 of the base 502 lie in a common plane.

After making the femoral resections 206, 214, 216, 218, and/or 220, the surgical procedure may turn to the tibia 104. The next step may be to align the tibia to the mechanical axis 202 of the leg as described for FIGS. 80A-80C. Alternately, the next steps may include coupling the tibial cut guide 328 (with the desired slope) to the proximal tibial bone pins previously placed using the tibial pin guide 510 and creating a final proximal tibial resection 210 through the tibial cut guide 328.

Figure 88:
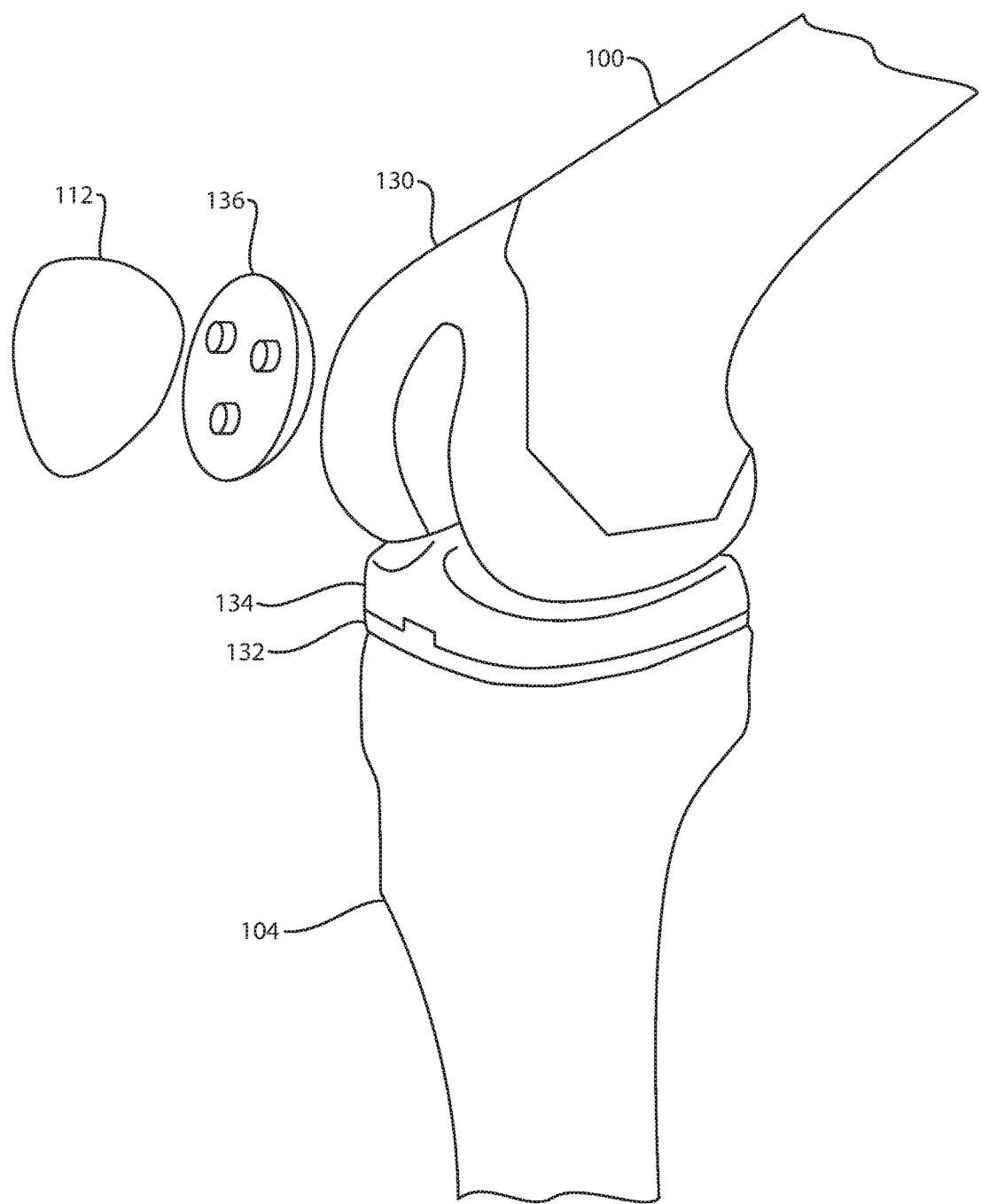
FIG. 88 is an isometric view of a knee joint with implanted femoral component, tibial component, articular insert, and patellar component, the patellar component shown exploded from the patella for clarity.

Referring to FIG. 88, after the femur 100, tibia 104, and optionally patella 112 are prepared, knee arthroplasty implants may be secured to the prepared bone surfaces. FIG. 88 is an isometric view of a knee joint with a femoral component 130, a tibial component 132, an articular insert 134, and a patellar component 136. The patellar component 136 is shown exploded from the patella for clarity, since the patellar component would otherwise be hidden by the patella in this view. Unicondylar or unicompartmental implants may be implanted instead of the total knee components shown.

FIGS. 89-120 illustrate yet another instrument system 1500.

Figure 89:
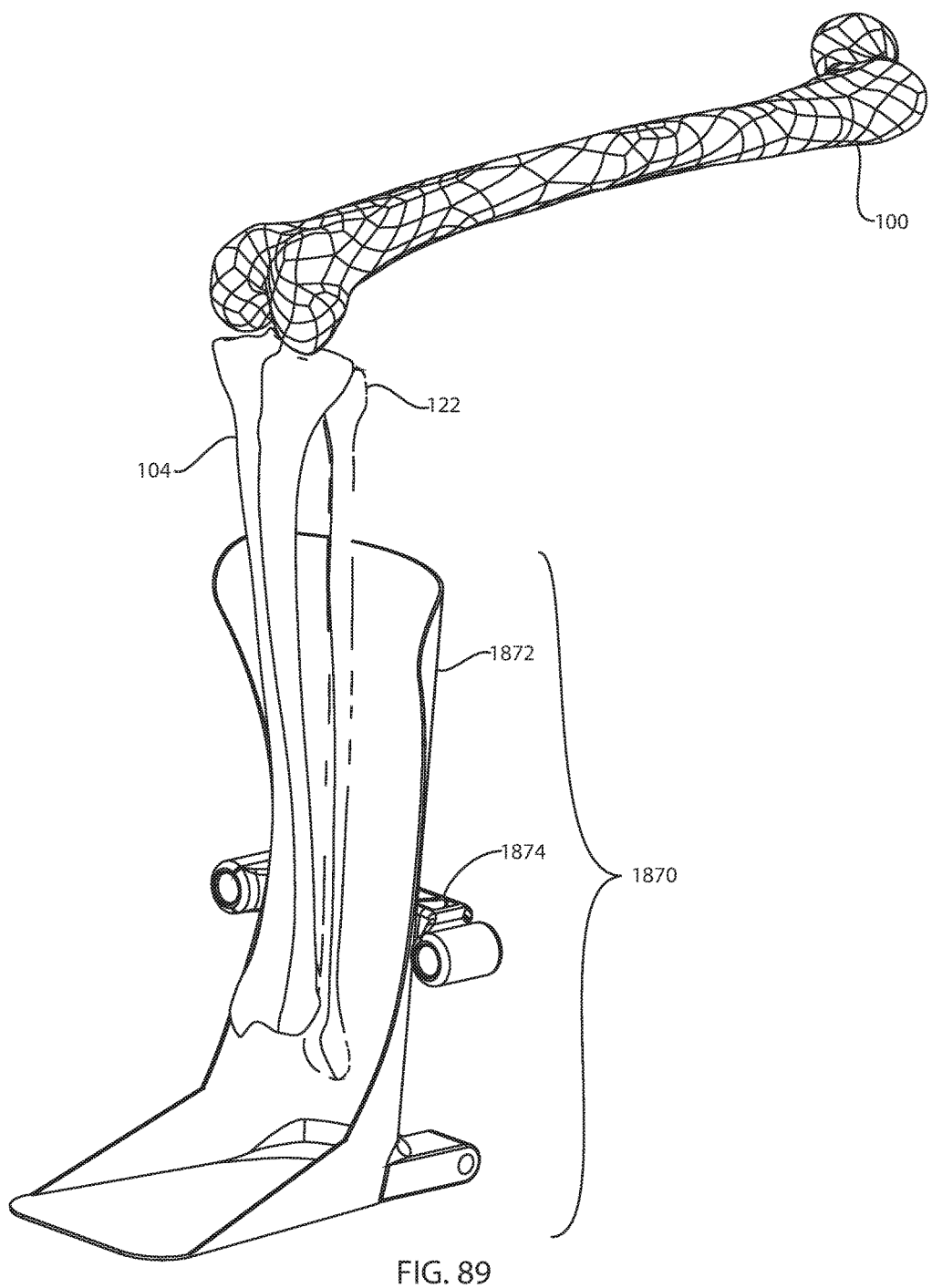
FIG. 89 is a perspective view of a femur, tibia, and fibula with a foot receiver and a lower bar of a foot holder assembly.
Figure 94:
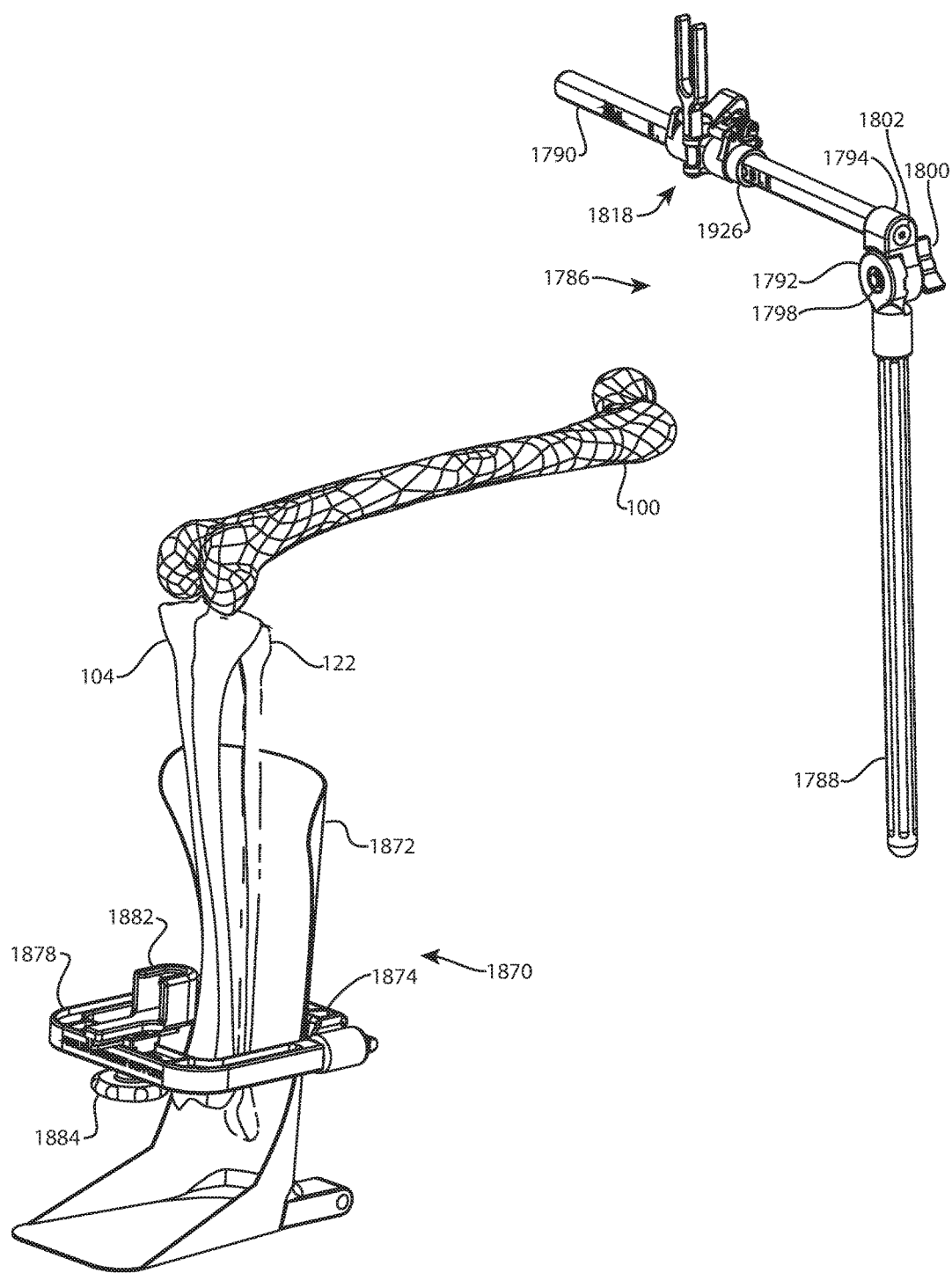
FIG. 94 is a perspective view of the femur, tibia, fibula, foot receiver, lower bar, femoral support arm assembly, collar, and target clamp assembly of FIG. 93 with a complete foot holder assembly including a bridge, target mounting block, dovetail lock, target, and thumbscrew coupled to the lower bar and the foot receiver.
Figure 95A:
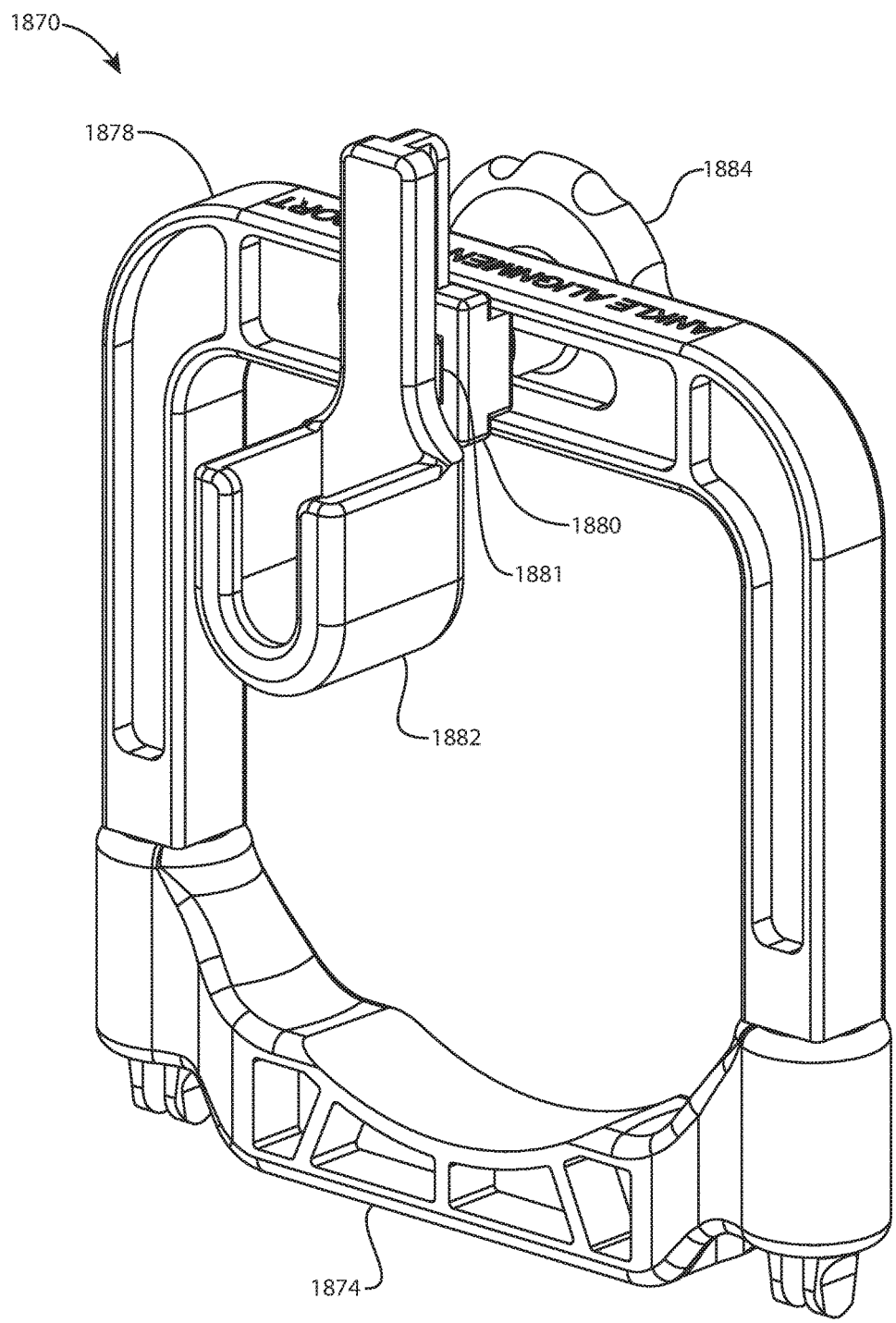
FIG. 95A is a perspective view of the foot holder assembly of FIG. 94.
Figure 95B:
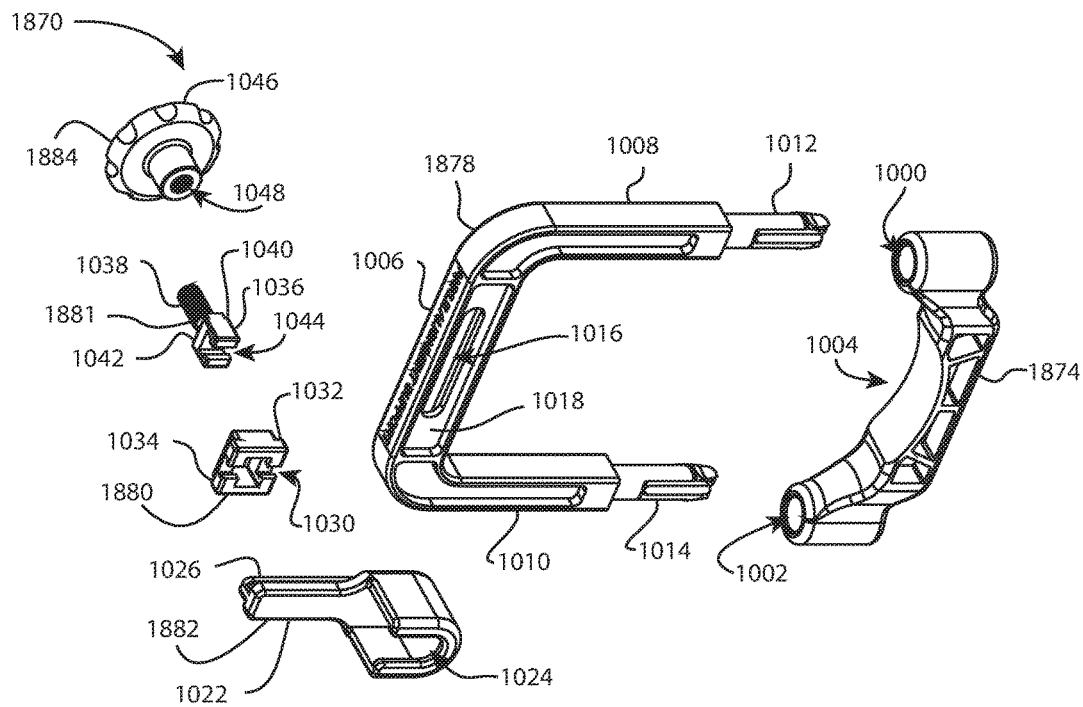
FIG. 95B is an exploded perspective view of the foot holder assembly of FIG. 94.
Figure 95C:
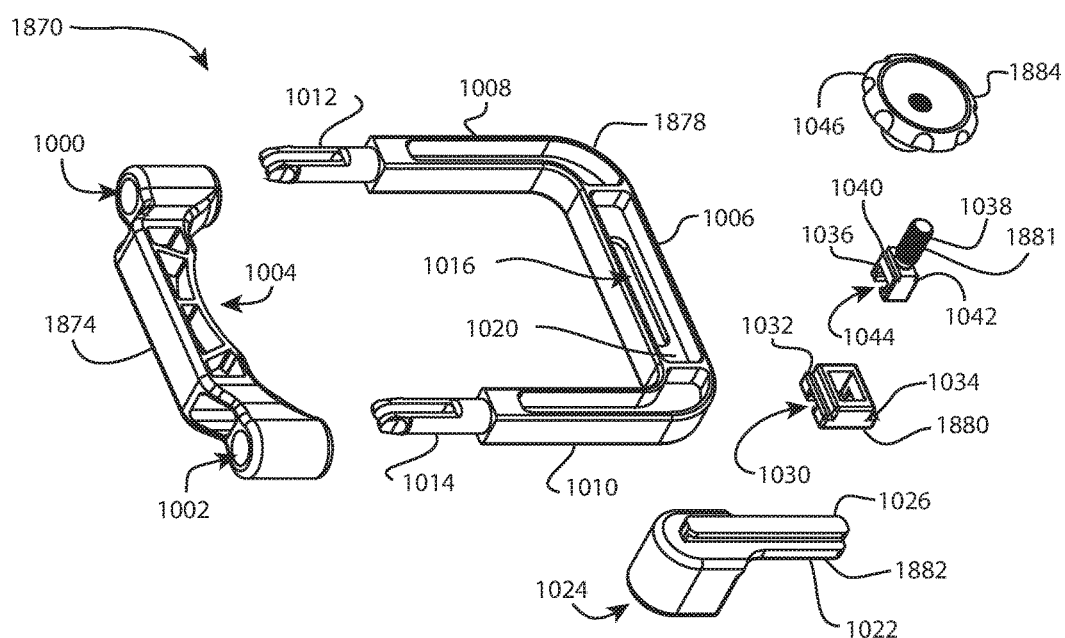
FIG. 95C is another exploded perspective view of the foot holder assembly of FIG. 94 from a different direction.

FIG. 89 shows the step of securing a foot (not shown, the lower leg is represented by the tibia 104 and fibula 122) in a portion of a foot holder assembly 1870. The foot holder assembly 1870 includes a foot receiver 1872, a lower bar 1874, a bridge 1878, a target mounting block 1880, a dovetail lock 1881, a target 1882, and a thumbscrew 1884. The bridge 1878, target mounting block 1880, dovetail lock 1881, target 1882, and thumbscrew 1884 are shown in FIGS. 94-95C.

Figure 90:
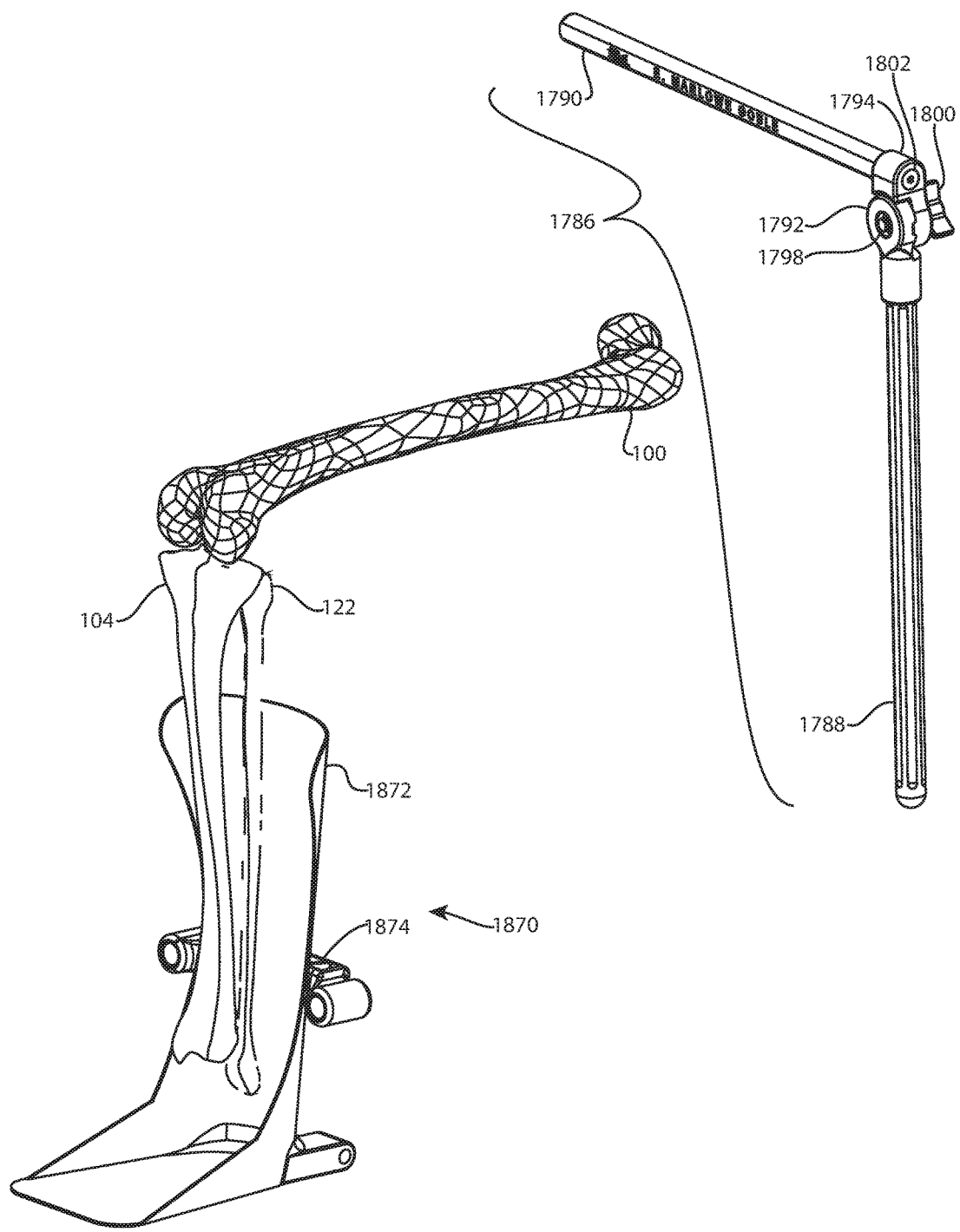
FIG. 90 is a perspective view of the femur, tibia, fibula, foot receiver, and lower bar of FIG. 89 with a femoral support arm assembly.

FIG. 90 shows the step of securing a femoral support arm assembly 1786 to an operating table (not shown) so that a portion of the femoral support arm assembly extends over the hip area. This step may be similar to or identical to the step of FIG. 69. The femoral support arm assembly 1786 includes a post 1788, a bar 1790, a first clamp body 1792, a second clamp body 1794, a spring 1796, a retaining ring 1798, a thumbscrew 1800, and a screw 1802. The femoral support arm assembly 1786 may be similar to or identical to the femoral support arm assembly 786 or 2786.

Figure 91:
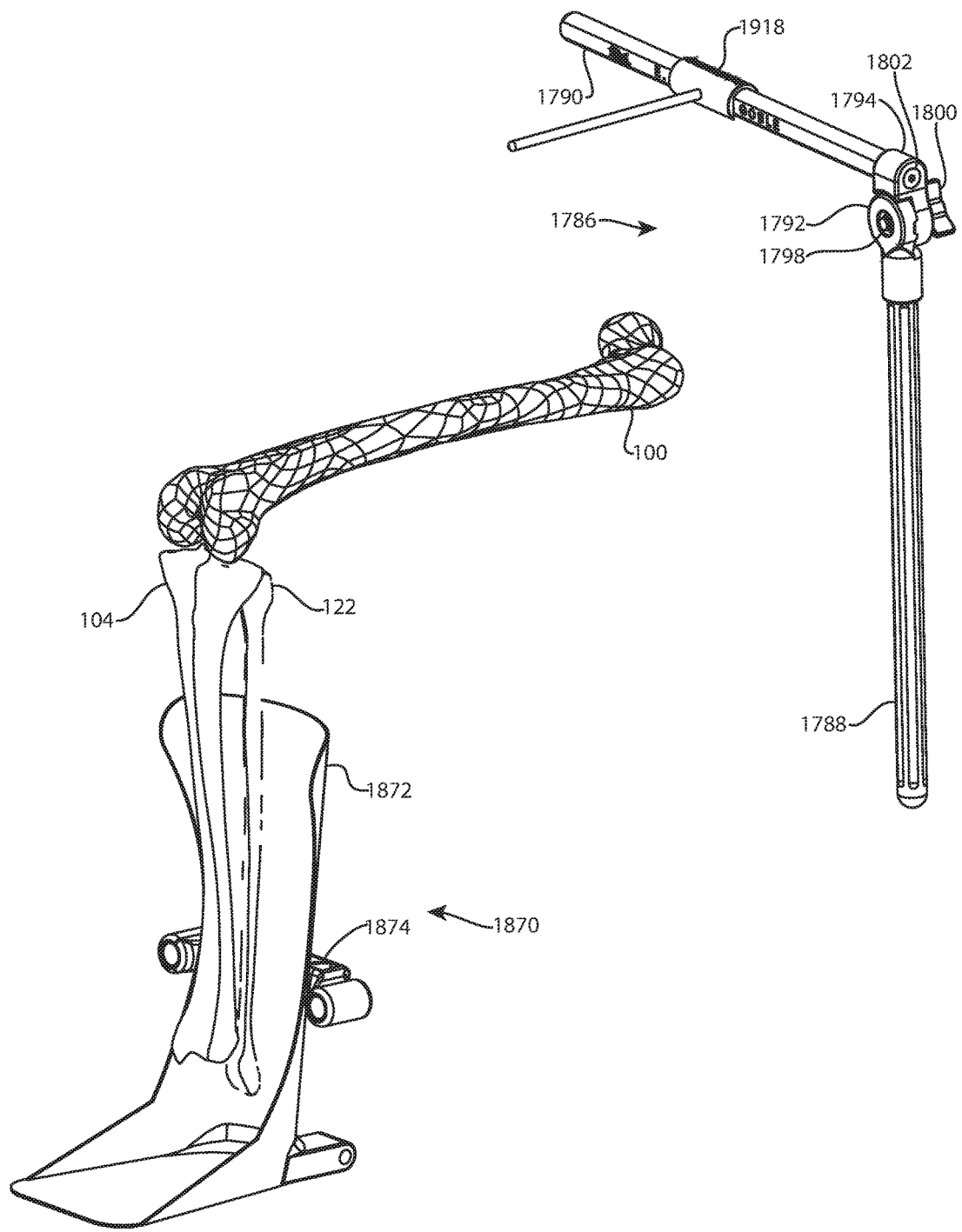
FIG. 91 is a perspective view of the femur, tibia, fibula, foot receiver, lower bar, and femoral support arm assembly of FIG. 90 with a femoral head finder coupled to the femoral support arm assembly.

FIG. 91 shows the step of positioning a femoral head finder 1918 to extend over the center 120 of the head 118 of the femur 100. This alignment may be verified using imaging, for example fluoroscopy. 70. The femoral head finder 1918 may be similar to or identical to the femoral head finder 918 or 2918.

Figure 92:
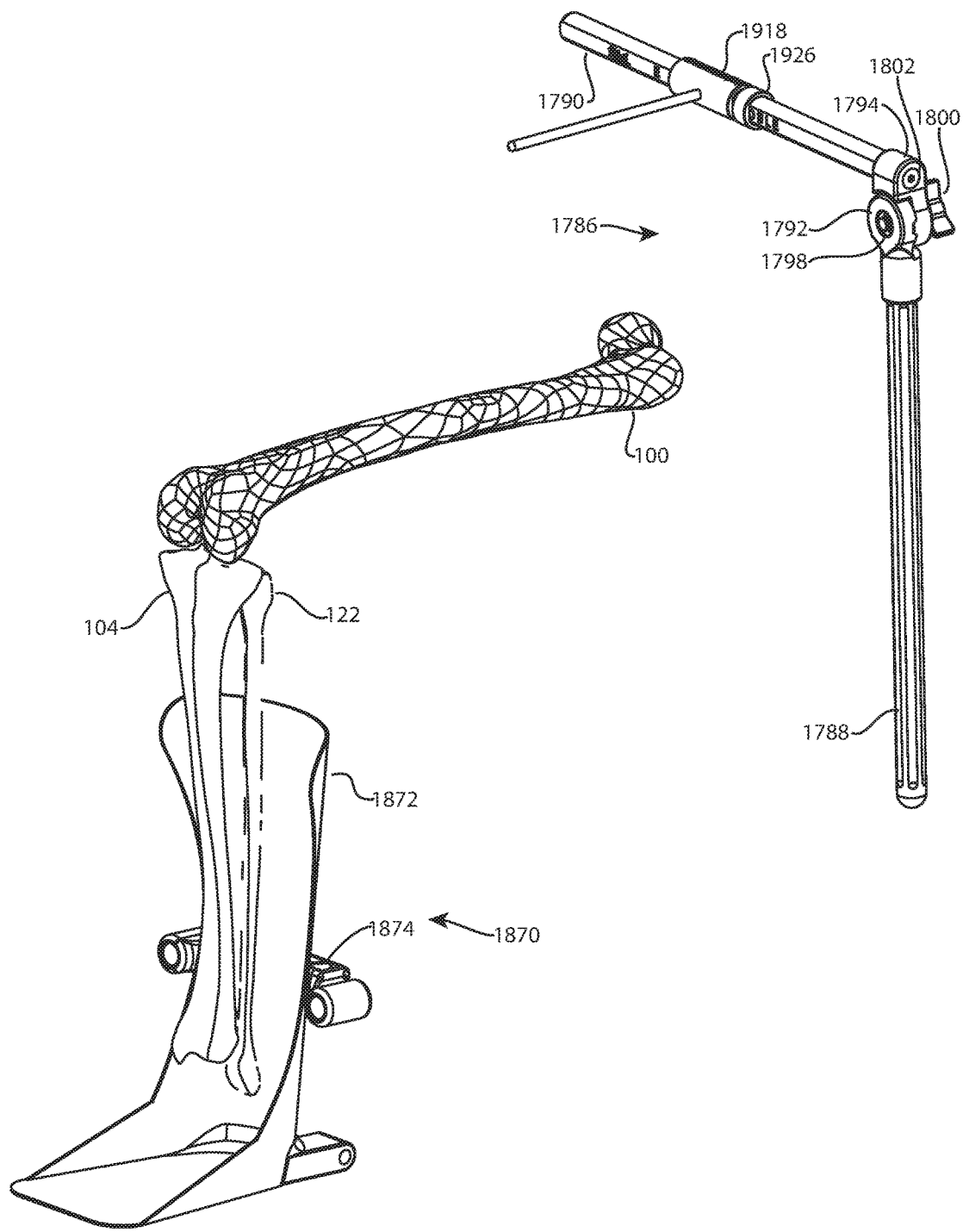
FIG. 92 is a perspective view of the femur, tibia, fibula, foot receiver, lower bar, femoral support arm assembly, and femoral head finder of FIG. 91 with a collar coupled to the femoral support arm assembly next to the femoral head finder.

FIG. 92 shows the step of securing a collar 1926 to the bar 1790 beside the femoral head finder 1918. The steps of FIGS. 91 and 92 may be similar to or identical to the step of FIG. 70. The collar 1926 may be similar to or identical to the collar 926 or 2926. Preferably, the steps of FIGS. 89-92 may occur before sterile draping of the patient.

Figure 93:
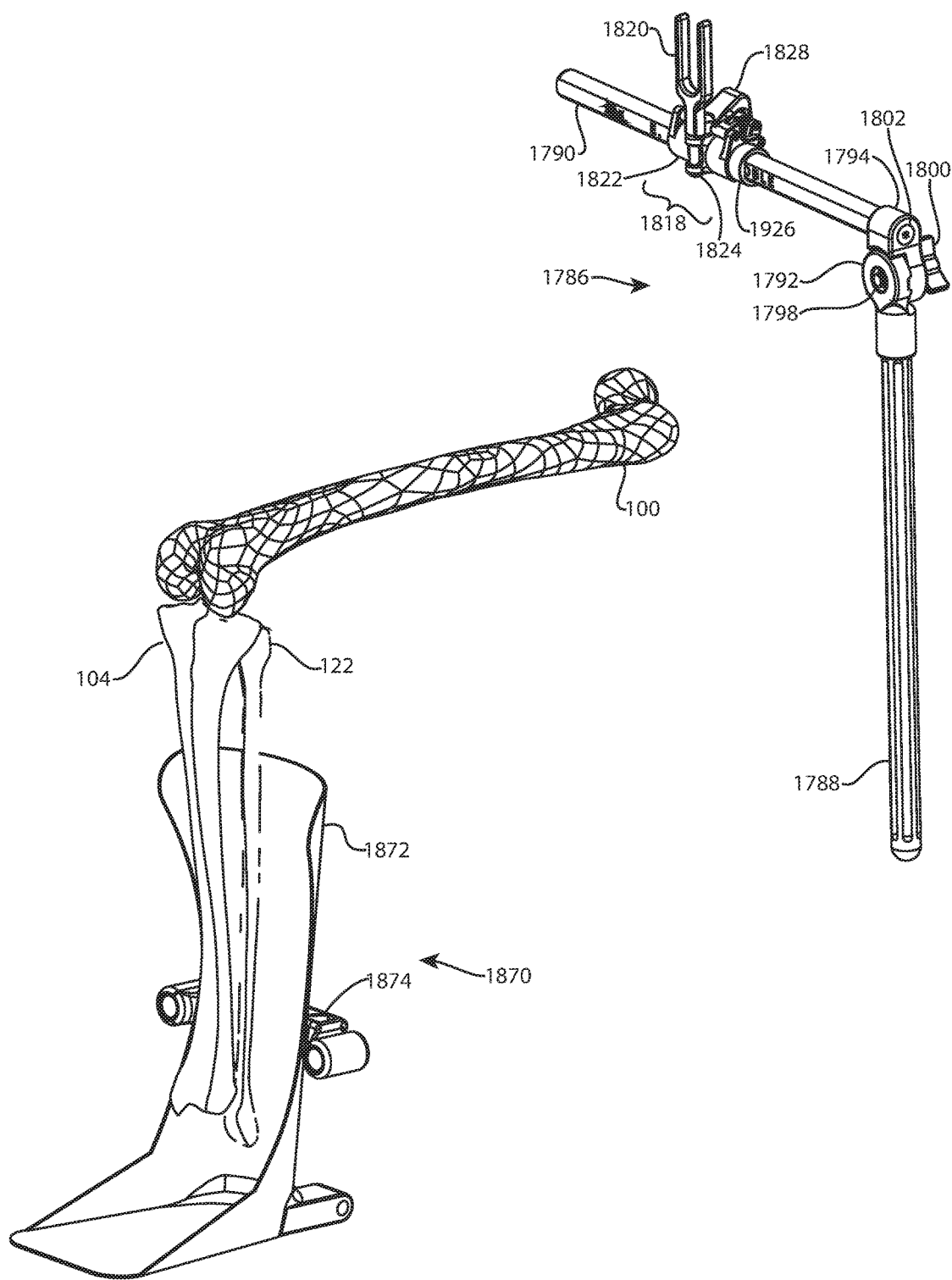
FIG. 93 is a perspective view of the femur, tibia, fibula, foot receiver, lower bar, femoral support arm assembly, and collar of FIG. 92 with a target clamp assembly coupled to the femoral support arm assembly next to the collar.

FIG. 93 shows the step of removing the femoral head finder 1918 and securing a target clamp assembly 1818 to the bar 1790 beside the collar 1926. This step may be similar to or identical to the step of FIG. 71. Preferably, this step may occur after the femoral support arm assembly 1786 has been covered with a sterile drape, such as drape 902 of FIG. 71. Thus the collar 1926 and the femoral support arm assembly 1786 may be nonsterile under the drape, and the target clamp assembly 1818 may be sterile above the drape. The target clamp assembly 1818 includes a target 1820, a retaining ring 1822, a first clamp body 1824, a second clamp body 1826, a lever 1828, a link 1830, and a pin 1832. The example shows two links 1830 and eight pins 1832. The target clamp assembly 1818 may be similar to or identical to the target clamp assembly 818 or 2818.

FIG. 94 shows the step of assembling the bridge 1878, target mounting block 1880, dovetail lock 1881, target 1882, and thumbscrew 1884 to the lower bar 1874 and the foot receiver 1872 to form a complete foot holder assembly 1870. FIGS. 95A-95C show the foot holder assembly 1870.

The lower bar 1874 includes bilateral sockets 1000, 1002 on either side of a concave portion 1004. The lower bar 1874 may be similar to or identical to the lower bar 874 or 2874. The bridge 1878 is a horseshoe-shaped or U-shaped part with a central bridge 1006 and two legs 1008, 1010, each leg extending from an end of the bridge 1006 and terminating in a free end. The free ends have tabs 1012, 1014, respectively. Each tab bifurcates at its tip to form a resilient snap feature. The bridge 1006 includes a through slot 1016 that extends between back to back pockets 1018, 1020. The target 1882 is a generally spoon-shaped or ladle-shaped part with an elongated stem 1022 that terminates in a bowl 1024 at one end. The stem 1022 includes an undercut rail 1026 that extends along the length of the stem. The target mounting block 1880 has a generally rectangular or square body with a rectangular or square through hole 1028. An undercut channel 1030 extends across one side of the target mounting block 1880 and across the hole 1028. The opposite side of the target mounting block 1880 includes bilateral shelves or ledges 1032, 1034 that extend transverse to, or perpendicular to, the undercut channel 1030. The dovetail lock 1881 is an elongated part that includes a generally rectangular or square body 1036 with a threaded shaft 1038 extending from one side of the body. Bilateral shelves or ledges 1038, 1040 extend across this side of the body on opposite sides of the shaft 1038. Opposite the shaft 1038, an undercut channel 1044 extends across the body 1036 transverse to, or perpendicular to, the bilateral ledges 1038, 1040. The thumbscrew 1884 includes a mushroom-shaped body 1046 with a threaded socket 1048 opposite the enlarged mushroom "cap." The foot receiver 1872 may be similar to or identical to the foot holder 872 or the foot receiver 2872.

The tab 1012 is received in the socket 1000 and the tab 1014 is received in the socket 1002. The tabs 1012, 1014 may snap into and out of engagement with the sockets 1000, 1002. The target mounting block 1880 is at least partially received in the pocket 1018 or 1020 so that the ledges 1032, 1034 rest atop the pocket walls. The target mounting block 1880 is shown in the pocket 1018. The body 1036 of the dovetail lock 1881 is at least partially received in the hole 1028 in the target mounting block 1880 so that the undercut channels 1030, 1044 face the same direction and are aligned, and so that the shaft 1038 extends through the slot 1016 of the bridge 1878 and threads into the socket 1048 of the thumbscrew 1884. The thumbscrew 1884 is partially received in the pocket 1018 or 1020, whichever one is not occupied by the target mounting block 1880. The thumbscrew 1884 is shown in the pocket 1020. The undercut rail 1026 of the target 1882 is received in the undercut channels 1030, 1044. Tightening the thumbscrew 1884 locks the undercut rail 1026 in position relative to the bridge 1878. Loosening the thumbscrew 1884 permits the target 1882 to be moved relative to the bridge 1878 in the anterior to posterior direction and in the medial to lateral direction.

Figure 96A:
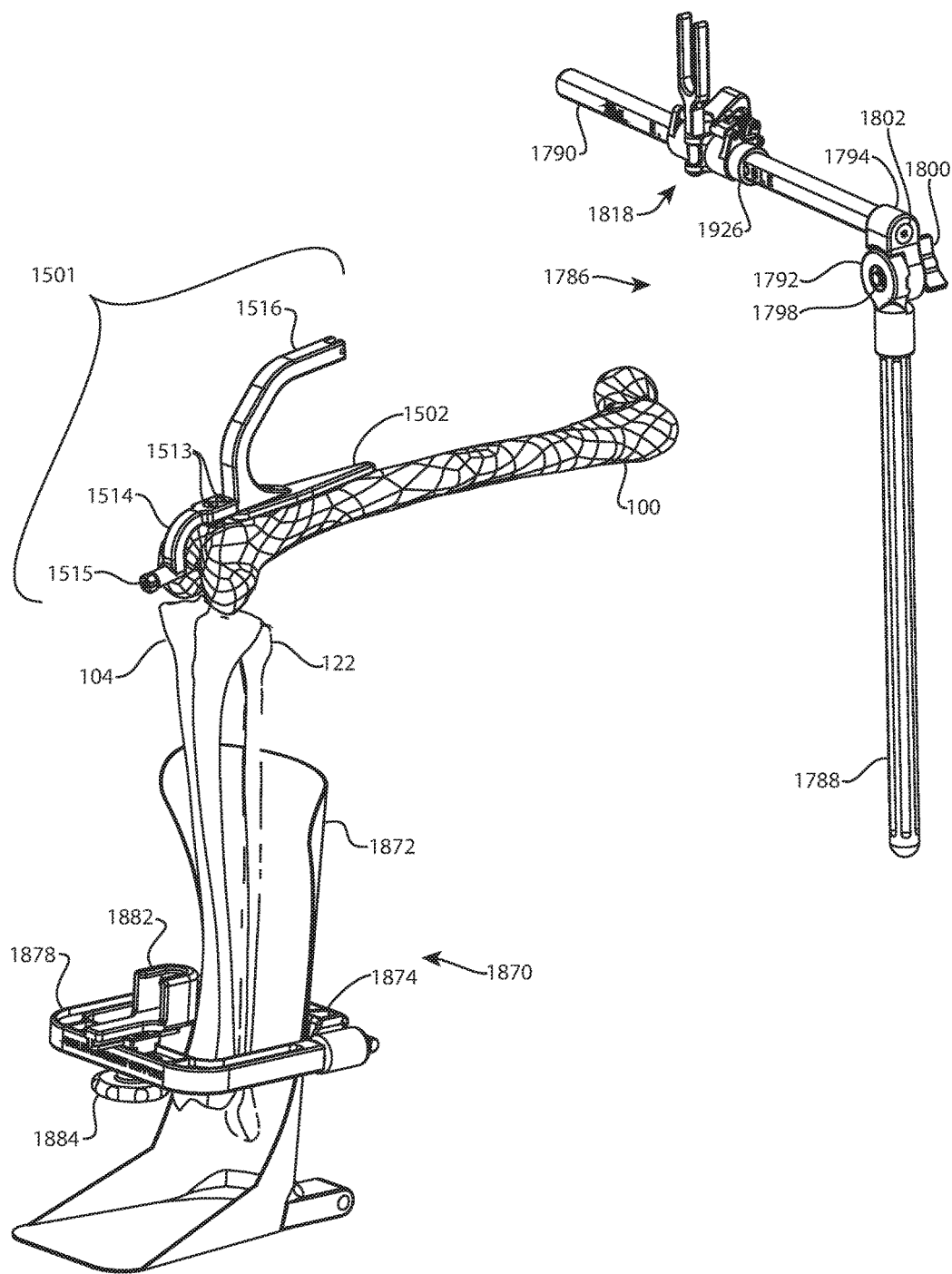
FIG. 96A is a perspective view of the femur, tibia, fibula, femoral support arm assembly, collar, target clamp assembly, and foot holder assembly of FIG. 94 with a femoral pin guide assembly coupled to the anterior distal femur.
Figure 96B:
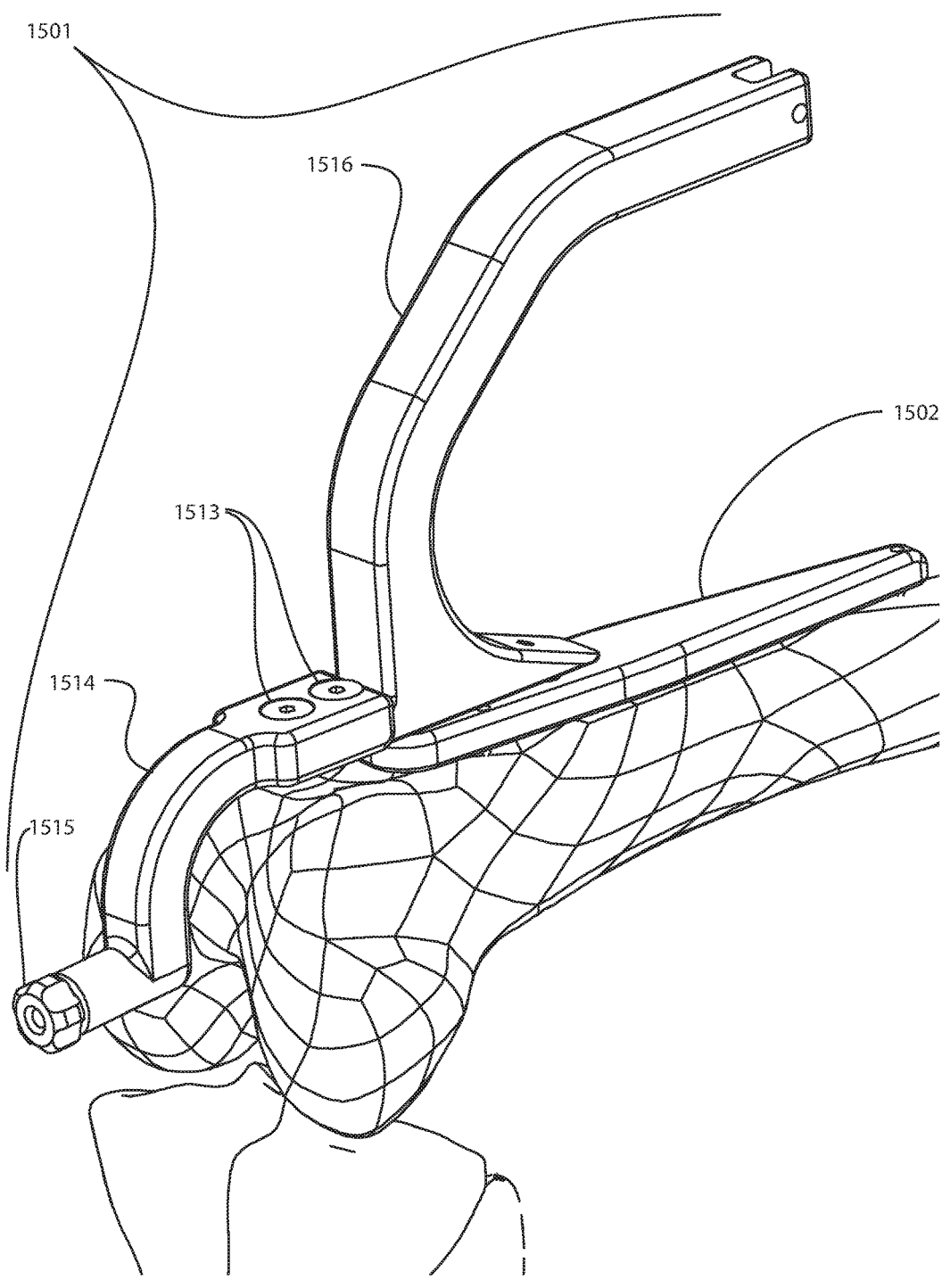
FIG. 96B is a detail perspective view of the femur, tibia, fibula, and femoral pin guide assembly of FIG. 96A.
Figure 97A:
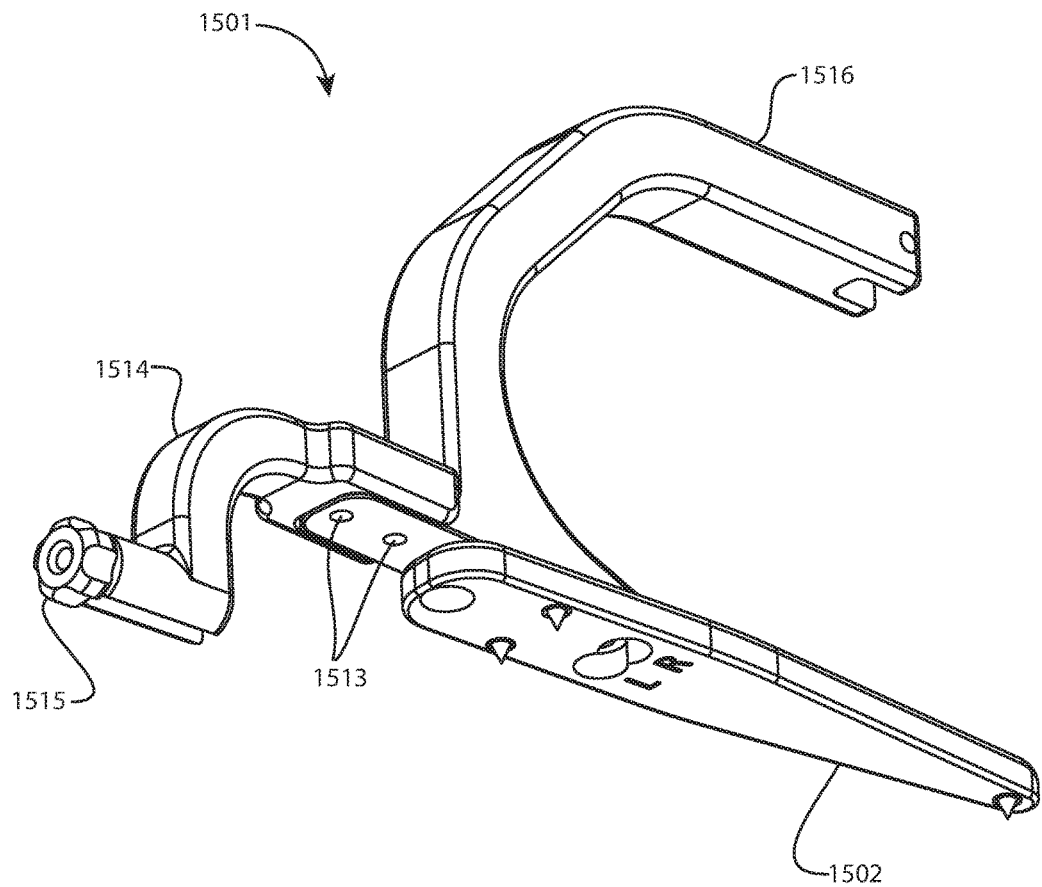
FIG. 97A is a perspective view of the femoral pin guide assembly of FIG. 96A.
Figure 97B:
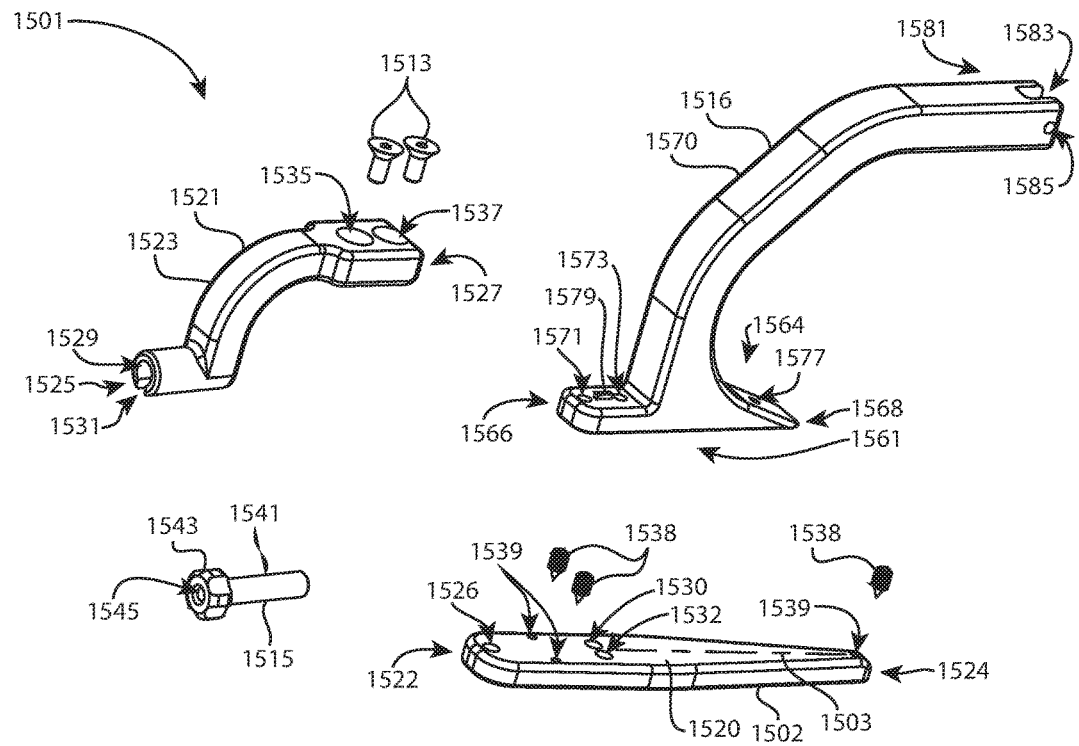
FIG. 97B is an exploded perspective view of the femoral pin guide assembly of FIG. 96A.
Figure 97C:
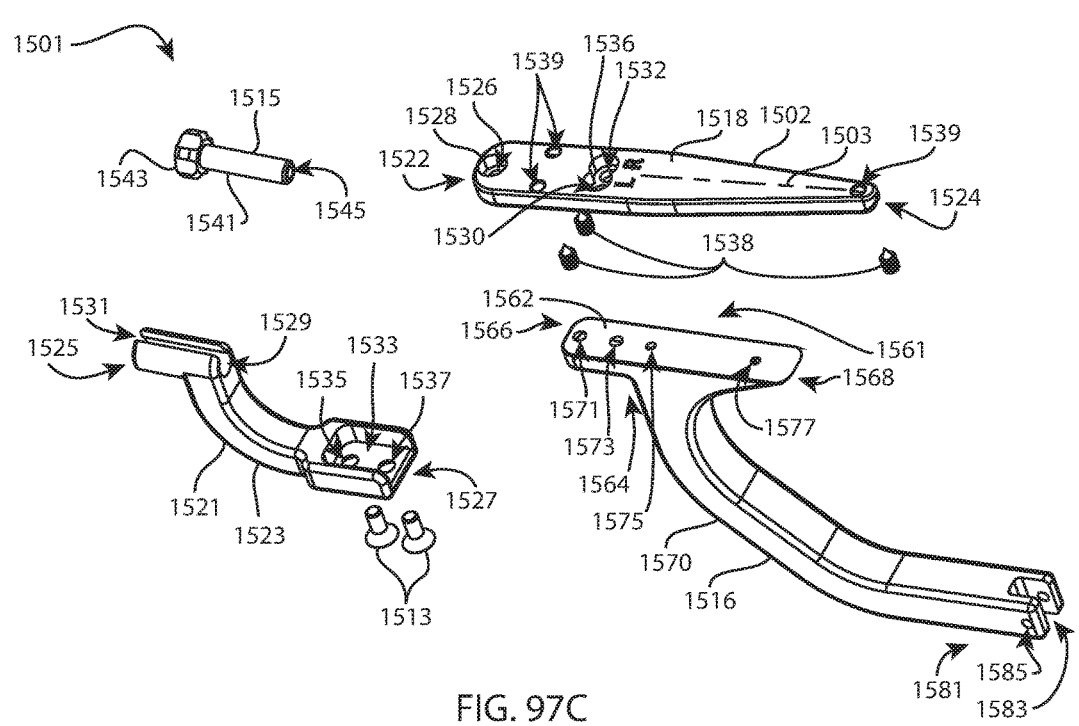
FIG. 97C is another exploded perspective view of the femoral pin guide assembly of FIG. 96A from a different direction.
Figure 107:
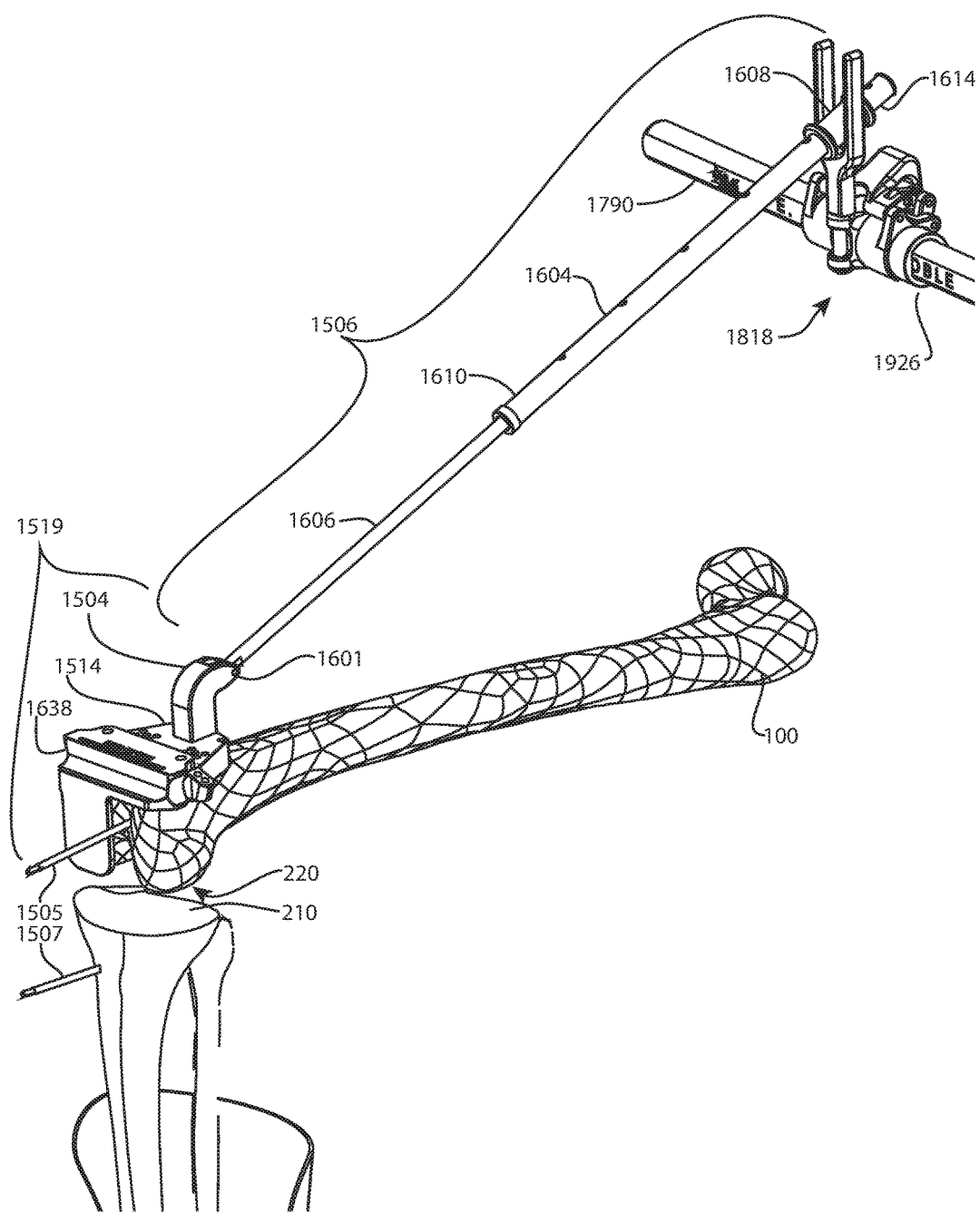
FIG. 107 is a perspective view of the femur, tibia, fibula, femoral pin, and tibial pin of FIG. 106 and a portion of the femoral support arm assembly, collar, target clamp assembly, and a portion of the foot holder assembly of FIG. 96A with a distal femoral cut guide assembly coupled to the distal femur and the target clamp assembly via a femoral extension rod assembly.
Figure 108A:
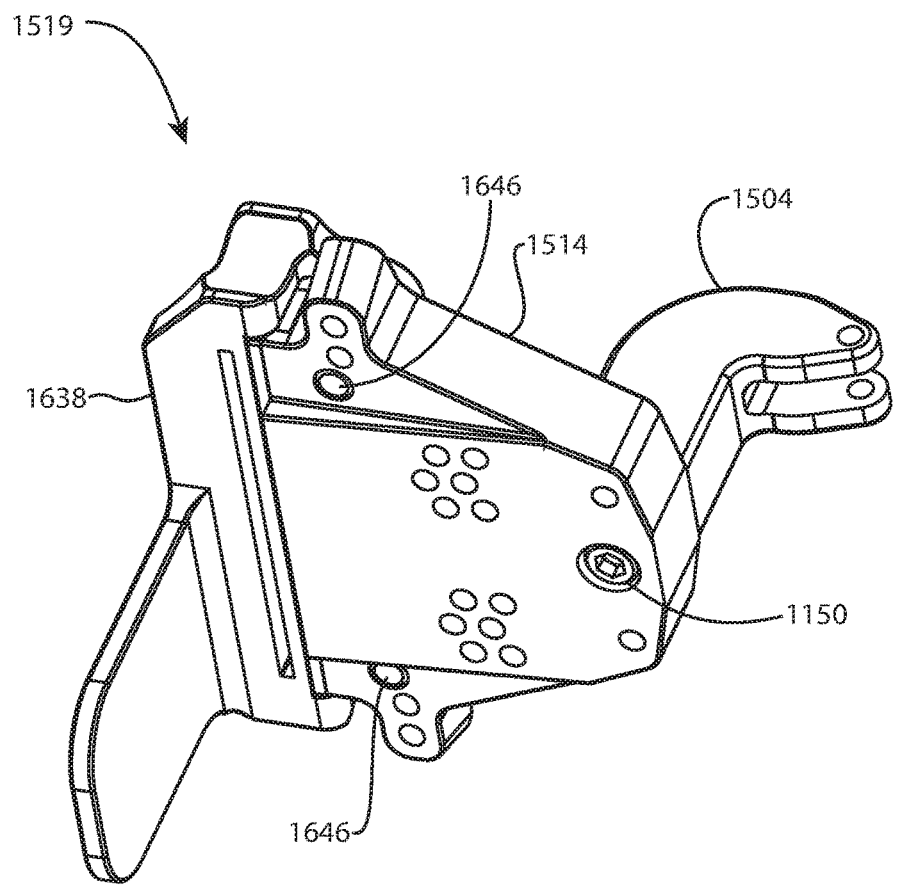
FIG. 108A is a perspective view of the distal femoral cut guide assembly of FIG. 107.
Figure 108B:
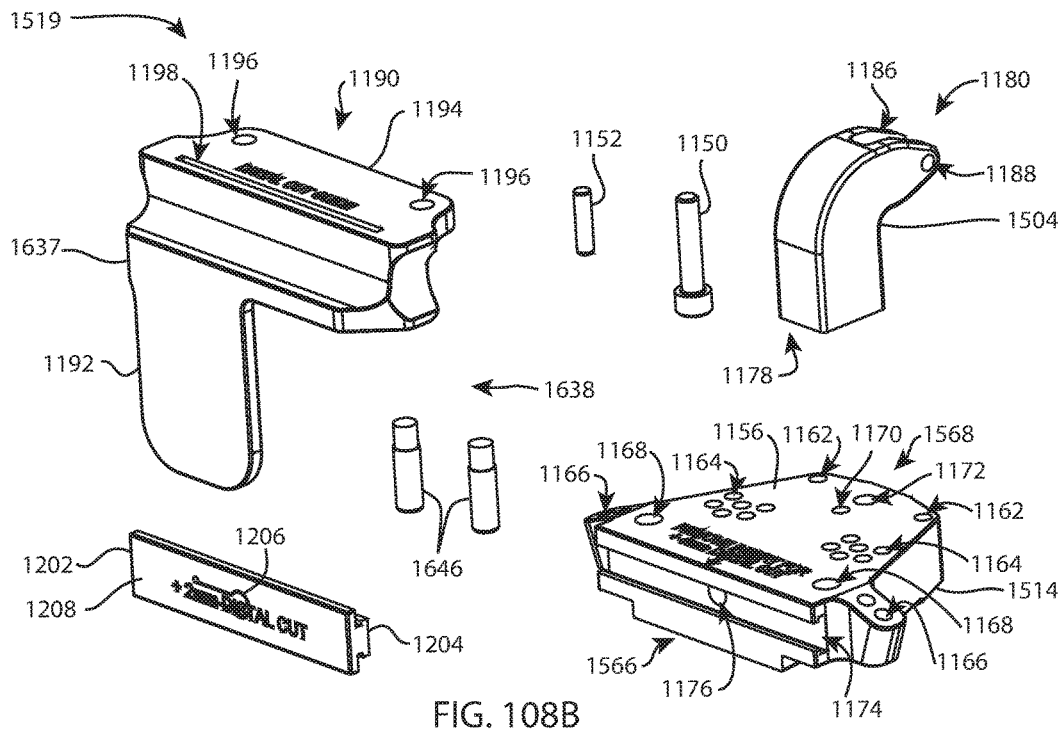
FIG. 108B is an exploded perspective view of the distal femoral cut guide assembly of FIG. 107.
Figure 108C:
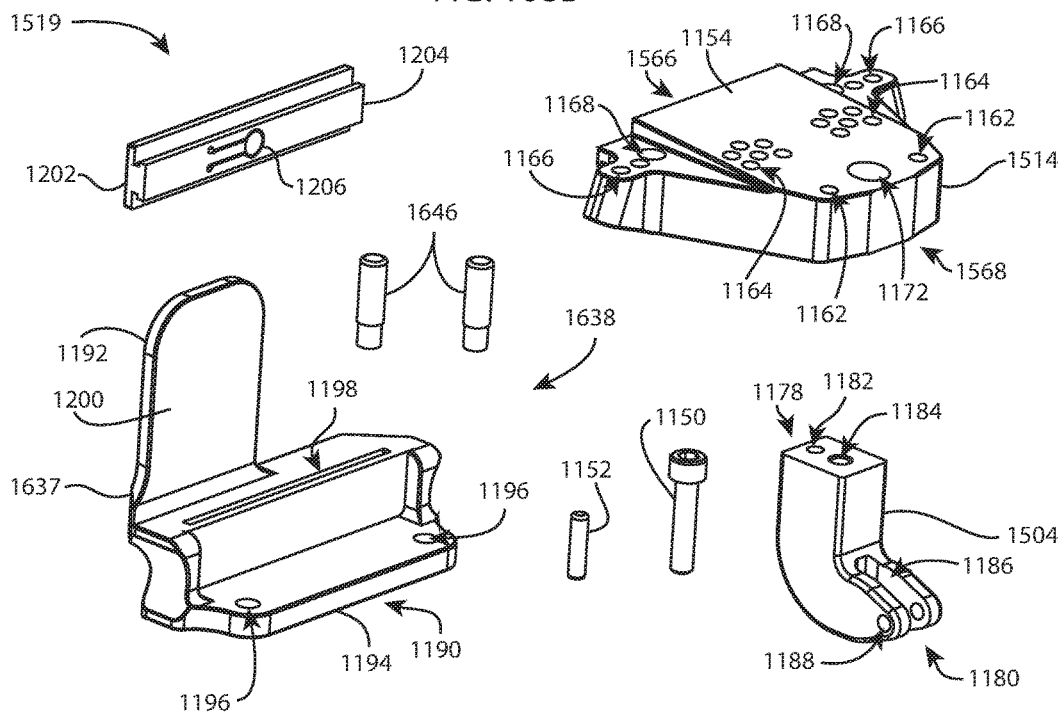
FIG. 108C is another exploded perspective view of the distal femoral cut guide assembly of FIG. 107 from a different direction.

FIGS. 96A and 96B show the step of coupling a femoral pin guide assembly 1501 to the anterior distal femur. This step may be similar to or identical to the step of FIG. 72. This step may include coupling the femoral pin guide assembly 1501 to the target 1820 of the target clamp assembly 1818 via a femoral extension rod assembly 1506 (FIG. 107). This step may include aligning the femoral pin guide assembly 1501 and/or the femoral extension rod assembly 1506 with the mechanical axis 202 of the leg as it extends through the femur 100. FIGS. 97A-97C show the femoral pin guide assembly 1501, which includes a base 1502, a handle 1516, a pin guide 1521, a screw 1513, and a pin sleeve 1515. The example shows two screws 1513.

Aligning the femoral pin guide assembly 1501 and/or the femoral extension rod assembly 1506 with the mechanical axis 202 of the leg may include centering the base 1502 in the medial-lateral width of the distal femur and at the same time aligning the femoral extension rod assembly 1506 to pass over the center 120 of the femoral head 118. This step may include positioning a distal edge of the bone contacting surface 1518 at the place on the distal anterior femur where the anterior femoral resection 214 is planned to exit the femur.

The base 1502 is an elongated plate with a bone contacting surface 1518 and an opposite top surface 1520. The base 1502 has a distal portion 1522 and a proximal portion 1524 which tapers to a proximal tip which is narrower than the distal portion. A longitudinal axis 1503 extends along the length of the base 1502 between the distal and proximal portions 1522, 1524; only a portion of the axis 1503 is shown for clarity. The base 1502 includes a hole 1526 through the distal portion 1522. A pocket 1528 is recessed into the bone contacting surface 1518 around the hole 1526. The pocket 1528 may be described as a counterbore around the hole 1526. The base 302 includes two through holes 1530, 1532 between the distal and proximal portions 1522, 1524. Each hole 1530, 1532, 1534 includes a shelf 1536 on at least one side wall. The shelves 1536 are illustrated as counterbores around the holes 1530, 1532, 1534 but may be unilaterally positioned instead. The base 1502 may include one or more frictional elements, such as spikes 1538 protruding from the bone contacting surface 1518. The spikes 1538 in this example are separate set screws with sharp leading tips inserted into corresponding holes 1539 in the base 1502.

The handle 1516 includes a base portion 1561 with a bone facing surface 1562 and an opposite top side 1564. The base portion 1561 has a distal portion 1566 and a proximal portion 1568. The base portion 1561 has a series of holes 1571, 1573, 1575, 1577 arranged from distal to proximal. An optional tab 1579 may extend from the top side between holes 1571, 1573. A stalk 1570 protrudes from the top side 1564 between the distal and proximal portions 1566, 1568. The stalk 1570 terminates in a proximal free end 1581 with a slot 1583 and through hole 1585.

The pin guide 1521 has a generally arcuate body 1523 that extends between a distal portion 1525 and a proximal portion 1527. The distal portion 1525 includes a longitudinal hole 1529 with a longitudinal slot 1531. The hole 1529 and slot 1531 extend in the distal-proximal direction. The proximal portion 1527 includes a pocket 1533 and holes 1535, 1537 which intersect the pocket. The pin sleeve 1515 includes a cylindrical shaft 1541 with an enlarged head 1543 at one end and a longitudinal through hole 1545.

The shaft 1541 of the pin sleeve 1515 is received in the hole 1529 of the pin guide 1521 so that the head 1543 is distal. The distal portion 1566 of the handle 1516 is received in the pocket 1533 of the pin guide 1521. One of the screws 1513 extends through the holes 1535, 1571 and the other screw 1513 extends through the holes 1537, 1573 to secure the pin guide 1521 to the handle 1516. The spikes 1538 are received in the holes 1539; the spikes may optionally be integrally formed with the base 1502. A fastener (not shown) extends through the holes 1526, 1575 and a second fastener extends through the holes 1530, 1577 (for a left knee) or the holes 1532, 1577 (for a right knee) to secure the base 1502 to the handle. When the pin sleeve 1515, pin guide 1521, handle 1516, and base 1502 are coupled together as described, the hole 1545 may be aligned with the bone contacting surface 1518, or a theoretical bone contacting plane defined by the spikes 1538 where the spikes contact the distal anterior femur. Preferably, the hole 1545 may be parallel to the bone contacting surface 1518, parallel to the upcoming anterior femoral resection 214, or perpendicular to the upcoming distal femoral resection 206. The inner rod 1606 of the femoral extension rod assembly 1506 is received in the slot 1583 and the pin 1601 extends through hole 1585 and the inner rod to form a hinge about which the femoral extension rod assembly pivots in use.

Figure 98:
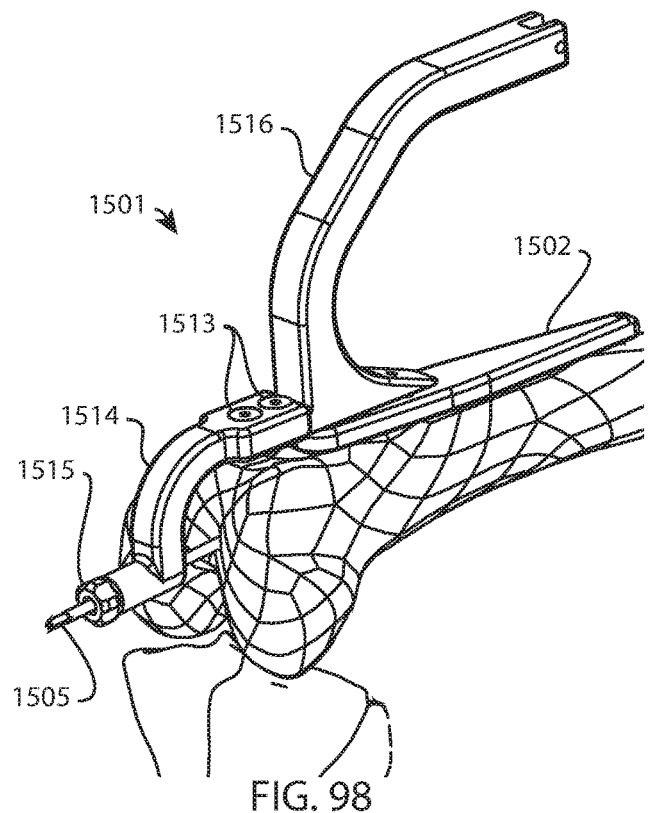
FIG. 98 is a perspective view of the femur, tibia, fibula, and femoral pin guide assembly of FIG. 96B with a femoral pin inserted through the femoral pin guide assembly into the distal femur.

FIG. 98 shows the step of placing a femoral pin 1505 into the distal femur through the pin sleeve 1515 of the femoral pin guide assembly 1501. The femoral pin 1505 is received in the hole 1545. Preferably, this step occurs while the bone contacting surface 1518 and/or the spikes 1538 of the base 1502 contact the distal anterior femur, and while the femoral pin guide assembly 1501 and/or the femoral extension rod assembly 1506 are aligned with the mechanical axis 202 of the leg. Preferably, the femoral pin 1505 is placed in strong, dense subtrochlear bone anterior to the femoral intramedullary canal and posterior to the intended location of the upcoming anterior femoral resection 214.

Figure 99:
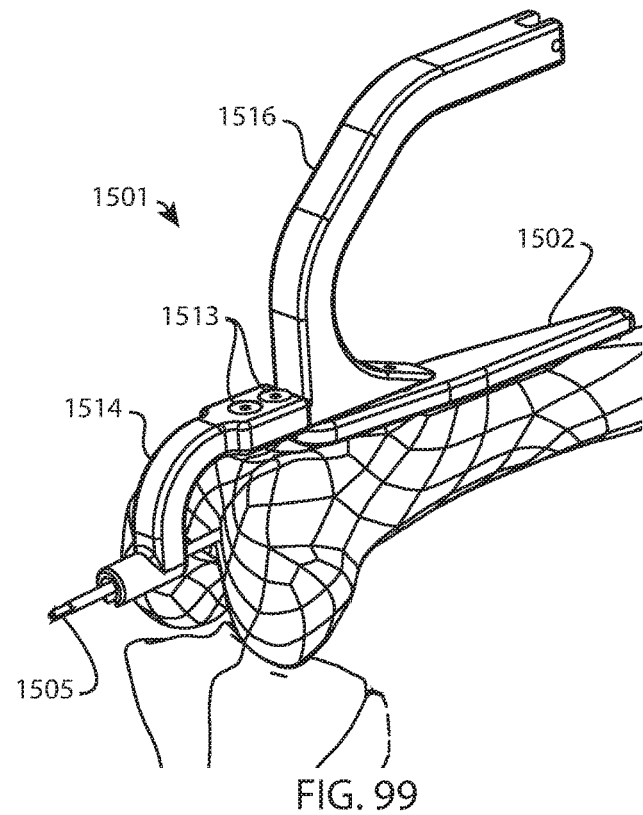
FIG. 99 is a perspective view of the femur, tibia, fibula, femoral pin guide assembly, and femoral pin of FIG. 98 with a pin sleeve of the femoral pin guide assembly removed.

FIG. 99 shows the step of removing the pin sleeve 1515 after the femoral pin 1505 has been placed into the distal femur. The pin sleeve 1515 slides distally out of the hole 1529 and distally along the femoral pin 1505. This exposes the slot 1531.

Figure 100:
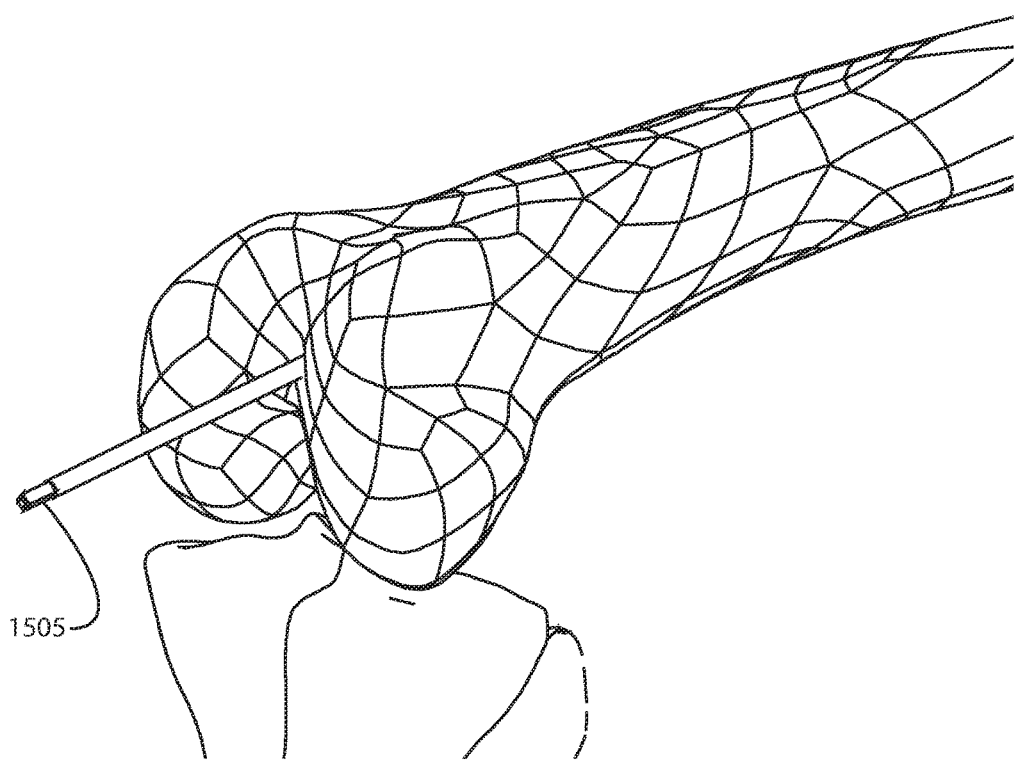
FIG. 100 is a perspective view of the femur, tibia, fibula, and femoral pin of FIG. 99 with the rest of the femoral pin guide assembly removed.

FIG. 100 shows the step of removing the femoral pin guide assembly 1501 after the femoral pin 1505 has been placed into the distal femur. The femoral pin guide assembly 1501 may be lifted anteriorly so that the femoral pin 1505 exits through the slot 1531. This step may include removing the spool 1608 anteriorly from the target 1820. The femoral pin 1505 encodes information about 1) the proper varus/valgus orientation of the distal femoral resection 206, 2) the flexion/extension orientation of the anterior femoral resection 214 and the posterior femoral resection 220, and 3) the middle of the trochlear groove (Whiteside's line). The femoral pin 1505 enables rotational adjustment of cut guides about the pin 1505, which ensures proper tracking of the patella. More specifically, femoral cut guides may be adjusted for varus-valgus rotation about the pin 1505.

Figure 101:
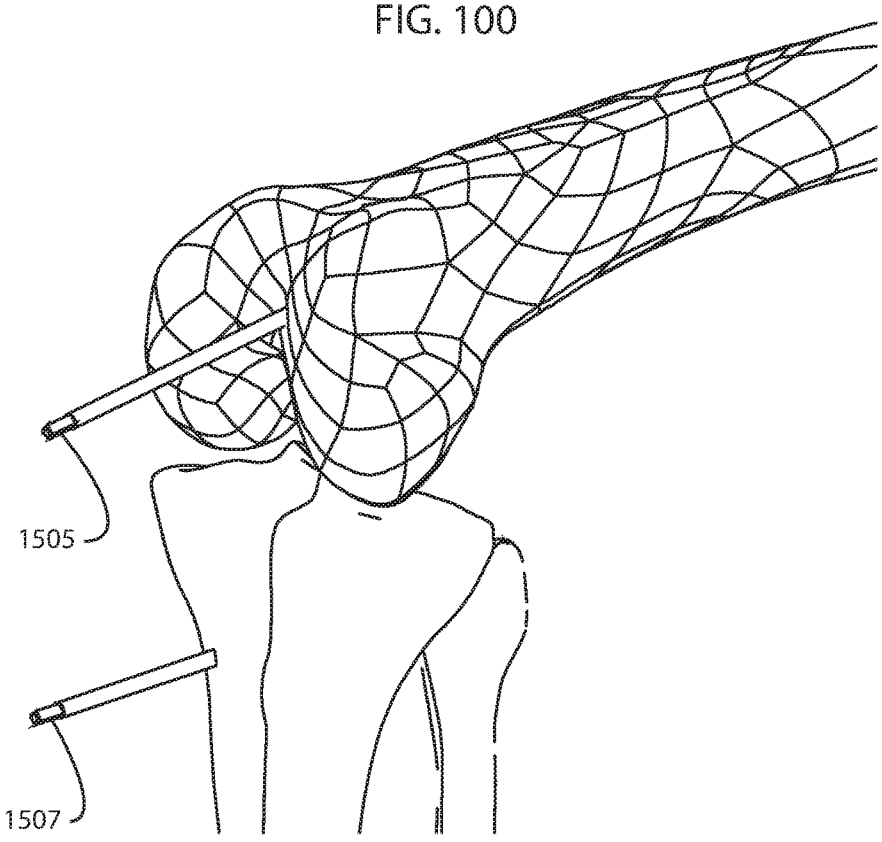
FIG. 101 is a perspective view of the femur, tibia, fibula, and femoral pin of FIG. 100 with a tibial pin inserted into the tibial tuberosity.

FIG. 101 shows the step of placing a tibial centering pin 1507 in the tibial tuberosity to serve as a proximal tibial target. The tibial centering pin 1507 may be placed freehand or with a guide (not shown). The tibial centering pin 1507 may be centered in the medial-lateral width of the proximal tibia 106 and/or centered in the medial-lateral width of the tibial tuberosity.

Figure 102A:
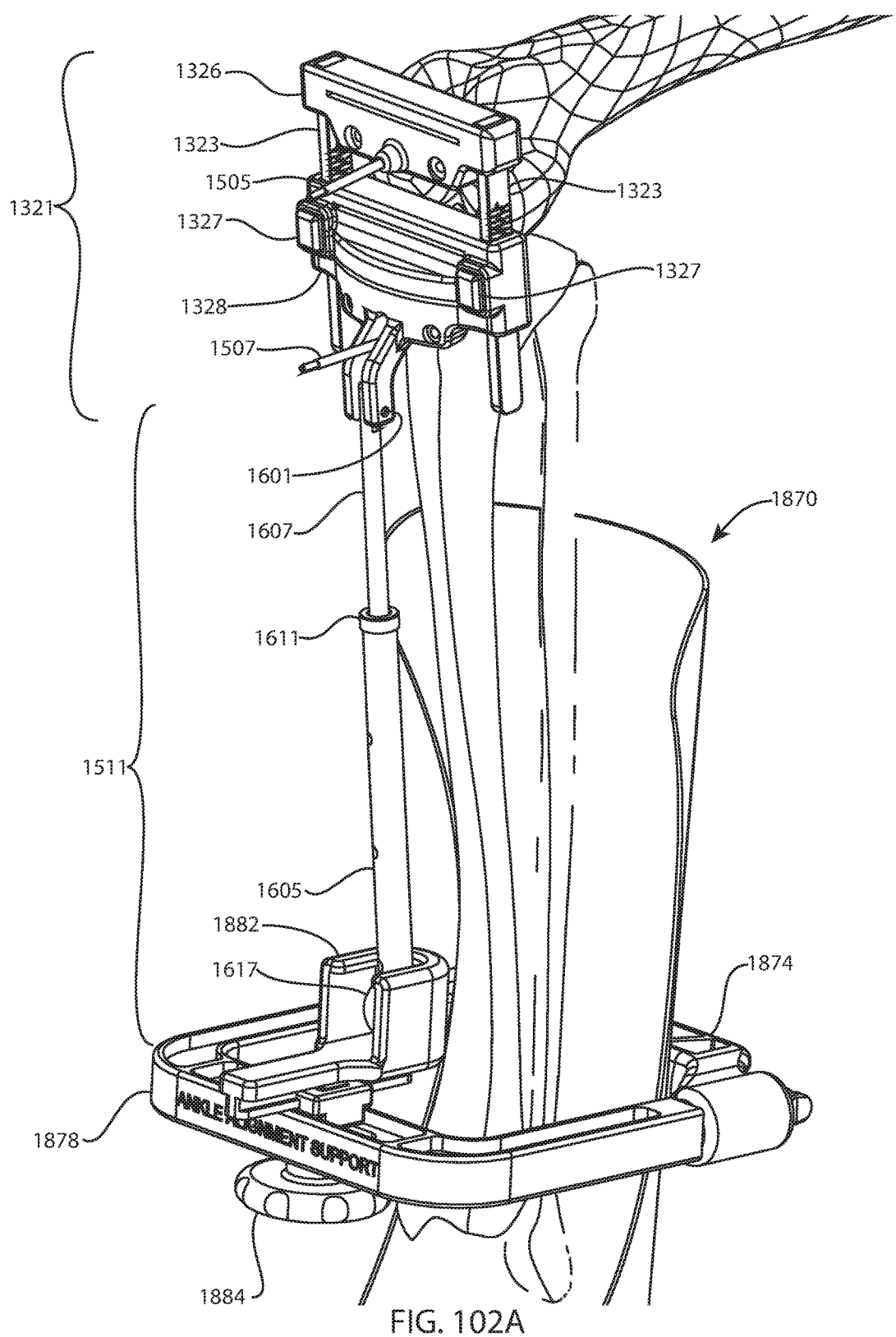
FIG. 102A is a perspective view of the femur, tibia, fibula, femoral pin, and tibial pin of FIG. 101 and the foot holder assembly of FIG. 96A with a three in one cut guide assembly coupled to the femoral pin and distal femur, the tibial pin and tibia, and the foot holder assembly via a tibial extension rod assembly.
Figure 102B:
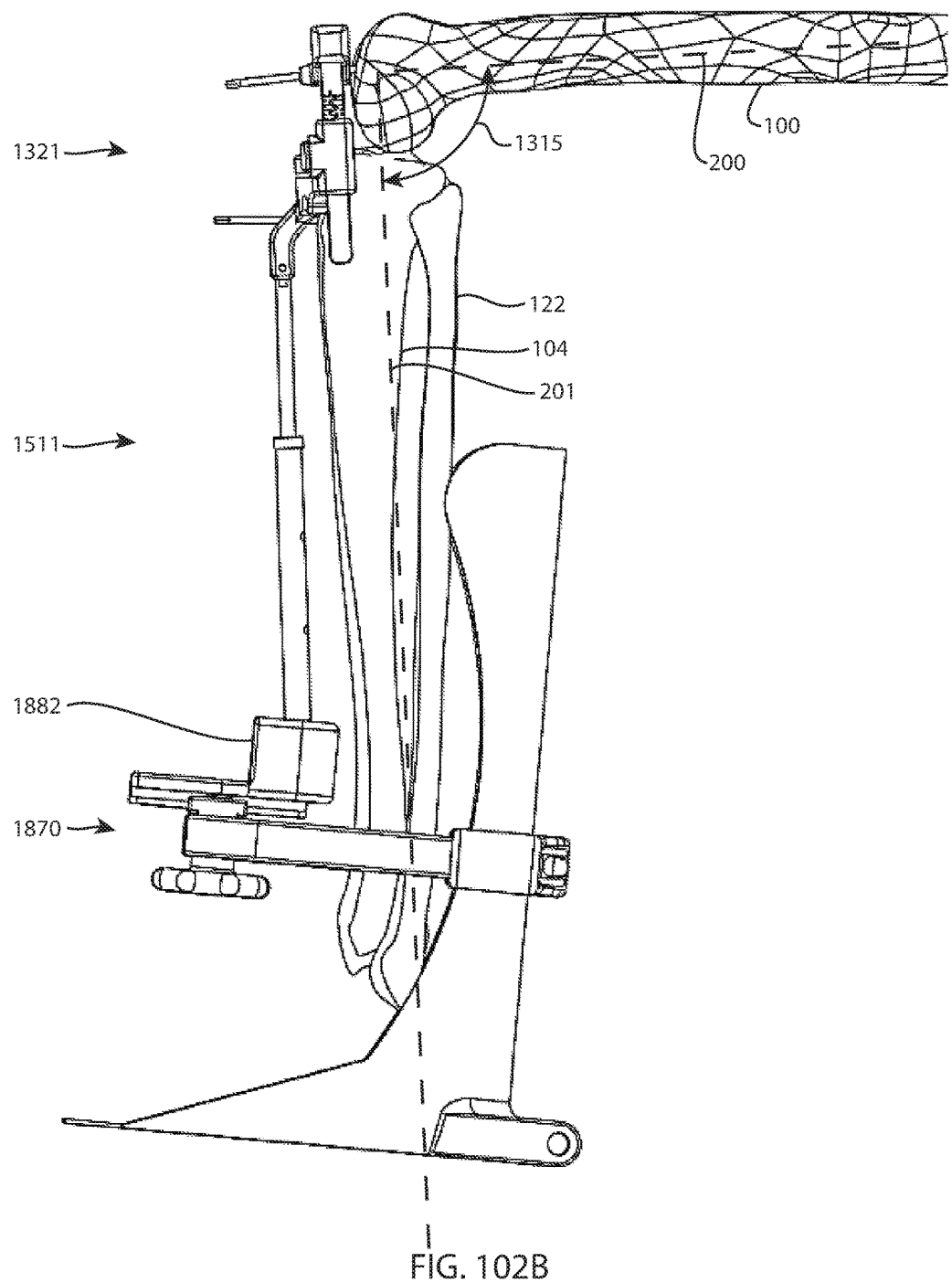
FIG. 102B is a lateral view of the femur, tibia, fibula, femoral pin, tibial pin, foot holder assembly, three in one cut guide assembly, and tibial extension rod assembly of FIG. 102A.
Figure 103A:
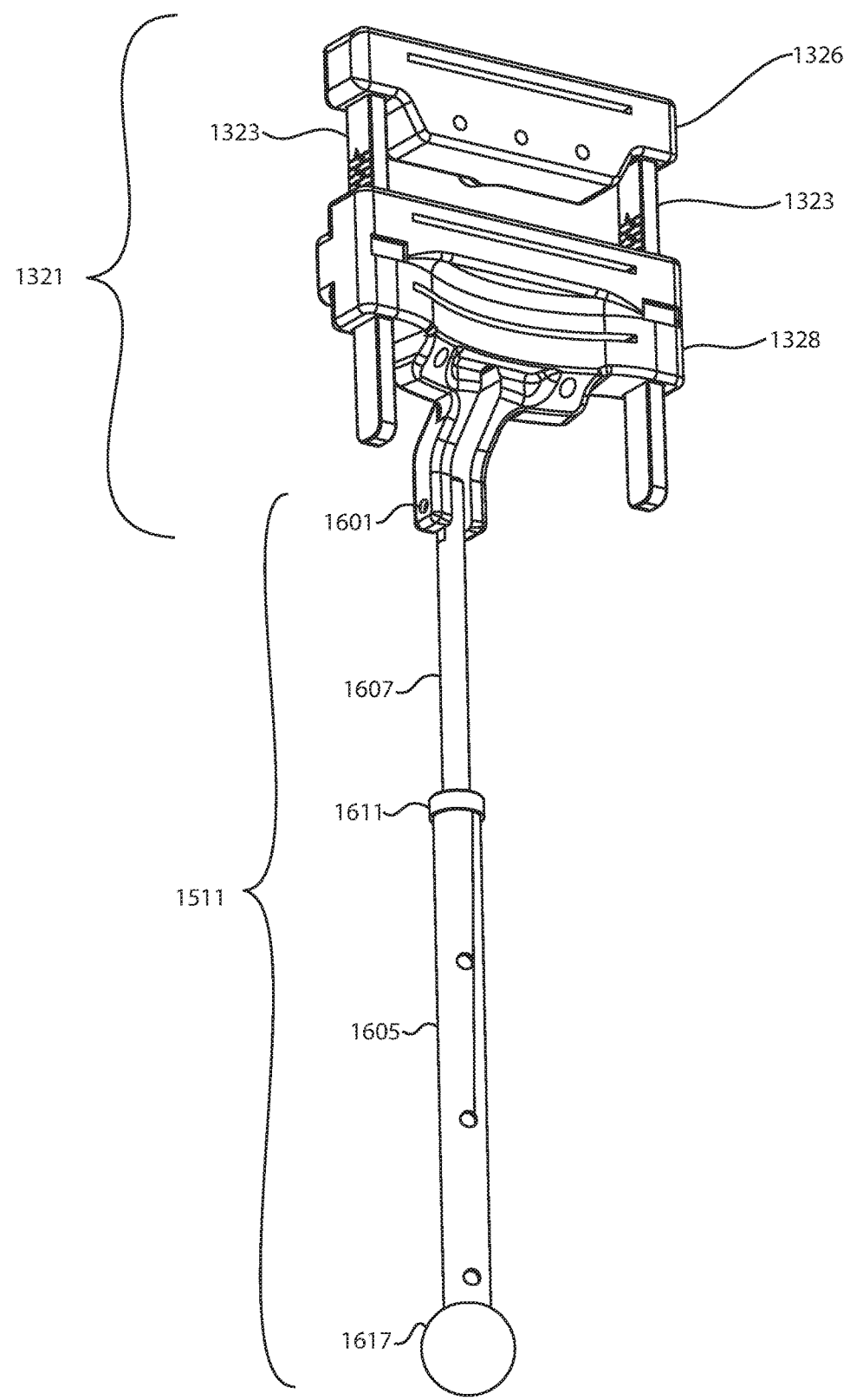
FIG. 103A is a perspective view of the three in one cut guide assembly and tibial extension rod assembly of FIG. 102A.
Figure 103B:
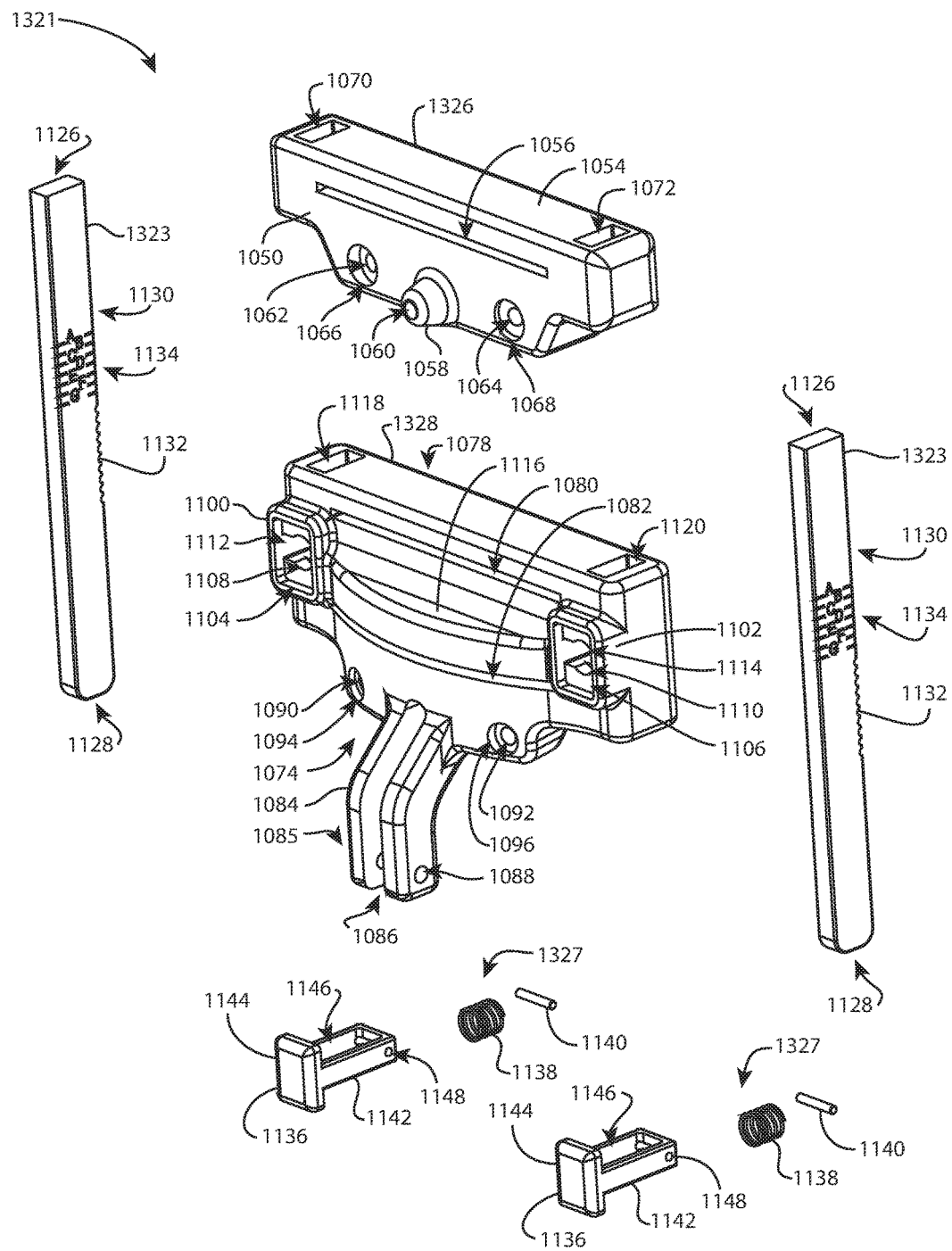
FIG. 103B is an exploded perspective view of the three in one cut guide assembly of FIG. 103A.
Figure 103C:
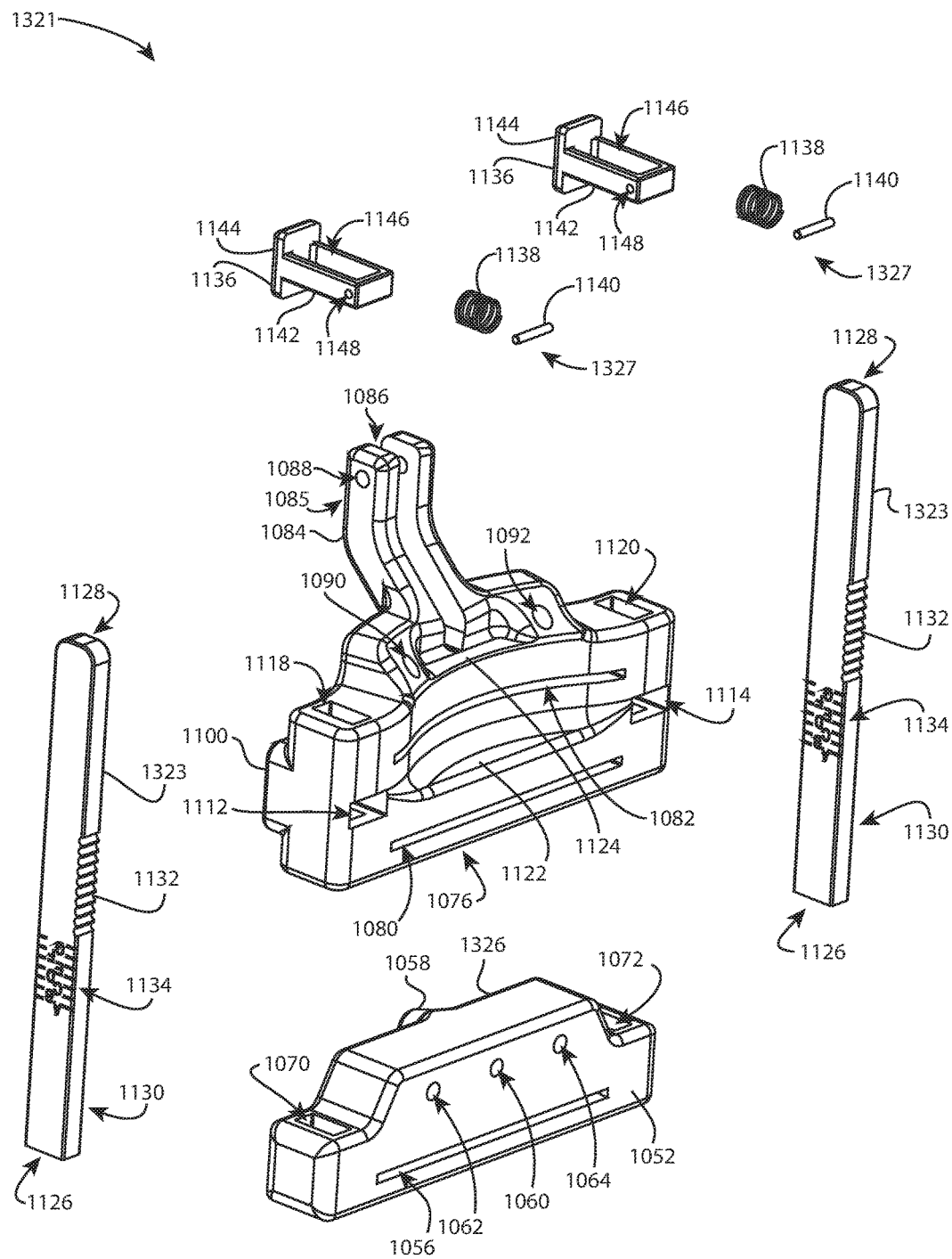
FIG. 103C is another exploded perspective view of the three in one cut guide assembly of FIG. 103A from a different direction.

FIGS. 102A and 102B show the step of coupling a three in one cut guide assembly 1321 to the femur 100, the tibia 104, and the foot holder assembly 1870. This step may include sliding a hole of the three in one cut guide assembly 1321 over the femoral pin 1505. This step may include sliding a slot of the three in one cut guide assembly 1321 over the tibial pin 1507. The three in one cut guide assembly 1321 may pivot around the femoral pin 1505 to a rotational position in which the slot accepts the tibial pin 1507. This step may include coupling the three in one cut guide assembly 1321 to a tibial extension rod assembly 1511, and coupling the tibial extension rod assembly to a target 1882 of the foot holder assembly 1870. This step may include aligning the three in one cut guide assembly 1321 and/or the tibial extension rod assembly 1511 with the mechanical axis of the leg as it extends through the tibia 104. The three in one cut guide assembly 1321 shown in FIGS. 103A-103C includes an anterior femoral cut guide 1326, a posterior femoral and tibial cut guide 1328, a tibial rail 1323, and a button assembly 1327. The three in one cut guide assembly 1321 is coupled to a tibial extension rod assembly 1511, which is coupled to the foot holder assembly 1870. FIG. 102B shows that it is preferable for the tibia 104 to be positioned so that a tibial shaft axis 201 forms a ninety degree angle 1315 with the femoral shaft axis 200 of the femur 100. The anterior femoral cut guide 1326 and the posterior femoral and tibial cut guide 1328 are pinned to the distal femur and proximal tibia, respectively, with femoral pin 1505 and tibial pin 1507. The example shows two tibial rails 1323 and two button assemblies 1327. The button assembly 1327 includes a button, a spring, and a dowel pin. The tibial extension rod assembly 1511 (FIG. 107) includes an outer rod 1605, an inner rod 1607, a sleeve 1611, a ring 1613, a pin 1601, and a ball 1617. The tibial extension rod assembly 1511 may be similar to or identical to the tibial extension rod 313, 511, 2511 or the femoral extension rod 306, 506, 1506, 2506. Aligning the three in one cut guide assembly 1321 and/or the tibial extension rod assembly 1511 with the mechanical axis of the leg may include centering the posterior femoral and tibial cut guide 1328 over the tibial pin 1507 and at the same time aligning the tibial extension rod assembly 1511 to pass over the medial-lateral center of the ankle, the second toe, or anterior tibial spine.

The anterior femoral cut guide 1326 has a distal side 1050, an opposite proximal side 1052, and an anterior side 1054. A saw slot 1056 extends through the anterior femoral cut guide 1326 in a distal to proximal direction. A boss 1058 extends from a middle portion of the distal side 1050. A through hole 1060 extends through the boss 1058. The through hole 1060 receives the femoral pin 1505, thereby positioning the saw slot 1056 so that the anterior femoral resection 214 will exit the femur at the planned location. Bilateral through holes 1062, 1064 are located on either side of the boss 1058. The holes 1062, 1064 may include counterbores 1066, 1068 as shown in the distal side 1050. The holes 1062, 1064 may converge as they extend from distal to proximal. Bilateral rectangular or square through holes 1070, 1072 are located on either side of the boss 1058; the holes 1070, 1072 are shown outboard of the holes 1062, 1064, but could be inboard instead. The holes 1070, 1072 extend through the anterior femoral cut guide 1326 in an anterior to posterior direction passing through the anterior side 1054.

The posterior femoral and tibial cut guide 1328 has a distal side 1074, an opposite proximal side 1076, and an anterior side 1078. Saw slots 1080, 1082 extend through the posterior femoral and tibial cut guide 1328 in a distal to proximal direction. The saw slots 1080, 1082 may be parallel or there may be an acute angle between them. An arm 1084 extends distally and posteriorly from a middle portion of the distal side 1074. The free end 1085 of the arm 1084 includes a lengthwise slot 1086 and a hole 1088 that extends through the arm and across the slot. Bilateral through holes 1090, 1092 are located on either side of the arm 1084. The holes 1090, 1092 may include counterbores 1094, 1096 as shown in the distal side 1074. The holes 1062, 1064 may converge as they extend from distal to proximal. Bilateral rectangular or square bosses 1100, 1102 extend from the distal side 1074 on either side of the arm 1084. The bosses 1100, 1102 are shown outboard of the holes 1090, 1092, but could be inboard instead. Rectangular or square pockets 1104, 1106 are recessed into the distal aspect of the bosses 1100, 1102. Circular holes 1108, 1110 are recessed into the proximal ends of the pockets 1104, 1106. Rectangular or square through holes 1112, 1114 extend through the bosses 1100, 1102 in a distal to proximal direction. An anterior facing shelf 1116 is formed between anterior and posterior portions of the posterior femoral and tibial cut guide 1328. Bilateral rectangular or square through holes 1118, 1120 are located on either side of the boss arm; the holes 1118, 1120 are shown outboard of the holes 1090, 1092, but could be inboard instead. The holes 1118, 1120 extend through the posterior femoral and tibial cut guide 1328 in an anterior to posterior direction passing through the anterior side 1078. Posterior facing shelves 1122, 1124 are formed in the proximal side of the posterior femoral and tibial cut guide 1328. The shelf 1122 rests on the proximal aspect of the tibia when the three in one cut guide 1321 is adjusted to an implant size that matches the patient's anatomy.

The tibial rail 1323 is a generally rectangular elongated part with an anterior end 1126, a posterior end 1128, and a proximal side 1130. A series of detents 1132, in this example grooves, extends along a middle portion of the proximal side 1130. Indicia 1134 may be present on the tibial rail 1323.

The button assembly 1327 includes a button body 1136, a spring 1138, and a pin 1140. The button body 1136 includes a generally rectangular shaft 1142 with an enlarged head 1144 at one end. A generally rectangular through hole 1146 extends transversely through the shaft 1142. A through hole 1148 extends transversely through the shaft 1142 and across the hole 1146.

The anterior ends 1126 of the tibial rails 1323 are received in the holes 1070, 1072 of the anterior femoral cut guide 1326 so that the posterior ends 1128 project posteriorly and the proximal sides 1052, 1130 face the same direction. The anterior ends 1126 may be fixed in the holes 1070, 1072. A spring 1138 is received in each hole 1146 of the button bodies 1136. The button bodies 1136 are received in the posterior femoral and tibial cut guide 1328 so that the shafts 1142 are in the holes 1112, 1114, the springs 1138 are in the holes 1108, 1110, the heads 1144 are in the pockets 1104, 1106, and the holes 1148 are exposed proximally to receive the pins 1140. The posterior ends 1128 of the tibial rails 1323, with attached anterior femoral cut guide 1326, are received in the anterior ends of the holes 1118, 1120 of the posterior femoral and tibial cut guide 1328 and advanced through the holes 1146 of the button bodies 1136 so that the springs 1138 are distal to the tibial rails 1323 and the pins 1140 engage the detents 1132. The inner rod 1607 of the tibial extension rod assembly 1511 is received in the slot 1086 and the pin 1601 extends through hole 1088 and the inner rod to form a hinge about which the tibial extension rod assembly pivots in use.

Figure 104:
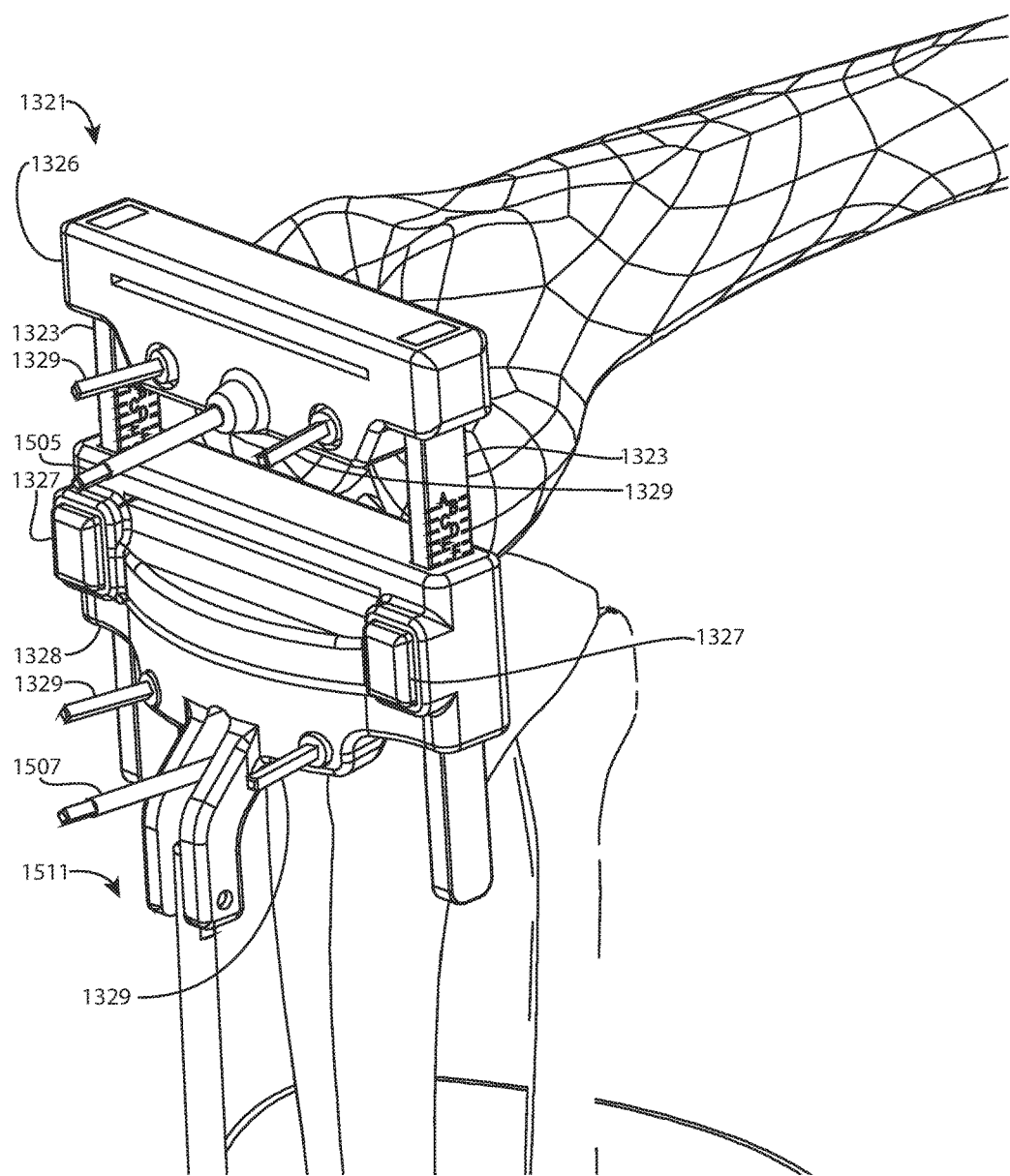
FIG. 104 is a perspective view of the femur, tibia, fibula, femoral pin, tibial pin, three in one cut guide assembly, and tibial extension rod assembly of FIG. 102A with bone pins inserted through the three in one cut guide assembly into the distal femur and proximal tibia.

FIG. 104 shows the step of further securing the three in one cut guide assembly 1321 to the femur 100 and the tibia 104 by driving bone pins 1329 through the anterior femoral cut guide 1326 and the posterior femoral and tibial cut guide 1328. Preferably, this step occurs while the three in one cut guide assembly 1321 and/or the tibial extension rod assembly 1511 are aligned with the mechanical axis 202 of the leg.

FIG. 105 shows the step of making an anterior femoral resection 214, a posterior femoral resection 220, and a proximal tibial resection 210. The anterior femoral resection 214 is made through the saw slot 1056 in the anterior femoral cut guide 1326, which is carried on the femoral pin 1505, which was positioned in the distal femur while directly referencing the distal anterior femoral cortex, notably the desired exit point for the anterior femoral resection 214. The posterior femoral resection 220 is made through the femoral saw slot 1080 in the posterior femoral and tibial cut guide 1328. The proximal tibial resection 210 is made through the tibial saw slot 1082 in the posterior femoral and tibial cut guide 1328. Note that the proximal tibial resection 210 is made while the soft tissues surrounding the knee joint are intact and loaded by the natural anatomy. Thus the conventional step of balancing soft tissues may be greatly reduced or eliminated altogether.

Figure 106:
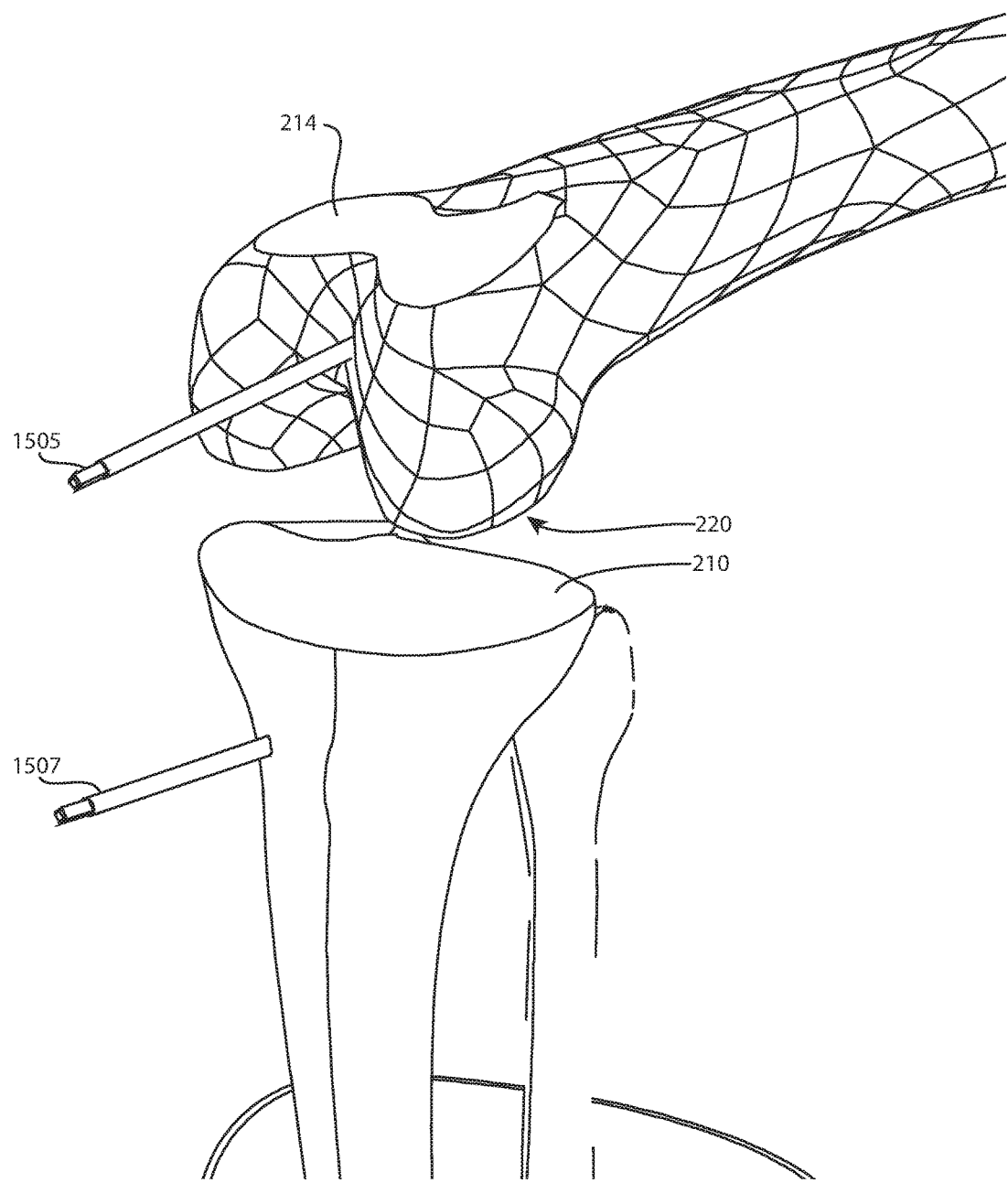
FIG. 106 is a perspective view of the femur, tibia, fibula, femoral pin, tibial pin, anterior femoral resection, posterior femoral resection, and proximal tibial resection of FIG. 105 with the three in one cut guide assembly and related bone pins removed.

FIG. 106 shows the step of removing the three in one cut guide assembly 1321 after making the anterior femoral resection 214, the posterior femoral resection 220, and the proximal tibial resection 210.

FIG. 107 shows the step of coupling a distal femoral cut guide assembly 1519 to the femur 100. This step may include coupling the distal femoral cut guide assembly 1519 to the anterior distal femur and the target 1820 of the target clamp assembly 1818 via the femoral extension rod assembly 1506. This step may include aligning the distal femoral cut guide assembly 1519 and/or the femoral extension rod assembly 1506 with the mechanical axis 202 of the leg as it extends through the femur 100. The distal femoral cut guide assembly 1519 shown in FIGS. 108A-108C includes a femoral pin block 1514, a femoral riser 1504, a screw 1150, a pin 1152, and a distal femoral cut block assembly 1638. The distal femoral cut guide assembly 1519 is coupled to a femoral extension rod assembly 1506. The femoral extension rod assembly 1506 includes an outer rod 1604, an inner rod 1606, a spool 1608, a sleeve 1610, a ring 1612, a retaining ring 1614, and the pin 1601. The femoral extension rod assembly 1506 may be similar to or identical to the femoral extension rod 306, 506, 2506 or the tibial extension rod 313, 511, 1511, 2511. The distal femoral cut block assembly 1638 shown in FIGS. 108A-108C includes a distal femoral cut block 1637 and two pegs 1646. Aligning the distal femoral cut guide assembly 1519 and/or the femoral extension rod assembly 1506 with the mechanical axis 202 of the leg may include centering the femoral pin block 1514 in the medial-lateral width of the distal femur and at the same time aligning the femoral extension rod assembly 1506 to pass over the center 120 of the femoral head 118. This step may reference four anatomical reference points: the distal margin of the medial femoral condyle, the femoral pin 1505 (which was placed by referencing the distal anterior femoral cortex and the mechanical axis of the leg), the anterior femoral resection 214, and the mechanical axis 202 of the leg (directly).

The femoral pin block 1514 is a roughly triangular plate with a bone facing surface 1154 and an opposite top surface 1156. The bone facing surface 1154 is positioned against the anterior femoral resection 214. The femoral pin block 1514 has a distal portion 1566 and a proximal portion 1568. The femoral pin block 1514 is illustrated with several through holes 1162, 1164, 1166 which receive bone pins; two mounting holes 1168 are shown as well. Two proximal holes 1162 are shown, twelve middle holes 1164 are shown, and four distal holes 1166 are shown, although any number of holes may be provided. The left and right holes 1162 may converge together as they approach the bone facing surface 1154. The left group and the right group of holes 1164 may also converge together as they approach the bone facing surface 1154. The left group and the right group of holes 1166 may include individual holes that are spaced apart widely enough in the medial-lateral direction that femoral resections may be cut while the femoral pin block 514 remains secured to the femur 100. These widely spaced holes 1166 may be located outboard of the mounting holes 1168 so that bone pins driven through the widely spaced holes 1166 penetrate the epicondyles. The femoral pin block 1514 may be widened as shown to support the widely spaced holes 1166. The femoral pin block 514 includes a blind hole 1170 and a through hole 1172. All of the preceding holes 1162, 1164, 1166, 1168, 1170, 1172 extend at least through the top surface 1154 of the femoral pin block. The distal portion 1566 includes a transverse undercut channel 1174 with a dimple 1176 in its proximal surface.

The femoral riser 1504 is a generally curved bar with a distal portion 1178 and a proximal portion 1180. Two holes 1182, 1184 extend anteriorly into the distal portion 1178. The proximal portion 1180 includes a longitudinal slot 1186 and a transverse hole 1188 that extends across the slot 1186.

The distal femoral cut block 1637 includes a proximal mounting portion 1190 and a distal paddle 1192. The mounting portion 1190 includes a bar 1194 with a peg 1646 extending from each end of the bar. The pegs 1646 are parallel, and in this example they are separate pins which are coupled to holes 1196 in the bar 1194; the pegs 1646 may be integral with the bar 1194 instead. The bar 1194 includes a saw slot 1198 which extends in an anterior-posterior direction through the bar 1194. The paddle 1192 includes a proximal surface 1200 which is positioned against the distal medial condyle. The saw slot 1198 is offset 9 mm from the proximal surface 1200 in the example shown.

The pin 1152 is received in the hole 1170 of the femoral pin block 1514 and the hole 1182 of the femoral riser 1504. The screw 1150 extends through the holes 1172, 1184 to secure the femoral pin block 514 and the femoral riser 1504 together. The pegs 1646 are received in the holes 1196 of the distal femoral cut block 1637, and may be press fit or otherwise fixed in place. The pegs are also received in the holes 1168 of the femoral pin block 514 to couple the distal femoral cut block assembly 1638 to the femoral pin block.

FIG. 109 shows the step of further securing the distal femoral cut guide assembly 1519 to the distal femur with bone pins 1329. Preferably, this step occurs while the bone facing surface 1154 of the femoral pin block 1514 contacts the anterior femoral resection 214, and while the femoral pin guide assembly 1501 and/or the femoral extension rod assembly 1506 are aligned with the mechanical axis 202 of the leg. This improves the accuracy of the distal femoral resection 206.

FIG. 110 shows the step of removing the femoral pin 1505 and making a distal femoral resection 206. The distal femoral resection 206 is made through the saw slot 1198 in the distal femoral cut block 1637.

FIGS. 111A and 111B show the step of removing the distal femoral cut block assembly 1638 and illustrate the adjustability provided by the distal femoral cut block 1637, an optional insert 1202, and the femoral pin block 1514. The optional insert 1202 may be included in the distal femoral cut guide assembly 1519 to provide adjustability to the distal femoral cut. A cut made through the saw slot 1198 of the distal femoral cut block 1637 is in the standard or zero position. If the distal femoral cut block assembly 1638 is removed, a cut made against the distal surface 1208 of the insert 1202 is 2 mm proximal to the standard position. If the insert 1202 is removed, a cut made against the distal surface 1566 of the femoral pin block 1514 is 4 mm proximal to the standard position. The insert 1202 is an elongated bar with a longitudinal proximal undercut rail 1204 and a retention tab 1206 on the rail.

FIG. 112 shows the step of coupling a chamfer cut guide 1751 to the femoral pin block 1514 in place of the distal femoral cut block assembly 1638. FIGS. 112-113 show views of the chamfer cut guide 1751. The chamfer cut guide 1751 includes a generally rectangular body 1210 with a distal surface 1212, an opposite proximal surface 1214, and an anterior surface 1216. The chamfer cut guide 1751 has two saw slots 1218, 1220 which intersect at the distal surface 1212 and diverge anteriorly and posteriorly as they extend toward the proximal surface 1214. Bilateral tabs 1222, 1242 extend from the chamfer cut guide 1751 on either side of the saw slots 1218, 1220. Bilateral through holes 1226, 1228 extend through the tabs 1222, 1242, respectively, in a distal to proximal direction. An L-shaped plate 1230 extends anteriorly and proximally from the anterior surface 1216. The L-shaped plate 1230 includes an anterior plate 1231 and a proximal plate 1234. The proximal plate 1234 includes a posterior surface 1236. The proximal surface 1214 is positioned against the distal femoral resection 206 and the posterior surface 1236 is positioned against the top surface 1156 of the femoral pin block 1514 so that the tabs 1222, 1224 extend medially and laterally relative to the distal femur 100.

FIG. 114 shows the step of further securing the chamfer cut guide 1751 to the distal femur with bone pins 1329. Preferably, this step occurs while the proximal surface 1214 is in close contact with the distal femoral resection 206 and the posterior surface 1236 is in close contact with the top surface 1156.

FIG. 115A shows the step of making an anterior chamfer cut 216 and a posterior chamfer cut 218. The anterior chamfer cut 216 is made through the anterior saw slot 1218 in the chamfer cut guide 1751. The posterior chamfer cut 218 is made through the posterior saw slot 1220 in the chamfer cut guide 1751.

The chamfer cut guide 1751 may be removed so that the distal femoral resection 206 may be adjusted as illustrated in FIG. 111B. The chamfer cut guide 1751 may then be repositioned so that the anterior and posterior chamfer cuts 216, 218 can also be adjusted.

FIG. 115B shows an optional step of coupling an implant trial 1238 to the posterior femoral resection 220 and the chamfer cut guide 1751 so that the knee may be moved through a range of motion to verify that the proper flexion/extension gaps have been established. Preferably, this step occurs while the chamfer cut guide 1751 and the distal femoral cut block assembly 1638 remain secured to the femur.

FIGS. 116A-119B illustrate a group of steps for making the distal femoral resection 206 and the anterior and posterior chamfer cuts 216, 218 that may be performed as an alternative to the steps illustrated in FIGS. 106-115B.

FIG. 116A shows the step of coupling a distal femoral cut guide 1240 to the distal anterior femur 100 and the three in one cut guide assembly 1321 of FIG. 105 with bone pins 1329. An advantage of this step is that the original alignment to the mechanical axis 202 of the leg established in FIG. 96A is maintained via the femoral pin 1505, the tibial pin 1507, the tibial extension rod assembly 1511, and the target 1882. Referring to FIGS. 116B and 116C, the distal femoral cut guide 1240 includes a distal surface 1242, a proximal surface 1244, an anterior surface 1246, and a posterior surface 1262. A saw slot 1248 and one or more holes 1250 extend through the distal femoral cut guide 1240 in an anterior to posterior direction. Five holes 1250, 1252, 1254, 1256, 1258 are shown. The holes may be counterbored at the anterior surface 1246. A tab 1260 extends distally from the distal surface 1242. The posterior surface 1262 is positioned against the anterior femoral resection 214, the tab 1242 is received in the saw slot 1056 of the anterior femoral cut guide 1326, and the distal surface 1242 is positioned against the proximal surface 1052.

FIG. 117A shows the step of removing the femoral pin 1505, three in one cut guide assembly 1321 and tibial extension rod assembly 1511 and making the distal femoral resection 206 through the saw slot 1248 of the distal femoral cut guide 1240.

FIG. 118A shows the step of coupling a chamfer cut guide 1264 to the distal femur and the distal femoral cut guide 1240 with bone pins 1329. The chamfer cut guide 1264 includes a distal surface 1266, a proximal surface 1268, and an anterior surface 1270. The chamfer cut guide 1264 has two saw slots 1272, 1274 which intersect at the distal surface 1266 and diverge anteriorly and posteriorly as they extend toward the proximal surface 1268. Bilateral tabs 1276, 1278 extend from the chamfer cut guide 1264 on either side of the saw slots 1272, 1274. Bilateral through holes 1280, 1282 extend through the tabs 1276, 1278, respectively, in a distal to proximal direction. A plate 1284 extends anteriorly from the anterior surface 1270. A slot 1286 extends through the plate 1284 in a distal to proximal direction. The proximal surface 1268 is positioned against the distal femoral resection 206, the tab 1260 of the distal femoral cut guide 1240 is received in the slot 1286 of the chamfer cut guide 1264, and the plate 1284 may be positioned against the distal surface 1242.

FIGS. 119A and 119B show the step of making anterior and posterior chamfer cuts 216, 218. The anterior chamfer cut 216 is made through the saw slot 1272 of the chamfer cut guide 1264 and the posterior chamfer cut 218 is made through the saw slot 1274.

FIG. 120 shows the femur 100, tibia 104, and fibula 122 after making the anterior femoral resection 214, the anterior chamfer cut 216, the distal femoral resection 206, the posterior chamfer cut 218, the posterior femoral resection 220, and the proximal tibial resection 210, and after removing all instruments. FIG. 120 represents an endpoint for the steps shown in FIGS. 106-115B or for the steps shown in FIGS. 116A-119B.

FIGS. 121-146B illustrate yet another instrument system 2500.

FIG. 121 shows the step of securing a foot (not shown) in a portion of a foot holder assembly 2870. This step may be similar to or identical to the step of FIG. 89. The foot holder assembly 2870 includes a foot receiver 2872, a lower bar 2874, a bridge 2878, a target mounting block 2880, a dovetail lock 2881, a target 2882, and a thumbscrew 2884. The bridge 2878, target mounting block 2880, dovetail lock 2881, target 2882, and thumbscrew 2884 are shown in FIG. 126. The foot holder assembly 2870 may be similar to or identical to the foot holder assembly 870 or 1870.

FIG. 122 shows the step of securing a femoral support arm assembly 2786 to an operating table (not shown) so that a portion of the femoral support arm assembly extends over the hip area. This step may be similar to or identical to the step of FIG. 69 and/or FIG. 90. The femoral support arm assembly 2786 includes a post 2788, a bar 2790, a first clamp body 2792, a second clamp body 2794, a spring 2796, a retaining ring 2798, a thumbscrew 2800, and a screw 2802. The femoral support arm assembly 2786 may be similar to or identical to the femoral support arm assembly 786 or 1786.

FIGS. 123A-123B show the step of positioning a femoral head finder 2918 to extend over a center 120 of a head of the femur 100. This step may be similar to or identical to the step of FIG. 70 and/or FIG. 91. FIG. 123A is a perspective view and FIG. 123B is a top view. The femoral head finder 2918 may be similar to or identical to the femoral head finder 918 or 1918. Imaging, such as radiographs, fluoroscopy, a C-arm, and the like, may facilitate positioning the femoral head finder 2918 accurately over the center 120 of the femoral head.

Alternatively, the center of the femoral head may be located using ultrasound. Ultrasound equipment may already be present in the operating room for preoperative identification of the femoral nerve or other neurovascular structures. The inventors have observed that the arcs of the femoral head and acetabulum show up clearly on ultrasound. The arc of the femoral head or acetabulum may be used to determine the location of the center of the femoral head. A skin mark may be made over the center of the femoral head. The skin mark may be made with a pen, an adhesive sticker, a clip or skin staple, a skin-piercing stud, or the like. A skin-pinching or skin-penetrating mark may be preferable in the presence of ultrasound gel. The skin mark may be transferred to the femoral support arm assembly 2786 with a plumb line, which may be supported by the femoral head finder 2918 on the bar 2790. Line 119 in FIG. 123A indicates the plumb line supported by the femoral head finder 2918 and positioned over the skin mark over the center 120 of the femoral head.

FIG. 124 shows the step of securing a collar 2926 to the bar 2790 beside the femoral head finder 2918. This step may be similar to or identical to the step of FIG. 70 and/or FIG. 92. The collar 2926 may be similar to or identical to the collar 926 or 1926.

The preceding steps may be performed before the patient is sterile draped. This is advantageous as it occurs before operative time begins to toll.

FIG. 125 shows the step of removing the femoral head finder 2918 and securing a target clamp assembly 2818 to the bar 2790 beside the collar 2926. This step may be similar to or identical to the step of FIG. 71 and/or FIG. 93. The target clamp assembly 2818 includes a target 2820, a retaining ring 2822, a first clamp body 2824, a second clamp body 2826, a lever 2828, a link 2830, and a pin 2832. The example shows two links 2830 and eight pins 2832. The target clamp assembly 2818 may be similar to or identical to the target clamp assembly 818 or 1818. The femoral support arm assembly 2786 with attached collar 2926 may be covered by a sterile drape after the femoral head finder 2918 is removed and before the target clamp assembly 2818 is coupled to the bar 2790, in a manner similar to that shown in FIG. 71.

FIG. 126 shows the step of assembling the bridge 2878, target mounting block 2880, dovetail lock 2881, target 2882, and thumbscrew 2884 to the lower bar 2874 and the foot receiver 2872 to form a complete foot holder assembly 2870. This step may be similar to or identical to the step of FIG. 94.

FIG. 127 shows the step of making a small provisional proximal tibial resection 209 at the base of the tibial eminence at the level of the normal lateral tibial plateau, which may optionally be referred to as a tibial sizing notch in situations where the resection 209 is limited to a small area such as the center of the lateral articular surface. The provisional proximal tibial resection 209 may involve the anterior portion of the tibial plateau as shown, or it may be less extensive or more extensive than shown. For example, the provisional proximal tibial resection 209 may involve only the tibial eminence. The provisional proximal tibial resection 209 marks the level of the unworn lateral tibial plateau and the actual joint line of the femoral-tibial joint.

FIGS. 128A-128B show the step of coupling a femoral pin block assembly 2501 to the anterior distal femur. This step may be similar to or identical to the step of FIG. 72 and/or FIG. 96A. FIG. 128A is a perspective view and FIG.

128B is a top view. The femoral pin block assembly 2501 includes a base 2502, a handle 2516, a pin guide 2514, a screw 2513, and a pin sleeve 2515. The example shows two screws 2513. The femoral pin block assembly 2501 is coupled to a femoral extension rod assembly 2506. The femoral extension rod assembly 2506 includes an outer rod 2604, an inner rod 2606, a spool 2608, a sleeve 2610, a ring 2612, a retaining ring 2614, and a pin 2601. The femoral extension rod assembly 2506 may be similar to or identical to the femoral extension rod 306, 506, 1506 or the tibial extension rod 313, 511, 1511, 2511. The spool 2608 rests in the target 2820 so that the femoral extension rod assembly 2506 extends over the center 120 of the femoral head.

FIGS. 129A-129B show perspective views of the femoral pin block assembly 2501. The pin guide 2514 includes a first hole 2519 and a second hole 2521. The femoral pin block assembly 2501 may be similar to the femoral pin guide assembly 1501 of FIG. 97A. The first hole 2519 includes a longitudinal slot 2523. The first hole 2519 receives the pin sleeve 2515. The first hole 2519 may be parallel to the bone contacting surface 2518 of the base 2502, or a theoretical bone contacting plane defined by spikes 2538 protruding from the bone contacting surface of the base. The second hole 2521 is anteriorly spaced apart from the first hole. The second hole 2521 may be parallel to the bone contacting surface 2518 of the base 2502, or a theoretical bone contacting plane defined by spikes 2538 protruding from the bone contacting surface of the base, parallel to the first hole 2519, or aligned to correspond to the upcoming anterior femoral resection 214, in other words coplanar with the anterior femoral resection 214. The second hole 2521 may be located so that a guide wire, k-wire, pin, drill, or the like passed through the second hole is aligned with the bone contacting surface 2518 of the base 2502, or a theoretical bone contacting plane defined by spikes 2538 protruding from the bone contacting surface of the base, or the anterior femoral resection 214 (which may be at an angle to the bone contacting surface 2518 or the theoretical bone contacting plane). Preferably, the second hole 2521 is located so that the guide wire, etc. exits the anterior femoral cortex at the distal edge 2517 of the base 2502. The second hole 2521 may be used to confirm that the distal anterior femoral resection 214, discussed below, will intersect the distal anterior femoral cortex at a satisfactory location. This ensures that the distal anterior femoral resection 214 is not too deep, so that it notches the anterior femur, and not too shallow, so that the final implant sits above the bone surface.

In an alternate arrangement, the hole 2519 may be parallel to the femoral transverse plane, or in other words, perpendicular to the upcoming distal femoral resection 206. The hole 2521 may also be parallel to the femoral transverse plane, or in other words, perpendicular to the distal femoral resection 206. Optionally, the femoral pin block assembly 2501 may enable the first and second holes to be adjusted, together or separately, with respect to the bone contacting surface 2518 and/or with respect to the mechanical axis 202 of the femur/leg. Preferably, the adjustability occurs between the distal part of pin guide 2514 and the distal part of base 2502.

FIG. 130 shows the step of placing a femoral pin 2505 into the distal femur through the pin sleeve 2515 and the first hole 2519 of the femoral pin block assembly 2501. This step may be similar to or identical to the step of FIG. 98. The femoral pin 2505 encodes information about 1) the proper varus/valgus orientation of the distal femoral resection 206, 2) the flexion/extension orientation of the distal anterior femoral resection 214 and the distal posterior femoral resection 220, 3) the middle of the trochlear groove (Whiteside's line). The femoral pin 2505 enables rotational adjustment of the femoral four-in-one cut guide assembly 3010 about the pin 2505, which ensures proper tracking of the patella. More specifically, the femoral four-in-one cut guide assembly 3010 may be adjusted for varus-valgus rotation about the femoral post 3122, which rotates within the hole 3004 created by the femoral pin 2505. The distal femoral resection 206, distal anterior femoral resection 214, distal posterior femoral resection 220, femoral four-in-one cut guide assembly 3010, femoral post 3122, and hole 3004 are discussed in greater detail below. FIG. 130 also shows the step of placing a femoral pin 2507 into the distal femur through the second hole 2521. The femoral pin 2507 may be placed into the distal femur temporarily to verify that the distal anterior femoral resection 214 will intersect the distal anterior femoral cortex at a satisfactory location, and then removed. The femoral pin 2505 is preferably a 5 mm diameter drill. The femoral pin 2507 is preferably a 3.2 mm diameter pin. Note that the femoral pin block assembly 2501 is not pinned to the anterior surface of the femur 100.

FIG. 131 shows the step of removing the pin sleeve 2515 from the first hole 2519 after the femoral pin 2505 has been placed into the distal femur. This step may be similar to or identical to the step of FIG. 99. FIG. 131 also shows the step of removing the femoral pin 2507 from the second hole 2521.

FIG. 132 shows the step of removing the femoral pin block assembly 2501 after the femoral pin 2505 has been placed into the distal femur and the pin sleeve 2515 has been removed from the first hole 2519. This step may be similar to or identical to the step of FIG. 100. The femoral pin 2505 slides laterally out of the first hole 2519 through the slot 2523 (FIG. 129B). In other words, the femoral pin block assembly 2501 slides anteriorly off of the femoral pin 2505.

FIGS. 133A-133B show the step of setting the knee angle to 90 degrees with a knee angle guide 2930. FIG. 133A is a perspective view and FIG. 133B is a side view. The knee angle guide 2930 includes a knee angle frame 2932 and a rod 2934. The knee angle frame 2932 includes a hole 2936 which receives the femoral pin 2505 and bilateral holes 2938, 2940 which receive the rod 2934. The hole 2938 is used with a right knee and the hole 2940 is used with a left knee as illustrated. The holes 2938, 2940 are parallel to each other. Referring to FIG. 133B, the femoral pin 2505 has a central longitudinal axis 2942. The rod 2934 has a central longitudinal axis 2944. The orientation of axis 2944 is set by hole 2940 which receives the rod 2934, or hole 2938 for a right knee. A 90 degree angle 2946 exists between axis 2944 and axis 2948 of the left arm 2950 of the knee angle frame 2932. A small acute angle 2952 may optionally exist between axis 2942 and 2948. The angle 2952 may be greater than or equal to zero degrees. The illustrated angle 2952 is 3 degrees. In other words, the illustrated axis 2942 is parallel to the distal anterior femoral cortex, thus parallel to the distal anterior femoral resection 214, and is at an angle of 3 degrees to the distal femoral resection 206. In other examples, the axis 2942 may be perpendicular to the distal femoral resection 206 and would thus form a small acute angle with the distal anterior femoral resection 214. The illustrated knee angle guide 2930 holds the rod 2934 (axis 2944) parallel to the distal femoral resection 206 so that when the proximal tibial resection 210 is made, its slope is accurate.

FIG. 134 shows the step of coupling a distal femoral cut guide assembly 2960 to the femur 100. The distal femoral cut guide assembly 2960 includes a distal plate 2962, a distal femoral cut guide 2964, and an interlock 2966. The distal plate 2962 slides over the femoral pin 2505. The interlock 2966 couples the distal femoral cut guide 2964 to the distal plate 2962 so that the distal femoral cut guide 2964 is free to slide in the anterior-posterior direction relative to the distal plate 2962. Two pins 2968, 2970 are shown securing the distal femoral cut guide 2964 to the femur 100.

FIGS. 135A-135B show exploded perspective views of the distal femoral cut guide assembly 2960. The distal plate 2962 includes a medial plate portion 2972, a lateral plate portion 2974, and holes 2976, 2978, 2980, 2982, 2984. The distal femoral cut guide 2964 includes a slot 2986, holes 2988, 2990, and holes 2992, 2994, 2996. Each of the holes 2992, 2994, 2996 may optionally be a cluster of holes as shown. The interlock 2966 includes a body 2998 and two posts 3000, 3002. The femoral pin 2505 is received in hole 2976. The post 3000 is received in holes 2988 and 2978. The post 3002 is received in holes 2990 and 2980. The pin 2968 is received in hole 2992 or another hole in its cluster. The pin 2970 is received in hole 2994 or another hole in its cluster. Another pin (not shown) may optionally be received in hole 2996 or another hole in its cluster. A saw blade (not shown) is received in the slot 2986 to make a distal femoral resection 206.

FIG. 136 shows the step of removing the interlock 2966, the distal plate 2962, the femoral pin 2505, and making a distal femoral resection 206. The distal femoral resection 206 is made through the saw slot 2986 in the distal femoral cut guide 2964. Removing the femoral pin 2505 leaves a hole 3004 in the distal femur. The hole 3004 is anterior to the femoral intramedullary canal in dense strong subtrochlear bone.

FIGS. 137A-137D show the step of coupling a femoral four-in-one cut guide assembly 3010 to the femur 100 and a proximal tibial cut guide 3012 to the tibia 104. This step may be similar to the step of FIG. 102A. FIG. 137A is a perspective view. FIG. 137B is a detail view of a portion of FIG. 137A. FIG. 137C is a front view. FIG. 137D is a side view. The four-in-one cut guide assembly 3010 is an adjustable assembly. The four-in-one cut guide assembly 3010 includes an anterior cut guide 3014, an anterior chamfer guide 3016, a posterior chamfer guide 3018, a posterior cut guide 3020, a gear assembly 3022, and a screw 3024. Four screws 3024 are shown, two in the anterior chamfer guide 3016 and two in the posterior chamfer guide 3018. The four-in-one cut guide assembly 3010 and the proximal tibial cut guide 3012 are adjustably coupled together by a latch mechanism 3026. The proximal tibial cut guide 3012 is coupled to a tibial extension rod assembly 2511. The tibial extension rod assembly 2511 includes an outer rod 2605, an inner rod 2607, a sleeve 2611, a ring 2613, a pin 2601, and a ball 2617. The tibial extension rod assembly 2511 may be similar to or identical to the tibial extension rod 313, 511, 1511 or the femoral extension rod 306, 506, 1506, 2506. The ball 2617 rests in the target 2882 so that the tibial extension rod assembly 2511 extends over the center of the distal tibia 104. The femoral four-in-one cut guide assembly 3010 and the proximal tibial cut guide 3012 may be adjusted for varus-valgus rotation about the femoral post 3122 in the hole 3004 to position the ball 2617 in the target 2882.

FIGS. 138A-138D show the femoral four-in-one cut guide assembly 3010, the proximal tibial cut guide 3012, and the latch mechanism 3026. FIGS. 138A-138B are perspective views. FIGS. 138C-138D are exploded perspective views. The proximal tibial cut guide 3012 includes a body 3028 with a proximal undercut channel 3030 defined by side walls 3032, 3034, a saw slot 3036, holes 3038, 3040, 3042, a distal arm 3044 which bifurcates into arms 3046, 3048, which are separated by a slot 3050, and terminates in a compliant pin receiver 3052. The slot 3050 may receive the tibial pin 1507 in the manner shown in FIG. 102A. The pin receiver 3052 receives pin 2601 of the tibial extension rod assembly 2511. The holes 3038, 3040, 3042 may be clusters of holes as shown. The latch mechanism 3026 includes a body 3054, a lever 3056, and pins 3058, 3060. The body 3054 includes a proximal undercut rail 3062, a distal undercut rail 3064, a grip portion 3066, a recess 3068, and holes 3070, 3072. The lever 3056 includes a tooth 3074, a notch 3076, a button 3078, a hole 3080, and a spring arm 3082. The lever 3056 is received in the recess 3068 with the tooth 3074 opposite the grip portion 3066 and the button 3078 exposed. The pin 3060 is received in the hole 3070 and the notch 3076. The pin 3058 is received in the holes 3072, 3080. The distal undercut rail 3064 is received in the proximal undercut channel 3030 so that the proximal tibial cut guide 3012 may be adjusted relative to the femoral four-in-one cut guide assembly 3010 in the proximal-distal or superior-inferior direction (relative to the femur).

Optionally, for the purpose of making a provisional tibial resection 209, the proximal tibial cut guide 3012 can be positioned anterior and distal to its illustrated position in FIG. 138A, in other words distal to the posterior cut guide 3020, so that the undercut channel 3180 and the undercut channel 3030 are aligned to form a continuous undercut channel so that the proximal tibial cut guide 3012 may be adjusted relative to the femoral four-in-one cut guide assembly 3010 in the proximal-distal or superior-inferior direction (relative to the femur). The latch mechanism 3026 including body 3054 and lever 3056 would of course be reconfigured to complement this arrangement.

Optionally, the femoral four-in-one cut guide assembly 3010 and the proximal tibial cut guide 3012 may be combined together as a five-in-one cut guide assembly. In this arrangement, the proximal tibial cut guide 3012 may be adjustable relative to the femoral four-in-one cut guide assembly 3010 in the anterior-posterior direction (relative to the femur), and may also be adjustable in the proximal-distal direction. The gear assembly 3022 would of course be reconfigured with additional gears and a rack to complement this arrangement.

FIGS. 139A-139E show the femoral four-in-one cut guide assembly 3010. FIG. 139A is a front view. FIG. 139B is a cross sectional view taken along line 139B-139B of FIG. 139A. FIG. 139C is a cross sectional view taken along line 139C-139C of FIG. 139A. FIGS. 139D-139E are exploded perspective views. The anterior cut guide 3014 includes a medial saw slot 3124, a lateral saw slot 3126, a plate 3128 with a medial rack 3130, a generally rectangular hole 3132, a round hole 3134, a boss 3136, and a femoral post 3122. The generally rectangular hole 3132 includes a medial channel 3250 and a lateral channel 3252. The femoral post 3122 is shown as a separate part coupled to the boss 3136, but the femoral post 3122 may be integrally formed with the boss 3136. The illustrated femoral post 3122 is oriented to match a femoral pin 2505 that is parallel to the bone contacting surface 2518, or theoretical bone contacting plane, however the femoral post 3122 may be oriented to match a femoral pin 2505 that is parallel to the femoral transverse plane, or in other words, perpendicular to the distal femoral resection 206. Optionally, the femoral four-in-one cut guide assembly 3010 may be designed with a through hole, similar to hole 2976 of distal plate 2962, instead of the femoral post 3122 and boss 3136. The through-hole design may affect many of the parts in the assembly 3010. The anterior chamfer guide 3016 includes a medial saw slot 3138, a lateral saw slot 3140, holes 3142, 3144, holes 3146, 3148, 3150, 3152, and a generally rectangular channel 3154. The holes 3142, 3144 receive screws 3024. The holes 3146, 3148, 3150, 3152 may receive bone screws (not shown) and may be counterbored as shown so that bone screw heads do not occlude the saw slots 3138, 3140. The generally rectangular channel 3154 includes a medial channel 3254, a lateral channel 3256, a medial lip 3262, and a lateral lip 3264. The posterior chamfer guide 3018 includes a medial saw slot 3156, a lateral saw slot 3158, holes 3160, 3162, holes 3164, 3166, 3168, 3170, and a generally rectangular channel 3172. The holes 3160, 3162 receive screws 3024. The holes 3164, 3166, 3168, 3170 may receive bone screws (not shown) and may be counterbored as shown so that bone screw heads do not occlude the saw slots 3156, 3158. By placing bone screws through some or all of holes 3146, 3148, 3150, 3152, 3164, 3166, 3168, 3170, the anterior chamfer guide 3016 and posterior chamfer guide 3018 are locked in place during the sawing process. The bone screws may serve in lieu of, and may be replaced by, a locking mechanism in the femoral four-in-one cut guide assembly 3010. The bone screws or locking mechanism serve to isolate the gear assembly 3022 from loads generated during the sawing process. The generally rectangular channel 3172 includes a medial channel 3258, a lateral channel 3260, a medial lip 3266, and a lateral lip 3268. The plate 3128 slides against the inner surfaces of the lips 3262, 3264, 3266, 3268. The posterior cut guide 3020 includes a medial saw slot 3174, a lateral saw slot 3176, a generally rectangular socket 3178, and a distal undercut channel 3180 defined by side walls 3182, 3184. The proximal undercut rail 3062 is received in the distal undercut channel 3180 so that the proximal tibial cut guide 3012 may be adjusted relative to the femoral four-in-one cut guide assembly 3010 in the proximal-distal or superior-inferior direction (relative to the femur). The gear assembly 3022 is received in the hole 3132, channels 3154, 3172, and socket 3178.

The femoral post 3122 may optionally be included on a bone-facing side of a conventional four-in-one cut guide, integrally formed or as a separate part, for engagement with the hole 3004. Alternatively, the conventional four-in-one cut guide may optionally include a through hole that receives the femoral pin 2505. Any of these optional arrangements enable the conventional four-in-one cut guide to be rotationally adjusted in the manner described herein for the femoral four-in-one cut guide assembly 3010.

FIGS. 140A-140B are exploded perspective views of the gear assembly 3022. The gear assembly 3022 includes a housing 3084, a bolt 3086, a bolt head pin 3088, an optional second bolt head pin 3090, a saddle block 3092, an anterior rack 3094, a posterior rack 3096, a first medial gear 3098, a second medial gear 3100, a third medial gear 3102, a first lateral gear 3104, a second lateral gear 3106, a third lateral gear 3108, a fourth lateral gear 3110, a first shaft 3112, a second shaft 3114, a third shaft 3116, a fourth shaft 3118, and a fifth shaft 3120.

The housing 3084 includes holes 3188, 3190, 3192, 3194, 3196, 3198, 3200, 3202, 3204, rectangular bosses 3206, 3208, a medial rail 3210, a lateral rail 3212, and a window 3214. The hole 3188 receives the bolt 3086. The hole 3190 receives the bolt head pin 3088. The optional hole 3192 receives the optional second bolt head pin 3090. The boss 3206 surrounds the hole 3194. The boss 3208 surrounds the hole 3196. The medial rail 3210 is received in the medial channels 3250, 3254, 3258. The lateral rail 3212 is received in the lateral channels 3252, 3256, 3260. Preferably, the rails 3210, 3212 and channels 3250, 3252, 3254, 3256, 3258, 3260 are complementary undercut shapes, such as dovetails (illustrated). The undercut engagement acts to prevent the generally rectangular channels 3154, 3172 from spreading during heavy use.

The bolt 3086 includes a head 3216, a circumferential groove 3218, a shaft 3220, and a torque drive feature 3222. The groove 3218 receives the bolt head pin 3088 and the optional second bolt head pin 3090, if present. The shaft 3220 is at least partially threaded from the end opposite the head 3216.

The saddle block 3092 includes a generally rectangular body 3224, a threaded hole 3226, a boss 3228, and an indentation 3229. The body 3224 is received in the window 3214 so that the boss 3228 protrudes from the housing 3084 near the rails 3210, 3212 and the indentation 3229 faces the first medial gear 3098. The threaded hole 3226 receives the shaft 3220. The boss 3228 is received in the hole 3134.

The anterior rack 3094 includes a rack 3230, a hole 3232, and a hole 3234. The holes 3232, 3234 receive screws 3024.

The posterior rack 3096 includes a rack 3236, a hole 3238, and a hole 3240. The holes 3238, 3240 receive screws 3024.

Referring to FIGS. 139B-139C, the medial rack 3130 meshes with the first medial gear 3098, which is mounted on a hexagonal boss of the second lateral gear 3106. The second lateral gear 3106 thus rotates with the first medial gear 3098. The second lateral gear 3106 meshes with the first lateral gear 3104, which meshes with the anterior rack 3094, which is fastened to the anterior chamfer guide 3016 with screws 3024. The second lateral gear 3106 also meshes with the third lateral gear 3108. The third lateral gear 3108 meshes with the fourth lateral gear 3110, which is mounted on a hexagonal boss of the second medial gear 3100. The second medial gear 3100 thus rotates with the fourth lateral gear 3110. The second medial gear 3100 meshes with the third medial gear 3102, which meshes with the posterior rack 3096, which is fastened to the posterior chamfer guide 3018 with screws 3024.

The first shaft 3112 bears the first medial gear 3098 and the second lateral gear 3106. The first shaft 3112 is received in hole 3196. The second shaft 3114 bears the second medial gear 3100 and the fourth lateral gear 3110. The second shaft 3114 is received in hole 3198. The third shaft 3116 bears the third medial gear 3102. The third shaft 3116 is received in hole 3200 and is cantilevered in the window 3214. The fourth shaft 3118 bears the first lateral gear 3104. The fourth shaft 3118 is received in hole 3202 and is cantilevered in the window 3214. The fifth shaft 3120 bears the third lateral gear 3108. The fifth shaft 3120 is received in hole 3204 and is cantilevered in the window 3214.

The four-in-one cut guide assembly 3010 can be adjusted to position the saw slots 3138, 3140, 3156, 3158, 3174, 3176 of the guides 3016, 3018, 3020 (respectively) to correspond to the progressive arrangement of resection surfaces for the range of femoral component sizes of a knee system. The saw slots 3124, 3126 of the anterior cut guide 3014 are stationary with respect to the femur 100 because in use the femoral post 3122 is in the femoral hole 3004. In the example shown, the anterior-posterior location of each guide 3016, 3018, 3020 is independently adjustable relative to the anterior cut guide in a controlled and synchronized manner. The guides are independently adjustable because each guide may move relative to the anterior cut guide at its own rate or speed. The adjustments made to each guide are controlled and synchronized by the gear assembly 3022 so that turning the bolt 3088 clockwise and counterclockwise causes each guide to move at its own speed, and the relative speeds of the guides are selected so that when the four-in-one cut guide assembly 3010 is adjusted to a particular size, the saw slots are all positioned to correspond to that size. Note the indicia 3186 shown on the housing 3084 in FIG. 140A to indicate prosthesis sizes. An audible, visual, or tactile feedback may be provided to positively indicate that the femoral four-in-one cut guide assembly 3010 is set to a discrete implant size. Optionally, in an arrangement that lacks such positive indicators, a spacer may be used to verify that the femoral four-in-one cut guide assembly 3010 is set to a discrete implant size. As one example, a spacer may have one or more prongs, plates, or fingers that engage one or more of the gaps 3015, 3017, 3019 (FIGS. 141C-141D) that occur between the anterior cut guide 3014, the anterior chamfer guide 3016, the posterior chamfer guide 3018, and the posterior cut guide 3020 of the femoral four-in-one cut guide assembly 3010. The spacer may be removed before making any resections. The relative speeds of the guides are a matter of design choice and will change from one knee system to the next. The example shown provides proportional motion of the guides 3016, 3018, 3020 relative to the anterior cut guide 3014. It is also contemplated that non-proportional motion may be provided, so that one or more of the guides may move sometimes faster and sometimes slower, according to the design rationale of the particular knee system.

FIGS. 141A-141D show the step of adjusting the femoral four-in-one cut guide assembly 3010, adjusting the proximal tibial cut guide 3012, and pinning the femoral four-in-one cut guide assembly 3010 and the proximal tibial cut guide 3012 to the femur 100 and the tibia 104, respectively. The femoral four-in-one cut guide assembly 3010 and the proximal tibial cut guide 3012 may be adjusted for varus-valgus rotation about the femoral post 3122 in the hole 3004. The femoral four-in-one cut guide assembly 3010 may be adjusted for size by rotating the bolt 3088 clockwise and counterclockwise to change the anterior-posterior locations of the saw slots 3138, 3140, 3156, 3158, 3174, 3176 of the guides 3016, 3018, 3020 (respectively). The proximal tibial cut guide 3012 is coupled to the femoral four-in-one cut guide assembly 3010 by the latch mechanism 3026, which fixes the saw slot 3036 a predetermined anterior-posterior distance from the saw slots 3174, 3176 and allows the proximal tibial cut guide 3012 to slide in and out over the tibial plateau. Preferably, the femoral four-in-one cut guide assembly 3010 is adjusted by first rotating the bolt 3088 until the femoral four-in-one cut guide assembly 3010 is in its closed or smallest state (shown in FIGS. 137A-139C) and then rotating the bolt 3088 in the opposite direction to move the femoral four-in-one cut guide assembly 3010 toward its fully open or largest state, until the proximal tibial cut guide 3012 contacts the provisional tibial resection 209 (shown in FIGS. 141B-142). At this point, if the femoral four-in-one cut guide assembly 3010 is between sizes, the bolt 3088 may be rotated to adjust the femoral four-in-one cut guide assembly 3010 to the next smaller size. Pins 3242, 3244, 3246, 3248 secure the femoral four-in-one cut guide assembly 3010 and the proximal tibial cut guide 3012 to the femur 100 and tibia 104, respectively. Pin 3242 is received in hole 3194, pin 3244 is received in hole 3038, pin 3246 is received in hole 3040, and pin 3248 is received in slot 3050.

FIG. 142 shows the step of making an anterior femoral resection 214, an anterior chamfer cut 216, a posterior chamfer cut 218, a posterior femoral resection 220, and a proximal tibial resection 210. The anterior femoral resection 214 is made through the saw slots 3124, 3126 in the anterior cut guide 3014. The anterior chamfer cut 216 is made through the saw slots 3138, 3140 in the anterior chamfer guide 3016. The posterior chamfer cut 218 is made through the saw slots 3156, 3158 in the posterior chamfer guide 3018. The posterior femoral resection 220 is made through the saw slots 3174, 3176 in the posterior cut guide 3020. The proximal tibial resection 210 is made through the saw slot 3036 in the proximal tibial cut guide 3012.

FIG. 143 shows the step of removing the femoral four-in-one cut guide assembly 3010, the proximal tibial cut guide 3012, the tibial extension rod assembly 2511, and related pins after making the anterior femoral resection 214, the anterior chamfer cut 216, the posterior chamfer cut 218, the posterior femoral resection 220, and the proximal tibial resection 210. This step may be similar to or identical to the step of FIG. 120.

FIG. 144 shows the step of implanting a femoral component 130, a tibial component 132, an articular insert 134, and a patellar component 136 in the prepared knee joint. This step may be similar to or identical to the step of FIG. 88. The femoral component 130 is fixed to the distal femur 100, the tibial component 132 is fixed to the proximal tibia 104, the articular insert 134 is coupled to the tibial component 132, and the patellar component 136 is fixed to the patella 112. The implant components shown in FIG. 144 are one example of a set of implant components for knee arthroplasty. A subset of the components shown may also be used. Unicompartmental components may also be used.

FIG. 145 shows the step of converting from an intramedullary referencing system or other conventional referencing system to the system disclosed herein by coupling another femoral pin block assembly 3270 of the present system to a distal femoral cut guide 3272 of the conventional referencing system and placing a femoral pin 2505 into the distal femur through the pin sleeve 2515. This step may take place instead of the steps of coupling the femoral pin block assembly 2501 to the anterior distal femur, as shown in FIG. 128A, and placing the femoral pin 2505 into the distal femur through the pin sleeve 2515 and the first hole 2519 of the femoral pin block assembly 2501, as shown in FIG. 130. The step of FIG. 145 may result in equivalent positioning of the femoral pin 2505 in the distal femur, as shown in FIG. 132, including formation of an equivalent hole 3004. The step of FIG. 145 may occur after a distal femoral resection 206 and a provisional proximal tibial resection 209 have been made.

FIGS. 146A-146B are exploded perspective views of the femoral pin block assembly 3270 and the distal femoral cut guide 3272. The femoral pin block assembly 3270 includes a body 3274, the pin sleeve 2515, an anterior referencing pin 3276, and a thumbscrew 3278.

The body 3274 includes a pin guide arm 3280, a distal femoral paddle 3282, and an anterior referencing arm 3284. The pin guide arm 3280 includes a first hole 3286 with a longitudinal slot 3288, equivalent to the first hole 2519 and longitudinal slot 2523. The first hole 3286 receives the pin sleeve 2515, which receives the femoral pin 2505. The slot 3288 is wider than the femoral pin 2505. The pin guide arm 3280 may include an optional second hole (not shown) equivalent to the second hole 2521. The anterior referencing arm 3284 includes a first hole 3290, a slot 3292, and a second hole 3294. The first hole 3290 receives the anterior referencing pin 3276. The slot 3292 splits the first hole 3290 longitudinally and bifurcates the free end of the arm 3284. The second hole 3294 extends through the bifurcated free ends of the arm 3284 transverse to the first hole 3290. The second hole 3294 threadedly receives the thumbscrew 3278, which can be tightened so that the first hole 3290 grips the anterior referencing pin 3276, or loosened so that the anterior referencing pin is movable within the first hole.

The anterior referencing pin 3276 extends between a narrow distal end 3296 and a broad proximal end 3298. The distal end 3296 contacts the anterior distal femoral cortex in use, while the proximal end 3298 serves as a handle. The distal end 3296 may taper to a point as shown. The proximal end 3298 may include grip features 3300 such as grooves (shown), knurling, threads, bumps, or a rough surface texture. The anterior referencing pin 3276 may optionally include indicia 3302, best seen in the enlarged detail provided in FIG. 146B. The indicia 3302 may include reference lines, numerals, icons, or other marks.

The distal femoral cut guide 3272 includes a saw slot 3304, pin holes 3306, 3308, 3310, and holes 3312, 3314. The saw slot 3304 receives a saw blade (not shown) to make the distal femoral resection 206. The saw slot 3304 also receives the distal femoral paddle 3282 as shown in FIG. 145. The pin holes 3306, 3308, 3310 receive bone pins 3316. Each pin hole 3306, 3308, 3310 may be a cluster of holes as shown. Indicia 3318 may be present.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the technology disclosed herein without departing from the spirit and scope of the invention as claimed.

The invention claimed is:

1. A method for inserting pins in a femur, comprising:
attaching a bone contacting surface of a base to an anterior distal femoral cortex of the femur;
positioning a distal edge of the bone contacting surface of the base at a place on the anterior distal femoral cortex where an anterior femoral resection is planned to exit the femur;
coupling an alignment rod to the base;
aligning the alignment rod with a mechanical axis of the femur;
coupling a pin guide to the base, wherein when the bone contacting surface of the base is attached to the anterior distal femoral cortex, the distal edge of the bone contacting surface of the base is positioned at the place, the alignment rod is coupled to the base and aligned with the mechanical axis of the femur, and the pin guide is coupled to the base, a first hole extending through the pin guide is aimed at a first point on a distal end of the femur that is located along a Whiteside's line associated with the femur that corresponds to a center of a trochlear groove of the femur, a second hole extending through the pin guide is aimed at a second point on the distal end of the femur that is in the trochlear groove, the first and second points are located between the anterior distal femoral cortex and an intramedullary canal of the femur, and the first and second holes of the pin guide are aligned with the mechanical axis of the femur and the bone contacting surface of the base; and
inserting a first pin through the first hole of the pin guide, through the first point, and into the femur and inserting a second pin through the second hole of the pin guide, through the second point, and into the femur so that a leading end of the second pin exits the femur at the place to indicate that the anterior femoral resection will intersect the anterior distal femoral cortex at the place, wherein the first and second pins are inserted while the bone contacting surface of the base is attached to the anterior distal femoral cortex, the distal edge of the bone contacting surface of the base is positioned at the place, the alignment rod is coupled to the base and aligned with the mechanical axis of the femur, and the pin guide is coupled to the base, such that the first and second pins are located between the anterior distal femoral cortex and the intramedullary canal of the femur.

2. The method of claim 1, wherein aligning the alignment rod with the mechanical axis of the femur comprises centering a proximal end of the alignment rod over a rotational center of an articular head of the femur.

3. The method of claim 2, wherein aligning the alignment rod with the mechanical axis of the femur further comprises centering a distal end of the alignment rod over the distal end of the femur, opposite the articular head, while the proximal end of the alignment rod is centered over the rotational center of the articular head of the femur.

4. The method of claim 3, wherein the distal end of the alignment rod is coupled to the base while the proximal end of the alignment rod is centered over the rotational center of the articular head of the femur and the distal end of the alignment rod is centered over the distal end of the femur.

5. The method of claim 1, wherein when the first pin is inserted into the femur, in an anterior view of the femur, the first pin is parallel to the mechanical axis.

6. The method of claim 1, wherein the bone contacting surface of the base is planar.

7. The method of claim 1, wherein when the first pin is inserted into the femur:

in an anterior view of the femur, the first pin is collinear with the mechanical axis of the femur, and, in a lateral view of the femur, the first pin is parallel to at least one of:

the anterior distal femoral cortex, and the anterior femoral resection.

8. The method of claim 7, wherein when the second pin is inserted into the femur:

in an anterior view of the femur, the second pin is collinear with the mechanical axis of the femur.

9. A method for inserting pins into a femur along desired trajectories, the method comprising:

attaching a base to an anterior distal femoral cortex of the femur;

coupling an alignment rod to the base;

aligning the alignment rod with a mechanical axis of the femur;

coupling a pin guide to the base, wherein when the base is attached to the anterior distal femoral cortex, the alignment rod is coupled to the base and aligned with the mechanical axis of the femur, and the pin guide is coupled to the base, a first hole through the pin guide is aimed along a first trajectory at a first point located on a distal end of the femur and located along a Whiteside's line associated with the femur that corresponds to a center of a trochlear groove of the femur, a second hole through the pin guide is aimed along a second trajectory at a second point located on the distal end of the femur and located in the trochlear groove, and the first and second points are located between the anterior distal femoral cortex and an intramedullary canal of the femur;

inserting a first pin through the first hole of the pin guide, along the first trajectory, through the first point and into the femur at a defined orientation relative to the anterior distal femoral cortex, intersecting the Whiteside's line, and aligned with the mechanical axis of the femur; and inserting a second pin through the second hole of the pin guide, along the second trajectory, through the second point, and into the femur, such that a leading end of the second pin exits the femur at a third point located at a distal edge of the base and located along the second trajectory, to indicate that an anterior femoral resection will intersect the anterior distal femoral cortex at the third point;

wherein the first and second pins are inserted while the base is attached to the anterior distal femoral cortex, the alignment rod is coupled to the base and aligned with the mechanical axis of the femur, and the pin guide is coupled to the base, wherein the first and second pins are located between the anterior distal femoral cortex and the intramedullary canal of the femur.

10. The method of claim 9, wherein aligning the alignment rod with the mechanical axis of the femur comprises centering a proximal end of the alignment rod over a rotational center of an articular head of the femur.

11. The method of claim 10, wherein aligning the alignment rod with the mechanical axis of the femur further comprises centering a distal end of the alignment rod over the distal end of the femur, opposite the articular head of the femur, while the proximal end of the alignment rod is centered over the rotational center of the articular head of the femur.

12. The method of claim 11, wherein the distal end of the alignment rod is coupled to the base while the proximal end of the alignment rod is centered over the rotational center of the articular head of the femur and the distal end of the alignment rod is centered over the distal end of the femur.

13. The method of claim 9, wherein when the first pin is in the defined orientation along the first trajectory, in an anterior view of the femur, the first pin is parallel to the mechanical axis.

14. The method of claim 9, wherein:

in an anterior view of the femur, the first trajectory is collinear with the mechanical axis of the femur; and in a lateral view of the femur, the first trajectory is parallel to at least one of the anterior distal femoral cortex and the anterior femoral resection.

15. The method of claim 14, wherein in in an anterior view of the femur, the second trajectory is collinear with the mechanical axis of the femur.

16. A method for inserting pins in a femur, the method comprising:

attaching a base to an anterior distal femoral cortex of the femur;

coupling an alignment rod to the base;

aligning the alignment rod with a mechanical axis of the femur;

coupling a pin guide to the base, wherein when the base is attached to the anterior distal femoral cortex, the alignment rod is coupled to the base and aligned with the mechanical axis of the femur, and the pin guide is coupled to the base, a first hole extending through the pin guide is aimed at a first point located on a distal end of the femur and located along a Whiteside's line along a center of a trochlear groove of the femur, a second hole extending through the pin guide is aimed at a second point located on the distal end of the femur and located in the trochlear groove, and the first and second points are located between the anterior distal femoral cortex and an intramedullary canal of the femur;

inserting a first pin through the first hole of the pin guide, through the first point, and into the femur at a defined orientation relative to the anterior distal femoral cortex, intersecting the Whiteside's line, and aligned with the mechanical axis of the femur; and inserting a second pin through the second hole of the pin guide, through the second point, and into the distal end of the femur so that a leading end of the second pin exits the femur at a distal edge of the base, in order to verify that an anterior femoral resection will intersect the anterior distal femoral cortex at the distal edge of the base;

wherein the first and second pins are inserted while the base is attached to the anterior distal femoral cortex, the alignment rod is coupled to the base and aligned with the mechanical axis of the femur, and the pin guide is coupled to the base, wherein the first and second pins are located between the anterior distal femoral cortex and the intramedullary canal of the femur.

17. The method of claim 16, wherein aligning the alignment rod with the mechanical axis of the femur comprises centering a proximal end of the alignment rod over a rotational center of an articular head of the femur.

18. The method of claim 17, wherein aligning the alignment rod with the mechanical axis of the femur further comprises centering a distal end of the alignment rod over the distal end of the femur, opposite the articular head of the femur, while the proximal end of the alignment rod is centered over the rotational center of the articular head of the femur.

19. The method of claim 18, wherein the distal end of the alignment rod is coupled to the base while the proximal end of the alignment rod is centered over the rotational center of the articular head of the femur and the distal end of the alignment rod is centered over the distal end of the femur.

20. The method of claim 16, wherein when the first pin is in the defined orientation, in an anterior view of the femur, the first pin is parallel to the mechanical axis.

21. The method of claim 16, wherein when the first pin is in the defined orientation:
   in an anterior view of the femur, the first pin is collinear with the mechanical axis of the femur; and
   in a lateral view of the femur, the first pin is parallel to at least one of the anterior distal femoral cortex and the anterior femoral resection.

22. The method of claim 16, wherein the second pin is inserted into the distal end of the femur so that in an anterior view of the femur, the second pin is collinear with the mechanical axis of the femur.

* * * * *